(12) United States Patent
Barry

(10) Patent No.: US 11,746,334 B2
(45) Date of Patent: Sep. 5, 2023

(54) ADENOVIRUSES AND METHODS FOR USING ADENOVIRUSES

(71) Applicant: MAYO FOUNDATION FOR MEDICAL EDUCATION AND RESEARCH, Rochester, MN (US)

(72) Inventor: Michael A. Barry, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 681 days.

(21) Appl. No.: 16/690,733

(22) Filed: Nov. 21, 2019

(65) Prior Publication Data

US 2020/0157510 A1 May 21, 2020

Related U.S. Application Data

(60) Provisional application No. 62/770,631, filed on Nov. 21, 2018.

(51) Int. Cl.
*C12N 7/00* (2006.01)
*A61K 35/761* (2015.01)

(52) U.S. Cl.
CPC .............. *C12N 7/00* (2013.01); *A61K 35/761* (2013.01); *C12N 2750/14122* (2013.01); *C12N 2750/14132* (2013.01); *C12N 2750/14143* (2013.01)

(58) Field of Classification Search
None
See application file for complete search history.

(56) References Cited

U.S. PATENT DOCUMENTS

| | | |
|---|---|---|
| 6,153,435 A | 11/2000 | Crystal |
| 7,332,337 B2 | 2/2008 | Van Es |
| 7,741,099 B2 | 6/2010 | Havenga |
| 7,951,585 B2 | 5/2011 | Ke |
| 8,834,863 B2 | 9/2014 | Roy |
| 9,546,206 B2 | 1/2017 | Ring et al. |
| 9,562,087 B2 | 2/2017 | Ring et al. |
| 9,683,025 B2 | 6/2017 | Zhang et al. |
| 10,588,938 B2 | 3/2020 | Giaccia et al. |
| 10,800,830 B2 | 10/2020 | Ring et al. |
| 2002/0150557 A1 | 10/2002 | Ramachandra |
| 2003/0219899 A1 | 11/2003 | Korokhov |
| 2004/0191222 A1 | 9/2004 | Emini |
| 2005/0265973 A1 | 12/2005 | Harden |

(Continued)

FOREIGN PATENT DOCUMENTS

| | | |
|---|---|---|
| EP | 1785488 | 5/2007 |
| JP | 2002527455 | 8/2006 |

(Continued)

OTHER PUBLICATIONS

Khare et al. (Molecular Therapy. 2011; 19(7): 1254-1262).*

(Continued)

*Primary Examiner* — Shanon A. Foley
(74) *Attorney, Agent, or Firm* — HUESCHEN AND SAGE

(57) ABSTRACT

This invention relates to methods and materials for nucleic acid delivery, vaccination, and/or treating cancer. More specifically, methods and materials for nucleic acid delivery, vaccination, and/or treating cancer using one or more recombinant adenoviruses (Ads) as an oncolytic agent are provided.

12 Claims, 82 Drawing Sheets

Specification includes a Sequence Listing.

(56) References Cited

U.S. PATENT DOCUMENTS

| | | |
|---|---|---|
| 2011/0318373 A1 | 12/2011 | Sasikumar |
| 2012/0264192 A1 | 10/2012 | Yamamoto |
| 2014/0348791 A1 | 11/2014 | Barouch |
| 2015/0250837 A1 | 9/2015 | Nolin |
| 2017/0157188 A1 | 6/2017 | Silvestre |
| 2018/0346571 A1 | 12/2018 | Gurney |
| 2019/0153471 A1 | 5/2019 | Paul |
| 2019/0382793 A1 | 12/2019 | Stewart |
| 2020/0339654 A1 | 10/2020 | Barry |

FOREIGN PATENT DOCUMENTS

| | | |
|---|---|---|
| JP | 2008522630 | 7/2008 |
| JP | 2015506372 | 3/2015 |
| WO | WO2000022136 | 4/2000 |
| WO | WO2006065827 | 6/2006 |
| WO | WO 2011/043719 | 4/2011 |
| WO | WO 2012/083297 | 6/2012 |
| WO | WO2013112966 | 8/2013 |
| WO | WO2015166082 | 11/2015 |
| WO | WO2017075570 | 5/2017 |
| WO | WO2018006005 | 1/2018 |
| WO | WO2018157165 | 8/2018 |
| WO | WO2019202118 | 10/2019 |

OTHER PUBLICATIONS

Walsh et al. (Journal of Clinical Microbiology. 2011; 3482-3490).*
Weaver et al. (Virology. 2011; 412: 19-27).*
Howe et al. (PNAS. 1990; 87: 5883-5887).*
International Preliminary Report on Patentability for PCT/US2020/030240 dated Mar. 24, 2021.
Brahmer, et al. The New England Journal of Medicine, 366:2455-65, 2012.
Davison, AJ. Journal of General Virology, 84(11):2895-2908, 2003.
Iwai, et al. "Involvement of PD-1 on tumor cells in the escape from host immune system and tumor immunotherapy by PD-L1 blockade", Proceedings of the National Academy of Sciences, 99(19):12293-97, 2002.
Maute, et al. Proceedings of the National Academy of Sciences, 112(47), E6506-E6514, published online Nov. 10, 2015.
Miao, et al. "Netralizing PD-L1 and PD-L2 Enhances teh Efficacy of Immune Checkpoint Inhibitors in Ovarian Cancer", bioRxiv, published online Jan. 20, 2020.
Weaver, et al. Virology, 412(1):19-27, 2011.
Barry, Michael, "Single-cycle adenovirus vectors in the current vaccine landscape", Expert Review of Vaccines, 17(2), Jan. 18, 2018, pp. 163-173.
International Search Report for PCT/US2019/062547 dated Feb. 5, 2020.
Chen, Christopher, Y., et al., "Targeting adenoviruses with factor x-single-chain antibody fusion proteins",Human Gene Therapy, vol. 21, No. 6, Jun. 1, 2010, pp. 739-749.
Fromm, George, et al., "Agonist redirected checkpoint, PD1-Fc-OX40L, for cancer immunotherapy", Journal for Immunotherapy of Cancer, 6:149, 2018, pp. 1-16.
Gao, Wenda, et al., "Stimulating PD-1-negative signals concurrent with blocking CD154 co-stimulation induces long-term islet allograft survival", Transplantation, vol. 76, No. 6, Sep. 1, 2003, pp. 994-999.
Herrmann, Monika, et al., "Bifunctional PD-1×αCD3×αCD33 fusion protein reverses adaptive immune escape in acute myeloid leukemia", Blood, vol. 132, No. 23, Dec. 6, 2018, pp. 2484-2494.
International Search Report for PCT/US2020/030240 dated Aug. 13, 2020.
Nguyen, Tien, V., et al., "Oncolytic adenovirus Ad657 for systemic virotherapy again prostate cancer", Oncolytic Virotherapy, vol. 7, May 1, 2018, pp. 43-51.
Stepanenko, Aleksei, et al., "Tropism and transduction on oncolytic adenovirus 5 vectors in cancer therapy: focus on fiber chimerism and mosaicism, hexon, and pIX", Virus Research, vol. 257, Sep. 1, 2018, pp. 40-51.
Wang, Gongze, et al., "Modification of sPD1 with CRT induces potent anti-tumor immune responses in vitro and in vivo", Biomedicine and Pharmacotherapy, vol. 76, Nov. 10, 2015, pp. 57-64.
Yoon, A-Rum, et al., "A vesicular stomatitis virus glycoprotein epitope-incorporated oncolytic adenovirus overcomes CAR-dependency and shows markedly enhanced cancer cell killing and suppression of tumor growth", Oncotarget, vol. 6, No. 33, Oct. 27, 2015, pp. 34875-34891.
Borovjagin, et al., "Adenovirus-based vectors for the development of prophylactic and therapeutic vaccines", Novel Technologies for Vaccine Development, publisher—Springer-Verlad Wien, chptr 8, pp. 203-271, 20114.
Cholanigiocarcinoma accessed Mar. 12, 2017 URL surgery.usc.edu/divisions/tumor/pancreasdiseases/web%20pages/BILIARY%20SYSTEM/cholaangiocarc 2 pages, 2017.
Kiesler, "Why a new immunotherapy for lung cancer works only for some people", accessed Feb, 12, 2018 at URL mskcc.org/blog/why-new-immunotherapy-lung-works-only-some-people, Apr. 2015, pp. 1-4.
McDermott, et al., "PD-1 as a potential target in cancer therapy", Cancer Medicine 2(5): 662-673, 2013.
Merck Manual Bladder cancer accessed Aug. 21, 2014 URL merckmanuals.com/home/kidney_and_urinary_tract_disorders/cancers_of_the_kidney_and_genitouriner 2 pages, 2014.
Merck Manual Colorectal cancer accessed Aug. 21, 2014 URL merckmanuals.com/home/digestive_disorders/tumors_of_the_digestive_system/colorectal_cancer.htm, 5 pages, 2013.
Merck Manual Prostate cancer accessed Aug. 21, 2014 URL merckmanuals.com/home/kidney_and_urinary_tracr_disorders/cancers_of_the_kidney_and_genitourinarcancer&alt=sh, 8 pages, 2013.
Merck Manuals Lung carcinoma accessed Mar. 12, 2017 URL merckmanuals.com/professional/pulmonaar-disorders/tumors-of-the-lungs/lung-carcinoma, 18 pages, 2017.
Merck Manuals Neuroblastoma accessed Mar. 12, 2017 URL merckmanuals.com/professional/pediatrics/pediatric-cancers/neuroblastoma, 4 pages, 2017.
National Institute of Cancer—understanding and related topics, accessed Aug. 21, 2014 at URL cancer.gov/cancertopics/understandingcancer, 63 pages, 2017.
Renal Cell Carcinoma accessed Mar. 12, 2017 URL merckmanuals.com/professional/genitourinary-disorders/genitourinary-cancer/renal-cell-carcinoma, 6 pages, 2017.
Teng, et al., "Classifying cancers based on T-cell infiltration and PD-L1", Am. Assoc. Cancer Res. J., 75:2139-2145, 2015.
Thyroid Cancer accessed Mar. 12, 2017 URL www.merckmanuals.com/professional/endocrine-and-metabolic-disorders/thyroid-disorders-cancers, 4 pages, 2016.
Lukashev, et al. "Evidence of frequent recombination among human adenoviruses", Journal of General Virology, 2008, 89:380-388.
Lu, Shao-Chia, et al., "Modulating oncolytic adenovirus immunotherapy by driving two axes of the immune system by expressing 4-IBBL and CD40L", Human Gene Therapy, vol. 33, No. 5-6, 2021, pp. 258-261.

* cited by examiner

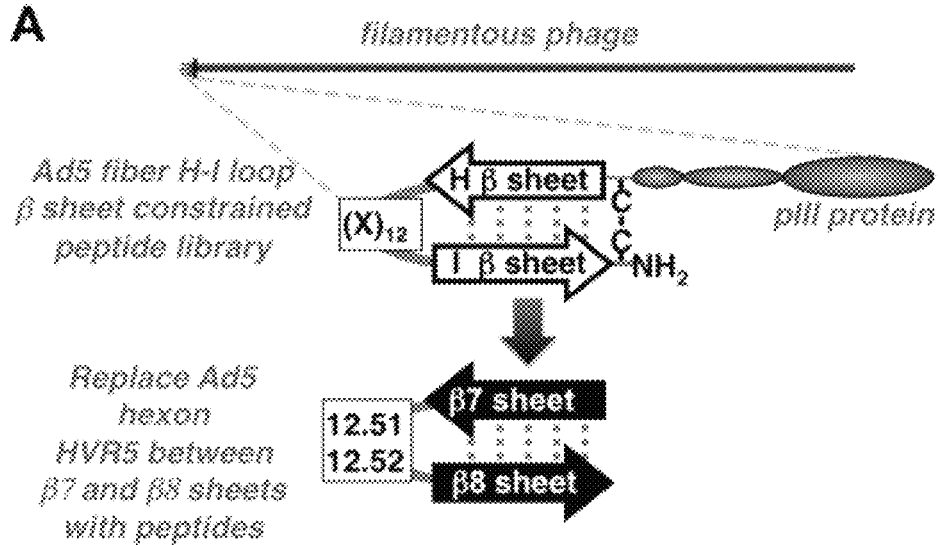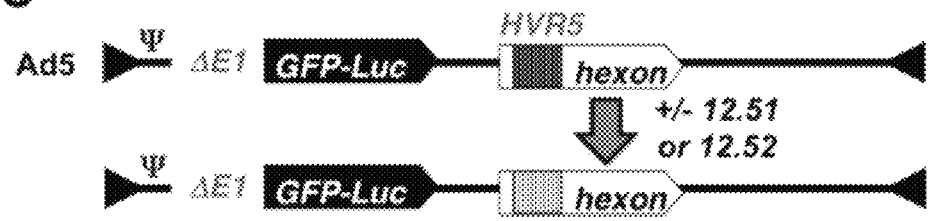
FIG. 1

```
              HVR 1
Ad5 hexon   YNALAPKGAPNPCEWDEAAT---ALEINLEEEDDNEDEVDEQAEQQKTHVFDAPYSGI
Ad6 hexon   YNALAPKGAPNSCEWEDMETAGVDADELDEEENEAQAFEQEQAKKTHVYAQAPLSGI
Ad57 hexon  YNALAPKGAPNSCEWDEDDT-QVQWAAEDDQDDEFEEQLPQQNQKKTHVYAQAPFAGE HVR 2                                              HVR 3
Ad5 hexon   NITKEGIQIG----VEGQ-TPKYADKTFQPEPQIGESQWYETEINHAAGRVLKKTTPMK
Ad6 hexon   KITKEGLQIGTADATVAGAGKEIFADKTFQPEPQVGESQWNEADATAGGRVLKKTTPMK
Ad57 hexon  KINKNGLQIGTNGAATEGN-KEIYADKTYQPEPQIGESQWNEAESSVAGGRVLKKTTPMK HVR 4                                              HVR 5
Ad5 hexon   PCYGSYARPTNENGGQGILVKQGNGKLESQVEMQFFSTIEATAGNGDNLTPKVVLYSEDV
Ad6 hexon   PCYGSYARPTNSNGGQGVMVEQ-NGKLESQVEMQFFSTSTNAINELNNIQPKVVLYSEDV
Ad57 hexon  PCYGSYARPTNSNGGQGVMVEQ-NGKLESQVEMQFFSTSVNAMNEANAIQPKLVLYSEDV HVR 6
Ad5 hexon   DIETPDTHISYMFTIDKEGNSRELVGQQSMPNRPNYIAFRDNFIGLMYYNSTGNMGVLAGQ
Ad6 hexon   NMETPDTHLSYKFKMGQKNAKMNLGQQAMPNRPNYIAFRDNFIGLMYYNSTGNMGVLAGQ
Ad57 hexon  NMETPDTHLSYKFGKSDDNSKAMLGQQSMPNRPNYIAFRDNFIGLMYYNSTGNMGVLAGQ Ad5 hexon   ASQLNAVVDLQDRNTELSYQLLLDSIGDRTRYFSMWNQAVDSYDPDVRIIENHGTEDELP
Ad6 hexon   ASQLNAVVDLQDRNTELSYQLLLDSIGDRTRYFSMWNQAVDSYDPDVRIIENHGTEDELP
Ad57 hexon  ASQLNAVVDLQDRNTELSYQLLLDSIGDRTRYFSMWNQAVDSYDPDVRIIENHGTEDELP HVR 7
Ad5 hexon   NYCFPLGGVINTETLTKVKPKTGQE----NGWEKDATEFSDKNEIRVGNNFAMEINLNAN
Ad6 hexon   NYCFPLGGIGIDTFQAVKITAANGDQGNTTWQKDS-TFAERNEIGVGNNFAMEINLNAN
Ad57 hexon  NYCFPLGGIGVTDTYQAIKAITNGNG--GATTWACDN-TFAERNEIGVGNNFAMEINLNAN Ad5 hexon   LWRNFLYSNIALYLPDKLKYSPSNVKISDNPNTYDYMNKRVVAPGLVDCYINLGARWSLD   SEQ ID NO: 71
Ad6 hexon   LWRNFLYSNIALYLPDKLKYNPTNVEISDNPNTYDYMNKRVVAPGLVDCYINLGARWSLE   SEQ ID NO: 72
Ad57 hexon  LWRNFLYSNIALYLPDKLKYNPTNVEISDNPNTYDYMNKRVVAPGLVDCYINLGARWSLD   SEQ ID NO: 73
```

Combining different HVRs from Ad6 and Ad657 and inserting cell targeting and detargeting ligands
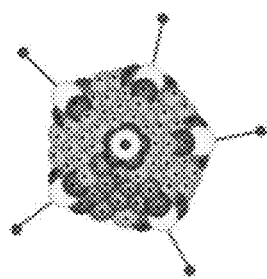
Insert combination of different HVRs
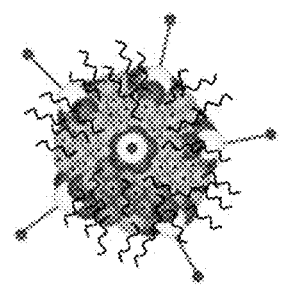
Insert peptides into different HVRs
FIG. 33

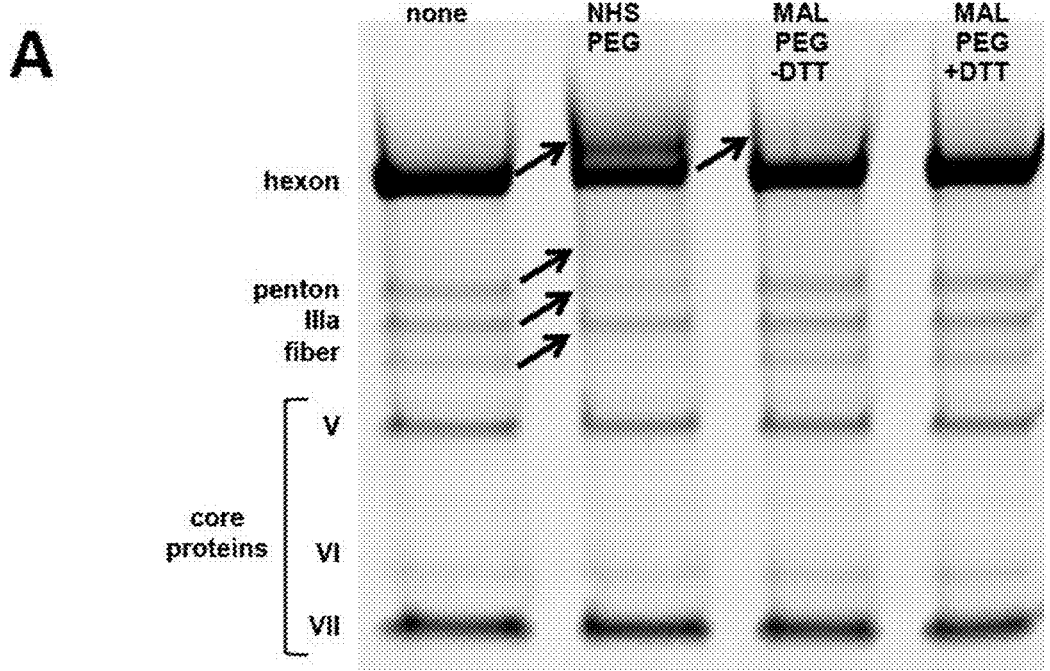
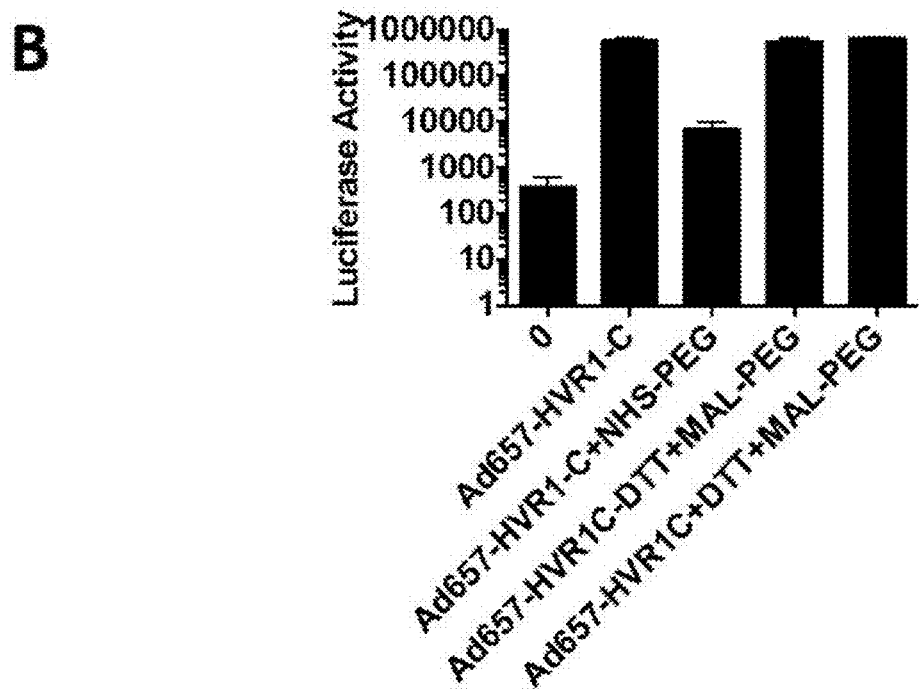
FIG. 36

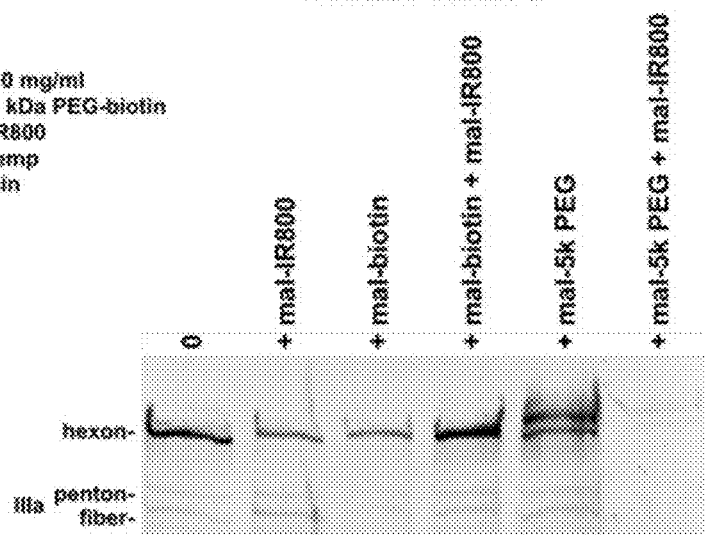
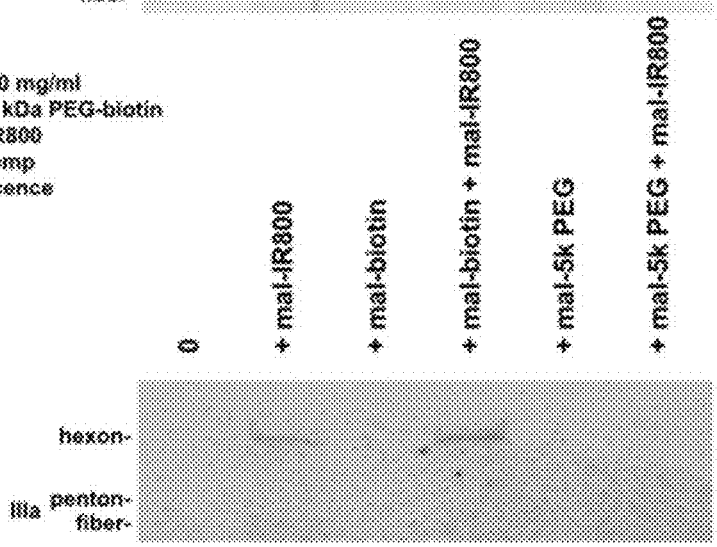
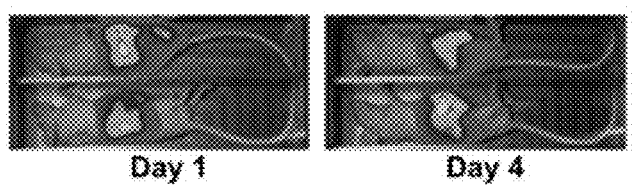
FIG. 37

RC-Ad

*E1 expression controlled by native E1 promoter*

CRAd-Probasin-E1A (Ad-PB)

*E1 expression
controlled by prostate-specific probasin promoter*

**CRAd-*dl*/1101**

*p300 pathway binding ablated, susceptible to IFN pathway
in normal cells*

**CRAd-*dl*/1107**

*pRB binding ablated allows virus to kill cancer cells with RB
pathway disruptions, but repressed in RB+ normal cells.*

**CRAd-*dl*/1101/07**

*p300 pathway binding ablated, susceptible to IFN pathway
pRB binding ablated allows virus to kill cancer cells with
RB pathway disruptions, but repressed in RB+
normal cells.*

Figure 43

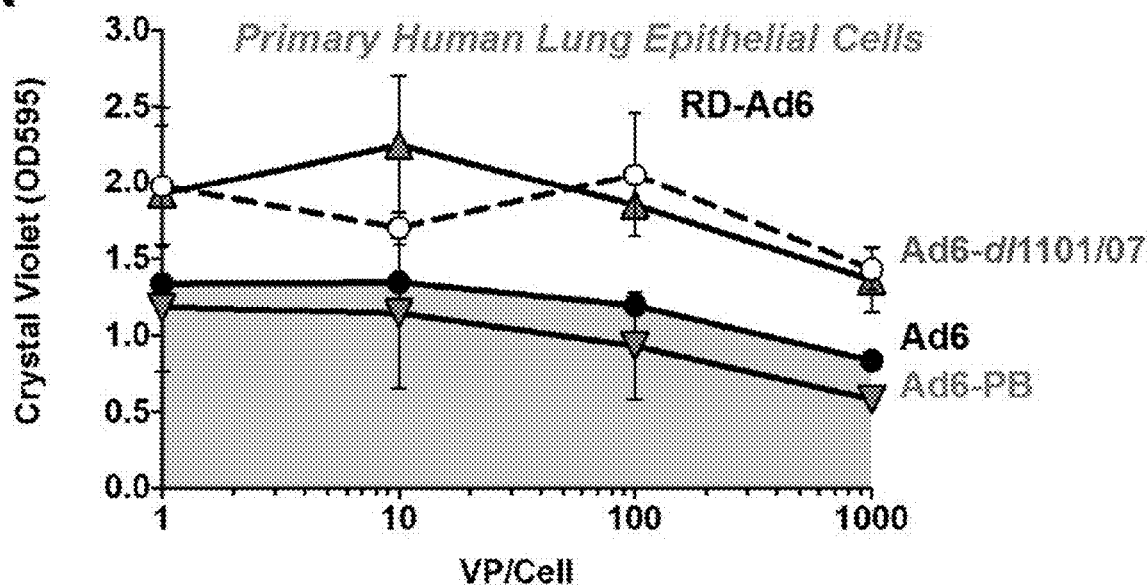
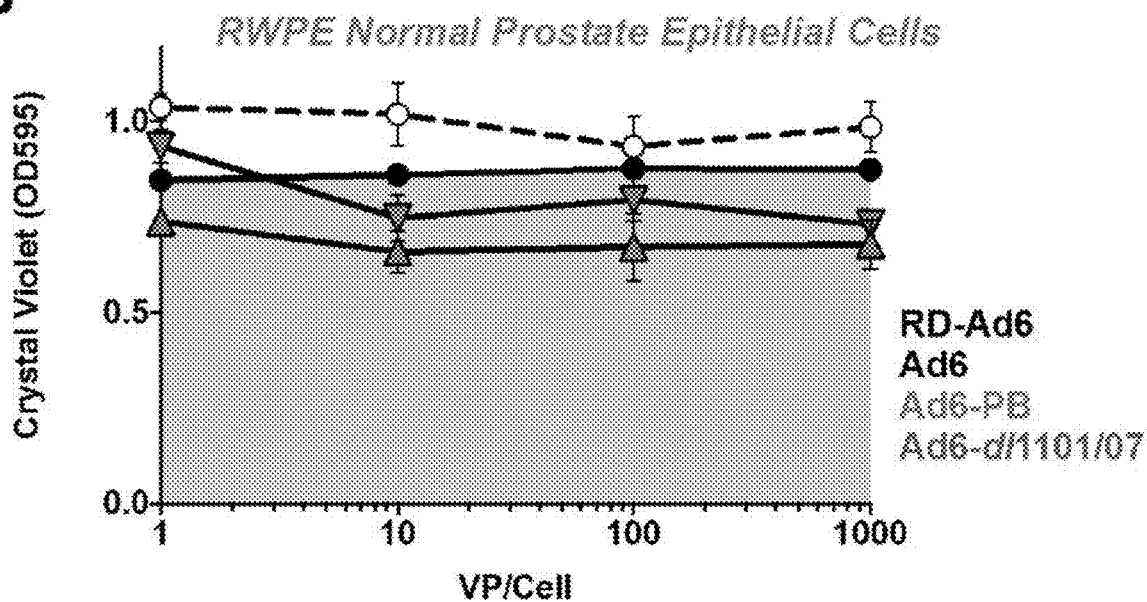
Figure 44

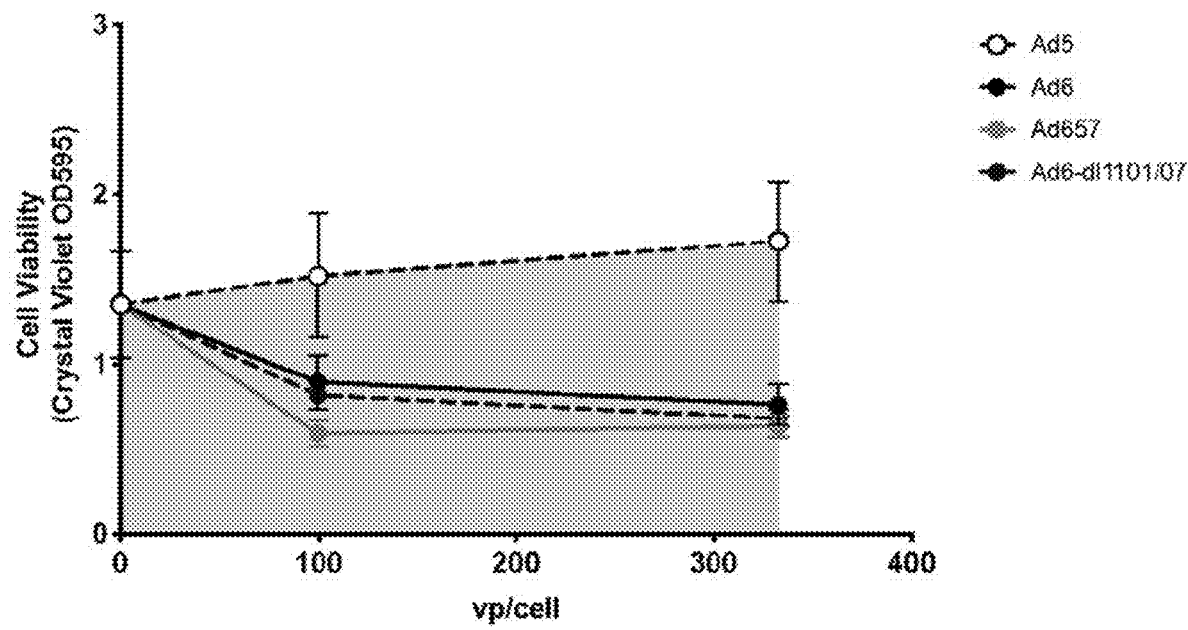
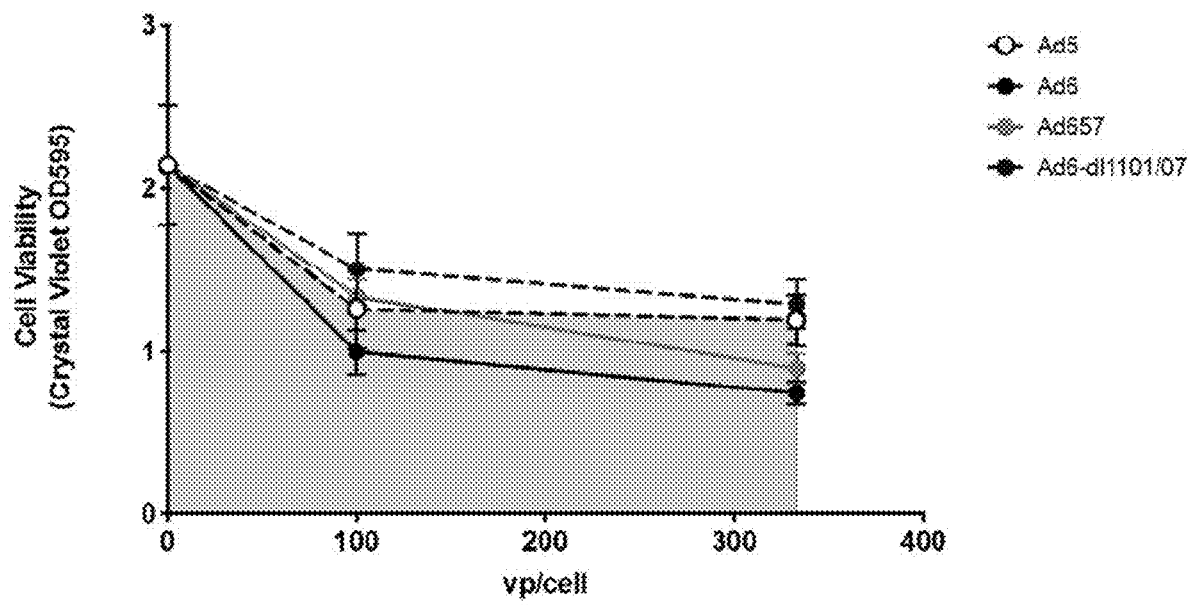
FIGURE 45 wild-type E1A N-terminus

MRHIICHGGVITEEMAASLLDQLIEEVLADNLPPPSHFEPPTLHELYDLDVT
APEDPNEEAVSQIFPESVMLAVQEGIDLFTFPPAPGSPEPPHLSRQPEQP
EQRALGPVSMPNLVPEVIDLTCHEAGFPPS (SEQ ID NO:42)

E1A dl1101 N-terminus

MRHIEEVLADNLPPPSHFEPPTLHELYDLDVTAPEDPNEEAVSQIFPESV
MLAVQEGIDLFTFPPAPGSPEPPHLSRQPEQPEQRALGPVSMPNLVPEVI
DLTCHEAGFPPS (SEQ ID NO:43)

E1A dl1107 N-terminus

MRHIICHGGVITEEMAASLLDQLIEEVLADNLPPPSHFEPPTLHELYDLDVT
APEDPNEEAVSQIFPESVMLAVQEGIDLFTFPPAPGSPEPPHLSRQPEQP
EQRALGPVCHEAGFPPS (SEQ ID NO:44)

E1A dl1101/1107 N-terminus

MRHIEEVLADNLPPPSHFEPPTLHELYDLDVTAPEDPNEEAVSQIFPESV
MLAVQEGIDLFTFPPAPGSPEPPHLSRQPEQPEQRALGPVCHEAGFPPS
(SEQ ID NO:45)

Figure 56

SEQUENCE LISTING

```
<160> NUMBER OF SEQ ID NOS: 78

<210> SEQ ID NO 1
<211> LENGTH: 12
<212> TYPE: PRT
<213> ORGANISM: Artificial Sequence
<220> FEATURE:
<223> OTHER INFORMATION: targeting polypeptide

<400> SEQUENCE: 1

Thr Ala Arg Gly Glu His Lys Glu Glu Glu Leu Ile
1               5                   10

<210> SEQ ID NO 2
<211> LENGTH: 12
<212> TYPE: PRT
<213> ORGANISM: Artificial Sequence
<220> FEATURE:
<223> OTHER INFORMATION: targeting polypeptide

<400> SEQUENCE: 2

Leu Arg Gln Thr Gly Ala Ala Ser Ala Val Trp Gly
1               5                   10

<210> SEQ ID NO 3
<211> LENGTH: 12
<212> TYPE: PRT
<213> ORGANISM: Artificial Sequence
<220> FEATURE:
<223> OTHER INFORMATION: targeting polypeptide

<400> SEQUENCE: 3

Ala Arg Arg Ala Asp Thr Gln Trp Arg Gly Leu Glu
1               5                   10

<210> SEQ ID NO 4
<211> LENGTH: 19
<212> TYPE: PRT
<213> ORGANISM: Artificial Sequence
<220> FEATURE:
<223> OTHER INFORMATION: targeting polypeptide

<400> SEQUENCE: 4

Gly Thr Trp Leu Asn Pro Gly Phe Pro Pro Gln Ser Cys Gly Tyr Ala
1               5                   10                  15
```

Thr Val Thr

<210> SEQ ID NO 5
<211> LENGTH: 9
<212> TYPE: PRT
<213> ORGANISM: Artificial Sequence
<220> FEATURE:
<223> OTHER INFORMATION: targeting polypeptide

<400> SEQUENCE: 5

Cys Asp Cys Arg Gly Asp Cys Phe Cys
1               5

<210> SEQ ID NO 6
<211> LENGTH: 10
<212> TYPE: PRT
<213> ORGANISM: Artificial Sequence
<220> FEATURE:
<223> OTHER INFORMATION: targeting polypeptide

<400> SEQUENCE: 6

Asn Met Ser Leu Asp Val Asn Arg Lys Ala
1               5                   10

<210> SEQ ID NO 7
<211> LENGTH: 12
<212> TYPE: PRT
<213> ORGANISM: Artificial Sequence
<220> FEATURE:
<223> OTHER INFORMATION: targeting polypeptide

<400> SEQUENCE: 7

Ile Ser Leu Ser Ser His Arg Ala Thr Trp Val Val
1               5                   10

<210> SEQ ID NO 8
<211> LENGTH: 20
<212> TYPE: PRT
<213> ORGANISM: Artificial Sequence
<220> FEATURE:
<223> OTHER INFORMATION: targeting polypeptide

<400> SEQUENCE: 8

Trp Thr Met Gly Leu Asp Gln Leu Arg Asp Ser Ser Trp Ala His Gly
1               5                   10                  15

Gly Phe Ser Ala
            20

<210> SEQ ID NO 9
<211> LENGTH: 20
<212> TYPE: PRT
<213> ORGANISM: Artificial Sequence
<220> FEATURE:
<223> OTHER INFORMATION: targeting polypeptide

<400> SEQUENCE: 9

Trp Thr Met Gly Leu Asp Gln Leu Arg Gly Asp Ser Ser Trp Ala His
1               5                   10                  15

Gly Gly Phe Ser
            20

<210> SEQ ID NO 10
<211> LENGTH: 20
<212> TYPE: PRT
<213> ORGANISM: Artificial Sequence
<220> FEATURE:

<223> OTHER INFORMATION: targeting polypeptide

<400> SEQUENCE: 10

Arg Ser Val Ser Gly Thr Glu Trp Val Pro Met Asn Glu Gln His Arg
1               5                   10                  15

Gly Ala Ile Trp
            20

<210> SEQ ID NO 11
<211> LENGTH: 20
<212> TYPE: PRT
<213> ORGANISM: Artificial Sequence
<220> FEATURE:
<223> OTHER INFORMATION: targeting polypeptide

<400> SEQUENCE: 11

Thr Glu Leu Arg Thr His Thr Ser Lys Glu Leu Thr Ile Arg Thr Ala
1               5                   10                  15

Ala Ser Ser Asp
            20

<210> SEQ ID NO 12
<211> LENGTH: 20
<212> TYPE: PRT
<213> ORGANISM: Artificial Sequence
<220> FEATURE:
<223> OTHER INFORMATION: targeting polypeptide

<400> SEQUENCE: 12

Asp Arg Ala Ile Gly Trp Gln Asp Lys Leu Tyr Lys Leu Pro Leu Gly
1               5                   10                  15

Ser Ile His Asn
            20

<210> SEQ ID NO 13
<211> LENGTH: 20
<212> TYPE: PRT
<213> ORGANISM: Artificial Sequence
<220> FEATURE:
<223> OTHER INFORMATION: targeting polypeptide

<400> SEQUENCE: 13

Met Gly Ser Trp Glu Lys Ala Ala Leu Trp Asn Arg Val Ser Ala Ser
1               5                   10                  15

Ser Gly Gly Ala
            20

<210> SEQ ID NO 14
<211> LENGTH: 20
<212> TYPE: PRT
<213> ORGANISM: Artificial Sequence
<220> FEATURE:
<223> OTHER INFORMATION: targeting polypeptide

<400> SEQUENCE: 14

Met Ala Met Gly Gly Lys Pro Glu Arg Pro Ala Asp Ser Asp Asn Val
1               5                   10                  15

Gln Val Arg Gly
            20

<210> SEQ ID NO 15
<211> LENGTH: 20
<212> TYPE: PRT
<213> ORGANISM: Artificial Sequence

```
<220> FEATURE:
<223> OTHER INFORMATION: targeting polypeptide

<400> SEQUENCE: 15

Met Ala Ser Arg Gly Asp Ala Gly Glu Gly Ser Thr Gln Ser Asn Thr
1               5                   10                  15

Asn Val Pro Ser
            20

<210> SEQ ID NO 16
<211> LENGTH: 20
<212> TYPE: PRT
<213> ORGANISM: Artificial Sequence
<220> FEATURE:
<223> OTHER INFORMATION: targeting polypeptide

<400> SEQUENCE: 16

Gly Pro Glu Asp Thr Ser Arg Ala Pro Glu Asn Gln Gln Lys Thr Phe
1               5                   10                  15

His Arg Arg Trp
            20

<210> SEQ ID NO 17
<211> LENGTH: 20
<212> TYPE: PRT
<213> ORGANISM: Artificial Sequence
<220> FEATURE:
<223> OTHER INFORMATION: targeting polypeptide

<400> SEQUENCE: 17

Met Gly Arg Glu Asp Val Gly Glu Gln Lys Leu Ile Ser Glu Glu Asp
1               5                   10                  15

Leu Gly Gly Ser
            20

<210> SEQ ID NO 18
<211> LENGTH: 11
<212> TYPE: PRT
<213> ORGANISM: Artificial Sequence
<220> FEATURE:
<223> OTHER INFORMATION: targeting polypeptide

<400> SEQUENCE: 18

Ala Cys Asp Cys Arg Gly Asp Cys Phe Cys Gly
1               5                   10

<210> SEQ ID NO 19
<211> LENGTH: 12
<212> TYPE: PRT
<213> ORGANISM: Artificial Sequence
<220> FEATURE:
<223> OTHER INFORMATION: targeting polypeptide

<400> SEQUENCE: 19

Ala Cys Asp Cys Arg Glu Asp Val Cys Phe Cys Gly
1               5                   10

<210> SEQ ID NO 20
<211> LENGTH: 20
<212> TYPE: PRT
<213> ORGANISM: Artificial Sequence
<220> FEATURE:
<223> OTHER INFORMATION: targeting polypeptide

<400> SEQUENCE: 20
```

```
Gly Gln Ile Pro Ile Thr Glu Pro Glu Leu Cys Cys Val Pro Trp Thr
1               5                   10                  15

Glu Ala Phe Tyr
            20

<210> SEQ ID NO 21
<211> LENGTH: 20
<212> TYPE: PRT
<213> ORGANISM: Artificial Sequence
<220> FEATURE:
<223> OTHER INFORMATION: targeting polypeptide

<400> SEQUENCE: 21

Pro Gln Pro Pro Asn Ser Thr Ala His Pro Asn Pro His Lys Ala Pro
1               5                   10                  15

Pro Asn Thr Thr
            20

<210> SEQ ID NO 22
<211> LENGTH: 20
<212> TYPE: PRT
<213> ORGANISM: Artificial Sequence
<220> FEATURE:
<223> OTHER INFORMATION: targeting polypeptide

<400> SEQUENCE: 22

Val Arg Trp Phe Pro Gly Gly Glu Trp Gly Val Thr His Pro Glu Ser
1               5                   10                  15

Leu Pro Pro Pro
            20

<210> SEQ ID NO 23
<211> LENGTH: 19
<212> TYPE: PRT
<213> ORGANISM: Artificial Sequence
<220> FEATURE:
<223> OTHER INFORMATION: targeting polypeptide

<400> SEQUENCE: 23

Lys Lys Lys Lys Lys Lys Lys Lys Lys Lys Lys Lys Lys Lys Lys Lys
1               5                   10                  15

Lys Lys Lys

<210> SEQ ID NO 24
<211> LENGTH: 14
<212> TYPE: PRT
<213> ORGANISM: Artificial Sequence
<220> FEATURE:
<223> OTHER INFORMATION: targeting polypeptide

<400> SEQUENCE: 24

Gly Leu Asn Asp Ile Phe Glu Ala Gln Lys Ile Glu Trp His
1               5                   10

<210> SEQ ID NO 25
<211> LENGTH: 23
<212> TYPE: PRT
<213> ORGANISM: Artificial Sequence
<220> FEATURE:
<223> OTHER INFORMATION: targeting polypeptide

<400> SEQUENCE: 25

Cys Ala Ala Ala Arg Trp Lys Lys Ala Phe Ile Ala Val Ser Ala Ala
1               5                   10                  15
```

Asn Arg Phe Lys Lys Ile Ser
            20

<210> SEQ ID NO 26
<211> LENGTH: 14
<212> TYPE: PRT
<213> ORGANISM: Artificial Sequence
<220> FEATURE:
<223> OTHER INFORMATION: targeting polypeptide

<400> SEQUENCE: 26

Glu Asp Pro Gly Phe Phe Asn Val Glu Ile Pro Glu Phe Pro
1               5                   10

<210> SEQ ID NO 27
<211> LENGTH: 20
<212> TYPE: PRT
<213> ORGANISM: Artificial Sequence
<220> FEATURE:
<223> OTHER INFORMATION: targeting polypeptide

<400> SEQUENCE: 27

Gly Gly His Gly Arg Val Leu Trp Pro Asp Gly Trp Phe Ser Leu Val
1               5                   10                  15

Gly Ile Ser Pro
            20

<210> SEQ ID NO 28
<211> LENGTH: 21
<212> TYPE: PRT
<213> ORGANISM: Artificial Sequence
<220> FEATURE:
<223> OTHER INFORMATION: targeting polypeptide

<400> SEQUENCE: 28

Met Ala Arg Thr Val Thr Ala Asn Val Pro Gly Met Gly Glu Gly Met
1               5                   10                  15

Val Val Val Pro Cys
            20

<210> SEQ ID NO 29
<211> LENGTH: 20
<212> TYPE: PRT
<213> ORGANISM: Artificial Sequence
<220> FEATURE:
<223> OTHER INFORMATION: targeting polypeptide

<400> SEQUENCE: 29

Gly Val Ser Lys Arg Gly Leu Gln Cys His Asp Phe Ile Ser Cys Ser
1               5                   10                  15

Gly Val Pro Trp
            20

<210> SEQ ID NO 30
<211> LENGTH: 20
<212> TYPE: PRT
<213> ORGANISM: Artificial Sequence
<220> FEATURE:
<223> OTHER INFORMATION: targeting polypeptide

<400> SEQUENCE: 30

Asn Gln Ser Ile Pro Lys Val Ala Gly Asp Ser Lys Val Phe Cys Trp
1               5                   10                  15

Trp Cys Ala Leu
            20

```
<210> SEQ ID NO 31
<211> LENGTH: 20
<212> TYPE: PRT
<213> ORGANISM: Artificial Sequence
<220> FEATURE:
<223> OTHER INFORMATION: targeting polypeptide

<400> SEQUENCE: 31

Gln Ser Thr Pro Pro Thr Lys His Leu Thr Ile Pro Arg His Leu Arg
1               5                   10                  15

Asn Thr Leu Ile
            20

<210> SEQ ID NO 32
<211> LENGTH: 20
<212> TYPE: PRT
<213> ORGANISM: Artificial Sequence
<220> FEATURE:
<223> OTHER INFORMATION: targeting polypeptide

<400> SEQUENCE: 32

Asp Met Ser Phe Gln Leu Val Thr Pro Phe Leu Lys Ala Leu Pro Thr
1               5                   10                  15

Gly Trp Arg Gly
            20

<210> SEQ ID NO 33
<211> LENGTH: 20
<212> TYPE: PRT
<213> ORGANISM: Artificial Sequence
<220> FEATURE:
<223> OTHER INFORMATION: targeting polypeptide

<400> SEQUENCE: 33

Gly Gly His Gly Arg Val Leu Trp Pro Asp Gly Trp Phe Ser Leu Val
1               5                   10                  15

Gly Ile Ser Pro
            20

<210> SEQ ID NO 34
<211> LENGTH: 8
<212> TYPE: PRT
<213> ORGANISM: Artificial Sequence
<220> FEATURE:
<223> OTHER INFORMATION: targeting polypeptide

<400> SEQUENCE: 34

Phe Ser Leu Val Gly Ile Ser Pro
1               5

<210> SEQ ID NO 35
<211> LENGTH: 20
<212> TYPE: PRT
<213> ORGANISM: Artificial Sequence
<220> FEATURE:
<223> OTHER INFORMATION: targeting polypeptide

<400> SEQUENCE: 35

Gln Ile Met Met Gly Pro Ser Leu Gly Tyr Tyr Met Pro Ser Glu Ser
1               5                   10                  15

Ile Phe Ala Tyr
            20
```

```
<210> SEQ ID NO 36
<211> LENGTH: 20
<212> TYPE: PRT
<213> ORGANISM: Artificial Sequence
<220> FEATURE:
<223> OTHER INFORMATION: targeting polypeptide

<400> SEQUENCE: 36

Ile Ser Trp Asp Ile Trp Arg Trp Trp Tyr Thr Ser Glu Asp Arg Asp
1               5                   10                  15

Ala Gly Ser Ala
            20

<210> SEQ ID NO 37
<211> LENGTH: 20
<212> TYPE: PRT
<213> ORGANISM: Artificial Sequence
<220> FEATURE:
<223> OTHER INFORMATION: targeting polypeptide

<400> SEQUENCE: 37

Val Trp Gly Met Thr Thr Ser Asp His Gln Arg Lys Thr Glu Arg Leu
1               5                   10                  15

Asp Ser Pro Glu
            20

<210> SEQ ID NO 38
<211> LENGTH: 20
<212> TYPE: PRT
<213> ORGANISM: Artificial Sequence
<220> FEATURE:
<223> OTHER INFORMATION: targeting polypeptide

<400> SEQUENCE: 38

Met Thr Ser Ala Gln Thr Ser Glu Lys Leu Lys Ala Glu Thr Asp Arg
1               5                   10                  15

His Thr Ala Glu
            20

<210> SEQ ID NO 39
<211> LENGTH: 19
<212> TYPE: PRT
<213> ORGANISM: Artificial Sequence
<220> FEATURE:
<223> OTHER INFORMATION: targeting polypeptide

<400> SEQUENCE: 39

Met Gly Ser Arg Ser Ala Val Gly Asp Phe Glu Ser Ala Glu Gly Ser
1               5                   10                  15

Arg Arg Pro

<210> SEQ ID NO 40
<211> LENGTH: 20
<212> TYPE: PRT
<213> ORGANISM: Artificial Sequence
<220> FEATURE:
<223> OTHER INFORMATION: targeting polypeptide

<400> SEQUENCE: 40

Met Gly Arg Thr Val Gln Ser Gly Asp Gly Thr Pro Ala Gln Thr Gln
1               5                   10                  15

Pro Ser Val Asn
            20
```

```
<210> SEQ ID NO 41
<211> LENGTH: 20
<212> TYPE: PRT
<213> ORGANISM: Artificial Sequence
<220> FEATURE:
<223> OTHER INFORMATION: targeting polypeptide

<400> SEQUENCE: 41

Met Ala Arg Thr Val Thr Ala Asn Val Pro Gly Met Gly Glu Gly Met
1               5                   10                  15

Val Val Val Pro
            20

<210> SEQ ID NO 42
<211> LENGTH: 132
<212> TYPE: PRT
<213> ORGANISM: Artificial Sequence
<220> FEATURE:
<223> OTHER INFORMATION: Adenovirus E1A N-terminus polypeptide

<400> SEQUENCE: 42

Met Arg His Ile Ile Cys His Gly Gly Val Ile Thr Glu Glu Met Ala
1               5                   10                  15

Ala Ser Leu Leu Asp Gln Leu Ile Glu Glu Val Leu Ala Asp Asn Leu
            20                  25                  30

Pro Pro Pro Ser His Phe Glu Pro Thr Leu His Glu Leu Tyr Asp
        35                  40                  45

Leu Asp Val Thr Ala Pro Glu Asp Pro Asn Glu Glu Ala Val Ser Gln
    50                  55                  60

Ile Phe Pro Glu Ser Val Met Leu Ala Val Gln Glu Gly Ile Asp Leu
65                  70                  75                  80

Phe Thr Phe Pro Pro Ala Pro Gly Ser Pro Glu Pro Pro His Leu Ser
                85                  90                  95

Arg Gln Pro Glu Gln Pro Glu Gln Arg Ala Leu Gly Pro Val Ser Met
            100                 105                 110

Pro Asn Leu Val Pro Glu Val Ile Asp Leu Thr Cys His Glu Ala Gly
        115                 120                 125

Phe Pro Pro Ser
    130

<210> SEQ ID NO 43
<211> LENGTH: 112
<212> TYPE: PRT
<213> ORGANISM: Artificial Sequence
<220> FEATURE:
<223> OTHER INFORMATION: E1A N-terminus polypeptide

<400> SEQUENCE: 43

Met Arg His Ile Glu Glu Val Leu Ala Asp Asn Leu Pro Pro Pro Ser
1               5                   10                  15

His Phe Glu Pro Pro Thr Leu His Glu Leu Tyr Asp Leu Asp Val Thr
            20                  25                  30

Ala Pro Glu Asp Pro Asn Glu Glu Ala Val Ser Gln Ile Phe Pro Glu
        35                  40                  45

Ser Val Met Leu Ala Val Gln Glu Gly Ile Asp Leu Phe Thr Phe Pro
    50                  55                  60

Pro Ala Pro Gly Ser Pro Glu Pro Pro His Leu Ser Arg Gln Pro Glu
65                  70                  75                  80

Gln Pro Glu Gln Arg Ala Leu Gly Pro Val Ser Met Pro Asn Leu Val
                85                  90                  95
```

```
Pro Glu Val Ile Asp Leu Thr Cys His Glu Ala Gly Phe Pro Pro Ser
            100                 105                 110
```

<210> SEQ ID NO 44
<211> LENGTH: 119
<212> TYPE: PRT
<213> ORGANISM: Artificial Sequence
<220> FEATURE:
<223> OTHER INFORMATION: E1A N-terminus polypeptide

<400> SEQUENCE: 44

```
Met Arg His Ile Ile Cys His Gly Gly Val Ile Thr Glu Glu Met Ala
1               5                   10                  15

Ala Ser Leu Leu Asp Gln Leu Ile Glu Glu Val Leu Ala Asp Asn Leu
            20                  25                  30

Pro Pro Pro Ser His Phe Glu Pro Pro Thr Leu His Glu Leu Tyr Asp
            35                  40                  45

Leu Asp Val Thr Ala Pro Glu Asp Pro Asn Glu Glu Ala Val Ser Gln
        50                  55                  60

Ile Phe Pro Glu Ser Val Met Leu Ala Val Gln Glu Gly Ile Asp Leu
65                  70                  75                  80

Phe Thr Phe Pro Pro Ala Pro Gly Ser Pro Glu Pro His Leu Ser
                85                  90                  95

Arg Gln Pro Glu Gln Pro Glu Arg Ala Leu Gly Pro Val Cys His
            100                 105                 110

Glu Ala Gly Phe Pro Pro Ser
            115
```

<210> SEQ ID NO 45
<211> LENGTH: 99
<212> TYPE: PRT
<213> ORGANISM: Artificial Sequence
<220> FEATURE:
<223> OTHER INFORMATION: E1A N-terminus polypeptide

<400> SEQUENCE: 45

```
Met Arg His Ile Glu Glu Val Leu Ala Asp Asn Leu Pro Pro Pro Ser
1               5                   10                  15

His Phe Glu Pro Pro Thr Leu His Glu Leu Tyr Asp Leu Asp Val Thr
            20                  25                  30

Ala Pro Glu Asp Pro Asn Glu Glu Ala Val Ser Gln Ile Phe Pro Glu
            35                  40                  45

Ser Val Met Leu Ala Val Gln Glu Gly Ile Asp Leu Phe Thr Phe Pro
        50                  55                  60

Pro Ala Pro Gly Ser Pro Glu Pro His Leu Ser Arg Gln Pro Glu
65                  70                  75                  80

Gln Pro Glu Gln Arg Ala Leu Gly Pro Val Cys His Glu Ala Gly Phe
                85                  90                  95

Pro Pro Ser
```

<210> SEQ ID NO 46
<211> LENGTH: 5
<212> TYPE: PRT
<213> ORGANISM: Artificial Sequence
<220> FEATURE:
<223> OTHER INFORMATION: Cell Binding Peptide

<400> SEQUENCE: 46

Arg Glu Asp Val Tyr

<210> SEQ ID NO 47
<211> LENGTH: 12
<212> TYPE: PRT
<213> ORGANISM: Artificial Sequence
<220> FEATURE:
<223> OTHER INFORMATION: Breast Cancer Binding Peptide

<400> SEQUENCE: 47

Ile Ser Leu Ser Ser His Arg Ala Thr Trp Val Val
1               5                   10

<210> SEQ ID NO 48
<211> LENGTH: 1608
<212> TYPE: DNA
<213> ORGANISM: Artificial Sequence
<220> FEATURE:
<223> OTHER INFORMATION: Probasin-E1 nucleic acid

<400> SEQUENCE: 48

```
tcgagcgacg gtatcgataa gcttggagct tatgatagca tcttgttctt agtcttttc      60
ttaataggga cataaagccc acaaataaaa atatgcctga agaatgggac aggcattggg    120
cattgtccat gcctagtaaa gtactccaag aacctatttg tatactagat gacacaatgt    180
tctagccaag cttggtagtc atcatgttta aacatctacc attccagtta agaaaatatg    240
atagcatctt gttcttagtc ttttcttaa tagggacata aagcccacaa ataaaaatat     300
gcctgaagaa tgggacaggc attgggcatt gtccatgcct agtaaagtac tccaagaacc    360
tatttgtata ctagatgaca caatgtcaat gtctgtgtac aactgccaac tgggatgcaa    420
gacactgccc atgccaatca tcctgaaaag cagctataaa aagcaggaag ctactctgca    480
ccttgtcagt gaggtccaga tacctccctc gagcggccgc gacgcgcagt gtatttatac    540
ccggtgagtt cctcaagagg ccactcttga gtgccagcga gtagagtttt ctcctccgag    600
ccgctccgac accgggactg aaaatgagac atattatctg ccacggaggt gttattaccg    660
aagaaatggc cgccagtctt ttggaccagc tgatcgaaga ggtactggct gataatcttc    720
cacctcctag ccattttgaa ccacctaccc ttcacgaact gtatgattta gacgtgacgg    780
ccccccgaaga tcccaacgag gaggcggttt cgcagatttt tcccgagtct gtaatgttgg    840
cggtgcagga agggattgac ttattcactt ttccgccggc gccggttct ccggagccgc     900
ctcaccttc cggcagccc gagcagccgg agcagagagc cttgggtccg gtttctatgc      960
caaaccttgt gccggaggtg atcgatctta cctgccacga ggctggcttt ccacccagtg   1020
acgacgagga tgaagagggt gaggagtttg tgttagatta tgtggagcac cccgggcacg   1080
gttgcaggtc ttgtcattat caccggagga atacggggga cccagatatt atgtgttcgc   1140
tttgctatat gaggacctgt ggcatgtttg tctacagtaa gtgaaaatta tgggcagtcg   1200
gtgatagagt ggtgggtttg gtgtggtaat ttttttttaa tttttacagt tttgtggttt   1260
aaagaatttt gtattgtgat tttttaaaag gtcctgtgtc tgaacctgag cctgagcccg   1320
agccagaacc ggagcctgca agacctaccc ggcgtcctaa attggtgcct gctatcctga   1380
gacgcccgac atcacctgtg tctagagaat gcaatagtag tacggatagc tgtgactccg   1440
gtccttctaa cacacctcct gagatacacc cggtggtccc gctgtgcccc attaaaccag   1500
ttgccgtgag agttggtggg cgtcgccagg ctgtggaatg tatcgaggac ttgcttaacg   1560
agtctgggca acctttggac ttgagctgta aacgccccag gccataag                 1608
```

<210> SEQ ID NO 49
<211> LENGTH: 959
<212> TYPE: PRT
<213> ORGANISM: Artificial Sequence
<220> FEATURE:
<223> OTHER INFORMATION: Hexon Polypeptide

<400> SEQUENCE: 49

```
Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Asp Glu Asp Thr Gln Val Gln Val
    130                 135                 140

Ala Ala Glu Asp Asp Gln Asp Asp Glu Glu Glu Gln Leu Pro
145                 150                 155                 160

Gln Gln Arg Asn Gly Lys Lys Thr His Val Tyr Ala Gln Ala Pro Phe
                165                 170                 175

Ala Gly Glu Ala Ile Asn Lys Asn Gly Leu Gln Ile Gly Thr Asn Gly
            180                 185                 190

Ala Ala Thr Glu Gly Asn Lys Glu Ile Tyr Ala Asp Lys Thr Tyr Gln
        195                 200                 205

Pro Glu Pro Gln Ile Gly Glu Ser Gln Trp Asn Glu Ala Glu Ser Ser
    210                 215                 220

Val Ala Gly Gly Arg Val Leu Lys Lys Thr Thr Pro Met Lys Pro Cys
225                 230                 235                 240

Tyr Gly Ser Tyr Ala Arg Pro Thr Asn Ser Asn Gly Gly Gln Gly Val
                245                 250                 255

Met Val Glu Gln Asn Gly Lys Leu Glu Ser Gln Val Glu Met Gln Phe
            260                 265                 270

Phe Ser Thr Ser Val Asn Ala Met Asn Glu Ala Asn Ala Ile Gln Pro
        275                 280                 285

Lys Leu Val Leu Tyr Ser Glu Asp Val Asn Met Glu Thr Pro Asp Thr
    290                 295                 300

His Leu Ser Tyr Lys Pro Gly Lys Ser Asp Asp Asn Ser Lys Ala Met
305                 310                 315                 320

Leu Gly Gln Gln Ser Met Pro Asn Arg Pro Asn Tyr Ile Ala Phe Arg
                325                 330                 335

Asp Asn Phe Ile Gly Leu Met Tyr Tyr Asn Ser Thr Gly Asn Met Gly
            340                 345                 350

Val Leu Ala Gly Gln Ala Ser Gln Leu Asn Ala Val Val Asp Leu Gln
        355                 360                 365
```

```
Asp Arg Asn Thr Glu Leu Ser Tyr Gln Leu Leu Asp Ser Ile Gly
370                 375                 380

Asp Arg Thr Arg Tyr Phe Ser Met Trp Asn Gln Ala Val Asp Ser Tyr
385                 390                 395                 400

Asp Pro Asp Val Arg Ile Ile Glu Asn His Gly Thr Glu Asp Glu Leu
            405                 410                 415

Pro Asn Tyr Cys Phe Pro Leu Gly Gly Ile Gly Val Thr Asp Thr Tyr
            420                 425                 430

Gln Ala Ile Lys Ala Thr Asn Gly Asn Gly Gly Ala Thr Thr Trp Ala
            435                 440                 445

Gln Asp Asn Thr Phe Ala Glu Arg Asn Glu Ile Gly Val Gly Asn Asn
450                 455                 460

Phe Ala Met Glu Ile Asn Leu Asn Ala Asn Leu Trp Arg Asn Phe Leu
465                 470                 475                 480

Tyr Ser Asn Ile Ala Leu Tyr Leu Pro Asp Lys Leu Lys Tyr Asn Pro
                485                 490                 495

Thr Asn Val Glu Ile Ser Asp Asn Pro Asn Thr Tyr Asp Tyr Met Asn
                500                 505                 510

Lys Arg Val Val Ala Pro Gly Leu Val Asp Cys Tyr Ile Asn Leu Gly
                515                 520                 525

Ala Arg Trp Ser Leu Asp Tyr Met Asp Asn Val Asn Pro Phe Asn His
530                 535                 540

His Arg Asn Ala Gly Leu Arg Tyr Arg Ser Met Leu Leu Gly Asn Gly
545                 550                 555                 560

Arg Tyr Val Pro Phe His Ile Gln Val Pro Gln Lys Phe Phe Ala Ile
                565                 570                 575

Lys Asn Leu Leu Leu Leu Pro Gly Ser Tyr Thr Tyr Glu Trp Asn Phe
                580                 585                 590

Arg Lys Asp Val Asn Met Val Leu Gln Ser Ser Leu Gly Asn Asp Leu
                595                 600                 605

Arg Val Asp Gly Ala Ser Ile Lys Phe Asp Ser Ile Cys Leu Tyr Ala
610                 615                 620

Thr Phe Phe Pro Met Ala His Asn Thr Ala Ser Thr Leu Glu Ala Met
625                 630                 635                 640

Leu Arg Asn Asp Thr Asn Asp Gln Ser Phe Asn Asp Tyr Leu Ser Ala
                645                 650                 655

Ala Asn Met Leu Tyr Pro Ile Pro Ala Asn Ala Thr Asn Val Pro Ile
                660                 665                 670

Ser Ile Pro Ser Arg Asn Trp Ala Ala Phe Arg Gly Trp Ala Phe Thr
                675                 680                 685

Arg Leu Lys Thr Lys Glu Thr Pro Ser Leu Gly Ser Gly Tyr Asp Pro
690                 695                 700

Tyr Tyr Thr Tyr Ser Gly Ser Ile Pro Tyr Leu Asp Gly Thr Phe Tyr
705                 710                 715                 720

Leu Asn His Thr Phe Lys Lys Val Ala Ile Thr Phe Asp Ser Ser Val
                725                 730                 735

Ser Trp Pro Gly Asn Asp Arg Leu Leu Thr Pro Asn Glu Phe Glu Ile
                740                 745                 750

Lys Arg Ser Val Asp Gly Glu Gly Tyr Asn Val Ala Gln Cys Asn Met
                755                 760                 765

Thr Lys Asp Trp Phe Leu Val Gln Met Leu Ala Asn Tyr Asn Ile Gly
770                 775                 780

Tyr Gln Gly Phe Tyr Ile Pro Glu Ser Tyr Lys Asp Arg Met Tyr Ser
```

```
785                 790                 795                 800
Phe Phe Arg Asn Phe Gln Pro Met Ser Arg Gln Val Val Asp Asp Thr
                805                 810                 815
Lys Tyr Lys Asp Tyr Gln Gln Val Gly Ile Ile His Gln His Asn Asn
                820                 825                 830
Ser Gly Phe Val Gly Tyr Leu Ala Pro Thr Met Arg Glu Gly Gln Ala
                835                 840                 845
Tyr Pro Ala Asn Val Pro Tyr Pro Leu Ile Gly Lys Thr Ala Val Asp
            850                 855                 860
Ser Ile Thr Gln Lys Lys Phe Leu Cys Asp Arg Thr Leu Trp Arg Ile
865                 870                 875                 880
Pro Phe Ser Ser Asn Phe Met Ser Met Gly Ala Leu Thr Asp Leu Gly
                    885                 890                 895
Gln Asn Leu Leu Tyr Ala Asn Ser Ala His Ala Leu Asp Met Thr Phe
                900                 905                 910
Glu Val Asp Pro Met Asp Glu Pro Thr Leu Leu Tyr Val Leu Phe Glu
            915                 920                 925
Val Phe Asp Val Val Arg Val His Gln Pro His Arg Gly Val Ile Glu
        930                 935                 940
Thr Val Tyr Leu Arg Thr Pro Phe Ser Ala Gly Asn Ala Thr Thr
945                 950                 955
```

<210> SEQ ID NO 50
<211> LENGTH: 967
<212> TYPE: PRT
<213> ORGANISM: Artificial Sequence
<220> FEATURE:
<223> OTHER INFORMATION: Hexon Polypeptide

<400> SEQUENCE: 50

```
Met Ala Thr Pro Ser Met Met Pro Gln Trp Ser Tyr Met His Ile Ser
1               5                   10                  15
Gly Gln Asp Ala Ser Glu Tyr Leu Ser Pro Gly Leu Val Gln Phe Ala
            20                  25                  30
Arg Ala Thr Glu Thr Tyr Phe Ser Leu Asn Asn Lys Phe Arg Asn Pro
        35                  40                  45
Thr Val Ala Pro Thr His Asp Val Thr Thr Asp Arg Ser Gln Arg Leu
    50                  55                  60
Thr Leu Arg Phe Ile Pro Val Asp Arg Glu Asp Thr Ala Tyr Ser Tyr
65                  70                  75                  80
Lys Ala Arg Phe Thr Leu Ala Val Gly Asp Asn Arg Val Leu Asp Met
                85                  90                  95
Ala Ser Thr Tyr Phe Asp Ile Arg Gly Val Leu Asp Arg Gly Pro Thr
            100                 105                 110
Phe Lys Pro Tyr Ser Gly Thr Ala Tyr Asn Ala Leu Ala Pro Lys Gly
        115                 120                 125
Ala Pro Asn Ser Cys Glu Trp Asp Glu Asp Thr Gln Val Gln Val
    130                 135                 140
Ala Ala Glu Asp Asp Gln Asp Asp Ser Ser Cys Ser Ser Gly Gly
145                 150                 155                 160
Thr Glu Glu Glu Glu Leu Pro Gln Gln Arg Asn Gly Lys Lys Thr
                165                 170                 175
His Val Tyr Ala Gln Ala Pro Phe Ala Gly Glu Ala Ile Asn Lys Asn
            180                 185                 190
Gly Leu Gln Ile Gly Thr Asn Gly Ala Ala Thr Glu Gly Asn Lys Glu
```

```
                195                 200                 205
Ile Tyr Ala Asp Lys Thr Tyr Gln Pro Glu Pro Gln Ile Gly Glu Ser
210                 215                 220

Gln Trp Asn Glu Ala Glu Ser Ser Val Ala Gly Gly Arg Val Leu Lys
225                 230                 235                 240

Lys Thr Thr Pro Met Lys Pro Cys Tyr Gly Ser Tyr Ala Arg Pro Thr
                245                 250                 255

Asn Ser Asn Gly Gly Gln Gly Val Met Val Glu Gln Asn Gly Lys Leu
                260                 265                 270

Glu Ser Gln Val Glu Met Gln Phe Phe Ser Thr Ser Val Asn Ala Met
        275                 280                 285

Asn Glu Ala Asn Ala Ile Gln Pro Lys Leu Val Leu Tyr Ser Glu Asp
290                 295                 300

Val Asn Met Glu Thr Pro Asp Thr His Leu Ser Tyr Lys Pro Gly Lys
305                 310                 315                 320

Ser Asp Asp Asn Ser Lys Ala Met Leu Gly Gln Gln Ser Met Pro Asn
                325                 330                 335

Arg Pro Asn Tyr Ile Ala Phe Arg Asp Asn Phe Ile Gly Leu Met Tyr
                340                 345                 350

Tyr Asn Ser Thr Gly Asn Met Gly Val Leu Ala Gly Gln Ala Ser Gln
        355                 360                 365

Leu Asn Ala Val Val Asp Leu Gln Asp Arg Asn Thr Glu Leu Ser Tyr
370                 375                 380

Gln Leu Leu Leu Asp Ser Ile Gly Asp Arg Thr Arg Tyr Phe Ser Met
385                 390                 395                 400

Trp Asn Gln Ala Val Asp Ser Tyr Asp Pro Asp Val Arg Ile Ile Glu
                405                 410                 415

Asn His Gly Thr Glu Asp Glu Leu Pro Asn Tyr Cys Phe Pro Leu Gly
                420                 425                 430

Gly Ile Gly Val Thr Asp Thr Tyr Gln Ala Ile Lys Ala Thr Asn Gly
        435                 440                 445

Asn Gly Gly Ala Thr Thr Trp Ala Gln Asp Asn Thr Phe Ala Glu Arg
450                 455                 460

Asn Glu Ile Gly Val Gly Asn Asn Phe Ala Met Glu Ile Asn Leu Asn
465                 470                 475                 480

Ala Asn Leu Trp Arg Asn Phe Leu Tyr Ser Asn Ile Ala Leu Tyr Leu
                485                 490                 495

Pro Asp Lys Leu Lys Tyr Asn Pro Thr Asn Val Glu Ile Ser Asp Asn
                500                 505                 510

Pro Asn Thr Tyr Asp Tyr Met Asn Lys Arg Val Val Ala Pro Gly Leu
        515                 520                 525

Val Asp Cys Tyr Ile Asn Leu Gly Ala Arg Trp Ser Leu Asp Tyr Met
530                 535                 540

Asp Asn Val Asn Pro Phe Asn His His Arg Asn Ala Gly Leu Arg Tyr
545                 550                 555                 560

Arg Ser Met Leu Leu Gly Asn Gly Arg Tyr Val Pro Phe His Ile Gln
                565                 570                 575

Val Pro Gln Lys Phe Phe Ala Ile Lys Asn Leu Leu Leu Leu Pro Gly
                580                 585                 590

Ser Tyr Thr Tyr Glu Trp Asn Phe Arg Lys Asp Val Asn Met Val Leu
        595                 600                 605

Gln Ser Ser Leu Gly Asn Asp Leu Arg Val Asp Gly Ala Ser Ile Lys
610                 615                 620
```

```
Phe Asp Ser Ile Cys Leu Tyr Ala Thr Phe Phe Pro Met Ala His Asn
625                 630                 635                 640

Thr Ala Ser Thr Leu Glu Ala Met Leu Arg Asn Asp Thr Asn Asp Gln
        645                 650                 655

Ser Phe Asn Asp Tyr Leu Ser Ala Ala Asn Met Leu Tyr Pro Ile Pro
            660                 665                 670

Ala Asn Ala Thr Asn Val Pro Ile Ser Ile Pro Ser Arg Asn Trp Ala
        675                 680                 685

Ala Phe Arg Gly Trp Ala Phe Thr Arg Leu Lys Thr Lys Glu Thr Pro
    690                 695                 700

Ser Leu Gly Ser Gly Tyr Asp Pro Tyr Tyr Thr Tyr Ser Gly Ser Ile
705                 710                 715                 720

Pro Tyr Leu Asp Gly Thr Phe Tyr Leu Asn His Thr Phe Lys Lys Val
                725                 730                 735

Ala Ile Thr Phe Asp Ser Ser Val Ser Trp Pro Gly Asn Asp Arg Leu
            740                 745                 750

Leu Thr Pro Asn Glu Phe Glu Ile Lys Arg Ser Val Asp Gly Glu Gly
        755                 760                 765

Tyr Asn Val Ala Gln Cys Asn Met Thr Lys Asp Trp Phe Leu Val Gln
770                 775                 780

Met Leu Ala Asn Tyr Asn Ile Gly Tyr Gln Gly Phe Tyr Ile Pro Glu
785                 790                 795                 800

Ser Tyr Lys Asp Arg Met Tyr Ser Phe Phe Arg Asn Phe Gln Pro Met
                805                 810                 815

Ser Arg Gln Val Val Asp Thr Lys Tyr Lys Asp Tyr Gln Gln Val
            820                 825                 830

Gly Ile Ile His Gln His Asn Asn Ser Gly Phe Val Gly Tyr Leu Ala
        835                 840                 845

Pro Thr Met Arg Glu Gly Gln Ala Tyr Pro Ala Asn Val Pro Tyr Pro
    850                 855                 860

Leu Ile Gly Lys Thr Ala Val Asp Ser Ile Thr Gln Lys Lys Phe Leu
865                 870                 875                 880

Cys Asp Arg Thr Leu Trp Arg Ile Pro Phe Ser Ser Asn Phe Met Ser
                885                 890                 895

Met Gly Ala Leu Thr Asp Leu Gly Gln Asn Leu Leu Tyr Ala Asn Ser
            900                 905                 910

Ala His Ala Leu Asp Met Thr Phe Glu Val Asp Pro Met Asp Glu Pro
        915                 920                 925

Thr Leu Leu Tyr Val Leu Phe Glu Val Phe Asp Val Val Arg Val His
    930                 935                 940

Gln Pro His Arg Gly Val Ile Glu Thr Val Tyr Leu Arg Thr Pro Phe
945                 950                 955                 960

Ser Ala Gly Asn Ala Thr Thr
                965

<210> SEQ ID NO 51
<211> LENGTH: 955
<212> TYPE: PRT
<213> ORGANISM: Artificial Sequence
<220> FEATURE:
<223> OTHER INFORMATION: Hexon Polypeptide

<400> SEQUENCE: 51

Met Ala Thr Pro Ser Met Met Pro Gln Trp Ser Tyr Met His Ile Ser
1               5                   10                  15
```

```
Gly Gln Asp Ala Ser Glu Tyr Leu Ser Pro Gly Leu Val Gln Phe Ala
             20                  25                  30

Arg Ala Thr Glu Thr Tyr Phe Ser Leu Asn Asn Lys Phe Arg Asn Pro
         35                  40                  45

Thr Val Ala Pro Thr His Asp Val Thr Thr Asp Arg Ser Gln Arg Leu
 50                  55                  60

Thr Leu Arg Phe Ile Pro Val Asp Arg Glu Asp Thr Ala Tyr Ser Tyr
 65                  70                  75                  80

Lys Ala Arg Phe Thr Leu Ala Val Gly Asp Asn Arg Val Leu Asp Met
                 85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Asp Glu Asp Thr Gln Val Gln Val
130                 135                 140

Ala Ala Glu Asp Asp Gln Asp Asp Glu Glu Glu Gln Leu Pro
145                 150                 155                 160

Gln Gln Arg Asn Gly Lys Lys Thr His Val Tyr Ala Gln Ala Pro Phe
                165                 170                 175

Ala Gly Glu Ala Ile Asn Lys Asn Gly Leu Gln Ile Gly Thr Asn Gly
            180                 185                 190

Ala Ala Thr Glu Gly Asn Lys Glu Ile Tyr Ala Asp Lys Thr Tyr Gln
        195                 200                 205

Pro Glu Pro Gln Ile Gly Glu Ser Gln Trp Asn Glu Ala Glu Ser Ser
    210                 215                 220

Val Ala Gly Gly Arg Val Leu Lys Lys Thr Thr Pro Met Lys Pro Cys
225                 230                 235                 240

Tyr Gly Ser Tyr Ala Arg Pro Thr Asn Ser Asn Gly Gly Gln Gly Val
                245                 250                 255

Met Val Glu Gln Asn Gly Lys Leu Glu Ser Gln Val Glu Met Gln Phe
            260                 265                 270

Phe Ser Thr Ser Ser Cys Ser Ser Gly Gly Thr Pro Lys Leu Val Leu
        275                 280                 285

Tyr Ser Glu Asp Val Asn Met Glu Thr Pro Asp Thr His Leu Ser Tyr
    290                 295                 300

Lys Pro Gly Lys Ser Asp Asp Asn Ser Lys Ala Met Leu Gly Gln Gln
305                 310                 315                 320

Ser Met Pro Asn Arg Pro Asn Tyr Ile Ala Phe Arg Asp Asn Phe Ile
                325                 330                 335

Gly Leu Met Tyr Tyr Asn Ser Thr Gly Asn Met Gly Val Leu Ala Gly
            340                 345                 350

Gln Ala Ser Gln Leu Asn Ala Val Val Asp Leu Gln Asp Arg Asn Thr
        355                 360                 365

Glu Leu Ser Tyr Gln Leu Leu Leu Asp Ser Ile Gly Asp Arg Thr Arg
    370                 375                 380

Tyr Phe Ser Met Trp Asn Gln Ala Val Asp Ser Tyr Asp Pro Asp Val
385                 390                 395                 400

Arg Ile Ile Glu Asn His Gly Thr Glu Asp Glu Leu Pro Asn Tyr Cys
                405                 410                 415

Phe Pro Leu Gly Gly Ile Gly Val Thr Asp Thr Tyr Gln Ala Ile Lys
            420                 425                 430
```

```
Ala Thr Asn Gly Asn Gly Gly Ala Thr Thr Trp Ala Gln Asp Asn Thr
            435                 440                 445

Phe Ala Glu Arg Asn Glu Ile Gly Val Gly Asn Asn Phe Ala Met Glu
450                 455                 460

Ile Asn Leu Asn Ala Asn Leu Trp Arg Asn Phe Leu Tyr Ser Asn Ile
465                 470                 475                 480

Ala Leu Tyr Leu Pro Asp Lys Leu Lys Tyr Asn Pro Thr Asn Val Glu
            485                 490                 495

Ile Ser Asp Asn Pro Asn Thr Tyr Asp Tyr Met Asn Lys Arg Val Val
            500                 505                 510

Ala Pro Gly Leu Val Asp Cys Tyr Ile Asn Leu Gly Ala Arg Trp Ser
            515                 520                 525

Leu Asp Tyr Met Asp Asn Val Asn Pro Phe Asn His His Arg Asn Ala
530                 535                 540

Gly Leu Arg Tyr Arg Ser Met Leu Leu Gly Asn Gly Arg Tyr Val Pro
545                 550                 555                 560

Phe His Ile Gln Val Pro Gln Lys Phe Ala Ile Lys Asn Leu Leu
                565                 570                 575

Leu Leu Pro Gly Ser Tyr Thr Tyr Glu Trp Asn Phe Arg Lys Asp Val
            580                 585                 590

Asn Met Val Leu Gln Ser Ser Leu Gly Asn Asp Leu Arg Val Asp Gly
            595                 600                 605

Ala Ser Ile Lys Phe Asp Ser Ile Cys Leu Tyr Ala Thr Phe Phe Pro
610                 615                 620

Met Ala His Asn Thr Ala Ser Thr Leu Glu Ala Met Leu Arg Asn Asp
625                 630                 635                 640

Thr Asn Asp Gln Ser Phe Asn Asp Tyr Leu Ser Ala Ala Asn Met Leu
            645                 650                 655

Tyr Pro Ile Pro Ala Asn Ala Thr Asn Val Pro Ile Ser Ile Pro Ser
            660                 665                 670

Arg Asn Trp Ala Ala Phe Arg Gly Trp Ala Phe Thr Arg Leu Lys Thr
            675                 680                 685

Lys Glu Thr Pro Ser Leu Gly Ser Gly Tyr Asp Pro Tyr Tyr Thr Tyr
690                 695                 700

Ser Gly Ser Ile Pro Tyr Leu Asp Gly Thr Phe Tyr Leu Asn His Thr
705                 710                 715                 720

Phe Lys Lys Val Ala Ile Thr Phe Asp Ser Ser Val Ser Trp Pro Gly
                725                 730                 735

Asn Asp Arg Leu Leu Thr Pro Asn Glu Phe Glu Ile Lys Arg Ser Val
            740                 745                 750

Asp Gly Glu Gly Tyr Asn Val Ala Gln Cys Asn Met Thr Lys Asp Trp
            755                 760                 765

Phe Leu Val Gln Met Leu Ala Asn Tyr Asn Ile Gly Tyr Gln Gly Phe
770                 775                 780

Tyr Ile Pro Glu Ser Tyr Lys Asp Arg Met Tyr Ser Phe Phe Arg Asn
785                 790                 795                 800

Phe Gln Pro Met Ser Arg Gln Val Val Asp Asp Thr Lys Tyr Lys Asp
                805                 810                 815

Tyr Gln Gln Val Gly Ile Ile His Gln His Asn Asn Ser Gly Phe Val
            820                 825                 830

Gly Tyr Leu Ala Pro Thr Met Arg Glu Gly Gln Ala Tyr Pro Ala Asn
            835                 840                 845

Val Pro Tyr Pro Leu Ile Gly Lys Thr Ala Val Asp Ser Ile Thr Gln
```

```
                    850                 855                 860
Lys Lys Phe Leu Cys Asp Arg Thr Leu Trp Arg Ile Pro Phe Ser Ser
865                 870                 875                 880

Asn Phe Met Ser Met Gly Ala Leu Thr Asp Leu Gly Gln Asn Leu Leu
                    885                 890                 895

Tyr Ala Asn Ser Ala His Ala Leu Asp Met Thr Phe Glu Val Asp Pro
                900                 905                 910

Met Asp Glu Pro Thr Leu Leu Tyr Val Leu Phe Glu Val Phe Asp Val
            915                 920                 925

Val Arg Val His Gln Pro His Arg Gly Val Ile Glu Thr Val Tyr Leu
        930                 935                 940

Arg Thr Pro Phe Ser Ala Gly Asn Ala Thr Thr
945                 950                 955

<210> SEQ ID NO 52
<211> LENGTH: 964
<212> TYPE: PRT
<213> ORGANISM: Artificial Sequence
<220> FEATURE:
<223> OTHER INFORMATION: Hexon Polypeptide

<400> SEQUENCE: 52

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Asp Glu Asp Thr Gln Val Gln Val
130                 135                 140

Ala Ala Glu Asp Asp Gln Asp Asp Ser Ser Gly Gly Thr Glu Glu
145                 150                 155                 160

Glu Glu Gln Leu Pro Gln Gln Arg Asn Gly Lys Lys Thr His Val Tyr
                165                 170                 175

Ala Gln Ala Pro Phe Ala Gly Glu Ala Ile Asn Lys Asn Gly Leu Gln
            180                 185                 190

Ile Gly Thr Asn Gly Ala Ala Thr Glu Gly Asn Lys Glu Ile Tyr Ala
        195                 200                 205

Asp Lys Thr Tyr Gln Pro Glu Pro Gln Ile Gly Glu Ser Gln Trp Asn
    210                 215                 220

Glu Ala Glu Ser Ser Val Ala Gly Gly Arg Val Leu Lys Lys Thr Thr
225                 230                 235                 240

Pro Met Lys Pro Cys Tyr Gly Ser Tyr Ala Arg Pro Thr Asn Ser Asn
                245                 250                 255

Gly Gly Gln Gly Val Met Val Glu Gln Asn Gly Lys Leu Glu Ser Gln
```

```
                260                 265                 270
Val Glu Met Gln Phe Phe Ser Thr Ser Val Asn Ala Met Asn Glu Ala
            275                 280                 285

Asn Ala Ile Gln Pro Lys Leu Val Leu Tyr Ser Glu Asp Val Asn Met
            290                 295                 300

Glu Thr Pro Asp Thr His Leu Ser Tyr Lys Pro Gly Lys Ser Asp Asp
305                 310                 315                 320

Asn Ser Lys Ala Met Leu Gly Gln Gln Ser Met Pro Asn Arg Pro Asn
                325                 330                 335

Tyr Ile Ala Phe Arg Asp Asn Phe Ile Gly Leu Met Tyr Tyr Asn Ser
            340                 345                 350

Thr Gly Asn Met Gly Val Leu Ala Gly Gln Ala Ser Gln Leu Asn Ala
            355                 360                 365

Val Val Asp Leu Gln Asp Arg Asn Thr Glu Leu Ser Tyr Gln Leu Leu
            370                 375                 380

Leu Asp Ser Ile Gly Asp Arg Thr Arg Tyr Phe Ser Met Trp Asn Gln
385                 390                 395                 400

Ala Val Asp Ser Tyr Asp Pro Asp Val Arg Ile Ile Glu Asn His Gly
                405                 410                 415

Thr Glu Asp Glu Leu Pro Asn Tyr Cys Phe Pro Leu Gly Gly Ile Gly
            420                 425                 430

Val Thr Asp Thr Tyr Gln Ala Ile Lys Ala Thr Asn Gly Asn Gly Gly
            435                 440                 445

Ala Thr Thr Trp Ala Gln Asp Asn Thr Phe Ala Glu Arg Asn Glu Ile
            450                 455                 460

Gly Val Gly Asn Asn Phe Ala Met Glu Ile Asn Leu Asn Ala Asn Leu
465                 470                 475                 480

Trp Arg Asn Phe Leu Tyr Ser Asn Ile Ala Leu Tyr Leu Pro Asp Lys
                485                 490                 495

Leu Lys Tyr Asn Pro Thr Asn Val Glu Ile Ser Asp Asn Pro Asn Thr
            500                 505                 510

Tyr Asp Tyr Met Asn Lys Arg Val Val Ala Pro Gly Leu Val Asp Cys
            515                 520                 525

Tyr Ile Asn Leu Gly Ala Arg Trp Ser Leu Asp Tyr Met Asp Asn Val
            530                 535                 540

Asn Pro Phe Asn His His Arg Asn Ala Gly Leu Arg Tyr Arg Ser Met
545                 550                 555                 560

Leu Leu Gly Asn Gly Arg Tyr Val Pro Phe His Ile Gln Val Pro Gln
                565                 570                 575

Lys Phe Phe Ala Ile Lys Asn Leu Leu Leu Pro Gly Ser Tyr Thr
            580                 585                 590

Tyr Glu Trp Asn Phe Arg Lys Asp Val Asn Met Val Leu Gln Ser Ser
            595                 600                 605

Leu Gly Asn Asp Leu Arg Val Asp Gly Ala Ser Ile Lys Phe Asp Ser
            610                 615                 620

Ile Cys Leu Tyr Ala Thr Phe Phe Pro Met Ala His Asn Thr Ala Ser
625                 630                 635                 640

Thr Leu Glu Ala Met Leu Arg Asn Asp Thr Asn Asp Gln Ser Phe Asn
                645                 650                 655

Asp Tyr Leu Ser Ala Ala Asn Met Leu Tyr Pro Ile Pro Ala Asn Ala
            660                 665                 670

Thr Asn Val Pro Ile Ser Ile Pro Ser Arg Asn Trp Ala Ala Phe Arg
            675                 680                 685
```

```
Gly Trp Ala Phe Thr Arg Leu Lys Thr Lys Glu Thr Pro Ser Leu Gly
            690                 695                 700

Ser Gly Tyr Asp Pro Tyr Tyr Thr Tyr Ser Gly Ile Pro Tyr Leu
705                 710                 715                 720

Asp Gly Thr Phe Tyr Leu Asn His Thr Phe Lys Lys Val Ala Ile Thr
                    725                 730                 735

Phe Asp Ser Ser Val Ser Trp Pro Gly Asn Asp Arg Leu Leu Thr Pro
            740                 745                 750

Asn Glu Phe Glu Ile Lys Arg Ser Val Asp Gly Glu Gly Tyr Asn Val
            755                 760                 765

Ala Gln Cys Asn Met Thr Lys Asp Trp Phe Leu Val Gln Met Leu Ala
770                 775                 780

Asn Tyr Asn Ile Gly Tyr Gln Gly Phe Tyr Ile Pro Glu Ser Tyr Lys
785                 790                 795                 800

Asp Arg Met Tyr Ser Phe Phe Arg Asn Phe Gln Pro Met Ser Arg Gln
                    805                 810                 815

Val Val Asp Asp Thr Lys Tyr Lys Asp Tyr Gln Gln Val Gly Ile Ile
            820                 825                 830

His Gln His Asn Asn Ser Gly Phe Val Gly Tyr Leu Ala Pro Thr Met
            835                 840                 845

Arg Glu Gly Gln Ala Tyr Pro Ala Asn Val Pro Tyr Pro Leu Ile Gly
850                 855                 860

Lys Thr Ala Val Asp Ser Ile Thr Gln Lys Lys Phe Leu Cys Asp Arg
865                 870                 875                 880

Thr Leu Trp Arg Ile Pro Phe Ser Ser Asn Phe Met Ser Met Gly Ala
                    885                 890                 895

Leu Thr Asp Leu Gly Gln Asn Leu Leu Tyr Ala Asn Ser Ala His Ala
            900                 905                 910

Leu Asp Met Thr Phe Glu Val Asp Pro Met Asp Glu Pro Thr Leu Leu
            915                 920                 925

Tyr Val Leu Phe Glu Val Phe Asp Val Val Arg Val His Gln Pro His
930                 935                 940

Arg Gly Val Ile Glu Thr Val Tyr Leu Arg Thr Pro Phe Ser Ala Gly
945                 950                 955                 960

Asn Ala Thr Thr

<210> SEQ ID NO 53
<211> LENGTH: 952
<212> TYPE: PRT
<213> ORGANISM: Artificial Sequence
<220> FEATURE:
<223> OTHER INFORMATION: Hexon Polypeptide

<400> SEQUENCE: 53

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80
```

-continued

```
Lys Ala Arg Phe Thr Leu Ala Val Gly Asp Asn Arg Val Leu Asp Met
                 85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Asp Glu Asp Thr Gln Val Gln Val
130                 135                 140

Ala Ala Glu Asp Asp Gln Asp Asp Glu Glu Glu Gln Leu Pro
145                 150                 155                 160

Gln Gln Arg Asn Gly Lys Lys Thr His Val Tyr Ala Gln Ala Pro Phe
                165                 170                 175

Ala Gly Glu Ala Ile Asn Lys Asn Gly Leu Gln Ile Gly Thr Asn Gly
            180                 185                 190

Ala Ala Thr Glu Gly Asn Lys Glu Ile Tyr Ala Asp Lys Thr Tyr Gln
        195                 200                 205

Pro Glu Pro Gln Ile Gly Glu Ser Gln Trp Asn Glu Ala Glu Ser Ser
210                 215                 220

Val Ala Gly Gly Arg Val Leu Lys Lys Thr Thr Pro Met Lys Pro Cys
225                 230                 235                 240

Tyr Gly Ser Tyr Ala Arg Pro Thr Asn Ser Asn Gly Gly Gln Gly Val
                245                 250                 255

Met Val Glu Gln Asn Gly Lys Leu Glu Ser Gln Val Glu Met Gln Phe
            260                 265                 270

Phe Ser Thr Ser Ser Gly Gly Thr Pro Lys Leu Val Leu Tyr Ser Glu
        275                 280                 285

Asp Val Asn Met Glu Thr Pro Asp Thr His Leu Ser Tyr Lys Pro Gly
290                 295                 300

Lys Ser Asp Asp Asn Ser Lys Ala Met Leu Gly Gln Gln Ser Met Pro
305                 310                 315                 320

Asn Arg Pro Asn Tyr Ile Ala Phe Arg Asp Asn Phe Ile Gly Leu Met
                325                 330                 335

Tyr Tyr Asn Ser Thr Gly Asn Met Gly Val Leu Ala Gly Gln Ala Ser
            340                 345                 350

Gln Leu Asn Ala Val Val Asp Leu Gln Asp Arg Asn Thr Glu Leu Ser
        355                 360                 365

Tyr Gln Leu Leu Leu Asp Ser Ile Gly Asp Arg Thr Arg Tyr Phe Ser
370                 375                 380

Met Trp Asn Gln Ala Val Asp Ser Tyr Asp Pro Asp Val Arg Ile Ile
385                 390                 395                 400

Glu Asn His Gly Thr Glu Asp Glu Leu Pro Asn Tyr Cys Phe Pro Leu
                405                 410                 415

Gly Gly Ile Gly Val Thr Asp Thr Tyr Gln Ala Ile Lys Ala Thr Asn
            420                 425                 430

Gly Asn Gly Gly Ala Thr Thr Trp Ala Gln Asp Asn Thr Phe Ala Glu
        435                 440                 445

Arg Asn Glu Ile Gly Val Gly Asn Asn Phe Ala Met Glu Ile Asn Leu
450                 455                 460

Asn Ala Asn Leu Trp Arg Asn Phe Leu Tyr Ser Asn Ile Ala Leu Tyr
465                 470                 475                 480

Leu Pro Asp Lys Leu Lys Tyr Asn Pro Thr Asn Val Glu Ile Ser Asp
                485                 490                 495

Asn Pro Asn Thr Tyr Asp Tyr Met Asn Lys Arg Val Val Ala Pro Gly
```

```
                500                 505                 510
Leu Val Asp Cys Tyr Ile Asn Leu Gly Ala Arg Trp Ser Leu Asp Tyr
            515                 520                 525

Met Asp Asn Val Asn Pro Phe Asn His His Arg Asn Ala Gly Leu Arg
530                 535                 540

Tyr Arg Ser Met Leu Leu Gly Asn Gly Arg Tyr Val Pro Phe His Ile
545                 550                 555                 560

Gln Val Pro Gln Lys Phe Phe Ala Ile Lys Asn Leu Leu Leu Leu Pro
            565                 570                 575

Gly Ser Tyr Thr Tyr Glu Trp Asn Phe Arg Lys Asp Val Asn Met Val
                580                 585                 590

Leu Gln Ser Ser Leu Gly Asn Asp Leu Arg Val Asp Gly Ala Ser Ile
            595                 600                 605

Lys Phe Asp Ser Ile Cys Leu Tyr Ala Thr Phe Phe Pro Met Ala His
            610                 615                 620

Asn Thr Ala Ser Thr Leu Glu Ala Met Leu Arg Asn Asp Thr Asn Asp
625                 630                 635                 640

Gln Ser Phe Asn Asp Tyr Leu Ser Ala Ala Asn Met Leu Tyr Pro Ile
                645                 650                 655

Pro Ala Asn Ala Thr Asn Val Pro Ile Ser Ile Pro Ser Arg Asn Trp
            660                 665                 670

Ala Ala Phe Arg Gly Trp Ala Phe Thr Arg Leu Lys Thr Lys Glu Thr
            675                 680                 685

Pro Ser Leu Gly Ser Gly Tyr Asp Pro Tyr Tyr Thr Tyr Ser Gly Ser
            690                 695                 700

Ile Pro Tyr Leu Asp Gly Thr Phe Tyr Leu Asn His Thr Phe Lys Lys
705                 710                 715                 720

Val Ala Ile Thr Phe Asp Ser Ser Val Ser Trp Pro Gly Asn Asp Arg
                725                 730                 735

Leu Leu Thr Pro Asn Glu Phe Glu Ile Lys Arg Ser Val Asp Gly Glu
            740                 745                 750

Gly Tyr Asn Val Ala Gln Cys Asn Met Thr Lys Asp Trp Phe Leu Val
            755                 760                 765

Gln Met Leu Ala Asn Tyr Asn Ile Gly Tyr Gln Gly Phe Tyr Ile Pro
            770                 775                 780

Glu Ser Tyr Lys Asp Arg Met Tyr Ser Phe Phe Arg Asn Phe Gln Pro
785                 790                 795                 800

Met Ser Arg Gln Val Val Asp Asp Thr Lys Tyr Lys Asp Tyr Gln Gln
                805                 810                 815

Val Gly Ile Ile His Gln His Asn Asn Ser Gly Phe Val Gly Tyr Leu
            820                 825                 830

Ala Pro Thr Met Arg Glu Gly Gln Ala Tyr Pro Ala Asn Val Pro Tyr
            835                 840                 845

Pro Leu Ile Gly Lys Thr Ala Val Asp Ser Ile Thr Gln Lys Lys Phe
            850                 855                 860

Leu Cys Asp Arg Thr Leu Trp Arg Ile Pro Phe Ser Ser Asn Phe Met
865                 870                 875                 880

Ser Met Gly Ala Leu Thr Asp Leu Gly Gln Asn Leu Leu Tyr Ala Asn
                885                 890                 895

Ser Ala His Ala Leu Asp Met Thr Phe Glu Val Asp Pro Met Asp Glu
            900                 905                 910

Pro Thr Leu Leu Tyr Val Leu Phe Glu Val Phe Asp Val Val Arg Val
            915                 920                 925
```

His Gln Pro His Arg Gly Val Ile Glu Thr Val Tyr Leu Arg Thr Pro
    930                 935                 940

Phe Ser Ala Gly Asn Ala Thr Thr
945                 950

<210> SEQ ID NO 54
<211> LENGTH: 1033
<212> TYPE: PRT
<213> ORGANISM: Artificial Sequence
<220> FEATURE:
<223> OTHER INFORMATION: Hexon Polypeptide

<400> SEQUENCE: 54

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Asp Glu Asp Thr Gln Val Gln Val
    130                 135                 140

Ala Ala Glu Asp Asp Gln Asp Asp Ser Thr Gly Glu Ile Pro Ala
145                 150                 155                 160

Pro Leu Ala Gly Thr Val Ser Lys Ile Leu Val Lys Glu Gly Asp Thr
                165                 170                 175

Val Lys Ala Gly Gln Thr Val Leu Val Leu Glu Ala Met Lys Met Glu
            180                 185                 190

Thr Glu Ile Asn Ala Pro Thr Asp Gly Lys Val Glu Lys Val Leu Val
        195                 200                 205

Lys Glu Arg Asp Ala Val Gln Gly Gly Gln Gly Leu Ile Lys Ile Gly
    210                 215                 220

Gly Gly Thr Glu Glu Glu Gln Leu Pro Gln Gln Arg Asn Gly Lys
225                 230                 235                 240

Lys Thr His Val Tyr Ala Gln Ala Pro Phe Ala Gly Glu Ala Ile Asn
                245                 250                 255

Lys Asn Gly Leu Gln Ile Gly Thr Asn Gly Ala Ala Thr Glu Gly Asn
            260                 265                 270

Lys Glu Ile Tyr Ala Asp Lys Thr Tyr Gln Pro Glu Pro Gln Ile Gly
        275                 280                 285

Glu Ser Gln Trp Asn Glu Ala Glu Ser Ser Val Ala Gly Gly Arg Val
    290                 295                 300

Leu Lys Lys Thr Thr Pro Met Lys Pro Cys Tyr Gly Ser Tyr Ala Arg
305                 310                 315                 320

Pro Thr Asn Ser Asn Gly Gly Gln Gly Val Met Val Glu Gln Asn Gly
                325                 330                 335

-continued

Lys Leu Glu Ser Gln Val Glu Met Gln Phe Ser Thr Ser Val Asn
              340                 345                 350

Ala Met Asn Glu Ala Asn Ala Ile Gln Pro Lys Leu Val Leu Tyr Ser
              355                 360                 365

Glu Asp Val Asn Met Glu Thr Pro Asp Thr His Leu Ser Tyr Lys Pro
370                 375                 380

Gly Lys Ser Asp Asp Asn Ser Lys Ala Met Leu Gly Gln Gln Ser Met
385                 390                 395                 400

Pro Asn Arg Pro Asn Tyr Ile Ala Phe Arg Asp Asn Phe Ile Gly Leu
              405                 410                 415

Met Tyr Tyr Asn Ser Thr Gly Asn Met Gly Val Leu Ala Gly Gln Ala
              420                 425                 430

Ser Gln Leu Asn Ala Val Val Asp Leu Gln Asp Arg Asn Thr Glu Leu
              435                 440                 445

Ser Tyr Gln Leu Leu Leu Asp Ser Ile Gly Asp Arg Thr Arg Tyr Phe
              450                 455                 460

Ser Met Trp Asn Gln Ala Val Asp Ser Tyr Asp Pro Asp Val Arg Ile
465                 470                 475                 480

Ile Glu Asn His Gly Thr Glu Asp Glu Leu Pro Asn Tyr Cys Phe Pro
              485                 490                 495

Leu Gly Gly Ile Gly Val Thr Asp Thr Tyr Gln Ala Ile Lys Ala Thr
              500                 505                 510

Asn Gly Asn Gly Gly Ala Thr Thr Trp Ala Gln Asp Asn Thr Phe Ala
              515                 520                 525

Glu Arg Asn Glu Ile Gly Val Gly Asn Asn Phe Ala Met Glu Ile Asn
              530                 535                 540

Leu Asn Ala Asn Leu Trp Arg Asn Phe Leu Tyr Ser Asn Ile Ala Leu
545                 550                 555                 560

Tyr Leu Pro Asp Lys Leu Lys Tyr Asn Pro Thr Asn Val Glu Ile Ser
              565                 570                 575

Asp Asn Pro Asn Thr Tyr Asp Tyr Met Asn Lys Arg Val Val Ala Pro
              580                 585                 590

Gly Leu Val Asp Cys Tyr Ile Asn Leu Gly Ala Arg Trp Ser Leu Asp
              595                 600                 605

Tyr Met Asp Asn Val Asn Pro Phe Asn His His Arg Asn Ala Gly Leu
              610                 615                 620

Arg Tyr Arg Ser Met Leu Leu Gly Asn Gly Arg Tyr Val Pro Phe His
625                 630                 635                 640

Ile Gln Val Pro Gln Lys Phe Phe Ala Ile Lys Asn Leu Leu Leu Leu
              645                 650                 655

Pro Gly Ser Tyr Thr Tyr Glu Trp Asn Phe Arg Lys Asp Val Asn Met
              660                 665                 670

Val Leu Gln Ser Ser Leu Gly Asn Asp Leu Arg Val Asp Gly Ala Ser
              675                 680                 685

Ile Lys Phe Asp Ser Ile Cys Leu Tyr Ala Thr Phe Phe Pro Met Ala
              690                 695                 700

His Asn Thr Ala Ser Thr Leu Glu Ala Met Leu Arg Asn Asp Thr Asn
705                 710                 715                 720

Asp Gln Ser Phe Asn Asp Tyr Leu Ser Ala Ala Asn Met Leu Tyr Pro
              725                 730                 735

Ile Pro Ala Asn Ala Thr Asn Val Pro Ile Ser Ile Pro Ser Arg Asn
              740                 745                 750

-continued

```
Trp Ala Ala Phe Arg Gly Trp Ala Phe Thr Arg Leu Lys Thr Lys Glu
            755                 760                 765

Thr Pro Ser Leu Gly Ser Gly Tyr Asp Pro Tyr Thr Tyr Ser Gly
    770                 775                 780

Ser Ile Pro Tyr Leu Asp Gly Thr Phe Tyr Leu Asn His Thr Phe Lys
785                 790                 795                 800

Lys Val Ala Ile Thr Phe Asp Ser Ser Val Ser Trp Pro Gly Asn Asp
                805                 810                 815

Arg Leu Leu Thr Pro Asn Glu Phe Glu Ile Lys Arg Ser Val Asp Gly
                820                 825                 830

Glu Gly Tyr Asn Val Ala Gln Cys Asn Met Thr Lys Asp Trp Phe Leu
            835                 840                 845

Val Gln Met Leu Ala Asn Tyr Asn Ile Gly Tyr Gln Gly Phe Tyr Ile
    850                 855                 860

Pro Glu Ser Tyr Lys Asp Arg Met Tyr Ser Phe Phe Arg Asn Phe Gln
865                 870                 875                 880

Pro Met Ser Arg Gln Val Val Asp Asp Thr Lys Tyr Lys Asp Tyr Gln
                885                 890                 895

Gln Val Gly Ile Ile His Gln His Asn Asn Ser Gly Phe Val Gly Tyr
            900                 905                 910

Leu Ala Pro Thr Met Arg Glu Gly Gln Ala Tyr Pro Ala Asn Val Pro
    915                 920                 925

Tyr Pro Leu Ile Gly Lys Thr Ala Val Asp Ser Ile Thr Gln Lys Lys
            930                 935                 940

Phe Leu Cys Asp Arg Thr Leu Trp Arg Ile Pro Phe Ser Ser Asn Phe
945                 950                 955                 960

Met Ser Met Gly Ala Leu Thr Asp Leu Gly Gln Asn Leu Leu Tyr Ala
                965                 970                 975

Asn Ser Ala His Ala Leu Asp Met Thr Phe Glu Val Asp Pro Met Asp
            980                 985                 990

Glu Pro Thr Leu Leu Tyr Val Leu Phe Glu Val Phe Asp Val Val Arg
    995                 1000                1005

Val His Gln Pro His Arg Gly Val Ile Glu Thr Val Tyr Leu Arg
    1010                1015                1020

Thr Pro Phe Ser Ala Gly Asn Ala Thr Thr
    1025                1030

<210> SEQ ID NO 55
<211> LENGTH: 1021
<212> TYPE: PRT
<213> ORGANISM: Artificial Sequence
<220> FEATURE:
<223> OTHER INFORMATION: Hexon Polypeptide

<400> SEQUENCE: 55

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80
```

```
Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Asp Glu Asp Thr Gln Val Gln Val
    130                 135                 140

Ala Ala Glu Asp Asp Gln Asp Asp Glu Glu Glu Gln Leu Pro
145                 150                 155                 160

Gln Gln Arg Asn Gly Lys Lys Thr His Val Tyr Ala Gln Ala Pro Phe
                165                 170                 175

Ala Gly Glu Ala Ile Asn Lys Asn Gly Leu Gln Ile Gly Thr Asn Gly
            180                 185                 190

Ala Ala Thr Glu Gly Asn Lys Glu Ile Tyr Ala Asp Lys Thr Tyr Gln
        195                 200                 205

Pro Glu Pro Gln Ile Gly Glu Ser Gln Trp Asn Glu Ala Glu Ser Ser
    210                 215                 220

Val Ala Gly Gly Arg Val Leu Lys Lys Thr Thr Pro Met Lys Pro Cys
225                 230                 235                 240

Tyr Gly Ser Tyr Ala Arg Pro Thr Asn Ser Asn Gly Gly Gln Gly Val
                245                 250                 255

Met Val Glu Gln Asn Gly Lys Leu Glu Ser Gln Val Glu Met Gln Phe
            260                 265                 270

Phe Ser Thr Ser Thr Gly Glu Ile Pro Ala Pro Leu Ala Gly Thr Val
        275                 280                 285

Ser Lys Ile Leu Val Lys Glu Gly Asp Thr Val Lys Ala Gly Gln Thr
    290                 295                 300

Val Leu Val Leu Glu Ala Met Lys Met Glu Thr Glu Ile Asn Ala Pro
305                 310                 315                 320

Thr Asp Gly Lys Val Glu Lys Val Leu Val Lys Glu Arg Asp Ala Val
                325                 330                 335

Gln Gly Gly Gln Gly Leu Ile Lys Ile Gly Gly Thr Pro Lys Leu
            340                 345                 350

Val Leu Tyr Ser Glu Asp Val Asn Met Glu Thr Pro Asp Thr His Leu
        355                 360                 365

Ser Tyr Lys Pro Gly Lys Ser Asp Asp Asn Ser Lys Ala Met Leu Gly
    370                 375                 380

Gln Gln Ser Met Pro Asn Arg Pro Asn Tyr Ile Ala Phe Arg Asp Asn
385                 390                 395                 400

Phe Ile Gly Leu Met Tyr Tyr Asn Ser Thr Gly Asn Met Gly Val Leu
                405                 410                 415

Ala Gly Gln Ala Ser Gln Leu Asn Ala Val Asp Leu Gln Asp Arg
            420                 425                 430

Asn Thr Glu Leu Ser Tyr Gln Leu Leu Asp Ser Ile Gly Asp Arg
        435                 440                 445

Thr Arg Tyr Phe Ser Met Trp Asn Gln Ala Val Asp Ser Tyr Asp Pro
    450                 455                 460

Asp Val Arg Ile Ile Glu Asn His Gly Thr Glu Asp Glu Leu Pro Asn
465                 470                 475                 480

Tyr Cys Phe Pro Leu Gly Gly Ile Gly Val Thr Asp Thr Tyr Gln Ala
                485                 490                 495

Ile Lys Ala Thr Asn Gly Asn Gly Gly Ala Thr Thr Trp Ala Gln Asp
```

```
                500             505             510
Asn Thr Phe Ala Glu Arg Asn Glu Ile Gly Val Gly Asn Asn Phe Ala
            515                 520                 525
Met Glu Ile Asn Leu Asn Ala Asn Leu Trp Arg Asn Phe Leu Tyr Ser
            530                 535                 540
Asn Ile Ala Leu Tyr Leu Pro Asp Lys Leu Lys Tyr Asn Pro Thr Asn
545                 550                 555                 560
Val Glu Ile Ser Asp Asn Pro Asn Thr Tyr Asp Tyr Met Asn Lys Arg
                565                 570                 575
Val Val Ala Pro Gly Leu Val Asp Cys Tyr Ile Asn Leu Gly Ala Arg
                580                 585                 590
Trp Ser Leu Asp Tyr Met Asp Asn Val Asn Pro Phe Asn His His Arg
            595                 600                 605
Asn Ala Gly Leu Arg Tyr Arg Ser Met Leu Leu Gly Asn Gly Arg Tyr
            610                 615                 620
Val Pro Phe His Ile Gln Val Pro Gln Lys Phe Phe Ala Ile Lys Asn
625                 630                 635                 640
Leu Leu Leu Leu Pro Gly Ser Tyr Thr Tyr Glu Trp Asn Phe Arg Lys
                645                 650                 655
Asp Val Asn Met Val Leu Gln Ser Ser Leu Gly Asn Asp Leu Arg Val
                660                 665                 670
Asp Gly Ala Ser Ile Lys Phe Asp Ser Ile Cys Leu Tyr Ala Thr Phe
            675                 680                 685
Phe Pro Met Ala His Asn Thr Ala Ser Thr Leu Glu Ala Met Leu Arg
            690                 695                 700
Asn Asp Thr Asn Asp Gln Ser Phe Asn Asp Tyr Leu Ser Ala Ala Asn
705                 710                 715                 720
Met Leu Tyr Pro Ile Pro Ala Asn Ala Thr Asn Val Pro Ile Ser Ile
                725                 730                 735
Pro Ser Arg Asn Trp Ala Ala Phe Arg Gly Trp Ala Phe Thr Arg Leu
                740                 745                 750
Lys Thr Lys Glu Thr Pro Ser Leu Gly Ser Gly Tyr Asp Pro Tyr Tyr
            755                 760                 765
Thr Tyr Ser Gly Ser Ile Pro Tyr Leu Asp Gly Thr Phe Tyr Leu Asn
            770                 775                 780
His Thr Phe Lys Lys Val Ala Ile Thr Phe Asp Ser Ser Val Ser Trp
785                 790                 795                 800
Pro Gly Asn Asp Arg Leu Leu Thr Pro Asn Glu Phe Glu Ile Lys Arg
                805                 810                 815
Ser Val Asp Gly Glu Gly Tyr Asn Val Ala Gln Cys Asn Met Thr Lys
                820                 825                 830
Asp Trp Phe Leu Val Gln Met Leu Ala Asn Tyr Asn Ile Gly Tyr Gln
            835                 840                 845
Gly Phe Tyr Ile Pro Glu Ser Tyr Lys Asp Arg Met Tyr Ser Phe Phe
            850                 855                 860
Arg Asn Phe Gln Pro Met Ser Arg Gln Val Val Asp Thr Lys Tyr
865                 870                 875                 880
Lys Asp Tyr Gln Gln Val Gly Ile Ile His Gln His Asn Asn Ser Gly
                885                 890                 895
Phe Val Gly Tyr Leu Ala Pro Thr Met Arg Glu Gly Gln Ala Tyr Pro
                900                 905                 910
Ala Asn Val Pro Tyr Pro Leu Ile Gly Lys Thr Ala Val Asp Ser Ile
            915                 920                 925
```

-continued

```
Thr Gln Lys Lys Phe Leu Cys Asp Arg Thr Leu Trp Arg Ile Pro Phe
    930                 935                 940

Ser Ser Asn Phe Met Ser Met Gly Ala Leu Thr Asp Leu Gly Gln Asn
945                 950                 955                 960

Leu Leu Tyr Ala Asn Ser Ala His Ala Leu Asp Met Thr Phe Glu Val
            965                 970                 975

Asp Pro Met Asp Glu Pro Thr Leu Leu Tyr Val Leu Phe Glu Val Phe
                980                 985                 990

Asp Val Val Arg Val His Gln Pro His Arg Gly Val Ile Glu Thr Val
        995                 1000                1005

Tyr Leu Arg Thr Pro Phe Ser Ala Gly Asn Ala Thr Thr
    1010                1015                1020
```

<210> SEQ ID NO 56
<211> LENGTH: 1015
<212> TYPE: PRT
<213> ORGANISM: Artificial Sequence
<220> FEATURE:
<223> OTHER INFORMATION: Hexon Polypeptide

<400> SEQUENCE: 56

```
Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Asp Glu Asp Thr Gln Val Gln Val
130                 135                 140

Ala Ala Glu Asp Asp Gln Asp Asp Glu Glu Glu Gln Leu Pro
145                 150                 155                 160

Gln Gln Arg Asn Gly Lys Lys Thr His Val Tyr Ala Gln Ala Pro Phe
                165                 170                 175

Ala Gly Glu Ala Ile Asn Lys Asn Gly Leu Gln Ile Gly Thr Asn Gly
            180                 185                 190

Ala Ala Thr Glu Gly Asn Lys Glu Ile Tyr Ala Asp Lys Thr Tyr Gln
        195                 200                 205

Pro Glu Pro Gln Ile Gly Glu Ser Gln Trp Asn Glu Ala Glu Ser Ser
    210                 215                 220

Val Ala Gly Gly Arg Val Leu Lys Lys Thr Thr Pro Met Lys Pro Cys
225                 230                 235                 240

Tyr Gly Ser Tyr Ala Arg Pro Thr Asn Ser Asn Gly Gly Gln Gly Val
                245                 250                 255

Met Val Glu Gln Asn Gly Lys Leu Glu Ser Gln Val Glu Met Gln Phe
            260                 265                 270
```

```
Phe Ser Thr Ser Ser Asn Phe Thr Arg Glu Gly Asn Val Thr Tyr
        275                 280                 285

Lys Glu Glu Met Asp Lys Val Lys Asn Cys Ser Phe Asn Val Thr Thr
    290                 295                 300

Gly Ile Arg Asp Lys Lys Gln Lys Val Asn Ala Leu Phe Tyr Arg Leu
305                 310                 315                 320

Asp Ile Thr Pro Leu Asp Glu Asn Asn Asn Ser Ser Glu Tyr Arg
                325                 330                 335

Leu Ile Asn Ser Gly Gly Thr Pro Lys Leu Val Leu Tyr Ser Glu Asp
                340                 345                 350

Val Asn Met Glu Thr Pro Asp Thr His Leu Ser Tyr Lys Pro Gly Lys
                355                 360                 365

Ser Asp Asp Asn Ser Lys Ala Met Leu Gly Gln Gln Ser Met Pro Asn
                370                 375                 380

Arg Pro Asn Tyr Ile Ala Phe Arg Asp Asn Phe Ile Gly Leu Met Tyr
385                 390                 395                 400

Tyr Asn Ser Thr Gly Asn Met Gly Val Leu Ala Gly Gln Ala Ser Gln
                    405                 410                 415

Leu Asn Ala Val Val Asp Leu Gln Asp Arg Asn Thr Glu Leu Ser Tyr
                420                 425                 430

Gln Leu Leu Leu Asp Ser Ile Gly Asp Arg Thr Arg Tyr Phe Ser Met
            435                 440                 445

Trp Asn Gln Ala Val Asp Ser Tyr Asp Pro Asp Val Arg Ile Ile Glu
    450                 455                 460

Asn His Gly Thr Glu Asp Glu Leu Pro Asn Tyr Cys Phe Pro Leu Gly
465                 470                 475                 480

Gly Ile Gly Val Thr Asp Thr Tyr Gln Ala Ile Lys Ala Thr Asn Gly
                485                 490                 495

Asn Gly Gly Ala Thr Thr Trp Ala Gln Asp Asn Thr Phe Ala Glu Arg
                500                 505                 510

Asn Glu Ile Gly Val Gly Asn Asn Phe Ala Met Glu Ile Asn Leu Asn
            515                 520                 525

Ala Asn Leu Trp Arg Asn Phe Leu Tyr Ser Asn Ile Ala Leu Tyr Leu
    530                 535                 540

Pro Asp Lys Leu Lys Tyr Asn Pro Thr Asn Val Glu Ile Ser Asp Asn
545                 550                 555                 560

Pro Asn Thr Tyr Asp Tyr Met Asn Lys Arg Val Val Ala Pro Gly Leu
                565                 570                 575

Val Asp Cys Tyr Ile Asn Leu Gly Ala Arg Trp Ser Leu Asp Tyr Met
                580                 585                 590

Asp Asn Val Asn Pro Phe Asn His His Arg Asn Ala Gly Leu Arg Tyr
                595                 600                 605

Arg Ser Met Leu Leu Gly Asn Gly Arg Tyr Val Pro Phe His Ile Gln
610                 615                 620

Val Pro Gln Lys Phe Phe Ala Ile Lys Asn Leu Leu Leu Leu Pro Gly
625                 630                 635                 640

Ser Tyr Thr Tyr Glu Trp Asn Phe Arg Lys Asp Val Asn Met Val Leu
                645                 650                 655

Gln Ser Ser Leu Gly Asn Asp Leu Arg Val Asp Gly Ala Ser Ile Lys
            660                 665                 670

Phe Asp Ser Ile Cys Leu Tyr Ala Thr Phe Phe Pro Met Ala His Asn
                675                 680                 685
```

Thr Ala Ser Thr Leu Glu Ala Met Leu Arg Asn Asp Thr Asn Asp Gln
        690                 695                 700

Ser Phe Asn Asp Tyr Leu Ser Ala Ala Asn Met Leu Tyr Pro Ile Pro
705                 710                 715                 720

Ala Asn Ala Thr Asn Val Pro Ile Ser Ile Pro Ser Arg Asn Trp Ala
            725                 730                 735

Ala Phe Arg Gly Trp Ala Phe Thr Arg Leu Lys Thr Lys Glu Thr Pro
        740                 745                 750

Ser Leu Gly Ser Gly Tyr Asp Pro Tyr Thr Tyr Ser Gly Ser Ile
        755                 760                 765

Pro Tyr Leu Asp Gly Thr Phe Tyr Leu Asn His Thr Phe Lys Lys Val
770                 775                 780

Ala Ile Thr Phe Asp Ser Ser Val Ser Trp Pro Gly Asn Asp Arg Leu
785                 790                 795                 800

Leu Thr Pro Asn Glu Phe Glu Ile Lys Arg Ser Val Asp Gly Glu Gly
                805                 810                 815

Tyr Asn Val Ala Gln Cys Asn Met Thr Lys Asp Trp Phe Leu Val Gln
                820                 825                 830

Met Leu Ala Asn Tyr Asn Ile Gly Tyr Gln Gly Phe Tyr Ile Pro Glu
        835                 840                 845

Ser Tyr Lys Asp Arg Met Tyr Ser Phe Phe Arg Asn Phe Gln Pro Met
850                 855                 860

Ser Arg Gln Val Val Asp Thr Lys Tyr Lys Asp Tyr Gln Gln Val
865                 870                 875                 880

Gly Ile Ile His Gln His Asn Asn Ser Gly Phe Val Gly Tyr Leu Ala
                885                 890                 895

Pro Thr Met Arg Glu Gly Gln Ala Tyr Pro Ala Asn Val Pro Tyr Pro
        900                 905                 910

Leu Ile Gly Lys Thr Ala Val Asp Ser Ile Thr Gln Lys Lys Phe Leu
        915                 920                 925

Cys Asp Arg Thr Leu Trp Arg Ile Pro Phe Ser Ser Asn Phe Met Ser
930                 935                 940

Met Gly Ala Leu Thr Asp Leu Gly Gln Asn Leu Leu Tyr Ala Asn Ser
945                 950                 955                 960

Ala His Ala Leu Asp Met Thr Phe Glu Val Asp Pro Met Asp Glu Pro
            965                 970                 975

Thr Leu Leu Tyr Val Leu Phe Glu Val Phe Asp Val Val Arg Val His
        980                 985                 990

Gln Pro His Arg Gly Val Ile Glu Thr Val Tyr Leu Arg Thr Pro Phe
        995                 1000                1005

Ser Ala Gly Asn Ala Thr Thr
    1010                1015

<210> SEQ ID NO 57
<211> LENGTH: 987
<212> TYPE: PRT
<213> ORGANISM: Artificial Sequence
<220> FEATURE:
<223> OTHER INFORMATION: Hexon Polypeptide

<400> SEQUENCE: 57

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

```
Arg Ala Thr Glu Thr Tyr Phe Ser Leu Asn Asn Lys Phe Arg Asn Pro
         35                  40                  45

Thr Val Ala Pro Thr His Asp Val Thr Thr Asp Arg Ser Gln Arg Leu
 50                  55                  60

Thr Leu Arg Phe Ile Pro Val Asp Arg Glu Asp Thr Ala Tyr Ser Tyr
 65                  70                  75                  80

Lys Ala Arg Phe Thr Leu Ala Val Gly Asp Asn Arg Val Leu Asp Met
                 85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
            115                 120                 125

Ala Pro Asn Ser Cys Glu Trp Asp Glu Asp Thr Gln Val Gln Val
130                 135                 140

Ala Ala Glu Asp Asp Gln Asp Asp Glu Glu Glu Gln Leu Pro
145                 150                 155                 160

Gln Gln Arg Asn Gly Lys Lys Thr His Val Tyr Ala Gln Ala Pro Phe
                165                 170                 175

Ala Gly Glu Ala Ile Asn Lys Asn Gly Leu Gln Ile Gly Thr Asn Gly
            180                 185                 190

Ala Ala Thr Glu Gly Asn Lys Glu Ile Tyr Ala Asp Lys Thr Tyr Gln
            195                 200                 205

Pro Glu Pro Gln Ile Gly Glu Ser Gln Trp Asn Glu Ala Glu Ser Ser
            210                 215                 220

Val Ala Gly Gly Arg Val Leu Lys Lys Thr Thr Pro Met Lys Pro Cys
225                 230                 235                 240

Tyr Gly Ser Tyr Ala Arg Pro Thr Asn Ser Asn Gly Gly Gln Gly Val
                245                 250                 255

Met Val Glu Gln Asn Gly Lys Leu Glu Ser Gln Val Glu Met Gln Phe
            260                 265                 270

Phe Ser Thr Ser Ser Gln Ala Glu Pro Asp Arg Ala His Tyr Asn Ile
            275                 280                 285

Val Thr Phe Cys Cys Lys Cys Asp Gln Leu Leu Arg Arg Glu Val Tyr
            290                 295                 300

Asp Phe Ala Phe Arg Asp Leu Ser Gly Gly Thr Pro Lys Leu Val Leu
305                 310                 315                 320

Tyr Ser Glu Asp Val Asn Met Glu Thr Pro Asp Thr His Leu Ser Tyr
                325                 330                 335

Lys Pro Gly Lys Ser Asp Asp Asn Ser Lys Ala Met Leu Gly Gln Gln
            340                 345                 350

Ser Met Pro Asn Arg Pro Asn Tyr Ile Ala Phe Arg Asp Asn Phe Ile
            355                 360                 365

Gly Leu Met Tyr Tyr Asn Ser Thr Gly Asn Met Gly Val Leu Ala Gly
            370                 375                 380

Gln Ala Ser Gln Leu Asn Ala Val Val Asp Leu Gln Asp Arg Asn Thr
385                 390                 395                 400

Glu Leu Ser Tyr Gln Leu Leu Leu Asp Ser Ile Gly Asp Arg Thr Arg
                405                 410                 415

Tyr Phe Ser Met Trp Asn Gln Ala Val Asp Ser Tyr Asp Pro Asp Val
            420                 425                 430

Arg Ile Ile Glu Asn His Gly Thr Glu Asp Glu Leu Pro Asn Tyr Cys
            435                 440                 445

Phe Pro Leu Gly Gly Ile Gly Val Thr Asp Thr Tyr Gln Ala Ile Lys
```

```
            450                 455                 460
Ala Thr Asn Gly Asn Gly Gly Ala Thr Thr Trp Ala Gln Asp Asn Thr
465                 470                 475                 480

Phe Ala Glu Arg Asn Glu Ile Gly Val Gly Asn Asn Phe Ala Met Glu
                485                 490                 495

Ile Asn Leu Asn Ala Asn Leu Trp Arg Asn Phe Leu Tyr Ser Asn Ile
                500                 505                 510

Ala Leu Tyr Leu Pro Asp Lys Leu Lys Tyr Asn Pro Thr Asn Val Glu
            515                 520                 525

Ile Ser Asp Asn Pro Asn Thr Tyr Asp Tyr Met Asn Lys Arg Val Val
530                 535                 540

Ala Pro Gly Leu Val Asp Cys Tyr Ile Asn Leu Gly Ala Arg Trp Ser
545                 550                 555                 560

Leu Asp Tyr Met Asp Asn Val Asn Pro Phe Asn His His Arg Asn Ala
                565                 570                 575

Gly Leu Arg Tyr Arg Ser Met Leu Leu Gly Asn Gly Arg Tyr Val Pro
            580                 585                 590

Phe His Ile Gln Val Pro Gln Lys Phe Phe Ala Ile Lys Asn Leu Leu
            595                 600                 605

Leu Leu Pro Gly Ser Tyr Thr Tyr Glu Trp Asn Phe Arg Lys Asp Val
610                 615                 620

Asn Met Val Leu Gln Ser Ser Leu Gly Asn Asp Leu Arg Val Asp Gly
625                 630                 635                 640

Ala Ser Ile Lys Phe Asp Ser Ile Cys Leu Tyr Ala Thr Phe Phe Pro
                645                 650                 655

Met Ala His Asn Thr Ala Ser Thr Leu Glu Ala Met Leu Arg Asn Asp
                660                 665                 670

Thr Asn Asp Gln Ser Phe Asn Asp Tyr Leu Ser Ala Ala Asn Met Leu
            675                 680                 685

Tyr Pro Ile Pro Ala Asn Ala Thr Asn Val Pro Ile Ser Ile Pro Ser
            690                 695                 700

Arg Asn Trp Ala Ala Phe Arg Gly Trp Ala Phe Thr Arg Leu Lys Thr
705                 710                 715                 720

Lys Glu Thr Pro Ser Leu Gly Ser Gly Tyr Asp Pro Tyr Tyr Thr Tyr
                725                 730                 735

Ser Gly Ser Ile Pro Tyr Leu Asp Gly Thr Phe Tyr Leu Asn His Thr
            740                 745                 750

Phe Lys Lys Val Ala Ile Thr Phe Asp Ser Ser Val Ser Trp Pro Gly
            755                 760                 765

Asn Asp Arg Leu Leu Thr Pro Asn Glu Phe Glu Ile Lys Arg Ser Val
770                 775                 780

Asp Gly Glu Gly Tyr Asn Val Ala Gln Cys Asn Met Thr Lys Asp Trp
785                 790                 795                 800

Phe Leu Val Gln Met Leu Ala Asn Tyr Asn Ile Gly Tyr Gln Gly Phe
                805                 810                 815

Tyr Ile Pro Glu Ser Tyr Lys Asp Arg Met Tyr Ser Phe Phe Arg Asn
            820                 825                 830

Phe Gln Pro Met Ser Arg Gln Val Val Asp Thr Lys Tyr Lys Asp
            835                 840                 845

Tyr Gln Gln Val Gly Ile Ile His Gln His Asn Asn Ser Gly Phe Val
850                 855                 860

Gly Tyr Leu Ala Pro Thr Met Arg Glu Gly Gln Ala Tyr Pro Ala Asn
865                 870                 875                 880
```

```
Val Pro Tyr Pro Leu Ile Gly Lys Thr Ala Val Asp Ser Ile Thr Gln
            885                 890                 895

Lys Lys Phe Leu Cys Asp Arg Thr Leu Trp Arg Ile Pro Phe Ser Ser
            900                 905                 910

Asn Phe Met Ser Met Gly Ala Leu Thr Asp Leu Gly Gln Asn Leu Leu
            915                 920                 925

Tyr Ala Asn Ser Ala His Ala Leu Asp Met Thr Phe Glu Val Asp Pro
            930                 935                 940

Met Asp Glu Pro Thr Leu Leu Tyr Val Leu Phe Glu Val Phe Asp Val
945                 950                 955                 960

Val Arg Val His Gln Pro His Arg Gly Val Ile Glu Val Tyr Leu
            965                 970                 975

Arg Thr Pro Phe Ser Ala Gly Asn Ala Thr Thr
            980                 985
```

<210> SEQ ID NO 58
<211> LENGTH: 959
<212> TYPE: PRT
<213> ORGANISM: Artificial Sequence
<220> FEATURE:
<223> OTHER INFORMATION: Hexon Polypeptide

<400> SEQUENCE: 58

```
Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
            35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65              70                  75                  80

Lys Ala Arg Phe Thr Leu Ala Val Gly Asp Asn Arg Val Leu Asp Met
            85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
            115                 120                 125

Ala Pro Asn Ser Cys Glu Trp Asp Glu Asp Thr Gln Val Gln Val
            130                 135                 140

Ala Ala Glu Asp Asp Gln Asp Asp Glu Glu Glu Gln Leu Pro
145                 150                 155                 160

Gln Gln Arg Asn Gly Lys Lys Thr His Val Tyr Ala Gln Ala Pro Phe
            165                 170                 175

Ala Gly Glu Ala Ile Asn Lys Asn Gly Leu Gln Ile Gly Thr Asn Gly
            180                 185                 190

Ala Ala Thr Glu Gly Asn Lys Glu Ile Tyr Ala Asp Lys Thr Tyr Gln
            195                 200                 205

Pro Glu Pro Gln Ile Gly Glu Ser Gln Trp Asn Glu Ala Glu Ser Ser
            210                 215                 220

Val Ala Gly Gly Arg Val Leu Lys Lys Thr Thr Pro Met Lys Pro Cys
225                 230                 235                 240

Tyr Gly Ser Tyr Ala Arg Pro Thr Asn Ser Asn Gly Gly Gln Gly Val
            245                 250                 255
```

```
Met Val Glu Gln Asn Gly Lys Leu Glu Ser Gln Val Glu Met Gln Phe
                260                 265                 270

Phe Ser Thr Ser Val Asn Ala Met Asn Glu Ala Asn Ala Ile Gln Pro
                275                 280                 285

Lys Leu Val Leu Tyr Ser Glu Asp Val Asn Met Glu Thr Pro Asp Thr
            290                 295                 300

His Leu Ser Tyr Lys Pro Gly Lys Ser Asp Asn Ser Lys Ala Met
305                 310                 315                 320

Leu Gly Gln Gln Ser Met Pro Asn Arg Pro Asn Tyr Ile Ala Phe Arg
                    325                 330                 335

Asp Asn Phe Ile Gly Leu Met Tyr Tyr Asn Ser Thr Gly Asn Met Gly
                340                 345                 350

Val Leu Ala Gly Gln Ala Ser Gln Leu Asn Ala Val Val Asp Leu Gln
                355                 360                 365

Asp Arg Asn Thr Glu Leu Ser Tyr Gln Leu Leu Asp Ser Ile Gly
            370                 375                 380

Asp Arg Thr Arg Tyr Phe Ser Met Trp Asn Gln Ala Val Asp Ser Tyr
385                 390                 395                 400

Asp Pro Asp Val Arg Ile Ile Glu Asn His Gly Thr Glu Asp Glu Leu
                405                 410                 415

Pro Asn Tyr Cys Phe Pro Leu Gly Gly Ile Gly Val Thr Asp Thr Tyr
                420                 425                 430

Gln Ala Ile Lys Ala Thr Asn Gly Asn Gly Gly Ala Thr Thr Trp Ala
                435                 440                 445

Gln Asp Asn Thr Phe Ala Glu Arg Asn Glu Ile Gly Val Gly Asn Asn
            450                 455                 460

Phe Ala Met Glu Ile Asn Leu Asn Ala Asn Leu Trp Arg Asn Phe Leu
465                 470                 475                 480

Tyr Ser Asn Ile Ala Leu Tyr Leu Pro Asp Lys Leu Lys Tyr Asn Pro
                485                 490                 495

Thr Asn Val Glu Ile Ser Asp Asn Pro Asn Thr Tyr Asp Tyr Met Asn
                500                 505                 510

Lys Arg Val Val Ala Pro Gly Leu Val Asp Cys Tyr Ile Asn Leu Gly
            515                 520                 525

Ala Arg Trp Ser Leu Asp Tyr Met Asp Asn Val Asn Pro Phe Asn His
                    535                 540
530

His Arg Asn Ala Gly Leu Arg Tyr Arg Ser Met Leu Leu Gly Asn Gly
545                 550                 555                 560

Arg Tyr Val Pro Phe His Ile Gln Val Pro Gln Lys Phe Phe Ala Ile
                565                 570                 575

Lys Asn Leu Leu Leu Leu Pro Gly Ser Tyr Thr Tyr Glu Trp Asn Phe
                580                 585                 590

Arg Lys Asp Val Asn Met Val Leu Gln Ser Ser Leu Gly Asn Asp Leu
            595                 600                 605

Arg Val Asp Gly Ala Ser Ile Lys Phe Asp Ser Ile Cys Leu Tyr Ala
            610                 615                 620

Thr Phe Phe Pro Met Ala His Asn Thr Ala Ser Thr Leu Glu Ala Met
625                 630                 635                 640

Leu Arg Asn Asp Thr Asn Asp Gln Ser Phe Asn Asp Tyr Leu Ser Ala
                645                 650                 655

Ala Asn Met Leu Tyr Pro Ile Pro Ala Asn Ala Thr Asn Val Pro Ile
                660                 665                 670
```

```
Ser Ile Pro Ser Arg Asn Trp Ala Ala Phe Arg Gly Trp Ala Phe Thr
            675                 680                 685

Arg Leu Lys Thr Lys Glu Thr Pro Ser Leu Gly Ser Gly Tyr Asp Pro
690                 695                 700

Tyr Tyr Thr Tyr Ser Gly Ser Ile Pro Tyr Leu Asp Gly Thr Phe Tyr
705                 710                 715                 720

Leu Asn His Thr Phe Lys Lys Val Ala Ile Thr Phe Asp Ser Ser Val
                725                 730                 735

Ser Trp Pro Gly Asn Asp Arg Leu Leu Thr Pro Asn Glu Phe Glu Ile
            740                 745                 750

Lys Arg Ser Val Asp Gly Glu Gly Tyr Asn Val Ala Gln Cys Asn Met
            755                 760                 765

Thr Lys Asp Trp Phe Leu Val Gln Met Leu Ala Asn Tyr Asn Ile Gly
            770                 775                 780

Tyr Gln Gly Phe Tyr Ile Pro Glu Ser Tyr Lys Asp Arg Met Tyr Ser
785                 790                 795                 800

Phe Phe Arg Asn Phe Gln Pro Met Ser Arg Gln Val Val Asp Asp Thr
                805                 810                 815

Lys Tyr Lys Asp Tyr Gln Gln Val Gly Ile Ile His Gln His Asn Asn
            820                 825                 830

Ser Gly Phe Val Gly Tyr Leu Ala Pro Thr Met Arg Glu Gly Gln Ala
            835                 840                 845

Tyr Pro Ala Asn Val Pro Tyr Pro Leu Ile Gly Lys Thr Ala Val Asp
            850                 855                 860

Ser Ile Thr Gln Lys Lys Phe Leu Cys Asp Arg Thr Leu Trp Arg Ile
865                 870                 875                 880

Pro Phe Ser Ser Asn Phe Met Ser Met Gly Ala Leu Thr Asp Leu Gly
                885                 890                 895

Gln Asn Leu Leu Tyr Ala Asn Ser Ala His Ala Leu Asp Met Thr Phe
            900                 905                 910

Glu Val Asp Pro Met Asp Glu Pro Thr Leu Leu Tyr Val Leu Phe Glu
            915                 920                 925

Val Phe Asp Val Val Arg Val His Gln Pro His Arg Gly Val Ile Glu
            930                 935                 940

Thr Val Tyr Leu Arg Thr Pro Phe Ser Ala Gly Asn Ala Thr Thr
945                 950                 955

<210> SEQ ID NO 59
<211> LENGTH: 962
<212> TYPE: PRT
<213> ORGANISM: Artificial Sequence
<220> FEATURE:
<223> OTHER INFORMATION: Hexon Polypeptide

<400> SEQUENCE: 59

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80
```

```
Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Glu Gln Asn Glu Thr Ala Gln Val Asp
    130                 135                 140

Ala Gln Glu Leu Asp Glu Glu Asn Glu Ala Asn Glu Ala Gln Ala
145                 150                 155                 160

Arg Glu Gln Glu Gln Ala Lys Lys Thr His Val Tyr Ala Gln Ala Pro
                165                 170                 175

Leu Ser Gly Glu Ala Ile Asn Lys Asn Gly Leu Gln Ile Gly Thr Asn
            180                 185                 190

Gly Ala Ala Thr Glu Gly Asn Lys Glu Ile Tyr Ala Asp Lys Thr Tyr
        195                 200                 205

Gln Pro Glu Pro Gln Ile Gly Glu Ser Gln Trp Asn Glu Ala Glu Ser
    210                 215                 220

Ser Val Ala Gly Gly Arg Val Leu Lys Lys Thr Thr Pro Met Lys Pro
225                 230                 235                 240

Cys Tyr Gly Ser Tyr Ala Arg Pro Thr Asn Ser Asn Gly Gln Gly
                245                 250                 255

Val Met Val Glu Gln Asn Gly Lys Leu Glu Ser Gln Val Glu Met Gln
            260                 265                 270

Phe Phe Ser Thr Ser Val Asn Ala Met Asn Glu Ala Asn Ala Ile Gln
        275                 280                 285

Pro Lys Leu Val Leu Tyr Ser Glu Asp Val Asn Met Glu Thr Pro Asp
    290                 295                 300

Thr His Leu Ser Tyr Lys Pro Gly Lys Ser Asp Asp Asn Ser Lys Ala
305                 310                 315                 320

Met Leu Gly Gln Gln Ser Met Pro Asn Arg Pro Asn Tyr Ile Ala Phe
                325                 330                 335

Arg Asp Asn Phe Ile Gly Leu Met Tyr Tyr Asn Ser Thr Gly Asn Met
            340                 345                 350

Gly Val Leu Ala Gly Gln Ala Ser Gln Leu Asn Ala Val Val Asp Leu
        355                 360                 365

Gln Asp Arg Asn Thr Glu Leu Ser Tyr Gln Leu Leu Leu Asp Ser Ile
    370                 375                 380

Gly Asp Arg Thr Arg Tyr Phe Ser Met Trp Asn Gln Ala Val Asp Ser
385                 390                 395                 400

Tyr Asp Pro Asp Val Arg Ile Ile Glu Asn His Gly Thr Glu Asp Glu
                405                 410                 415

Leu Pro Asn Tyr Cys Phe Pro Leu Gly Gly Ile Gly Ile Thr Asp Thr
            420                 425                 430

Phe Gln Ala Val Lys Thr Thr Ala Ala Asn Gly Asp Gln Gly Asn Thr
        435                 440                 445

Thr Trp Gln Lys Asp Ser Thr Phe Ala Glu Arg Asn Glu Ile Gly Val
    450                 455                 460

Gly Asn Asn Phe Ala Met Glu Ile Asn Leu Ala Asn Leu Trp Arg
465                 470                 475                 480

Asn Phe Leu Tyr Ser Asn Ile Ala Leu Tyr Leu Pro Asp Lys Leu Lys
                485                 490                 495

Tyr Asn Pro Thr Asn Val Glu Ile Ser Asp Asn Pro Asn Thr Tyr Asp
```

-continued

Tyr Met Asn Lys Arg Val Val Ala Pro Gly Leu Val Asp Cys Tyr Ile
500                     505                         510
Asn Leu Gly Ala Arg Trp Ser Leu Asp Tyr Met Asp Asn Val Asn Pro
    515                     520                     525
Phe Asn His Pro Arg His Ala Gly Leu Arg Tyr Arg Ser Met Leu Leu
545                     550                     555                     560
Gly Asn Gly Arg Tyr Val Pro Phe His Ile Gln Val Pro Gln Lys Phe
                565                     570                     575
Phe Ala Ile Lys Asn Leu Leu Leu Pro Gly Ser Tyr Thr Tyr Glu
        580                     585                     590
Trp Asn Phe Arg Lys Asp Val Asn Met Val Leu Gln Ser Ser Leu Gly
    595                     600                     605
Asn Asp Leu Arg Val Asp Gly Ala Ser Ile Lys Phe Asp Ser Ile Cys
    610                     615                     620
Leu Tyr Ala Thr Phe Phe Pro Met Ala His Asn Thr Ala Ser Thr Leu
625                     630                     635                     640
Glu Ala Met Leu Arg Asn Asp Thr Asn Asp Gln Ser Phe Asn Asp Tyr
                645                     650                     655
Leu Ser Ala Ala Asn Met Leu Tyr Pro Ile Pro Ala Asn Ala Thr Asn
            660                     665                     670
Val Pro Ile Ser Ile Pro Ser Arg Asn Trp Ala Ala Phe Arg Gly Trp
    675                     680                     685
Ala Phe Thr Arg Leu Lys Thr Lys Glu Thr Pro Ser Leu Gly Ser Gly
    690                     695                     700
Tyr Asp Pro Tyr Tyr Thr Tyr Ser Gly Ser Ile Pro Tyr Leu Asp Gly
705                     710                     715                     720
Thr Phe Tyr Leu Asn His Thr Phe Lys Lys Val Ala Ile Thr Phe Asp
                725                     730                     735
Ser Ser Val Ser Trp Pro Gly Asn Asp Arg Leu Leu Thr Pro Asn Glu
            740                     745                     750
Phe Glu Ile Lys Arg Ser Val Asp Gly Glu Gly Tyr Asn Val Ala Gln
    755                     760                     765
Cys Asn Met Thr Lys Asp Trp Phe Leu Val Gln Met Leu Ala Asn Tyr
    770                     775                     780
Asn Ile Gly Tyr Gln Gly Phe Tyr Ile Pro Glu Ser Tyr Lys Asp Arg
785                     790                     795                     800
Met Tyr Ser Phe Phe Arg Asn Phe Gln Pro Met Ser Arg Gln Val Val
                805                     810                     815
Asp Asp Thr Lys Tyr Lys Asp Tyr Gln Gln Val Gly Ile Ile His Gln
            820                     825                     830
His Asn Asn Ser Gly Phe Val Gly Tyr Leu Ala Pro Thr Met Arg Glu
    835                     840                     845
Gly Gln Ala Tyr Pro Ala Asn Val Pro Tyr Pro Leu Ile Gly Lys Thr
    850                     855                     860
Ala Val Asp Ser Ile Thr Gln Lys Lys Phe Leu Cys Asp Arg Thr Leu
865                     870                     875                     880
Trp Arg Ile Pro Phe Ser Ser Asn Phe Met Ser Met Gly Ala Leu Thr
                885                     890                     895
Asp Leu Gly Gln Asn Leu Leu Tyr Ala Asn Ser Ala His Ala Leu Asp
            900                     905                     910
Met Thr Phe Glu Val Asp Pro Met Asp Glu Pro Thr Leu Leu Tyr Val
    915                     920                     925

```
Leu Phe Glu Val Phe Asp Val Arg Val His Gln Pro His Arg Gly
        930                 935                 940

Val Ile Glu Thr Val Tyr Leu Arg Thr Pro Phe Ser Ala Gly Asn Ala
945                 950                 955                 960

Thr Thr

<210> SEQ ID NO 60
<211> LENGTH: 528
<212> TYPE: PRT
<213> ORGANISM: Artificial Sequence
<220> FEATURE:
<223> OTHER INFORMATION: Fiber Polypeptide

<400> SEQUENCE: 60

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
        35                  40                  45

Leu Arg Leu Ser Glu Pro Leu Val Thr Ser His Gly Met Leu Ala Leu
    50                  55                  60

Lys Met Gly Ser Gly Leu Ser Leu Asp Gln Ala Gly Asn Leu Thr Ser
65                  70                  75                  80

Asn Thr Ile Thr Val Ser Gln Pro Leu Lys Lys Thr Lys Ser Asn Ile
                85                  90                  95

Thr Leu Glu Thr Ser Ala Pro Leu Thr Val Ser Ser Gly Ala Leu Thr
            100                 105                 110

Met Ala Thr Thr Ser Pro Leu Val Val Ser Asp Asn Thr Leu Thr Met
        115                 120                 125

Gln Ser Gln Ala Pro Leu Thr Val Gln Asp Ser Lys Leu Ser Ile Ala
    130                 135                 140

Thr Lys Glu Pro Leu Thr Val Leu Asp Gly Lys Leu Ala Leu Gln Thr
145                 150                 155                 160

Ser Ala Pro Leu Ser Ala Thr Asp Asn Asn Ala Leu Thr Ile Thr Ala
                165                 170                 175

Ser Pro Pro Leu Thr Thr Ala Asn Gly Ser Leu Ala Val Thr Met Glu
            180                 185                 190

Asn Pro Leu Tyr Asn Asn Gly Lys Leu Gly Leu Lys Ile Gly Gly
        195                 200                 205

Pro Leu Gln Val Ala Thr Asp Ser His Ala Leu Thr Leu Gly Thr Gly
    210                 215                 220

Gln Gly Val Ala Val His Asn Asn Leu Leu His Thr Lys Val Thr Gly
225                 230                 235                 240

Ala Ile Gly Phe Asp Thr Ser Gly Asn Met Glu Leu Lys Thr Gly Asp
                245                 250                 255

Gly Leu Tyr Val Asp Ser Ala Gly Pro Asn Gln Lys Leu His Ile Asn
            260                 265                 270

Leu Asn Thr Thr Lys Gly Leu Ala Phe Asp Asn Thr Ala Ile Thr Ile
        275                 280                 285

Asn Ala Gly Lys Gly Leu Glu Phe Glu Thr Asp Ser Ser Asn Gly Asn
    290                 295                 300

Pro Ile Lys Thr Lys Ile Gly Ser Gly Ile Gln Tyr Asn Thr Asn Gly
305                 310                 315                 320
```

```
Ala Met Val Ala Lys Leu Gly Thr Gly Leu Ser Phe Asp Ser Ser Gly
                325                 330                 335

Ala Ile Thr Met Gly Ser Ile Asn Asn Asp Arg Leu Thr Leu Trp Thr
            340                 345                 350

Thr Pro Asp Pro Ser Pro Asn Cys Arg Ile Ala Ser Asp Lys Asp Cys
        355                 360                 365

Lys Leu Thr Leu Ala Leu Thr Lys Cys Gly Ser Gln Ile Leu Gly Thr
    370                 375                 380

Val Ser Ala Leu Ala Val Ser Gly Asn Met Ala Ser Ile Asn Gly Thr
385                 390                 395                 400

Leu Ser Ser Val Asn Leu Val Leu Arg Phe Asp Asp Asn Gly Val Leu
                405                 410                 415

Met Ser Asn Ser Ser Leu Asp Lys Gln Tyr Trp Asn Phe Arg Asn Gly
            420                 425                 430

Asp Ser Thr Asn Gly Gln Pro Tyr Thr Tyr Ala Val Gly Phe Met Pro
        435                 440                 445

Asn Leu Lys Ala Tyr Pro Lys Thr Gln Ser Lys Thr Ala Lys Ser Asn
    450                 455                 460

Ile Val Ser Gln Val Tyr Leu Asn Gly Asp Lys Ser Lys Pro Leu His
465                 470                 475                 480

Phe Thr Ile Thr Leu Asn Gly Thr Asp Glu Thr Asn Gln Val Ser Lys
                485                 490                 495

Tyr Ser Ile Ser Phe Ser Trp Ser Trp Asn Ser Gly Gln Tyr Thr Asn
            500                 505                 510

Asp Lys Phe Ala Thr Asn Ser Tyr Thr Phe Ser Tyr Ile Ala Gln Glu
        515                 520                 525

<210> SEQ ID NO 61
<211> LENGTH: 324
<212> TYPE: PRT
<213> ORGANISM: Artificial Sequence
<220> FEATURE:
<223> OTHER INFORMATION: Fiber Polypeptide

<400> SEQUENCE: 61

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Thr
        35                  40                  45

Leu Lys Cys Leu Thr Pro Leu Thr Thr Thr Gly Gly Ser Leu Gln Leu
    50                  55                  60

Lys Val Gly Gly Gly Leu Thr Val Asp Thr Asp Gly Thr Leu Gln
65                  70                  75                  80

Glu Asn Ile Arg Ala Thr Ala Pro Ile Thr Lys Asn Asn His Ser Val
                85                  90                  95

Glu Leu Ser Ile Gly Asn Gly Leu Glu Thr Gln Asn Asn Lys Leu Cys
            100                 105                 110

Ala Lys Leu Gly Asn Gly Leu Lys Phe Asn Asn Gly Asp Ile Cys Ile
        115                 120                 125

Lys Asp Ser Ile Asn Thr Leu Trp Thr Gly Ile Asn Pro Pro Asn
    130                 135                 140

Cys Gln Ile Val Glu Asn Thr Asn Thr Asn Asp Gly Lys Leu Thr Leu
145                 150                 155                 160
```

```
Val Leu Val Lys Asn Gly Gly Leu Val Asn Gly Tyr Val Ser Leu Val
            165                 170                 175

Gly Val Ser Asp Thr Val Asn Gln Met Phe Thr Gln Lys Thr Ala Asn
        180                 185                 190

Ile Gln Leu Arg Leu Tyr Phe Asp Ser Ser Gly Asn Leu Leu Thr Asp
            195                 200                 205

Glu Ser Asp Leu Lys Ile Pro Leu Lys Asn Lys Ser Ser Thr Ala Thr
    210                 215                 220

Ser Glu Thr Val Ala Ser Ser Lys Ala Phe Met Pro Ser Thr Thr Ala
225                 230                 235                 240

Tyr Pro Phe Asn Thr Thr Thr Arg Asp Ser Glu Asn Tyr Ile His Gly
                245                 250                 255

Ile Cys Tyr Tyr Met Thr Ser Tyr Asp Arg Ser Leu Phe Pro Leu Asn
            260                 265                 270

Ile Ser Ile Met Leu Asn Ser Arg Met Ile Ser Ser Asn Val Ala Tyr
        275                 280                 285

Ala Ile Gln Phe Glu Trp Asn Leu Asn Ala Ser Glu Ser Pro Glu Ser
            290                 295                 300

Asn Ile Ala Thr Leu Thr Thr Ser Pro Phe Phe Phe Ser Tyr Ile Thr
305                 310                 315                 320

Glu Asp Asp Asn

<210> SEQ ID NO 62
<211> LENGTH: 534
<212> TYPE: PRT
<213> ORGANISM: Artificial Sequence
<220> FEATURE:
<223> OTHER INFORMATION: Fiber Polypeptide

<400> SEQUENCE: 62

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
        35                  40                  45

Leu Arg Leu Ser Glu Pro Leu Val Thr Ser His Gly Met Leu Ala Leu
    50                  55                  60

Lys Met Gly Ser Gly Leu Ser Leu Asp Gln Ala Gly Asn Leu Thr Ser
65                  70                  75                  80

Asn Thr Ile Thr Val Ser Gln Pro Leu Lys Lys Thr Lys Ser Asn Ile
                85                  90                  95

Thr Leu Glu Thr Ser Ala Pro Leu Thr Val Ser Ser Gly Ala Leu Thr
            100                 105                 110

Met Ala Thr Thr Ser Pro Leu Val Val Ser Asp Asn Thr Leu Thr Met
        115                 120                 125

Gln Ser Gln Ala Pro Leu Thr Val Gln Asp Ser Lys Leu Ser Ile Ala
    130                 135                 140

Thr Lys Glu Pro Leu Thr Val Leu Asp Gly Lys Leu Ala Leu Gln Thr
145                 150                 155                 160

Ser Ala Pro Leu Ser Ala Thr Asp Asn Asn Ala Leu Thr Ile Thr Ala
                165                 170                 175

Ser Pro Pro Leu Thr Thr Ala Asn Gly Ser Leu Ala Val Thr Met Glu
            180                 185                 190

Asn Pro Leu Tyr Asn Asn Asn Gly Lys Leu Gly Leu Lys Ile Gly Gly
```

```
            195                 200                 205
Pro Leu Gln Val Ala Thr Asp Ser His Ala Leu Thr Leu Gly Thr Gly
    210                 215                 220

Gln Gly Val Ala Val His Asn Asn Leu Leu His Thr Lys Val Thr Gly
225                 230                 235                 240

Ala Ile Gly Phe Asp Thr Ser Gly Asn Met Glu Leu Lys Thr Gly Asp
                245                 250                 255

Gly Leu Tyr Val Asp Ser Ala Gly Pro Asn Gln Lys Leu His Ile Asn
            260                 265                 270

Leu Asn Thr Thr Lys Gly Leu Ala Phe Asp Asn Thr Ala Ile Thr Ile
        275                 280                 285

Asn Ala Gly Lys Gly Leu Glu Phe Glu Thr Asp Ser Ser Asn Gly Asn
    290                 295                 300

Pro Ile Lys Thr Lys Ile Gly Ser Gly Ile Gln Tyr Asn Thr Asn Gly
305                 310                 315                 320

Ala Met Val Ala Lys Leu Gly Thr Gly Leu Ser Phe Asp Ser Ser Gly
                325                 330                 335

Ala Ile Thr Met Gly Ser Ile Asn Asn Asp Arg Leu Thr Leu Trp Thr
            340                 345                 350

Thr Pro Asp Pro Ser Pro Asn Cys Arg Ile Ala Ser Asp Lys Asp Cys
        355                 360                 365

Lys Leu Thr Leu Ala Leu Thr Lys Cys Gly Ser Gln Ile Leu Gly Thr
    370                 375                 380

Val Ser Ala Leu Ala Val Ser Gly Asn Met Ala Ser Ile Asn Gly Thr
385                 390                 395                 400

Leu Ser Ser Val Asn Leu Val Leu Arg Phe Asp Asp Asn Gly Val Leu
                405                 410                 415

Met Ser Asn Ser Ser Leu Asp Lys Gln Tyr Trp Asn Phe Arg Asn Gly
            420                 425                 430

Asp Ser Thr Asn Gly Gln Pro Tyr Thr Tyr Ala Val Gly Phe Met Pro
        435                 440                 445

Asn Leu Lys Ala Tyr Pro Lys Thr Gln Ser Leu Thr Ala Lys Ser Asn
    450                 455                 460

Ile Val Ser Gln Val Tyr Leu Asn Gly Asp Lys Ser Lys Pro Leu His
465                 470                 475                 480

Phe Thr Ile Thr Leu Asn Gly Thr Asp Glu Thr Asn Gln Val Ser Lys
                485                 490                 495

Tyr Ser Ile Ser Phe Ser Trp Ser Trp Asn Ser Gly Gln Tyr Thr Asn
            500                 505                 510

Asp Lys Phe Ala Thr Asn Ser Tyr Thr Phe Ser Tyr Ile Ala Gln Glu
        515                 520                 525

Lys Lys Lys Lys Lys Lys
    530

<210> SEQ ID NO 63
<211> LENGTH: 425
<212> TYPE: PRT
<213> ORGANISM: Artificial Sequence
<220> FEATURE:
<223> OTHER INFORMATION: Fiber Polypeptide

<400> SEQUENCE: 63

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
```

```
            20                  25                  30
Phe Val Ser Pro Asn Gly Phe Gln Glu Ser Pro Pro Gly Val Leu Ser
        35                  40                  45
Leu Arg Leu Ser Glu Pro Leu Val Thr Lys Asn Gly Glu Ile Thr Leu
 50                  55                  60
Lys Leu Gly Glu Gly Val Asp Leu Asp Ser Gly Lys Leu Ile Ser
 65                  70                  75                  80
Asn Thr Ala Thr Lys Ala Ala Pro Leu Ser Phe Ser Asn Asn Thr
                85                  90                  95
Ile Ser Leu Asn Met Asp His Pro Phe Tyr Thr Lys Asp Gly Lys Leu
            100                 105                 110
Ser Leu Gln Val Ser Pro Pro Leu Asn Ile Leu Arg Thr Ser Ile Leu
            115                 120                 125
Asn Thr Leu Ala Leu Gly Phe Gly Ser Gly Leu Gly Leu Arg Gly Ser
            130                 135                 140
Ala Leu Ala Val Gln Leu Val Ser Pro Leu Thr Phe Asp Thr Asp Gly
145                 150                 155                 160
Asn Ile Lys Leu Thr Leu Asp Arg Gly Leu His Val Thr Thr Gly Asp
                165                 170                 175
Ala Ile Glu Ser Asn Ile Ser Trp Ala Lys Gly Leu Lys Phe Glu Asp
            180                 185                 190
Gly Ala Ile Ala Thr Asn Ile Gly Asn Gly Leu Glu Phe Gly Ser Ser
            195                 200                 205
Ser Thr Glu Thr Gly Val Asp Asp Ala Tyr Pro Ile Gln Val Lys Leu
            210                 215                 220
Gly Ser Gly Leu Ser Phe Asp Ser Thr Gly Ala Ile Met Ala Gly Asn
225                 230                 235                 240
Lys Glu Asp Asp Lys Leu Thr Leu Trp Thr Thr Pro Asp Pro Ser Pro
                245                 250                 255
Asn Cys Gln Ile Leu Ala Glu Asn Asp Ala Lys Leu Thr Leu Cys Leu
            260                 265                 270
Thr Lys Cys Gly Ser Gln Ile Leu Ala Thr Val Ser Val Leu Val Val
            275                 280                 285
Gly Ser Gly Asn Leu Asn Pro Ile Thr Gly Thr Val Ser Ser Ala Gln
290                 295                 300
Val Phe Leu Arg Phe Asp Ala Asn Gly Val Leu Leu Thr Glu His Ser
305                 310                 315                 320
Thr Leu Lys Lys Tyr Trp Gly Tyr Arg Gln Gly Asp Ser Ile Asp Gly
                325                 330                 335
Thr Pro Tyr Thr Asn Ala Val Gly Phe Met Pro Asn Leu Lys Ala Tyr
                340                 345                 350
Pro Lys Ser Gln Ser Ser Thr Thr Lys Asn Asn Ile Val Gly Gln Val
            355                 360                 365
Tyr Met Asn Gly Asp Val Ser Lys Pro Met Leu Leu Thr Ile Thr Leu
            370                 375                 380
Asn Gly Thr Asp Asp Ser Asn Ser Thr Tyr Ser Met Ser Phe Ser Tyr
385                 390                 395                 400
Thr Trp Thr Asn Gly Ser Tyr Val Gly Ala Thr Phe Gly Ala Asn Ser
                405                 410                 415
Tyr Thr Phe Ser Tyr Ile Ala Gln Glu
            420                 425

<210> SEQ ID NO 64
```

```
<211> LENGTH: 432
<212> TYPE: PRT
<213> ORGANISM: Artificial Sequence
<220> FEATURE:
<223> OTHER INFORMATION: Fiber Polypeptide

<400> SEQUENCE: 64

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
        35                  40                  45

Leu Arg Leu Ser Glu Pro Leu Val Thr Lys Asn Gly Glu Ile Thr Leu
50                  55                  60

Lys Leu Gly Glu Gly Val Asp Leu Asp Ser Ser Gly Lys Leu Ile Ser
65                  70                  75                  80

Asn Thr Ala Thr Lys Ala Ala Pro Leu Ser Phe Ser Asn Asn Thr
                85                  90                  95

Ile Ser Leu Asn Met Asp His Pro Phe Tyr Thr Lys Asp Gly Lys Leu
            100                 105                 110

Ser Leu Gln Val Ser Pro Pro Leu Asn Ile Leu Arg Thr Ser Ile Leu
        115                 120                 125

Asn Thr Leu Ala Leu Gly Phe Gly Ser Gly Leu Gly Leu Arg Gly Ser
130                 135                 140

Ala Leu Ala Val Gln Leu Val Ser Pro Leu Thr Phe Asp Thr Asp Gly
145                 150                 155                 160

Asn Ile Lys Leu Thr Leu Asp Arg Gly Leu His Val Thr Thr Gly Asp
                165                 170                 175

Ala Ile Glu Ser Asn Ile Ser Trp Ala Lys Gly Leu Lys Phe Glu Asp
            180                 185                 190

Gly Ala Ile Ala Thr Asn Ile Gly Asn Gly Leu Glu Phe Gly Ser Ser
        195                 200                 205

Ser Thr Glu Thr Gly Val Asp Asp Ala Tyr Pro Ile Gln Val Lys Leu
210                 215                 220

Gly Ser Gly Leu Ser Phe Asp Ser Thr Gly Ala Ile Met Ala Gly Asn
225                 230                 235                 240

Lys Glu Asp Asp Lys Leu Thr Leu Trp Thr Thr Pro Asp Pro Ser Pro
                245                 250                 255

Asn Cys Gln Ile Leu Ala Glu Asn Asp Ala Lys Leu Thr Leu Cys Leu
            260                 265                 270

Thr Lys Cys Gly Ser Gln Ile Leu Ala Thr Val Ser Val Leu Val Val
        275                 280                 285

Gly Ser Gly Asn Leu Asn Pro Ile Thr Gly Thr Val Ser Ser Ala Gln
290                 295                 300

Val Phe Leu Arg Phe Asp Ala Asn Gly Val Leu Leu Thr Glu His Ser
305                 310                 315                 320

Thr Leu Lys Lys Tyr Trp Gly Tyr Arg Gln Gly Asp Ser Ile Asp Gly
                325                 330                 335

Thr Pro Tyr Thr Asn Ala Val Gly Phe Met Pro Asn Leu Lys Ala Tyr
            340                 345                 350

Pro Lys Ser Gln Ser Ser Thr Thr Lys Asn Asn Ile Val Gly Gln Val
        355                 360                 365

Tyr Met Asn Gly Asp Val Ser Lys Pro Met Leu Leu Thr Ile Thr Leu
370                 375                 380
```

```
Asn Gly Thr Asp Asp Ser Asn Ser Thr Tyr Ser Met Ser Phe Ser Tyr
385                 390                 395                 400

Thr Trp Thr Asn Gly Ser Tyr Val Gly Ala Thr Phe Gly Ala Asn Ser
                405                 410                 415

Tyr Thr Phe Ser Tyr Ile Ala Gln Glu Lys Lys Lys Lys Lys Lys
            420                 425                 430

<210> SEQ ID NO 65
<211> LENGTH: 441
<212> TYPE: PRT
<213> ORGANISM: Artificial Sequence
<220> FEATURE:
<223> OTHER INFORMATION: Fiber Polypeptide

<400> SEQUENCE: 65

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
        35                  40                  45

Leu Arg Leu Ser Glu Pro Leu Val Thr Lys Asn Gly Glu Ile Thr Leu
50                  55                  60

Lys Leu Gly Glu Gly Val Asp Leu Asp Ser Ser Gly Lys Leu Ile Ser
65                  70                  75                  80

Asn Thr Ala Thr Lys Ala Ala Pro Leu Ser Phe Ser Asn Asn Thr
                85                  90                  95

Ile Ser Leu Asn Met Asp His Pro Phe Tyr Thr Lys Asp Gly Lys Leu
            100                 105                 110

Ser Leu Gln Val Ser Pro Pro Leu Asn Ile Leu Arg Thr Ser Ile Leu
        115                 120                 125

Asn Thr Leu Ala Leu Gly Phe Gly Ser Gly Leu Gly Leu Arg Gly Ser
    130                 135                 140

Ala Leu Ala Val Gln Leu Val Ser Pro Leu Thr Phe Asp Thr Asp Gly
145                 150                 155                 160

Asn Ile Lys Leu Thr Leu Asp Arg Gly Leu His Val Thr Thr Gly Asp
                165                 170                 175

Ala Ile Glu Ser Asn Ile Ser Trp Ala Lys Gly Leu Lys Phe Glu Asp
            180                 185                 190

Gly Ala Ile Ala Thr Asn Ile Gly Asn Gly Leu Glu Phe Gly Ser Ser
        195                 200                 205

Ser Thr Glu Thr Gly Val Asp Asp Ala Tyr Pro Ile Gln Val Lys Leu
    210                 215                 220

Gly Ser Gly Leu Ser Phe Asp Ser Thr Gly Ala Ile Met Ala Gly Asn
225                 230                 235                 240

Lys Glu Asp Asp Lys Leu Thr Leu Trp Thr Thr Pro Asp Pro Ser Pro
                245                 250                 255

Asn Cys Gln Ile Leu Ala Glu Asn Asp Ala Lys Leu Thr Leu Cys Leu
            260                 265                 270

Thr Lys Cys Gly Ser Gln Ile Leu Ala Thr Val Ser Val Leu Val Val
        275                 280                 285

Gly Ser Gly Asn Leu Asn Pro Ile Thr Gly Thr Val Ser Ser Ala Gln
    290                 295                 300

Val Phe Leu Arg Phe Asp Ala Asn Gly Val Leu Leu Thr Glu His Ser
305                 310                 315                 320
```

```
Thr Leu Lys Lys Tyr Trp Gly Tyr Arg Gln Gly Asp Ser Ile Asp Gly
            325                 330                 335

Thr Pro Tyr Thr Asn Ala Val Gly Phe Met Pro Asn Leu Lys Ala Tyr
            340                 345                 350

Pro Lys Ser Gln Ser Ser Thr Thr Lys Asn Asn Ile Val Gly Gln Val
            355                 360                 365

Tyr Met Asn Gly Asp Val Ser Lys Pro Met Leu Leu Thr Ile Thr Leu
            370                 375                 380

Asn Gly Thr Asp Asp Ser Gly Gly Ser Ser Gly Lys Lys Lys Lys
385                 390                 395                 400

Lys Lys Ala Ser Gly Gly Ser Ser Thr Tyr Ser Met Ser Phe Ser Tyr
                405                 410                 415

Thr Trp Thr Asn Gly Ser Tyr Val Gly Ala Thr Phe Gly Ala Asn Ser
            420                 425                 430

Tyr Thr Phe Ser Tyr Ile Ala Gln Glu
            435                 440

<210> SEQ ID NO 66
<211> LENGTH: 27
<212> TYPE: PRT
<213> ORGANISM: Mus musculus

<400> SEQUENCE: 66

Pro Val Thr Leu Thr Ile Thr Leu Thr Ala Arg Gly Glu His Lys Glu
1               5                   10                  15

Glu Glu Leu Ile Gly Ala Tyr Tyr Ser Met Ser
            20                  25

<210> SEQ ID NO 67
<211> LENGTH: 27
<212> TYPE: PRT
<213> ORGANISM: Mus musculus

<400> SEQUENCE: 67

Pro Val Thr Leu Thr Ile Thr Leu Leu Arg Gln Thr Gly Ala Ala Ser
1               5                   10                  15

Ala Val Trp Gly Gly Ala Tyr Tyr Ser Met Ser
            20                  25

<210> SEQ ID NO 68
<211> LENGTH: 23
<212> TYPE: PRT
<213> ORGANISM: Adenovirus type 5

<400> SEQUENCE: 68

Glu Met Gln Phe Phe Ser Thr Thr Glu Ala Thr Ala Gly Asn Gly Asp
1               5                   10                  15

Asn Leu Thr Pro Lys Val Val
            20

<210> SEQ ID NO 69
<211> LENGTH: 26
<212> TYPE: PRT
<213> ORGANISM: Artificial Sequence
<220> FEATURE:
<223> OTHER INFORMATION: Synthesized muscle targeting polypeptide

<400> SEQUENCE: 69

Glu Met Gln Phe Phe Ser Gly Ser Thr Ala Arg Gly Glu His Lys Glu
1               5                   10                  15
```

```
Glu Glu Leu Ile Gly Thr Pro Lys Val Val
            20                  25

<210> SEQ ID NO 70
<211> LENGTH: 27
<212> TYPE: PRT
<213> ORGANISM: Artificial Sequence
<220> FEATURE:
<223> OTHER INFORMATION: Synthesized muscle targeting polypeptide

<400> SEQUENCE: 70

Glu Met Gln Phe Phe Ser Gly Ser Met Leu Arg Gln Thr Gly Ala Ala
1               5                   10                  15

Ser Ala Val Trp Gly Gly Thr Pro Lys Val Val
            20                  25

<210> SEQ ID NO 71
<211> LENGTH: 407
<212> TYPE: PRT
<213> ORGANISM: Adenovirus type 5

<400> SEQUENCE: 71

Tyr Asn Ala Leu Ala Pro Lys Gly Ala Pro Asn Pro Cys Glu Trp Asp
1               5                   10                  15

Glu Ala Ala Thr Ala Leu Glu Ile Asn Leu Glu Glu Glu Asp Asp Asp
            20                  25                  30

Asn Glu Asp Glu Val Asp Glu Gln Ala Glu Gln Gln Lys Thr His Val
        35                  40                  45

Phe Ser Gln Ala Pro Tyr Ser Gly Ile Asn Ile Thr Lys Glu Gly Ile
    50                  55                  60

Gln Ile Gly Val Glu Gly Gln Thr Pro Lys Tyr Ala Asp Lys Thr Phe
65                  70                  75                  80

Gln Pro Glu Pro Gln Ile Gly Glu Ser Gln Trp Tyr Glu Thr Glu Ile
                85                  90                  95

Asn His Ala Ala Gly Arg Val Leu Lys Lys Thr Thr Pro Met Lys Pro
            100                 105                 110

Cys Tyr Gly Ser Tyr Ala Lys Pro Thr Asn Glu Asn Gly Gly Gln Gly
        115                 120                 125

Ile Leu Val Lys Gln Gln Asn Gly Lys Leu Glu Ser Gln Val Glu Met
    130                 135                 140

Gln Phe Phe Ser Thr Thr Glu Ala Thr Ala Gly Asn Gly Asp Asn Leu
145                 150                 155                 160

Thr Pro Lys Val Val Leu Tyr Ser Glu Asp Val Asp Ile Glu Thr Pro
                165                 170                 175

Asp Thr His Ile Ser Tyr Met Pro Thr Ile Lys Glu Gly Asn Ser Arg
            180                 185                 190

Glu Leu Met Gly Gln Gln Ser Met Pro Asn Arg Pro Asn Tyr Ile Ala
        195                 200                 205

Phe Arg Asp Asn Phe Ile Gly Leu Met Tyr Tyr Asn Ser Thr Gly Asn
    210                 215                 220

Met Gly Val Leu Ala Gly Gln Ala Ser Gln Leu Asn Ala Val Val Asp
225                 230                 235                 240

Leu Gln Asp Arg Asn Thr Glu Leu Ser Tyr Gln Leu Leu Leu Asp Ser
                245                 250                 255

Ile Gly Asp Arg Thr Arg Tyr Phe Ser Met Trp Asn Gln Ala Val Asp
            260                 265                 270
```

```
Ser Tyr Asp Pro Asp Val Arg Ile Ile Glu Asn His Gly Thr Glu Asp
            275                 280                 285

Glu Leu Pro Asn Tyr Cys Phe Pro Leu Gly Gly Val Ile Asn Thr Glu
        290                 295                 300

Thr Leu Thr Lys Val Lys Pro Lys Thr Gly Gln Glu Asn Gly Trp Glu
305                 310                 315                 320

Lys Asp Ala Thr Glu Phe Ser Asp Lys Asn Glu Ile Arg Val Gly Asn
                325                 330                 335

Asn Phe Ala Met Glu Ile Asn Leu Ala Asn Leu Trp Arg Asn Phe
                340                 345                 350

Leu Tyr Ser Asn Ile Ala Leu Tyr Leu Pro Asp Lys Leu Lys Tyr Ser
        355                 360                 365

Pro Ser Asn Val Lys Ile Ser Asp Asn Pro Asn Thr Tyr Asp Tyr Met
    370                 375                 380

Asn Lys Arg Val Val Ala Pro Gly Leu Val Asp Cys Tyr Ile Asn Leu
385                 390                 395                 400

Gly Ala Arg Trp Ser Leu Asp
                405

<210> SEQ ID NO 72
<211> LENGTH: 418
<212> TYPE: PRT
<213> ORGANISM: Adenovirus type 6

<400> SEQUENCE: 72

Tyr Asn Ala Leu Ala Pro Lys Gly Ala Pro Asn Ser Cys Glu Trp Glu
1               5                   10                  15

Gln Asn Glu Thr Ala Gln Val Asp Ala Gln Glu Leu Asp Glu Glu Glu
            20                  25                  30

Asn Glu Ala Asn Glu Ala Gln Ala Arg Glu Gln Glu Gln Ala Lys Lys
        35                  40                  45

Thr His Val Tyr Ala Gln Ala Pro Leu Ser Gly Ile Lys Ile Thr Lys
    50                  55                  60

Glu Gly Leu Gln Ile Gly Thr Ala Asp Ala Thr Val Ala Gly Ala Gly
65                  70                  75                  80

Lys Glu Ile Phe Ala Asp Lys Thr Phe Gln Pro Glu Pro Gln Val Gly
                85                  90                  95

Glu Ser Gln Trp Asn Glu Ala Asp Ala Thr Ala Ala Gly Gly Arg Val
            100                 105                 110

Leu Lys Lys Thr Thr Pro Met Lys Pro Cys Tyr Gly Ser Tyr Ala Arg
        115                 120                 125

Pro Thr Asn Ser Asn Gly Gly Gln Gly Val Met Val Glu Gln Asn Gly
    130                 135                 140

Lys Leu Glu Ser Gln Val Glu Met Gln Phe Phe Ser Thr Ser Thr Asn
145                 150                 155                 160

Ala Thr Asn Glu Val Asn Asn Ile Gln Pro Thr Val Val Leu Tyr Ser
                165                 170                 175

Glu Asp Val Asn Met Glu Thr Pro Asp Thr His Leu Ser Tyr Lys Pro
            180                 185                 190

Lys Met Gly Asp Lys Asn Ala Lys Val Met Leu Gly Gln Gln Ala Met
        195                 200                 205

Pro Asn Arg Pro Asn Tyr Ile Ala Phe Arg Asp Asn Phe Ile Gly Leu
    210                 215                 220

Met Tyr Tyr Asn Ser Thr Gly Asn Met Gly Val Leu Ala Gly Gln Ala
225                 230                 235                 240
```

```
Ser Gln Leu Asn Ala Val Val Asp Leu Gln Asp Arg Asn Thr Glu Leu
                245                 250                 255

Ser Tyr Gln Leu Leu Asp Ser Ile Gly Asp Arg Thr Arg Tyr Phe
            260                 265                 270

Ser Met Trp Asn Gln Ala Val Asp Ser Tyr Asp Pro Asp Val Arg Ile
        275                 280                 285

Ile Glu Asn His Gly Thr Glu Asp Glu Leu Pro Asn Tyr Cys Phe Pro
    290                 295                 300

Leu Gly Gly Ile Gly Ile Thr Asp Thr Phe Gln Ala Val Lys Thr Thr
305                 310                 315                 320

Ala Ala Asn Gly Asp Gln Gly Asn Thr Thr Trp Gln Lys Asp Ser Thr
                325                 330                 335

Phe Ala Glu Arg Asn Glu Ile Gly Val Gly Asn Asn Phe Ala Met Glu
            340                 345                 350

Ile Asn Leu Asn Ala Asn Leu Trp Arg Asn Phe Leu Tyr Ser Asn Ile
        355                 360                 365

Ala Leu Tyr Leu Pro Asp Lys Leu Lys Tyr Asn Pro Thr Asn Val Glu
    370                 375                 380

Ile Ser Asp Asn Pro Asn Thr Tyr Asp Tyr Met Asn Lys Arg Val Val
385                 390                 395                 400

Ala Pro Gly Leu Val Asp Cys Tyr Ile Asn Leu Gly Ala Arg Trp Ser
                405                 410                 415

Leu Glu

<210> SEQ ID NO 73
<211> LENGTH: 414
<212> TYPE: PRT
<213> ORGANISM: Adenovirus type 57

<400> SEQUENCE: 73

Tyr Asn Ala Leu Ala Pro Lys Gly Ala Pro Asn Ser Cys Glu Trp Asp
1               5                   10                  15

Glu Asp Asp Thr Gln Val Gln Val Ala Ala Glu Asp Asp Gln Asp Asp
                20                  25                  30

Asp Glu Glu Glu Gln Leu Pro Gln Gln Arg Asn Gly Lys Lys Thr
            35                  40                  45

His Val Tyr Ala Gln Ala Pro Phe Ala Gly Glu Ala Ile Asn Lys Asn
    50                  55                  60

Gly Leu Gln Ile Gly Thr Asn Gly Ala Ala Thr Glu Gly Asn Lys Glu
65                  70                  75                  80

Ile Tyr Ala Asp Lys Thr Tyr Gln Pro Glu Pro Gln Ile Gly Glu Ser
                85                  90                  95

Gln Trp Asn Glu Ala Glu Ser Ser Val Ala Gly Arg Val Leu Lys
            100                 105                 110

Lys Thr Thr Pro Met Lys Pro Cys Tyr Gly Ser Tyr Ala Arg Pro Thr
        115                 120                 125

Asn Ser Asn Gly Gly Gln Gly Val Met Val Glu Gln Asn Gly Lys Leu
    130                 135                 140

Glu Ser Gln Val Glu Met Gln Phe Phe Ser Thr Ser Val Asn Ala Met
145                 150                 155                 160

Asn Glu Ala Asn Ala Ile Gln Pro Lys Leu Val Leu Tyr Ser Glu Asp
                165                 170                 175

Val Asn Met Glu Thr Pro Asp Thr His Leu Ser Tyr Lys Pro Gly Lys
            180                 185                 190
```

```
Ser Asp Asp Asn Ser Lys Ala Met Leu Gly Gln Gln Ser Met Pro Asn
        195                 200                 205

Arg Pro Asn Tyr Ile Ala Phe Arg Asp Asn Phe Ile Gly Leu Met Tyr
210                 215                 220

Tyr Asn Ser Thr Gly Asn Met Gly Val Leu Ala Gly Gln Ala Ser Gln
225                 230                 235                 240

Leu Asn Ala Val Val Asp Leu Gln Asp Arg Asn Thr Glu Leu Ser Tyr
                245                 250                 255

Gln Leu Leu Leu Asp Ser Ile Gly Asp Arg Thr Arg Tyr Phe Ser Met
                260                 265                 270

Trp Asn Gln Ala Val Asp Ser Tyr Asp Pro Asp Val Arg Ile Ile Glu
        275                 280                 285

Asn His Gly Thr Glu Asp Glu Leu Pro Asn Tyr Cys Phe Pro Leu Gly
        290                 295                 300

Gly Ile Gly Val Thr Asp Thr Tyr Gln Ala Ile Lys Ala Thr Asn Gly
305                 310                 315                 320

Asn Gly Gly Ala Thr Thr Trp Ala Gln Asp Asn Thr Phe Ala Glu Arg
                325                 330                 335

Asn Glu Ile Gly Val Gly Asn Asn Phe Ala Met Glu Ile Asn Leu Asn
                340                 345                 350

Ala Asn Leu Trp Arg Asn Phe Leu Tyr Ser Asn Ile Ala Leu Tyr Leu
        355                 360                 365

Pro Asp Lys Leu Lys Tyr Asn Pro Thr Asn Val Glu Ile Ser Asp Asn
        370                 375                 380

Pro Asn Thr Tyr Asp Tyr Met Asn Lys Arg Val Val Ala Pro Gly Leu
385                 390                 395                 400

Val Asp Cys Tyr Ile Asn Leu Gly Ala Arg Trp Ser Leu Asp
                405                 410

<210> SEQ ID NO 74
<211> LENGTH: 348
<212> TYPE: PRT
<213> ORGANISM: Adenovirus type 1

<400> SEQUENCE: 74

Tyr Asn Ala Leu Ala Pro Lys Gly Ala Pro Asn Ser Cys Glu Trp Glu
1               5                   10                  15

Gln Glu Glu Pro Thr Gln Met Ala Glu Glu Leu Glu Asp Glu Glu Glu
                20                  25                  30

Glu Ala Glu Glu Glu Ala Glu Glu Ala Glu Ala Pro Gln Ala
            35                  40                  45

Asp Gln Lys Val Lys Lys Thr His Val Tyr Ala Gln Ala Pro Leu Ala
        50                  55                  60

Gly Glu Lys Ile Thr Ala Asn Gly Leu Gln Ile Val Ser Asp Thr Gln
65                  70                  75                  80

Thr Glu Gly Asn Pro Val Phe Ala Asp Pro Thr Tyr Gln Pro Glu Pro
                85                  90                  95

Gln Val Gly Glu Ser Gln Trp Asn Glu Ala Glu Ala Thr Ala Ser Gly
            100                 105                 110

Gly Arg Val Leu Lys Lys Thr Thr Pro Met Lys Pro Cys Tyr Gly Ser
        115                 120                 125

Tyr Ala Arg Pro Thr Asn Lys Asn Gly Gly Gln Gly Ile Leu Val Ala
        130                 135                 140

Asn Asn Gln Gly Ala Leu Glu Ser Lys Val Glu Met Gln Phe Phe Ala
```

-continued

```
            145                 150                 155                 160
        Pro Ser Gly Thr Ala Met Asn Glu Arg Asn Ala Val Gln Pro Ser Ile
                        165                 170                 175
        Val Leu Tyr Ser Glu Asp Val Asn Met Glu Thr Pro Asp Thr His Ile
                        180                 185                 190
        Ser Tyr Lys Pro Ser Lys Thr Asp Glu Asn Ser Lys Ala Met Leu Gly
                        195                 200                 205
        Gln Gln Ala Met Pro Asn Arg Pro Asn Tyr Ile Ala Phe Arg Asp Asn
                    210                 215                 220
        Phe Ile Gly Leu Met Tyr Tyr Asn Ser Thr Gly Asn Met Gly Val Leu
        225                 230                 235                 240
        Ala Gly Gln Ala Ser Gln Leu Asn Ala Val Val Asp Leu Gln Asp Arg
                        245                 250                 255
        Asn Thr Glu Leu Ser Tyr Gln Leu Leu Leu Asp Ser Ile Gly Asp Arg
                        260                 265                 270
        Thr Arg Tyr Phe Ser Met Trp Asn Gln Ala Val Asp Ser Tyr Asp Pro
                        275                 280                 285
        Asp Val Arg Ile Ile Glu Asn His Gly Thr Glu Asp Glu Leu Pro Asn
                    290                 295                 300
        Tyr Cys Phe Pro Leu Gly Gly Ile Gly Val Thr Asp Thr Tyr Gln Gly
        305                 310                 315                 320
        Ile Lys Ser Asn Gly Asn Gly Asn Pro Gln Asn Trp Thr Lys Asn Asp
                        325                 330                 335
        Asp Phe Ala Ala Arg Asn Glu Ile Gly Val Gly Asn
                        340                 345

<210> SEQ ID NO 75
<211> LENGTH: 352
<212> TYPE: PRT
<213> ORGANISM: Adenovirus type 2

<400> SEQUENCE: 75

Tyr Asn Ala Leu Ala Pro Lys Gly Ala Pro Asn Ser Cys Glu Trp Glu
        1               5                   10                  15
        Gln Thr Glu Asp Ser Gly Arg Ala Val Ala Glu Asp Glu Glu Glu
                    20                  25                  30
        Asp Glu Asp Glu Glu Glu Glu Glu Glu Gln Asn Ala Arg Asp Gln
                35                  40                  45
        Ala Thr Lys Lys Thr His Val Tyr Ala Gln Ala Pro Leu Ser Gly Glu
            50                  55                  60
        Thr Ile Thr Lys Ser Gly Leu Gln Ile Gly Ser Asp Asn Ala Glu Thr
        65                  70                  75                  80
        Gln Ala Lys Pro Val Tyr Ala Asp Pro Ser Tyr Gln Pro Glu Pro Gln
                        85                  90                  95
        Ile Gly Glu Ser Gln Trp Asn Glu Ala Asp Ala Asn Ala Ala Gly Gly
                    100                 105                 110
        Arg Val Leu Lys Lys Thr Thr Pro Met Lys Pro Cys Tyr Gly Ser Tyr
                115                 120                 125
        Ala Arg Pro Thr Asn Pro Phe Gly Gly Gln Ser Val Leu Val Pro Asp
                    130                 135                 140
        Glu Lys Gly Val Pro Leu Pro Lys Val Asp Leu Gln Phe Phe Ser Asn
        145                 150                 155                 160
        Thr Thr Ser Leu Asn Asp Arg Gln Gly Asn Ala Thr Lys Pro Lys Val
                        165                 170                 175
```

Val Leu Tyr Ser Glu Asp Val Asn Met Glu Thr Pro Asp Thr His Leu
            180                 185                 190

Ser Tyr Lys Pro Gly Lys Gly Asp Glu Asn Ser Lys Ala Met Leu Gly
        195                 200                 205

Gln Gln Ser Met Pro Asn Arg Pro Asn Tyr Ile Ala Phe Arg Asp Asn
    210                 215                 220

Phe Ile Gly Leu Met Tyr Tyr Asn Ser Thr Gly Asn Met Gly Val Leu
225                 230                 235                 240

Ala Gly Gln Ala Ser Gln Leu Asn Ala Val Val Asp Leu Gln Asp Arg
                245                 250                 255

Asn Thr Glu Leu Ser Tyr Gln Leu Leu Leu Asp Ser Ile Gly Asp Arg
            260                 265                 270

Thr Arg Tyr Phe Ser Met Trp Asn Gln Ala Val Asp Ser Tyr Asp Pro
        275                 280                 285

Asp Val Arg Ile Ile Glu Asn His Gly Thr Glu Asp Glu Leu Pro Asn
    290                 295                 300

Tyr Cys Phe Pro Leu Gly Gly Ile Gly Val Thr Asp Thr Tyr Gln Ala
305                 310                 315                 320

Ile Lys Ala Asn Gly Asn Gly Ser Gly Asp Asn Gly Asp Thr Thr Trp
                325                 330                 335

Thr Lys Asp Glu Thr Phe Ala Thr Arg Asn Glu Ile Gly Val Gly Asn
            340                 345                 350

<210> SEQ ID NO 76
<211> LENGTH: 336
<212> TYPE: PRT
<213> ORGANISM: Adenovirus type 5

<400> SEQUENCE: 76

Tyr Asn Ala Leu Ala Pro Lys Gly Ala Pro Asn Pro Cys Glu Trp Asp
1               5                   10                  15

Glu Ala Ala Thr Ala Leu Glu Ile Asn Leu Glu Glu Glu Asp Asp Asp
            20                  25                  30

Asn Glu Asp Glu Val Asp Glu Gln Ala Glu Gln Gln Lys Thr His Val
        35                  40                  45

Phe Ser Gln Ala Pro Tyr Ser Gly Ile Asn Ile Thr Lys Glu Gly Ile
    50                  55                  60

Gln Ile Gly Val Glu Gly Gln Thr Pro Lys Tyr Ala Asp Lys Thr Phe
65                  70                  75                  80

Gln Pro Glu Pro Gln Ile Gly Glu Ser Gln Trp Tyr Glu Thr Glu Ile
                85                  90                  95

Asn His Ala Ala Gly Arg Val Leu Lys Lys Thr Thr Pro Met Lys Pro
            100                 105                 110

Cys Tyr Gly Ser Tyr Ala Lys Pro Thr Asn Glu Asn Gly Gly Gln Gly
        115                 120                 125

Ile Leu Val Lys Gln Gln Asn Gly Lys Leu Glu Ser Gln Val Glu Met
    130                 135                 140

Gln Phe Phe Ser Thr Thr Glu Ala Thr Ala Gly Asn Gly Asp Asn Leu
145                 150                 155                 160

Thr Pro Lys Val Val Leu Tyr Ser Glu Asp Val Asp Ile Glu Thr Pro
                165                 170                 175

Asp Thr His Ile Ser Tyr Met Pro Thr Ile Lys Glu Gly Asn Ser Arg
            180                 185                 190

Glu Leu Met Gly Gln Gln Ser Met Pro Asn Arg Pro Asn Tyr Ile Ala
        195                 200                 205

```
Phe Arg Asp Asn Phe Ile Gly Leu Met Tyr Tyr Asn Ser Thr Gly Asn
            210                 215                 220
Met Gly Val Leu Ala Gly Gln Ala Ser Gln Leu Asn Ala Val Val Asp
225                 230                 235                 240
Leu Gln Asp Arg Asn Thr Glu Leu Ser Tyr Gln Leu Leu Asp Ser
            245                 250                 255
Ile Gly Asp Arg Thr Arg Tyr Phe Ser Met Trp Asn Gln Ala Val Asp
            260                 265                 270
Ser Tyr Asp Pro Asp Val Arg Ile Ile Glu Asn His Gly Thr Glu Asp
            275                 280                 285
Glu Leu Pro Asn Tyr Cys Phe Pro Leu Gly Gly Val Ile Asn Thr Glu
            290                 295                 300
Thr Leu Thr Lys Val Lys Pro Lys Thr Gly Gln Glu Asn Gly Trp Glu
305                 310                 315                 320
Lys Asp Ala Thr Glu Phe Ser Asp Lys Asn Glu Ile Arg Val Gly Asn
            325                 330                 335

<210> SEQ ID NO 77
<211> LENGTH: 347
<212> TYPE: PRT
<213> ORGANISM: Adenovirus type 6

<400> SEQUENCE: 77

Tyr Asn Ala Leu Ala Pro Lys Gly Ala Pro Asn Ser Cys Glu Trp Glu
1               5                   10                  15
Gln Asn Glu Thr Ala Gln Val Asp Ala Gln Glu Leu Asp Glu Glu Glu
            20                  25                  30
Asn Glu Ala Asn Glu Ala Gln Ala Arg Glu Gln Glu Gln Ala Lys Lys
        35                  40                  45
Thr His Val Tyr Ala Gln Ala Pro Leu Ser Gly Ile Lys Ile Thr Lys
    50                  55                  60
Glu Gly Leu Gln Ile Gly Thr Ala Asp Ala Thr Val Ala Gly Ala Gly
65                  70                  75                  80
Lys Glu Ile Phe Ala Asp Lys Thr Phe Gln Pro Glu Pro Gln Val Gly
                85                  90                  95
Glu Ser Gln Trp Asn Glu Ala Asp Ala Thr Ala Ala Gly Gly Arg Val
            100                 105                 110
Leu Lys Lys Thr Thr Pro Met Lys Pro Cys Tyr Gly Ser Tyr Ala Arg
        115                 120                 125
Pro Thr Asn Ser Asn Gly Gly Gln Gly Val Met Val Glu Gln Asn Gly
    130                 135                 140
Lys Leu Glu Ser Gln Val Glu Met Gln Phe Phe Ser Thr Ser Thr Asn
145                 150                 155                 160
Ala Thr Asn Glu Val Asn Asn Ile Gln Pro Thr Val Val Leu Tyr Ser
                165                 170                 175
Glu Asp Val Asn Met Glu Thr Pro Asp Thr His Leu Ser Tyr Lys Pro
            180                 185                 190
Lys Met Gly Asp Lys Asn Ala Lys Val Met Leu Gly Gln Gln Ala Met
        195                 200                 205
Pro Asn Arg Pro Asn Tyr Ile Ala Phe Arg Asp Asn Phe Ile Gly Leu
    210                 215                 220
Met Tyr Tyr Asn Ser Thr Gly Asn Met Gly Val Leu Ala Gly Gln Ala
225                 230                 235                 240
Ser Gln Leu Asn Ala Val Val Asp Leu Gln Asp Arg Asn Thr Glu Leu
```

```
                    245                 250                 255
Ser Tyr Gln Leu Leu Asp Ser Ile Gly Asp Arg Thr Arg Tyr Phe
            260                 265                 270

Ser Met Trp Asn Gln Ala Val Asp Ser Tyr Asp Pro Asp Val Arg Ile
        275                 280                 285

Ile Glu Asn His Gly Thr Glu Asp Glu Leu Pro Asn Tyr Cys Phe Pro
    290                 295                 300

Leu Gly Gly Ile Gly Ile Thr Asp Thr Phe Gln Ala Val Lys Thr Thr
305                 310                 315                 320

Ala Ala Asn Gly Asp Gln Gly Asn Thr Thr Trp Gln Lys Asp Ser Thr
                325                 330                 335

Phe Ala Glu Arg Asn Glu Ile Gly Val Gly Asn
            340                 345

<210> SEQ ID NO 78
<211> LENGTH: 343
<212> TYPE: PRT
<213> ORGANISM: Adenovirus type 57

<400> SEQUENCE: 78

Tyr Asn Ala Leu Ala Pro Lys Gly Ala Pro Asn Ser Cys Glu Trp Asp
1               5                   10                  15

Glu Asp Asp Thr Gln Val Gln Val Ala Ala Glu Asp Gln Asp Asp
            20                  25                  30

Asp Glu Glu Glu Gln Leu Pro Gln Gln Arg Asn Gly Lys Lys Thr
        35                  40                  45

His Val Tyr Ala Gln Ala Pro Phe Ala Gly Glu Ala Ile Asn Lys Asn
    50                  55                  60

Gly Leu Gln Ile Gly Thr Asn Gly Ala Ala Thr Glu Gly Asn Lys Glu
65                  70                  75                  80

Ile Tyr Ala Asp Lys Thr Tyr Gln Pro Glu Pro Gln Ile Gly Glu Ser
                85                  90                  95

Gln Trp Asn Glu Ala Glu Ser Ser Val Ala Gly Gly Arg Val Leu Lys
            100                 105                 110

Lys Thr Thr Pro Met Lys Pro Cys Tyr Gly Ser Tyr Ala Arg Pro Thr
        115                 120                 125

Asn Ser Asn Gly Gly Gln Gly Val Met Val Glu Gln Asn Gly Lys Leu
    130                 135                 140

Glu Ser Gln Val Glu Met Gln Phe Phe Ser Thr Ser Val Asn Ala Met
145                 150                 155                 160

Asn Glu Ala Asn Ala Ile Gln Pro Lys Leu Val Leu Tyr Ser Glu Asp
                165                 170                 175

Val Asn Met Glu Thr Pro Asp Thr His Leu Ser Tyr Lys Pro Gly Lys
            180                 185                 190

Ser Asp Asp Asn Ser Lys Ala Met Leu Gly Gln Gln Ser Met Pro Asn
        195                 200                 205

Arg Pro Asn Tyr Ile Ala Phe Arg Asp Asn Phe Ile Gly Leu Met Tyr
    210                 215                 220

Tyr Asn Ser Thr Gly Asn Met Gly Val Leu Ala Gly Gln Ala Ser Gln
225                 230                 235                 240

Leu Asn Ala Val Val Asp Leu Gln Asp Arg Asn Thr Glu Leu Ser Tyr
                245                 250                 255

Gln Leu Leu Leu Asp Ser Ile Gly Asp Arg Thr Arg Tyr Phe Ser Met
            260                 265                 270
```

-continued

```
Trp Asn Gln Ala Val Asp Ser Tyr Asp Pro Asp Val Arg Ile Ile Glu
        275                 280                 285

Asn His Gly Thr Glu Asp Glu Leu Pro Asn Tyr Cys Phe Pro Leu Gly
        290                 295                 300

Gly Ile Gly Val Thr Asp Thr Tyr Gln Ala Ile Lys Ala Thr Asn Gly
305                 310                 315                 320

Asn Gly Gly Ala Thr Thr Trp Ala Gln Asp Asn Thr Phe Ala Glu Arg
                325                 330                 335

Asn Glu Ile Gly Val Gly Asn
            340
```

ADENOVIRUSES AND METHODS FOR USING ADENOVIRUSES

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 65346 Bytes ASCII (Text) file named "SEQUENCE_LISTING.TXT," created on 21 Nov. 2019.

STATEMENT REGARDING PRIOR DISCLOSURES BY THE INVENTOR OR A JOINT INVENTOR QUALIFYING FOR THE GRACE PERIOD PROVIDED UNDER 35 USC § 102(b)(1)

The applicant submits that the following disclosures qualify under the grace period provided as noted above: Nguyen, et al., Oncolytic Virotherapy 8:43-51, May 3, 2018; Nguyen, et al., Virology 514:118-123, 15 Jan. 2018; Matchett, et al., J Virol., 93:1-18, May 1, 2019.

BACKGROUND OF THE INVENTION

Technical Field of the Invention

This invention relates to methods and materials for nucleic acid delivery, vaccination, and/or treating cancer. For example, the invention encompasses adenoviruses (Ads) and methods for using adenoviruses to treat medical conditions such as cancer. In an aspect of the invention, an adenovirus provided herein can be used as an oncolytic agent.

Despite vast efforts, cancer remains a major public health issue in the United States with over 1.6 million new cases in 2017 alone (National Cancer Institute, "Cancer Stat Facts: Cancer of Any Site," seer.cancer.gov/statfacts/html/all.html). Traditional therapies, such as chemotherapeutics, radiation therapy and surgery, often fail, especially when cancer is advanced. One of the reasons is for this that cancer cells can eliminate or modify the components that are targeted by these therapies and effectively avoid being killed.

Oncolytic virotherapy can provide an alternative approach to cancer treatment by utilizing selectively replicating viruses to destroy tumors, activate adaptive immune responses, and ensure a life-long immunity against the tumors (Russell et al., 2017 Molecular Therapy 25:1107-1116).

This invention provides methods and materials for nucleic acid delivery, vaccination, and/or treating cancer. For example, this invention provides methods and materials for treating cancer by administering one or more recombinant Ads (e.g., one or more of Ad657 and variants thereof) as an oncolytic agent. In an embodiment, a recombinant Ad can be derived from a first Ad (e.g., can include a genome of a first Ad, such as Ad6, also referred to as the recombinant Ad backbone) and can include hexon HVRs from a second Ad such as Ad57. In cases where a recombinant Ad includes an Ad6 genome and Ad57 hexon HVRs, the recombinant Ad can be a chimeric Ad referred to as Ad657. (See Nguyen, et al. Oncolytic Virotherapy 7:43-51, 2018, the disclosure of which is incorporated by reference).

In an aspect, this invention provides methods for vaccinating against infectious disease using one or more recombinant Ads (e.g., one or more of Ad657 and variants thereof). In an aspect, this invention provides methods for treating cancer using one or more recombinant Ads (e.g., one or more of Ad657 and variants thereof) as an oncolytic agent. In some cases, one or more recombinant Ads (e.g., one or more Ad657s) can be used to reduce the number of cancer cells (e.g., by infecting and killing cancer cells) in a mammal. In some cases, one or more recombinant Ads (e.g., one or more of Ad657 and variants thereof) can be used to stimulate anti-cancer immune responses in a mammal. In some cases, one or more recombinant Ads (e.g., one or more of Ad657 and variants thereof) can be used to stimulate immune responses against infectious diseases in a mammal.

As demonstrated herein, when Ad657 is delivered by intravenous injection to mice having subcutaneous human DU145 prostate cancer tumors, Ad657 first infects the liver and then reaches distant tumors. Both Ad6 and Ad657 mediated significant delays in tumor growth and extension of survival with Ad6 mediating higher efficacy.

This invention provides methods and materials for nucleic acid delivery, vaccination, and/or treating cancer. For example, this invention provides methods and materials for treating cancer by administering one or more recombinant Ads (e.g., one or more of Ad657 and variants thereof) as an oncolytic agent. In an embodiment, a recombinant Ad can be derived from a first Ad (e.g., can include a genome of a first Ad, such as Ad6, also referred to as the recombinant Ad backbone) and can include hexon HVRs from a second Ad such as Ad57. In cases where a recombinant Ad includes an Ad6 genome and Ad57 hexon HVRs, the recombinant Ad can be a chimeric Ad referred to as Ad657. In an aspect, this invention provides methods for vaccinating against infectious disease using one or more recombinant Ads (e.g., one or more of Ad657 and variants thereof). In an aspect, this invention provides methods for treating cancer using one or more recombinant Ads (e.g., one or more of Ad657 and variants thereof) as an oncolytic agent. In some cases, one or more recombinant Ads (e.g., one or more Ad657s) can be used to reduce the number of cancer cells (e.g., by infecting and killing cancer cells) in a mammal. In some cases, one or more recombinant Ads (e.g., one or more of Ad657 and variants thereof) can be used to stimulate anti-cancer immune responses in a mammal. In some cases, one or more recombinant Ads (e.g., one or more of Ad657 and variants thereof) can be used to stimulate immune responses against infectious diseases in a mammal.

As demonstrated herein, when Ad657 is delivered by intravenous injection to mice having subcutaneous human DU145 prostate cancer tumors, Ad657 first infects the liver and then reaches distant tumors. Both Ad6 and Ad657 mediated significant delays in tumor growth and extension of survival with Ad6 mediating higher efficacy.

Moreover, liver sequestration is a considerable problem for virtually any oncolytic virus if it is used as an intravenous systemic therapy. If the virus infects hepatocytes and kills them, this will result in liver damage at low doses and death at higher doses. Notably, administration of the Ads of the invention, i.e., Ad657 chimeric vector and variants thereof, mediated unexpected lower liver damage than either Ad5 or Ad6. Thus the unique combination of Ad6 platform with the HVRs 1-7 of Ad657 mediated changes in biodistribution and therapy not observed in natural viruses.

Also, as demonstrated herein, immunization of rhesus macaques with replicating single-cycle adenovirus (SC-Ad657) vaccines expressing only Glade B HIV-1 gp160 by intranasal (IN) and intramuscular (IM) routes was compared to mucosal and systemic routes of vaccination. SC-Ad vaccines by themselves generated significant circulating antibody titers against Env after only a single immunization. Animals immunized only by the IM route had high peripheral T follicular helper (pTfh) cells in blood, but low Tfh in lymph nodes, and had lower antibody-dependent cellular cytotoxicity (ADCC) antibody activity. Animals immunized by the IN route had high Tfh in lymph nodes, but low pTfh in the blood, and had higher ADCC antibodies. When immunized animals were challenged rectally with $SHIV_{SF162P3}$, they all became infected, but mucosally-primed animals had markedly lower viral loads their gastrointestinal tracts. Similarly, Ad657 carrying genes for hepatitis C antigens is able to generate cytotoxic T lymphocyte (CTL) responses against hepatitis and cytomegalovirus. Ad657 is able to delivery and express therapeutic genes including cytokines like 4-1BBL, granulocyte macrophage stimulating factor (GMCSF), and IL-21. The results provided herein demonstrate that recombinant Ads can be used as a local or systemic delivery vehicle for nucleic acid, vaccines, and/or oncolytic virotherapy for cancers.

BRIEF SUMMARY OF THE INVENTION

In general, one aspect of this invention features recombinant Ad comprising (a) an Ad genome from a first Ad strain and (b) a nucleic acid encoding a hexon polypeptide from a second Ad strain, where one or more of the hypervariable regions the hypervariable regions (HVRs) of the hexon polypeptide are different from the HVRs encoded by the Ad genome. The first Ad strain can be a first human Ad strain, and the second Ad strain can be a second human Ad strain which is different from the first human Ad strain. The first Ad strain and the second Ad strain can be serotypically distinct. The first Ad strain can be a human Ad6 strain, and the second Ad strain can be a human Ad57 strain. The recombinant Ad also can include one or more targeting polypeptides, antigenic polypeptides, enzymes, amino acid substitutions, PEGylation, ligands, tags and the like.

A recombinant Ad may be used as a vector for gene-based vaccination, for gene therapy application/delivery, or for oncolytic virotherapy.

In a further embodiment, the recombinant Ad comprises (a) an Ad genome from a first Ad strain and (b) a nucleic acid encoding at least one hexon polypeptide from one or more Ad strains, where the hypervariable regions (HVRs) of the hexon polypeptide from the one or more Ad strains are different from the HVRs encoded by the first Ad genome.

In a further embodiment, the recombinant Ad can be a replication competent or conditionally-replicating Ad (e.g., a CRAd).

In another aspect, this invention features a recombinant and/or chimeric Ad comprising (a) nucleic acid encoding a first hexon polypeptide and (b) a second hexon polypeptide, where the amino acid sequence of the first hexon polypeptide is different from the amino acid sequence of the second hexon polypeptide. The amino acid sequence of a hypervariable region (HVR) of the first hexon polypeptide can be different from the amino acid sequence of a hypervariable region of the second hexon polypeptide. The nucleic acid can be from a first Ad strain, and the second hexon polypeptide can be from a second Ad strain. The first Ad strain can be a first human Ad strain, and the second Ad strain can be a second human Ad strain different from the first human Ad strain. The first Ad strain and the second Ad strain can be serotypically distinct. The Ad strain can be a human Ad6 strain, and the second Ad strain can be a human Ad57 strain. The recombinant Ad also can include a targeting polypeptide. The targeting polypeptide can include the amino acid sequence TARGEHKEEELI (SEQ ID NO:1).

In a further embodiment, the recombinant Ad comprises a) nucleic acid encoding a first hexon polypeptide and (b) a second hexon polypeptide from one or more Ad strains, where the amino acid sequence of the first hexon polypeptide is different from the amino acid sequence of the second hexon polypeptide from the one or more Ad strains.

In a further embodiment, the recombinant Ad can be a replication competent Ad or conditionally-replicating Ad (e.g., a CRAd).

In another aspect, the invention provides materials and methods for treating a mammal having cancer. The methods can include, or consist essentially of, administering to a mammal having cancer, a recombinant Ad comprising (a) an Ad genome from a first Ad strain and (b) at least one hexon polypeptide from a one or more Ad strains, where one or more of the hypervariable regions (HVRs) of the hexon polypeptide are different from the HVRs encoded by the Ad genome and/or an Ad comprising (a) nucleic acid encoding a first hexon polypeptide and (b) a second hexon polypeptide, where the amino acid sequence of the first hexon polypeptide is different from the amino acid sequence of the second hexon polypeptide. The mammal can be a human The cancer can be prostate cancer, ovarian cancer, lung cancer, hepatocellular carcinoma, pancreatic cancer, kidney cancer, melanoma, brain cancer, colon cancer, lymphoma, myeloma, lymphocytic leukemia, or myelogenous leukemia. The administering can include systemic or local administration (e.g. intravenous, intratumoral, intramuscular, intraorgan, intralymph node administration).

It is demonstrated herein that Ad657 and variants thereof are able to deliver therapeutic genes to cells for expression of therapeutic polypeptides. Thus, recombinant Ads, including chimeric Ads, can be used as a local or systemic delivery vehicle for nucleic acid, vaccines, and/or oncolytic virotherapy for cancers.

An aspect of the invention relates to recombinant adenovirus (Ad) comprising (a) an Ad genome encoding hexon polypeptides from a first Ad strain and (b) a nucleic acid encoding at least one hexon polypeptide from one or more different Ad strains, wherein at least one hypervariable region (HVR) of the hexon polypeptide is different from the HVRs encoded by the Ad genome of the first Ad strain.

A further aspect of the invention relates to such a recombinant Ad, wherein the first Ad strain and the one or more different Ad strains are serotypically distinct.

A further aspect of the invention relates to such a recombinant Ad, wherein the first Ad strain is a human Ad6 strain, and wherein a second Ad strain is a human Ad57 strain.

A further aspect of the invention relates to such a recombinant Ad further comprising a nucleic acid encoding a targeting polypeptide, antigen, enzyme, receptor, ligand or tag.

A further aspect of the invention relates to such a recombinant Ad, wherein the targeting polypeptide comprises an amino acid sequence selected from SEQ ID NO: 1-41 and SEQ ID NO:46-47.

A further aspect of the invention relates to such a recombinant Ad, wherein said recombinant Ad is a replication competent Ad.

A further aspect of the invention relates to such a recombinant Ad, wherein the replication competent Ad is a single-cycle Ad or conditionally-replicating Ad (CRAd).

A further aspect of the invention relates to such a recombinant adenovirus (Ad) comprising (a) Ad capsid polypeptides from a first Ad strain and (b) at least one hexon polypeptide from one or more different Ad strains, wherein hypervariable regions (HVRs) of the hexon polypeptide or capsid polypeptides are different from the HVRs or capsid polypeptides of the first Ad strain.

A further aspect of the invention relates to such a recombinant adenovirus (Ad) comprising (a) a nucleic acid encoding a first hexon polypeptide and (b) a nucleic acid encoding a second hexon polypeptide, wherein the amino acid sequence of the first hexon polypeptide is different from the amino acid sequence of the second hexon polypeptide.

A further aspect of the invention relates to such a recombinant Ad, wherein the nucleic acid encoding at least one hexon polypeptide is different from the amino acid sequence of a hypervariable region of said second hexon polypeptide.

A further aspect of the invention relates to such a recombinant Ad, wherein said nucleic acid is from a first Ad strain, and wherein said second hexon polypeptide is from a second Ad strain.

A further aspect of the invention relates to such a recombinant Ad, wherein said first Ad strain is a first human Ad strain, and wherein said second Ad strain is a second human Ad strain different from said first human Ad strain.

A further aspect of the invention relates to such a recombinant Ad, wherein said first Ad strain and said second Ad strain are serotypically distinct.

A further aspect of the invention relates to such a recombinant Ad, wherein said first Ad strain is a human Ad6 strain, and wherein said second Ad strain is a human Ad57 strain.

A further aspect of the invention relates to such a recombinant Ad, further comprising a targeting polypeptide.

A further aspect of the invention relates to such a recombinant Ad, wherein said targeting polypeptide comprises an amino acid sequence TARGEHKEEELI (SEQ ID NO:1).

A further aspect of the invention relates to such a recombinant Ad, wherein said recombinant Ad is a replication competent Ad.

A further aspect of the invention relates to such a recombinant Ad, wherein said replication competent Ad is a single-cycle Ad or conditionally-replicating Ad (CRAd).

A further aspect of the invention relates to a method for treating a mammal having cancer, wherein said method comprises administering, to said mammal, a recombinant adenovirus (Ad) as described herein.

A further aspect of the invention relates to such a method, wherein said cancer is selected from the group consisting of prostate cancer, ovarian cancer, lung cancer, hepatocellular carcinoma, pancreatic cancer, kidney cancer, melanoma, brain cancer, colon cancer, lymphoma, myeloma, lymphocytic leukemia, and myelogenous leukemia.

A further aspect of the invention relates to such a method, wherein said administering comprises systemic administration.

A further aspect of the invention relates to such a method, wherein in systemic administration comprises intramuscular, intranasal, or intravenous administration.

A further aspect of the invention relates to such a method, wherein said administering comprises local administration.

A further aspect of the invention relates to such a method, wherein said local administration comprises intratumoral injection.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1 shows a translation of context-specific peptides from phage to adenovirus. A) Diagram of a phage display library containing the Ad5 fiber HI β sheets that structurally constrain a random 12-mer peptide library. Shown below is a depiction of the structurally similar site between the β7 and β8 sheets in the Ad5 HVR5 hexon. B) Primary amino acid alignments of 12.51 and 12.52 in the HI library and their location when inserted into HVR5 of hexon. C) Representation of Ad5 GFP-Luc expressing viruses modified with the peptides.

FIG. 15 shows plasma HIV neutralization titers. Neutralization of the indicated viruses was performed using the TZM-bl neutralization assay. All values were calculated as compared to virus-only wells. Each dot represents the mean value for each animal.

FIG. 21 shows protection against repeated rectal SHIV$_{SF162P3}$ challenge. The indicated groups were challenged rectally with 4.3 TCID50 (on rhesus PBMCs) of SHIVSF162P3 on a weekly basis. Plasma samples were analyzed for SHIV viral RNA copies. Animals with RNA copies above 10 were considered infected and the number of challenges required to infect that animal were used as events for Kaplan-Meier survival analysis.

FIG. 22 shows SHIV$_{SF162P3}$ acquisition and viral loads. A) Animals from FIG. 8 were grouped by their initial SC-Ad priming route (IM or IN) yielding groups of 8 and Kaplan-Meier analysis was performed. B) Plasma SHIVSF162P3 viral RNA levels over the course of the challenge study.

FIG. 25 shows saliva and vaginal HIV env binding titrations. ELISA OD450 levels are shown for the indicated samples at the indicated dilutions when tested against F8. The low level of antibodies in these mucosal samples prevent reaching saturation of the assay. For this reason, EC50 values cannot be reliably calculated for most animals. Rhesus macaque Rh13-091 in the IN-IM-IM group was the only animal in which an EC50 could be calculated (EC50=4580). Similar results were observed in ELISAs using SF162 gp140.

FIG. 36 shows conjugation of polyethylene glycol (PEG) to Ad657-HVR1-C. A) SDS-PAGE of Ad proteins with and without PEGylation. Arrows show size increases due to chemical modification of PEG to hexon. B) Effects of targeted PEGylation by maleimide-PEG and non-targeting NHS-PEG on virus infection.

FIG. 37 shows conjugation of polyethylene glycol (PEG) to Ad657-HVR5-C. A) SDS-PAGE of Ad proteins with and without PEGylation. B) Near infrared imaging of SDS-PAGE of Ad proteins with and without PEGylation and with and without the near infrared fluorescence imaging tag IR800. C) In vivo transduction after intraperitoneal injection of maleimide-PEGylated Ad657-HVR5-C by luciferase imaging.

FIG. 43 is a schematic of a replication competent Ad (RC-Ad), wherein E1 expression is controlled by the native E1 promoter; a variant CRAd—Probasin-E1A (Ad-PB), wherein E1 expression is controlled by prostate-specific probasin promoter; CRAd-dl1101, wherein p300 pathway binding ablated, susceptible to IFN pathway in normal cells; CRAd-dl1107, wherein pRB binding ablated allows virus to kill cancer cells with RB pathway disruptions, but is repressed in RB+ normal cells; CRAd-dl1101/07, wherein p300 pathway binding ablated, susceptible to IFN pathway pRB binding ablated allows virus to kill cancer cells with RB pathway disruptions, but is repressed in RB+ normal cells.

FIG. 44 (A and B) shows the effect of infection with replication-competent Ad5, Ad6, Ad657 on non-cancerous cells and modification of Ad6 and Ad657 to be conditionally-replicating Ads (CRAds).

FIG. 45 demonstrates killing of cancerous cells by replication-competent Ad5, Ad6, Ad657, and the indicated CRAds.

FIG. 56 shows amino acid sequences of the N-terminal portion of the wild-type E1A polypeptide and the E1A N-terminus of the CRAd variants, dl1101, dl1107 and dl1101/1107.

DETAILED DESCRIPTION OF THE INVENTION

Figure 2:
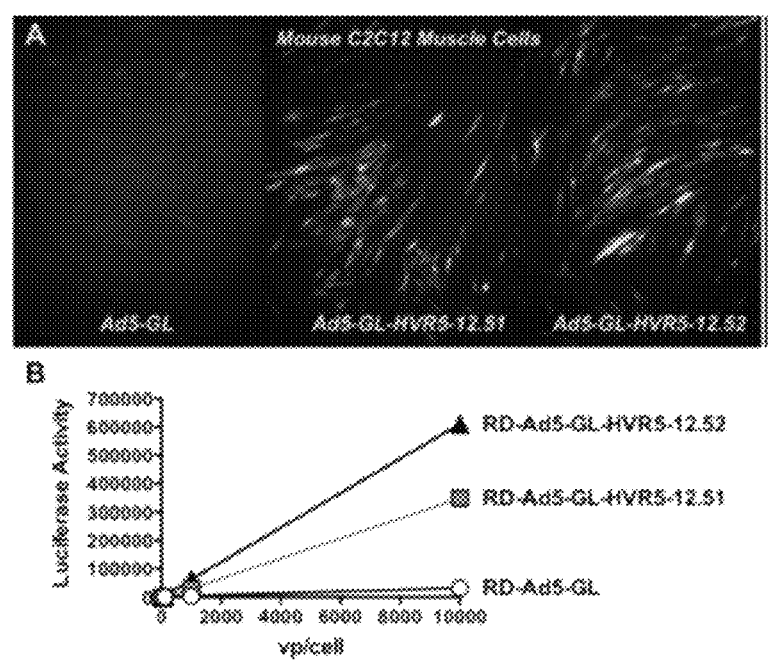
FIG. 2 shows in vitro transduction A) GFP expression by fluorescent microscopy of C2C12 cells infected with $10^4$ vp/cell of the indicated vectors 2 days after infection. B) Luciferase activity from C2C12 cells 2 days after infection with varied MOIs of the indicated Ads.

This invention provides methods and materials for nucleic acid delivery, vaccination, and/or treating cancer. For example, this invention provides methods and materials for nucleic acid delivery of proteins/polypeptides, vaccination, and/or treating cancer using one or more recombinant Ads (e.g., Ad657 and variants thereof) as an oncolytic agent.

An adenovirus icosahedron is made up of 720 copies of its hexon protein. The virus does not use this protein to bind receptors, but this nano-lattice of repeating proteins provides a matrix for interactions (e.g., natural interactions and unnatural interactions) with proteins, cells, and drugs. Antibodies that can neutralize Ads can target hypervariable regions (HVRs) of the hexon polypeptide on an Ads.

In some cases, this invention provides recombinant Ads having oncolytic anti-cancer activity. For example, a recombinant Ad can be derived from a first Ad and can include hexon HVRs from one or more different Ads. The HVRs may be derived from any species C Ads, for example Ad1, Ad2, Ad5, Ad6 and Ad57. In an embodiment, a recombinant Ad can be derived from a first Ad and can include one or more hexon HVRs from at least one other Ad, wherein at least one hexon HVR is different from the HVR(s) of the first Ad. The first Ad strain can be a human Ad6 strain, and the second Ad strain can be a human Ad57 strain. Hexon shuttle plasmid maps (FIG. 34) show the combination of the insertion of individual HVRs from different Ad serotypes with the insertion of cell targeting/detargeting peptides or novel amino acids such as cysteine into the hexon for targeted chemical modification and shielding. In an embodiment, the recombinant Ads comprise amino acid substitutions, for example, substitution of cysteines into polypeptides, and modifications such as PEGylation and BAPylation. The ability to target polymer and other chemical modifications to cysteines inserted in Ad657 hexon is demonstrated herein.

Ad657 as an oncolytic against human prostate cancer is demonstrated. The Ad6 HVRs were replaced with those from Ad57 to generate a chimeric species C oncolytic virus called Ad657. Ad657 and Ad6 were tested as systemic oncolytic therapies by single i.v. injection in nude mice bearing human cancerous tumors. Ad657 may be used as a local or systemic oncolytic virotherapy for cancers. These data also demonstrate surprising effects of serotype-switching with oncolytic species C Ads.

In some cases, this invention provides methods for using one or more recombinant Ads provided herein to treat a mammal having, or at risk of having, cancer, an infectious disease, and/or a genetic disease. For example, one or more recombinant Ads can be administered to a mammal having, or at risk of having, cancer to reduce the number of cancer cells (e.g., by infecting and killing cancer cells) in the mammal (e.g., a human) For example, one or more recombinant Ads can be administered to a mammal having, or at risk of having, cancer to stimulate anti-cancer immune responses in the mammal (e.g., a human).

In some cases, recombinant Ads described herein (e.g., recombinant Ads having oncolytic anti-cancer activity such as recombinant Ad657 and variants thereof) are not destroyed by a mammal's immune system. For example, a recombinant Ad is not destroyed by antigen presenting cells (APCs), macrophages, and/or other immune cells in a mammal that the recombinant Ad is administered to.

In some cases, recombinant Ads described herein (e.g., recombinant Ads having oncolytic anti-cancer activity such as recombinant Ad657 and variants thereof) can be administered for multiple (e.g., two or more) rounds of treatment. For example, a first recombinant Ad described herein can avoid antibodies that can neutralize a second recombinant Ad described herein, and vice versa. In cases where a mammal having cancer is treated with one or more recombinant Ads described herein, the mammal can be administered a first round of treatment with a first recombinant Ad and can subsequently be administered a second round of treatment with a second recombinant Ad.

In some cases, recombinant Ads described herein (e.g., recombinant Ads having oncolytic anti-cancer activity such as recombinant Ad657 and variants thereof) can be replication competent Ads (RC-Ads). For example, a RC-Ad can be a RC-Ad that includes a nucleic acid encoding an E1 polypeptide (e.g., an E1+RC-Ad). For example, a RC-Ad can be a single-cycle Ad (SC-Ad) that includes a deletion of one or more nucleic acids encoding one or more polypeptides associated with the production of infectious viral progeny (e.g., pIIIa and E3). For example, a RC-Ad can be a conditionally-replicating Ad (CRAd). Examples of single-cycle Ads and how to make and use them are provided elsewhere (International Patent Application Publication No. WO2009/111738).

In some cases, recombinant Ads described herein (e.g., recombinant Ads having oncolytic anti-cancer activity such as recombinant Ad657 and variants thereof) can be replication defective Ads (RD-Ads). For example, a RD-Ad can be a RD-Ad that includes a deletion of a nucleic acid encoding an E1 polypeptide (e.g., an E1-deleted RD-Ad).

It is demonstrated in the examples herein that CRAd 657 and variants thereof are conditionally-replicating Ads (CRAds) in cancerous cells and that infection of cells with CRAd 657 and variants thereof reduces cell viability and tumor volume. Thus, CRAd 657 and variants thereof may be used as a local or systemic oncolytic virotherapy in subjects with cancer.

What is more, it is demonstrated that CRAds can be used for expression of antigens and used as a vaccine for vaccinating against viruses, for example, against Human Immunodeficiency Virus (HIV), Human Papilloma Virus (HPV) and Hepatitis C Virus (HCV).

In some cases, recombinant Ads described herein (e.g., recombinant Ads having oncolytic anti-cancer activity such as recombinant Ad657 and variants thereof) can bind to a cell surface receptor (e.g., to facilitate viral entry to a cell). For example, a recombinant Ad described herein can bind to coxsackie-adenovirus receptors (CARs) and/or Fc receptors (e.g., FcµR and FcγR), complement receptors (e.g., CR3 and/or C2qR).

In an aspect of the invention, CRAds may comprise nucleic acids encoding polypeptides heterologous to the Ad, for example, antigens, cell surface receptors, cell targeting polypeptides and the like. For example, CRAd-657-dl1101/1107-FoIR is a recombinant Ad comprising intact E3 and expressing the human folate receptor alpha. It is demonstrated herein that CRAds may be used to generate antibodies against known cancer antigens, for example, folate receptor alpha.

In some cases, recombinant Ads described herein (e.g., recombinant Ads having oncolytic anti-cancer activity such as recombinant Ad657s) can avoid binding (e.g., do not bind) to a scavenger receptor (e.g., to facilitate viral entry to a cell). For example, a recombinant Ad described herein avoid binding to a SREC receptors and/or SR-A receptors.

In some cases, recombinant Ads described herein (e.g., recombinant Ads having oncolytic anti-cancer activity such as recombinant Ad657s) can avoid phagocytosis.

In some cases, recombinant Ads described herein (e.g., recombinant Ads having oncolytic anti-cancer activity such as recombinant Ad657s) are non-pathogenic (e.g., to a mammal being treated as described herein).

In some cases, recombinant Ads described herein (e.g., recombinant Ads having oncolytic anti-cancer activity such as recombinant Ad657s) can infect dividing cells (e.g., can infect only dividing cells).

A recombinant Ad described herein can be any appropriate recombinant Ad (e.g., a recombinant Ad having oncolytic anti-cancer activity) generated by recombinant DNA technology and methods known to those skilled in the art. A recombinant Ad can be any Ad generated by recombining material (e.g., nucleic acid and/or polypeptide) from any organism other than the Ad from which the recombinant Ad is derived. For example, a recombinant Ad can include one or more materials that do not naturally occur in that Ad (e.g., do no naturally occur in that Ad prior to recombination). In some cases, a recombinant Ad provided herein can be a chimeric Ad (e.g., can include viral elements from two or more (e.g., two, three, four, five, or more) different Ad genomes).

These embodiments have been applied also in the context of Ads which combine different HVRs from different Ads (i.e., shuffling HVRs). For example, HVR1 of Ad6 with HVRs 2-7 of Ad57 or HVR1 and 7 of Ad6 with HVRs 2-6 of Ad57, or HVRs 1 and 7 from Ad6 and HVRs 2-6 from Ad657.

Nucleic acid and/or polypeptides that do not naturally occur in the Ad can be from any appropriate source. In some cases, a nucleic acid and/or a polypeptide that does not naturally occur in that Ad can be from a non-viral organism. In some cases, a nucleic acid and/or a polypeptide that does not naturally occur in that Ad can be from a virus other than an Ad. In some cases, a nucleic acid and/or a polypeptide that does not naturally occur in that Ad can be from an Ad obtained from a different species. In some cases, a nucleic acid and/or a polypeptide that does not naturally occur in that Ad can be from a different strain of Ad (e.g., serotypically distinct strains). In some cases, a nucleic acid and/or a polypeptide that does not naturally occur in that Ad can be a synthetic nucleic acid and/or a synthetic polypeptide.

A recombinant Ad described herein (e.g., a recombinant Ad having oncolytic anti-cancer activity such as a recombinant Ad657) can be derived from (e.g., can include a genomic backbone from) any appropriate Ad. In some cases, a recombinant Ad described herein can be derived from an Ad having low seroprevalence. For example, 50% or fewer (e.g., 50%, 45%, 40%, 35%, 30%, 25%, 20%, 15%, 10%, 5%, or fewer) of mammals (e.g., human) can have been exposed to an Ad from which a recombinant Ad described herein is derived. With regard to seroprevalence, species C adenoviruses, Ad6 and Ad657 have lower prevalence than archetype Ad5 virus. In some cases, a recombinant Ad described herein can be derived from an Ad having reduced or eliminated side effects (e.g., phagocytosis and liver damage). A recombinant Ad can be derived from an Ad isolated from any appropriate species of animal. For example, Ads can be isolated from humans, non-human primates (e.g., monkeys such as Old World monkey species like rhesus macaques), fish, frogs, and snakes. In some cases, a recombinant Ad described herein can be derived from a human Ad (HAd or HAdV). A recombinant Ad can be derived from any species of Ad (e.g., A, B, C, D, E, F, or G). In some cases, a recombinant Ad described herein can be derived from an Ad C species (e.g., a human Ad C species (HAd-C)). A recombinant Ad can be derived from any appropriate Ad serotype (e.g., 2, 5, 6, or 57). In some cases, a recombinant Ad described herein can be derived from an Ad serotype 6 (Ad6; e.g., a human Ad6).

In some cases, a recombinant Ad described herein (e.g., a recombinant Ad having oncolytic anti-cancer activity such as a recombinant Ad657 and variants thereof) can include an Ad genome containing one or more modifications to one or more nucleic acids encoding a polypeptide (or fragments thereof) and/or one or more viral elements of the Ad genome. The one or more modifications can be any appropriate modification. In some cases, a modification can be effective to inhibit the ability of the modified polypeptide to bind another polypeptide such as p300 and/or pRB. In some cases, a modification can be effective to neutralize one or more interferon pathways. Examples of modifications that can be made to a nucleic acid encoding a polypeptide or to a viral element include, without limitation, substitutions, deletions, insertions, and mutations.

Ads, for example Ad657 and variants thereof, may be modified and retain all E1A genes, or modified to delete selected regions and functions of their encoded proteins.

Figure 57:
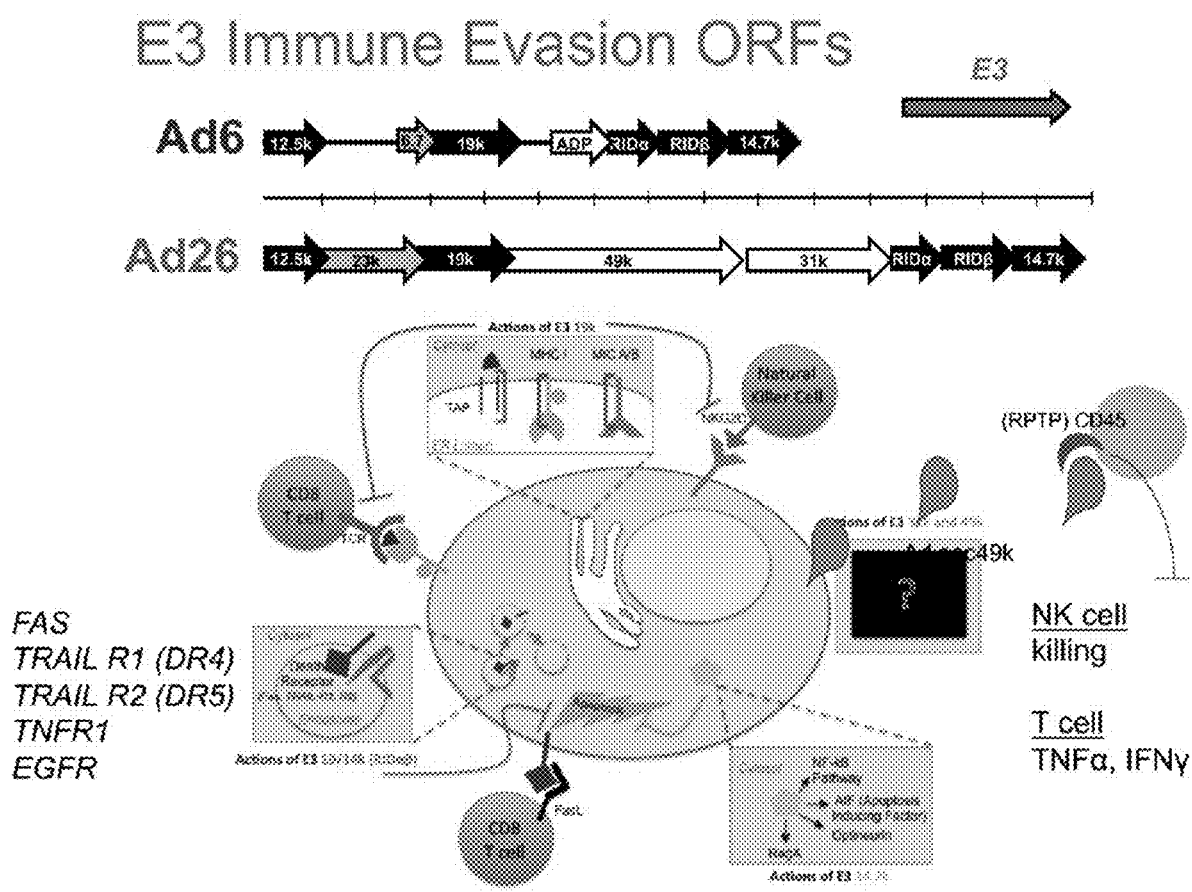
FIG. 57 shows as schematic of different E3 immune evasion genes in Ad species C exemplar Ad6 and Ad species D exemplar Ad26. Both Ads express size and sequence variants of E3 12.5K, 6.7K, 19K, 10.4K (RIDα), 14.5K (RIDβ), and 14.7K genes, as well as a depiction of the functions of these E3 encoded proteins.

FIG. 57 shows as schematic of different E3 immune evasion genes in Ad species C exemplar Ad6 and Ad species D exemplar Ad26, as well as a depiction of the functions of these E3 encoded proteins. Both Ads express size and sequence variants of E3 12.5K, 6.7K, 19K, 10.4K (RIDα), 14.5K (RIDβ), and 14.7K genes. 19K reduces display of MHC I and MIC proteins on the cell surface to protect infected cells from T cells and NK cells. RID proteins protect infected cells from death-inducing ligands (FAS, TRAIL, TNFR, and EGFR). 14.7K inhibits intrinsic activation of apoptosis in infected cells. Species C Ads also express the 11.6K known as the adenovirus death protein (ADP). Over-expression of ADP accelerates cell death, but overall cell death is equal. Species D viruses also express two novel variants called 49K and 31K. The secreted form of 49K binds to CD46 on T cells and NK cells leading to down-regulation of these cells and less-efficient cell killing of cells deficient in class I MHC by NK cells. Ad657 plasmids have been modified to retain all native E3 immune evasion genes (12.5K, 6.7K, 19K, 11.6K (ADP), 10.4K (RIDα), 14.5K (RIDβ), and 14.7K) and E4 34K or to delete selected regions. Ad657 and its variants are also modified with the addition of 49K and 31K to provide these extra functions to these species C viral platforms.

Ads, for example Ad657 and variants thereof, may be modified to retain all E3 immune evasion genes, or to delete selected regions and functions of their encoded proteins. With respect to E3 mutations: 19k downregulates MHCI and MIC proteins on infected cells; ADP over expression accelerates cell death, but does not increase the number of cells that are killed; 10k and 14k proteins (RIDα and RIDβ) combine to block cell killing by extrinsic apoptosis proteins like FAS, TRAIL, TNF, TNFR, and EGFR; 14.7k protein inhibits intrinsic apoptosis signaling.

Retaining these E3 proteins may allow oncolytic to persist longer, and deleting them may increase immune stimulation.

Data testing oncolytic efficacy suggests intact E3 mediates better efficacy.

DE3 constructs have deleted part of 12.5k through and including 14.7k, DE3A constructs have deleted part of E3 12.5k through and including 19k, and DE3ADP constructs have deleted part of E3 12.5k through and including ADP.

Surprisingly, deleting all E3 genes makes the oncolytic virus less effective in repressing tumor growth.

In an embodiment, the invention encompasses single-cycle adenovirus, for example SC-Ad657 and variants thereof. Recombinant SC-Ad viruses with heterologous nucleic acids encoding polypeptides were evaluated for use as a vaccine. SC-Ad657 vaccines by themselves generated significant circulating antibody titers against an HIV envelope protein after only a single immunization.

Similarly, Ad657 carrying genes for hepatitis B and C antigens is able to generate cytotoxic T lymphocyte (CTL) responses against hepatitis and cytomegalovirus.

Ad657 was modified by insertion of synthetic peptides from human papilloma virus into HVR5. In an embodiment, the amino acid sequence of the variant Ad657-HVR5-HPV hexon is defined in SEQ ID NO:57. The modification allows display of this antigen for vaccine purposes as well as retargeting by binding to proteins that interact with HPV peptides.

In a further embodiment, expression of Human Granulocyte-Macrophage Colony Stimulating Factor (GMCSF) by Ad657 is demonstrated herein.

Thus, from the examples herein, it is demonstrated that recombinant Ads, for example Ad657 and variants thereof, may be utilized for expression of heterologous proteins, for example, polypeptide antigens and cell targeting polypeptides.

In some cases, a recombinant Ad described herein (e.g., a recombinant Ad having oncolytic anti-cancer activity such as a recombinant Ad657) can include an Ad genome containing one or more substitutions. For example, one or more nucleic acids encoding a polypeptide (or fragments thereof) and/or one or more viral elements encoded by the Ad genome can be substituted. A substitution can be any appropriate substitution. In some cases, one or more nucleic acids encoding a capsid polypeptide of a genome of a first Ad can be substituted with one or more nucleic acids encoding a capsid polypeptide of a second Ad to generate a chimeric Ad. For example, when a recombinant Ad includes a genome from a first Ad where a nucleic acid encoding a capsid polypeptide in the genome is substituted for a nucleic acid encoding a capsid polypeptide from a second Ad (e.g., an Ad different from the Ad backbone), the nucleic acid encoding a capsid polypeptide form the second Ad can express one or more capsid polypeptides, and the expressed capsid polypeptide(s) can be incorporated into the capsid of the recombinant Ad. Examples of capsid polypeptides include, without limitation, hexon polypeptides, fiber polypeptides, penton base polypeptides, IIIa polypeptides, IX polypeptides, and pVI polypeptides.

The Ad fiber protein is a complex of three apparently identical subunits which mediates the initial cell attachment step. The native Ad6 fiber protein comprises the amino acid sequence set forth in SEQ ID NO:60 and binds CAR.

In an aspect of the invention, fiber-modified recombinant and chimeric Ads having fiber proteins which are not native to the parental or "backbone" Ad were generated.

A chimeric Ad, AdF35 fiber chimera, has the amino acid sequence of SEQ ID NO:61 and is shorter than Ad5 and Ad6 fiber proteins and retargets virus to CD46.

A fiber-modified recombinant Ad, comprising K7 Fiber having the sequence of SEQ ID NO:62, targets virus to heparin sulfate proteoglycans and negative charges on cells.

A recombinant, chimeric Ad, 6/FC68 Fiber comprising the sequence of SEQ ID NO:63, is a chimeric Ad having a fiber protein from chimpanzee adenovirus C68. The fiber protein is shorter than Ad5 or Ad6 fiber proteins and binds CAR.

A recombinant, chimeric Ad, 6/FC68-K7 Fiber comprising the sequence of SEQ ID NO:64, is a chimeric Ad having a fiber protein from chimpanzee adenovirus C68. The fiber protein is shorter than Ad5 or Ad6 fiber proteins. The 6/FC68-K7 Fiber binds CAR and is retargeted to heparin sulfate and negative charges.

A recombinant, chimeric Ad, 6/FC68-HI-K7 Fiber comprising the sequence of SEQ ID NO:65, is a chimeric Ad having a fiber protein from chimpanzee adenovirus C68. The fiber protein is shorter than Ad5 or Ad6 fiber proteins. The 6/FC68-HI-K7 Fiber binds CAR and is retargeted to heparin sulfate and negative charges.

In some cases, a recombinant Ad can include a genome from a first Ad where a nucleic acid encoding a hexon polypeptide (e.g., HVRs of a nucleic acid encoding a hexon polypeptide) in the genome is substituted for a nucleic acid encoding a hexon polypeptide (e.g., HVRs of a nucleic acid encoding a hexon polypeptide) from a second Ad. In some cases, a recombinant Ad described herein can include a genome from a first Ad that has one or more HVRs substituted for one or more HVRs from a second Ad. For example, a recombinant Ad can be a chimera, in particular Ad657 (e.g., can include an Ad6 genome where the hexon HVRs are substituted for Ad57 hexon HVRs). In cases where a recombinant Ad includes a genome from a first Ad where a nucleic acid encoding a hexon polypeptide in the genome is substituted for a nucleic acid encoding a hexon polypeptide from a second Ad, the recombinant Ad can include from about 1 to about 720 hexon polypeptides from the second Ad. For example, when a recombinant Ad is an Ad657, the Ad657 can include an Ad6 genome and 720 hexon polypeptides including Ad57 hexon HVRs.

In some cases, a recombinant Ad described herein (e.g., a recombinant Ad having oncolytic anti-cancer activity such as a recombinant Ad657) can include an Ad genome containing one or more nucleic acid deletions. A nucleic acid deletion can be any appropriate nucleic acid deletion. A nucleic acid deletion can be a full deletion (e.g., deletion of a nucleic acid encoding a polypeptide) or a partial deletion (e.g., deletion of one or more nucleotides within a nucleic acid encoding a polypeptide). A nucleic acid deletion can reduce or eliminate transcription and translation of a polypeptide encoded by the deleted nucleic acid. Any appropriate nucleic acid can be deleted. In some cases, a nucleic acid encoding a polypeptide associated with production of infectious progeny can be deleted. Examples of nucleic acids that can be deleted and/or modified in a recombinant Ad described herein may encode E1 (e.g., E1A and E1B), E2, E3, E4, pIIIA, fiber, E1B, and include viral enhancers and promoters. For example, a recombinant Ad described herein (e.g., a recombinant Ad having oncolytic anti-cancer activity such as a recombinant Ad657) can include an Ad genome containing a deletion of one or more nucleotides within a nucleic acid encoding an E1 polypeptide. In some cases, a recombinant Ad described herein can include one or more substitutions in a nucleic acid encoding an E1 polypeptide.

In particular embodiments, a recombinant Ad described herein is modified to comprise a probasin promoter comprising, for example, a nucleic acid of SEQ ID NO:48; a recombinant Ad described herein is modified to comprise a dl1101 deletion in a nucleic acid encoding an E1 polypeptide; a recombinant Ad described herein is modified to comprise a dl1107 deletion in a nucleic acid encoding an E1 polypeptide; a recombinant Ad described herein is modified to comprise a dl1101 deletion and a dl1107 deletion. See the examples herein and FIG. 56 for N-terminal amino acid sequences of the E1A polypeptide, for example, wild-type Ad E1A, and CRAd-657-dl1101, CRAd-657-dl1107 and CRAd-657-dl1101/1107 variants.

In an embodiment, a variant CRAd-657-dl1101/1107-FoIR comprises intact E3 and expresses the human folate receptor alpha found on cancer cells.

In general, Ads may be modified to include CRAd modifications described herein.

In some cases, a recombinant Ad described herein (e.g., a recombinant Ad having oncolytic anti-cancer activity such as a recombinant Ad657) can include an Ad genome containing one or more nucleic acid insertions. For example, a nucleic acid insertion can include a nucleic acid encoding a polypeptide. A nucleic acid can be inserted into any appropriate location within a genome of a recombinant Ad described herein. In some cases, a nucleic acid encoding a polypeptide can be inserted into a HVR (e.g., HVR 5 loop) of a genome of a recombinant Ad described herein. For example, when a nucleic acid encoding a polypeptide is inserted into a HVR of a genome of a recombinant Ad described herein, the nucleic acid encoding a polypeptide can express one or more polypeptides, and the expressed polypeptide(s) can be incorporated into the capsid of the recombinant Ad. In cases where a nucleic acid encoding a polypeptide is inserted into a HVR of a genome of a recombinant Ad described herein, the recombinant Ad can present from about 1 to about 720 polypeptides encoded by the inserted nucleic acid on its surface. A nucleic acid insertion can be nucleic acid encoding any appropriate polypeptide. In some cases, a nucleic acid insertion can encode a polypeptide antigen.

In some cases, a nucleic acid insertion can encode a targeting polypeptide. Examples of targeting polypeptides that can be included in a recombinant Ad described herein include, without limitation peptide 12.51 (TARGEHKEEELI; SEQ ID NO:1), peptide 12.52 (LRQTGAASAVWG; SEQ ID NO:2), 12.53 (ARRADTQWRGLE; SEQ ID NO:3), VSV (GTWLNPGFPPQSCGYATVT; SEQ ID NO:4), RGD (CDCRGDCFC; SEQ ID NO:5), alpha4 integrin binding peptide (NMSLDVNRKA; SEQ ID NO:6), Met 3-4 (ISLSSHRATWVV; SEQ ID NO:7), L10.1F (WTMGLDQLRDSSWAHGGFSA; SEQ ID NO:8), L10.1RGDF (WTMGLDQLRGDSSWAHGGFS; SEQ ID NO:9), L10.2F (RSVSGTEWVPMNEQHRGAIW; SEQ ID NO:10), L10.5F (TELRTHTSKELTIRTAASSD; SEQ ID NO:11), S5.1 (DRAIGWQDKLYKLPLGSIHN; SEQ ID NO:12), DU9C.1 (MGSWEKAALWNRVSASSGGA; SEQ ID NO:13), DU9C.2 (MAMGGKPERPADSDNVQVRG; SEQ ID NO:14), DU9A.7 (MASRGDAGEGSTQSNTNVPS; SEQ ID NO:15), XS.1 (GPEDTSRAPENQQKTFHRRW; SEQ ID NO:16), REDVmyc (MGREDVGEQKLISEEDLGGS; SEQ ID NO:17), RGD-4C (ACDCRGDCFCG; SEQ ID NO:18), REDV-4C (ACDCREDVCFCG; SEQ ID NO:19), SKBR5C1 (GQIPITEPELCCVPWTEAFY; SEQ ID NO:20), 231R10.1 (PQPPNSTAHPNPHKAPPNTT; SEQ ID NO:21), HepaCD8 (VRWFPGGEWGVTHPESLPPP;

SEQ ID NO:22), K20 (KKKKKKKKKKKKKKKKKKKK; SEQ ID NO:23), BAP (GLNDIFEAQKIEWH; SEQ ID NO:24), CALM BP (CAAARWKKAFIAVSAANRFKKIS; SEQ ID NO:25), EBV (EDPGFFNVEIPEFP; SEQ ID NO:26), #1-5 (GGHGRVLWPDGWFSLVGISP; SEQ ID NO:27), ##4*-5 (MARTVTANVPGMGEGMVVVPC; SEQ ID NO:28), 1-1 (GVSKRGLQCHDFISCSGVPW; SEQ ID NO:29), 1-2 (NQSIPKVAGDSKVFCWWCAL; SEQ ID NO:30), 1-3 (QSTPPTKHLTIPRHLRNTLI; SEQ ID NO:31), 1-4 (DMSFQLVTPFLKALPTGWRG; SEQ ID NO:32), 1-5 (GGHGRVLWPDGWFSLVGISP; SEQ ID NO:33), 1-5con (FSLVGISP; SEQ ID NO:34), 1-6 (QIMMGPSLGYYMPSESIFAY; SEQ ID NO:35), 2-11 (ISWDIWRWWYTSEDRDAGSA; SEQ ID NO:36), 2-14 (VWGMTTSDHQRKTERLDSPE; SEQ ID NO:37), 2-20 (MTSAQTSEKLKAETDRHTAE; SEQ ID NO:38), 2-9 (MGSRSAVGDFESAEGSRRP; SEQ ID NO:39), 3b-6 (MGRTVQSGDGTPAQTQPSVN; SEQ ID NO:40), 4*-5 (MARTVTANVPGMGEGMVVVP; SEQ ID NO:41), CLL peptides, PD-1, GLA polypeptides (e.g., Factor X), antigen genes, fusion proteins, fusogenic glycoproteins, single-chain antibodies, and capsid proteins from other viruses. A targeting polypeptide can target any appropriate type of cell. Examples of types of cells that can be targeted by a targeting polypeptide included in a recombinant Ad described herein include, without limitation, muscle cells (e.g., skeletal muscle cells), tumors, cancer cells, kidney cells, liver cells, mucosal cells, carbohydrates, and cell membranes.

This example demonstrates that peptides selected in a compatible structural context on phage libraries can be translated into the Ad hexon protein. For example, for the 12.51 peptide, this insertion site increases muscle transduction while decreasing off target infection in the liver. Thus, such a recombinant Ad which targets muscle tissue may be used as a vector for gene-based muscle vaccination or for gene therapy application/delivery to the muscle.

In some cases, a nucleic acid insertion can detarget the virus (e.g., by disrupting cell and protein interactions that occur on a given HVR). In some cases, a nucleic acid insertion can encode a detectable label. Examples of detectable labels include, without limitation, fluorophores (e.g., green fluorescent protein (GFP), mCherry, and mBFP), and enzymes (e.g., luciferase, DNAses, proteases, transporters, and polymerases).

Also provided herein are expression vectors containing a recombinant Ad described herein (e.g., a recombinant Ad having oncolytic anti-cancer activity such as a recombinant Ad657 and variants thereof). Expression vectors can carry a recombinant Ad described herein into another cell (e.g., a cancer cell), where it can be replicated and/or expressed. An expression vector, also commonly referred to as an expression construct, is typically a plasmid or vector having an enhancer/promoter region controlling expression of a specific nucleic acid. When introduced into a cell, the expression vector can use cellular protein synthesis machinery to produce the virus in the cell. In some cases, expression vectors containing recombinant Ads described herein can be viral vectors. For example, an expression vector containing a recombinant Ad described herein can be a retroviral vector. In some cases, expression vectors including a recombinant Ad described herein also can be designed to allow insertion of one or more transgenes (e.g., at a multi-cloning site). For example, expression vectors including a recombinant Ad described herein also can include a nucleic acid encoding a detectable label. Examples of detectable labels include, without limitation, fluorophores (e.g., green fluorescent protein (GFP), mCherry, and mBFP), and enzymes (e.g., luciferase, recombinases, nucleases, and transcription factors).

This invention also provides methods and materials for using one or more recombinant Ads described herein (e.g., recombinant Ads having oncolytic anti-cancer activity such as recombinant Ad657s). In some cases, a recombinant Ad provided herein can used for treating a mammal having, or at risk of having, cancer. For example, methods for treating a mammal having, or at risk of having, cancer can include administering one or more recombinant Ads described herein to the mammal. In some cases, methods for treating a mammal having, or at risk of having, cancer can include administering one or more expression vectors that encode a recombinant Ad described herein or nucleic acid encoding a recombinant Ad described herein to the mammal. In some cases, one or more recombinant Ads described herein can be administered to a mammal to reduce the number of cancer cells in the mammal (e.g., suppress and/or delay tumor growth) and/or to increase survival of the mammal.

Figure 9:
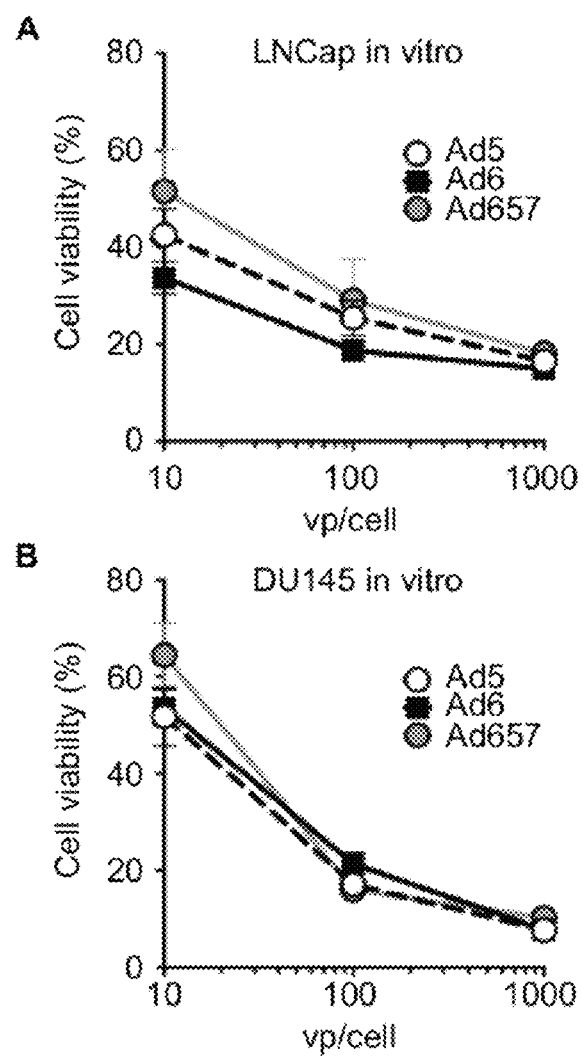
FIG. 9 shows in vitro oncolytic activity. LNCaP and DU145 cells were treated with the indicated viruses with the indicated vp/cell for 5 days. The cells were stained with crystal violet and cell viability was measured by OD595. Cell viability (%) was calculated by dividing the OD of the samples by the mean OD of untreated control cells on the same 96-well plate and multiplying this number by 100. (A) LNCaP cell killing. (B) DU145 killing. Abbreviation: vp, viral particle.

Targeting a cancerous tumor by serotype-switching oncolytic adenoviruses is demonstrated. Mice bearing DU145 or LNCaP prostate tumors on their flanks were treated one by intravenous (IV) injection with Ad657. These mice were treated a second time with alternate Ad6 or Ad6/57/6 oncolytic virus variants with fiber modifications and expressing GFPLuciferase and luciferase activity was measured by imaging. Ad6 has Ad6 hexon and fiber that targets CAR. Ad6-F35 has Ad6 hexon and the Ad35 fiber that targets CD46. Ad6/57/6 has HVR1 and 7 from Ad6 and HVRs 2-6 from Ad57. Ad6/57/6 viruses have Ad6 fiber, AdC68 fiber, or Ad35 fiber. These data in FIG. 9 show the surprising ability to serotype-switch oncolytics with viruses targeting the tumor with lower off-target infection of the liver.

Figure 70:
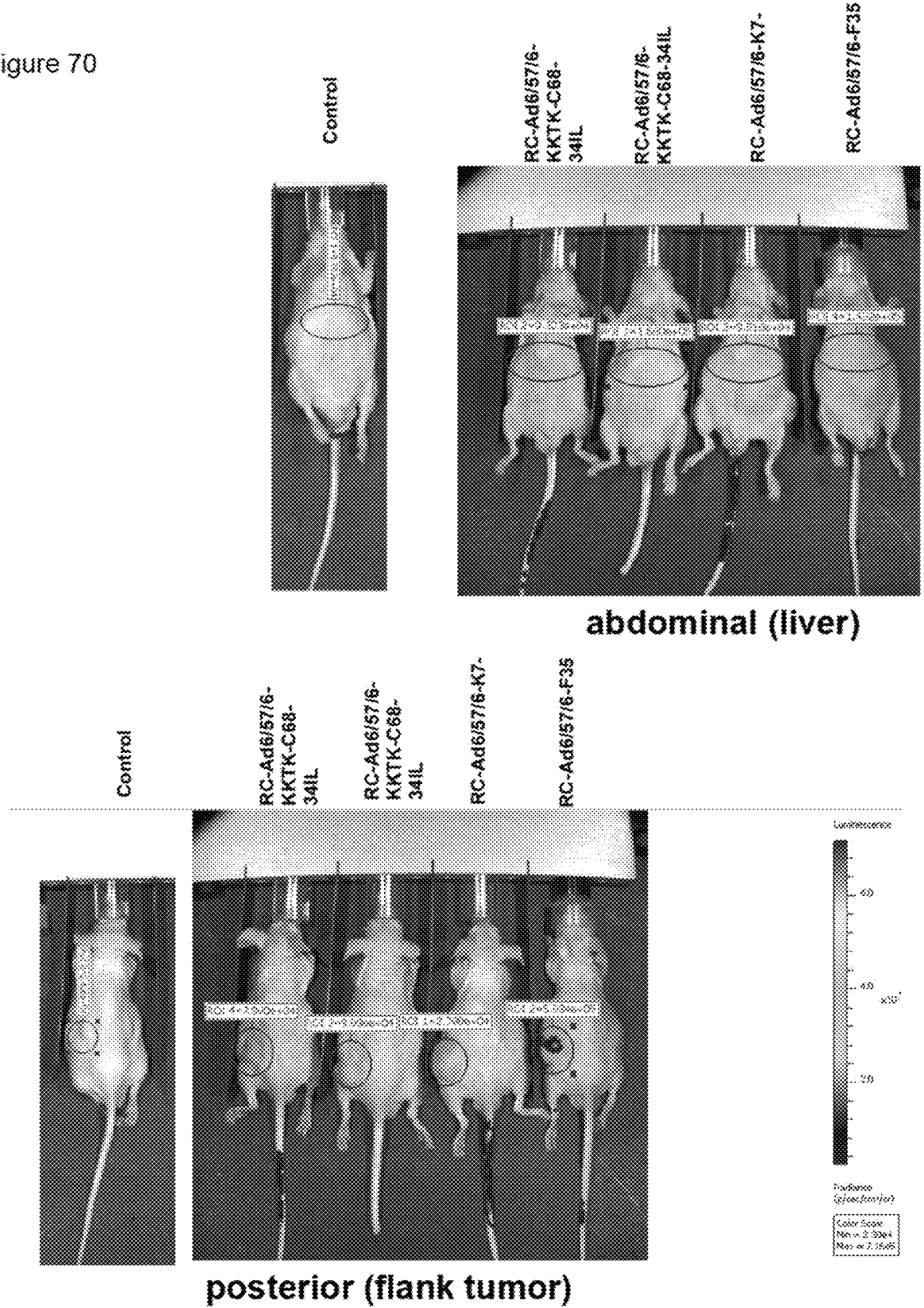
FIG. 70 shows luciferase imaging after serotype switching. Mice bearing LNCaP prostate tumors on their flanks were treated by a single IV injection of Ad657 or CRAd657. Mice with residual tumors 5 months after single IV injection were treated by serotype-switching of the indicated Ad6/57/6 variants expressing GFPLuciferase with and without variant fibers and a codon-optimized E4 34K gene. The indicated Ad6/57/6 variants include Ad6/57/6 virus having different fiber modifications including an added 7 lysine on fiber (K7), chimpanzee C68 fiber grafted onto Ad6 fiber after its KKTK flexibility domain and with an Ad35 fiber. Mice were imaged for luciferase activity 7 days later.
Figure 71:
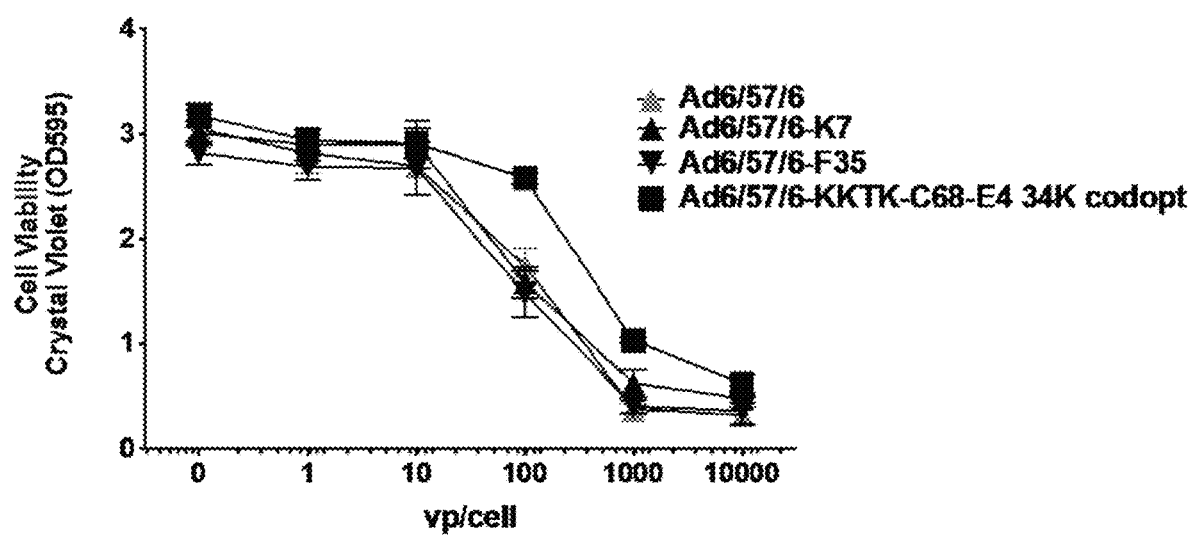
FIG. 71 shows A549 human lung cancer cells which were treated with the indicated viral particles (vp) per cell of Ad6/57/6 with and without variant fibers and a codon-optimized E4 34K gene. 7 days later, the cells were stained with crystal violet and the wells were analyzed in a plate reader. High OD indicates the presence of viable cells. Low OD indicates death and loss of adherent cells.

In another example of serotype-switching, mice bearing LNCaP prostate tumors on their flanks were treated by a single intravenous (IV) injection with Ad657 or CRAd657. These mice were treated a second time 5 months later with alternate Ad6/57/6 oncolytic virus expressing GFPLuciferase and fiber variants K7 (with 7 lysines added), F35 (with the Ad35 fiber), or KKTK-C68 (chimpanzee C68 fiber fused after the Ad6 KKTK flexibility domain. KKTK-C68 virus also has an added codon-optimized E4 34K gene to enhance viral productivity. Luciferase activity was measured by imaging. All Ad6/57/6's have a hexon with HVR1 and 7 from Ad6 and HVRs 2-6 from Ad57. Ad6/57/6 and KKTK-C68 have fibers that targets CAR. Ad6/57/6-F35 has the Ad35 fiber that targets CD46. K7 increases binding to negative charges on cells including binding heparin sulfate proteoglycans. FIG. 70 demonstrates the capability to serotype-switch oncolytics with viruses targeting a tumor with lower off-target infection of the liver.

Any appropriate mammal having, or at risk of having, cancer, an infectious disease, and/or a genetic disease can be treated as described herein. For example, humans, non-human primates (e.g., monkeys), horses, bovine species, porcine species, dogs, cats, mice, rats, and feed animals having cancer, an infectious disease, and/or a genetic disease can be treated for cancer as described herein. In some cases, a human having cancer can be treated. In some cases, a mammal (e.g., a human) treated as described herein is not a natural host of an Ad used to generate a recombinant Ad described herein (e.g., a recombinant Ad having oncolytic anti-cancer activity such as a recombinant Ad657). For example, a human being treated with a recombinant Ad657 described herein can lack any pre-existing adaptive immunity to Ad6.

A mammal having any type of cancer can be treated as described herein. In some cases, a cancer can include one or more solid tumors. In some cases, a cancer can be a blood cancer. Examples of cancers that can be treated as described herein include, without limitation, prostate cancer, ovarian cancer, lung cancer, hepatocellular carcinoma, pancreatic cancer, kidney cancer, melanoma, brain cancer, colon cancer, lymphoma, myeloma, and leukemias (e.g., lymphocytic leukemias and myelogenous leukemias).

In some cases, methods described herein also can include identifying a mammal as having cancer. Examples of methods for identifying a mammal as having cancer include, without limitation, physical examination, laboratory tests (e.g., blood and/or urine), biopsy, imaging tests (e.g., X-ray, PET/CT, MRI, and/or ultrasound), nuclear medicine scans (e.g., bone scans), endoscopy, and/or genetic tests. Once identified as having cancer, an infectious disease, and/or a genetic disease, a mammal can be administered or instructed to self-administer one or more a recombinant Ads described herein (e.g., recombinant Ads having oncolytic anti-cancer activity such as recombinant Ad657s) or a nucleic acid (e.g., an expression vector) encoding one or more a recombinant Ads described herein (e.g., recombinant Ads having oncolytic anti-cancer activity such as recombinant Ad657s).

One or more recombinant Ads described herein (e.g., recombinant Ads having oncolytic anti-cancer activity such as recombinant Ad657s) can be administered by any appropriate route. In some cases, administration can be local administration. In some cases, administration can be systemic administration. Examples of routes of administration include, without limitation, intravenous, intramuscular, subcutaneous, oral, intranasal, inhalation, transdermal, parenteral, intratumoral, retro-ureter, sub-capsular, vaginal, and rectal administration. In cases where multiple rounds of treatment are administered, a first round of treatment can include administering one or more recombinant Ads described herein to a mammal (e.g., a human) by a first route (e.g., intravenously), and a second round of treatment can include administering one or more recombinant Ads described herein to a mammal (e.g., a human) by a second route (e.g., intramuscularly).

As used herein, the term "pharmaceutical composition" refers to the combination of one or more recombinant and/or chimeric Ads of the present invention with a carrier, inert or active, making the composition especially suitable for therapeutic use. One or more recombinant Ads described herein (e.g., recombinant Ads having oncolytic anti-cancer activity such as recombinant Ad657s) can be formulated into a composition (e.g., a pharmaceutical composition) for administration to a mammal (e.g., a mammal having, or at risk of having, cancer). For example, one or more recombinant Ads can be formulated into a pharmaceutically acceptable composition for administration to a mammal having, or at risk of having, cancer. In some cases, one or more recombinant Ads can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, wafers, and granules. Pharmaceutically acceptable carriers, fillers, and vehicles that may be used in a pharmaceutical composition described herein include, without limitation, saline (e.g., phosphate-buffered saline, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinylpyrrolidone, cellulose-based substances, sodium carboxymethylcellulose, polyacrylates, waxes, polyethylene-polyoxypropylene-block polymers, polyethylene glycol, and wool fat. Suitable pharmaceutical carriers are described in "Remington's Pharmaceutical Sciences" by E. W. Martin, 18th Edition. The selection and use of suitable excipients is taught in Gennaro, ed., Remington: The Science and Practice of Pharmacy, 20th Ed. (Lippincott Williams & Wilkins 2003).

A composition (e.g., a pharmaceutical composition) including one or more recombinant Ads described herein (e.g., recombinant Ads having oncolytic anti-cancer activity such as recombinant Ad657s) can be administered to a mammal (e.g., a mammal having, or at risk of having, cancer) as a vaccine. A vaccine can be prophylactic or therapeutic.

In some cases, methods described herein also can include administering to a mammal (e.g., a mammal having cancer) one or more additional agents used to treat a cancer. The one or more additional agents used to treat a cancer can include any appropriate cancer treatment. In some cases, a cancer treatment can include surgery. In some cases, a cancer treatment can include radiation therapy. In some cases, a cancer treatment can include administration of a pharmacotherapy such as a chemotherapy, hormone therapy, targeted therapy, and/or cytotoxic therapy. For example, a mammal having cancer can be administered one or more a recombinant Ads described herein (e.g., recombinant Ads having oncolytic anti-cancer activity such as recombinant Ad657 and variants thereof) and administered one or more additional agents used to treat a cancer. In cases where a mammal having cancer is treated with one or more a recombinant Ads described herein and is treated with one or more additional agents used to treat a cancer, an infectious disease, and/or a genetic disease, the additional agents used to treat a cancer, an infectious disease, and/or a genetic disease can be administered at the same time or independently. For example, one or more a recombinant Ads described herein and one or more additional agents used to treat a cancer, an infectious disease, and/or a genetic disease can be formulated together to form a single composition. In some cases, one or more a recombinant Ads described herein can be administered first, and the one or more additional agents used to treat a cancer, an infectious disease, and/or a genetic disease administered second, or vice versa.

EXAMPLES

Example 1

Adenoviruses

For 50 years, there were only four known species C human species Ads including Ad1, Ad2, Ad5, and Ad6 (see, e.g., Weaver et al., 2011 *Virology.* 412:19-27). In 2001, a fifth species C adenovirus was identified as field isolate strain #16700, and virus neutralization testing with antisera against Ad1, 2, 5, and 6 demonstrated high levels of neutralization (reciprocal titers of 500-16,000) when each antisera was used against its cognate virus (Lukashev et al., 2008 J Gen Virol. 89:380-388). In contrast, anti-Ad1, 2, and 5 antibodies have weak cross-reactivity against #16700 (reciprocal titers of 32-64). Anti-Ad6 sera demonstrated higher cross-reactivity against #16700, but neutralization required 10-fold higher concentrations of sera to neutralize #16700 when compared with Ad6 itself. Subsequent sequence comparisons confirmed #16700 as a novel species C adenovirus and renamed it as Ad57 (see, e.g., Walsh et al., 2011 *J. Clin Microbiol.* 49:3482-3490).

15 human Ads were evaluated for oncolytic activity against breast, ovarian, liver, prostate, kidney, and B cell malignancies. In tests against DU145 human prostate tumors, species C Ad6 was more potent after single intratumoral or intravenous (i.v.) injection than species C Ad5 or species B viruses Ad 11 and Ad35. Ad6 was also more effective than Ad5 and Ad 11 in immunocompetent Syrian hamsters.

Construction of Recombinant Adenoviruses

Recombinant adenoviruses were constructed by recombinant DNA technology utilizing methods known to those skilled in the art. A recombinant Ad is derived from a first Ad (e.g., can include a genome of a first Ad, such as Ad6) and may include hexon HVRS from a second Ad such as Ad57. In cases where a recombinant Ad includes an Ad6 genome and Ad57 hexon HVRS, the recombinant Ad can be a chimeric Ad referred to as Ad657.

To obtain Ad657, an Ad57 HVR sequence was synthesized and inserted into the Ad6 hexon in a plasmid with an FRT-Zeocin®-FRT cassette between pVI and hexon. This was recombined into various pAd6 plasmids to generate Ad657 and variants thereof. The amino acid sequence of the Ad657 hexon is set forth in SEQ ID NO:49. See FIGS. 34 and 59-65 for plasmid maps of Ad657 variants.

With respect to variants of Ad657, the Ad57 HVR sequence was synthesized with HVR1 modified with a cysteine, flexibility amino acids, and restriction sites to allow insertions of other peptides. This was inserted into the Ad6 hexon in a plasmid with an FRT-Zeocin®-FRT cassette between pVI and hexon. This was recombined into various pAd6 plasmids to generate Ad657 variants with cysteine in HVR1, the variant referred to as Ad657-HVR1-XXA comprises the hexon having the amino acid sequence of SEQ ID NO:50.

With respect to variants of Ad657, the Ad57 HVR sequence was synthesized with HVRS modified with a cysteine, flexibility amino acids, and restriction sites to allow insertions of other peptides. This was inserted into the Ad6 hexon in a plasmid with an FRT-Zeocin®-FRT cassette between pVI and hexon. This was recombined into various pAd6 plasmids to generate Ad657 variants with cysteine in HVRS, the variant referred to as Ad657-HVRS-XXA comprises the hexon having the amino acid sequence of SEQ ID NO:51.

With respect to variants of Ad657, the Ad57 HVR sequence was synthesized with HVR1 modified with a cysteine, flexibility amino acids, and restriction sites to allow insertions of other peptides. This was inserted into the Ad6 hexon in a plasmid with an FRT-Zeocin®-FRT cassette between pVI and hexon. This was recombined into various pAd6 plasmids to generate Ad657 variants without cysteine in HVR1, but with restriction sites allowing peptide insertions into HVR1, the variant referred to as Ad657-HVR1-XA comprises the hexon having the amino acid sequence of SEQ ID NO:52.

With respect to variants of Ad657, the Ad57 HVR sequence was synthesized with HVR5 modified with a cysteine, flexibility amino acids, and restriction sites to allow insertions of other peptides. This was inserted into the Ad6 hexon in a plasmid with an FRT-Zeocin®-FRT cassette between pVI and hexon. This was recombined into various pAd6 plasmids to generate Ad657 variants without cysteine in HVR5, but with restriction sites allowing peptide insertions into HVR5, the variant referred to as Ad657-HVR5-XA comprises the hexon having the amino acid sequence of SEQ ID NO:53.

With respect to variants of Ad657, the Ad657 HVR1-XA sequence was modified by insertion of a biotin acceptor peptide into HVR1. This was recombined into various pAd6 plasmids to generate Ad657 variants a BAP in HVR1, the variant referred to as Ad657-HVR1-PSTCD comprises the hexon having the amino acid sequence of SEQ ID NO:54.

The insertion of a biotin acceptor peptide detargets the virus variants from the liver, allows the virus to be retargeted with avidin or streptavidin and biotinylated ligands, and allows the virus to be purified on monomeric avidin or streptavidin columns.

With respect to variants of Ad657, the Ad657 HVR1-XA sequence was modified by insertion of a biotin acceptor peptide into HVR1. This was recombined into various pAd6 plasmids to generate Ad657 variants a BAP in HVR1, the variant referred to as Ad657-HVR5-PSTCD comprises the hexon having the amino acid sequence of SEQ ID NO:55.

With respect to variants of Ad657, the Ad657 HVR5-XA sequence was modified by insertion of a synthetic V1/V2 loop from HIV envelope into HVR5, the variant referred to as Ad657-HVR5-V1/V2 comprises the hexon having the amino acid sequence of SEQ ID NO:56.

The insertion of a synthetic V1/V2 loop from HIV envelope allows display of this antigen to serve as a vaccine as well as retargeting by binding to proteins that interact with HIV envelope.

With respect to variants of Ad657, the Ad657 HVR5-XA sequence was modified by insertion of synthetic peptides from human papilloma virus into HVR5, the variant referred to as Ad657-HVR5-HPV comprises the hexon having the amino acid sequence of SEQ ID NO:57.

The insertion of synthetic peptides from human papilloma virus allows display of HPV peptides as antigens for vaccine purposes as well as for retargeting by binding to proteins that interact with HPV peptides.

In another aspect of the invention, chimeric Ads were generated which have an Ad6 HVR1 and Ad57 HVRs 2-7, the chimera, referred to as Ad6/57 HVR chimera, comprises the hexon having the amino acid sequence of SEQ ID NO:58.

In yet another aspect of the invention, chimeric Ads were generated which have Ad6 HVR1 and 7 and Ad57 HVRs 2-6, the chimera, referred to as Ad6/57/6 HVR chimera, comprises the hexon having the amino acid sequence of SEQ ID NO:59.

Example 2

Retargeted and Detargeted Recombinant Adenovirus for Gene Delivery

Adenoviruses are robust vectors for gene delivery and gene-based immunization. The archetype adenovirus used for the vast majority of these application has been human species C adenovirus serotype 5 (HAdV-C5 or Ad5). In vitro, Ad5 binds and enters cells through the combined interactions of its fiber and penton base proteins with cell surface receptors. The trimeric fiber binds the coxsackie-adenovirus receptor (CAR), and cells that lack CAR are relatively resistant to infection unless they also express $\alpha_v$ integrins that can be bound by an RGD motif on the penton base.

In vivo, these interactions are still utilized, but their importance varies by injection route. If injected directly into a solid tissue or tumor, CAR and integrin interactions dominate. If injected intravenously (IV), these interactions become secondary due to the effects of Ad5 binding to vitamin-K-dependent blood clotting factors. Blood factor X (FX) binds with subnanomolar affinity to the hexons of Ad5 and, consequently, enables Ad5 to efficiently transduce liver hepatocytes after IV injection. In the absence of FX, liver transduction is drastically reduced.

Adenoviral vectors are somewhat unique in their ability to carry very large cDNA sequences of up to 36 kilobase pairs (kbp) when compared to other vectors like adeno-associated virus (AAV) vectors with only 4.5 kb of DNA sequence. This payload capacity justified early exploration of Ad vectors for muscle gene therapy when delivering very large transgenes like the 14 kbp dystrophin cDNA. IV administration in newborn mice can mediate muscle gene delivery, but this ability is lost in adult mice. The decreased transfection with age is due in part to the very large size of Ad virions (i.e. 100 nm) as well as the loss of CAR receptor on muscle cells with aging. The intramuscular (IM) route is by far the most popular route for gene-based vaccines when using Ad5 and other serotypes despite the fact that CAR is absent on skeletal muscle cells.

Therefore, Ad5 and other Ad serotype transduction of muscle can be adequate for gene therapy or gene-based vaccination. However, the absence of the virus' primary receptor in the muscle reduces the efficacy of the virus and requires more vector to be delivered to achieve desired effects.

Construction of Peptide-Modified Hexons in Adenovirus.

12 amino acid (12-mer) peptides on C2C12 mouse muscle cells were selected from a random peptide library displayed between the H and I β sheets from the knob region of Ad5 (FIG. 1A). Peptides 12.51 (TARGEHKEEELI; SEQ ID NO:1) and 12.52 (LRQTGAASAVWG; SEQ ID NO:2) were selected against myoblasts with pre-clearing against non-target cells to obtain peptides which would be specific for binding muscle cells. In most cases, small peptides have relatively low affinity. It was therefore reasoned that displaying these muscle-selected peptides on the 720 copies of the Ad5 hexon might enable better muscle gene delivery. This insertion site would also have the benefit of inactivating FX binding to the hexon to "detarget" the vector from the liver if any vector leaked into the blood after IM injection.

Inserting these muscle-selected peptides between two other β sheets which also constrains a hypervariable loop on the virus, the ability of the modified Ads to modulate tropism was evaluated. Peptides 12.51 and 12.52 were introduced into the hypervariable region (HVR) 5 loop constrained by the β7 and β8 sheets in Ad5 hexon. The in vivo ability of these viruses to transduce tissues after intravenous and intramuscular injections in mice and in hamsters was evaluated.

Adenoviruses

E1-deleted Ad5-GL (RD-Ad5-GL) expresses a green fluorescent protein-luciferase (GFP-Luciferase, GL) fusion protein as described elsewhere (see., e.g., Crosby et al., 2002 *J. Virol.*, 76:6893-6899; Khare et al., 2011 *Mol. Ther.*, 19:1254-1262; and Khare et al., 2012 *J. Virol.*, 86:2293-2301). Muscle selected peptides 12.51 and 12.52 were inserted in place of HVR5 on Ad5 hexon between its β7 and β8 sheets which structurally similar to the H and I β sheets from the knob region of Ad5 (FIG. 1A) according to methods known to those skilled in the art. The peptides with a flexibility leader replaced the entire HVR5 loop in Ad5 (FIG. 1B). These modified hexon sequences were introduced into replication-defective Ad5 expressing a green fluorescent protein-luciferase (RD-Ad5-GL) fusion protein by red recombination in bacteria (see, e.g., Campos et al., 2004 *Hum. Gene Ther.*, 15:1125-1130). Peptide modified Ads were constructed by insertion of annealed oligonucleotides encoding the peptides 12.51 and 12.52 (FIG. 1B) into the plasmid pHVR5 display (FIG. 1A bottom) to yield recombinant Ads, Ad5-HVRS-12.51 and Ad5-HVRS-12.52.

The resulting plasmids were digested and used for red recombination into pAd5-GL. These vectors were rescued in 293 cells, purified on two consecutive CsCl gradients and were desalted on Econopac 10-DG chromatography columns (Bio-Rad) into 50 mM Tris pH 8 with 0.5 M sucrose and stored at −80° C.

In Vitro Virus Testing

C2C12 mouse myoblasts were purchased from American Type Tissue Culture (Manassas, Va.). 293 cells were obtained from Microbix, Toronto, Ontario, Canada. Cells were maintained in DMEM with 10% FBS Invitrogen.

C2C12 muscle cells were plated in 6 well plates (Corning) the day before infection. Viruses were used to infect cells in DMEM with 5% FBS. The cells were incubated for 2 days prior to observation under green fluorescence.

Animal experiments were performed with approval by the Mayo Clinic Institutional Animal Care and Use Committee under the provisions of the Animal Welfare Act, PHS Animal Welfare Policy and principles of the NIH Guide for the Care and Use of Laboratory Animals. Female CD-1 mice (Charles River) were anesthetized and injected intramuscularly (IM) or intravenously (IV) with $10^{10}$ vp of the indicated viruses at indicated times. The animals were anesthetized and injected with 3 mg of d-luciferin (Molecular Imaging Products) and were imaged on a Xenogen imaging system. At later times, the animals were anesthetized and blood was collected in serum separators for ELISA.

ELISA was performed as follows Immulon 4 HBX plates (Thermo) were incubated with 100 ng per well of GFP protein in 1X phosphate-buffered saline (PBS) at 4° C. overnight, washed, and blocked with 5% milk in TRIS-buffered saline with 0.1% Tween 20 (TBST) at room temperature for 2 hours. 1:100,000 to 1:1,1000 dilutions of each serum sample were prepared in blocking buffer. Wells were washed and 100 μL of each were added to GFP-coated plates in triplicate and incubated for 3 hours at room temperature. Wells were washed and a 1/10,000 dilution of goat anti-mouse-HRP secondary antibody (Pierce Chemical) was added to each well. Plates were incubated for 2 hours at room temperature, washed, and 50 μL of 1 Step Ultra TMB ELISA (Thermo Fisher Scientific Inc.) was added for HRP detection followed by 50 μL of 2 M $H_2SO_4$. Absorbance at 450 nm was determined with a Beckman Coulter DTX 880.

Statistical analyses were performed with Prism (Graphpad). Statistical significance was calculated by one-way ANOVA followed by Tukey's HSD In Vitro Transduction in Mouse C2C12 Muscle Cells RD-Ad5-GL, RD-Ad5-GL-HVR5-12.51, and RD-Ad5-HVR5-12.52 were used to infect mouse C2C12 myoblast cells at varied multiplicities of infection (MOI) in terms of virus particles (vp)/cell. When green fluorescence from the GFP fusion protein was observed by fluorescence microscopy, both of the peptide-modified vectors mediated significantly better transduction than RD-Ad5-GL (FIG. 2A). When luciferase activity was measured, significant increases were observed in RD-Ad5-GL-12.51 and 12.52 infected cells (FIG. 2B). When one of the peptides, 12.51, was inserted back into the knob region of Ad5, the peptide increased in vitro transduction 14-fold on C2C12 myoblasts.

Figure 3:
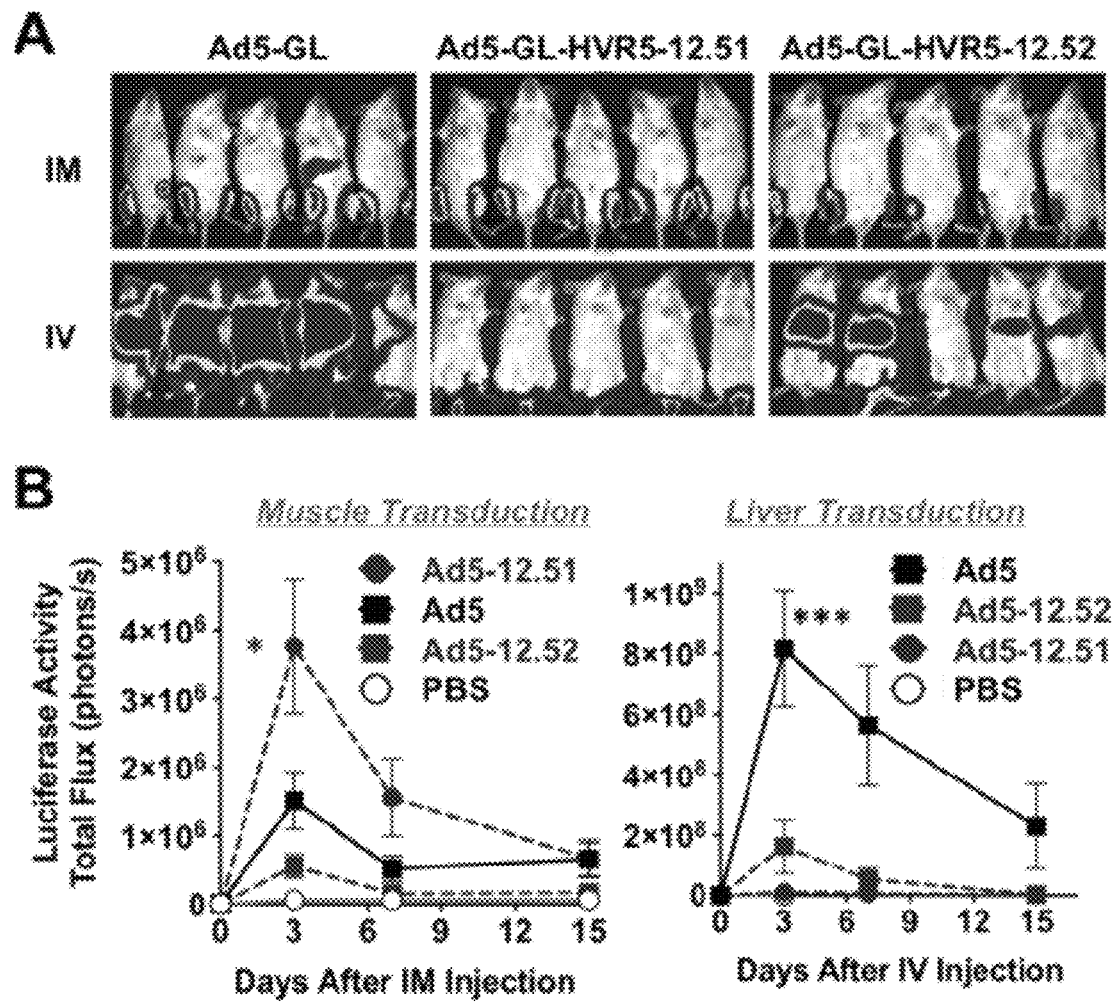
FIG. 3 shows in vivo transduction in mice. A) Luciferase imaging of mice 1 day after injection by the intravenous (IV) or intramuscular (IM) routes. IM injected mice received $10^9$ vp into each quadricep. IV injected mice received $10^{10}$ vp by tail vein. B) Quantitation of luciferase activity by imaging on the indicated days after injection. *$p<0.05$ by one way ANOVA. ***$p<0.001$ by one way ANOVA.

In Vivo Transduction after Intramuscular Injection in Mice $10^9$ vp of Ad5-GL, Ad5-GL-HVR5-12.51, and Ad5-GL-HVR5-12.52 were injected by the IM route into both quadriceps muscles in mice and luciferase imaging was performed at varied times (FIG. 3A top). Ad5-GL-HVR5-12.51 produced 2 to 3-fold higher luciferase activity than Ad5-GL at all the time points (p <0.05 at day 1 by one-way ANOVA) (FIG. 3B left). Ad5-GL-HVR5-12.52 activity in the muscle was lower than both Ad5-GL and HVR5-12.51 in contrast to its stronger activity in vitro.

In Vivo Transduction after Intravenous Injection in Mice $3 \times 10^{10}$ vp of Ad5-GL, Ad5-GL-HVR5-12.51, and Ad5-GL-HVR5-12.52 were injected by the IV route in mice and luciferase imaging was performed (FIG. 3A bottom). In contrast to the results in the muscle, only unmodified Ad5-GL mediated strong liver transduction. Liver transduction by Ad5-GL was 60-fold higher than both Ad5-GL-HVR5-12.51 and Ad5-GL-HVR5-12.52 (p<0.001 at day 1 by one-way ANOVA) (FIG. 3B right) demonstrating that the recombinant Ads target muscle tissue while decreasing off target infection in the liver.

In Vivo Transduction after Intramuscular Injection in Hamsters

Figure 4:
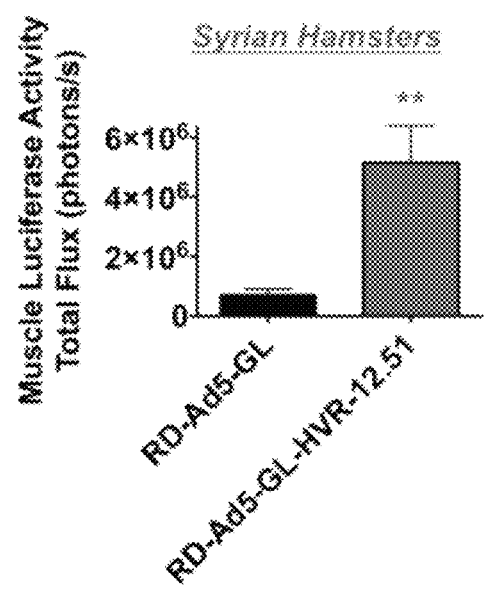
FIG. 4 shows in vivo transduction in hamsters. A) Luciferase activity in the muscles of hamsters 1 day after injection with $10^{10}$ vp by the IM route. **$p<0.01$ by T test.

To test if the 12.51 modified vector works in other species than mice, $10^{10}$ vp of Ad5-GL and Ad5-GL-HVR5-12.51 were injected IM into both quadriceps of larger Syrian hamsters and luciferase imaging was performed 24 hours later (FIG. 4). In this case, Ad5-GL-HVR5-12.51 mediated 7-fold higher luciferase activity than Ad5-GL (p<0.01 at day 1 by one-way ANOVA).

Figure 5:
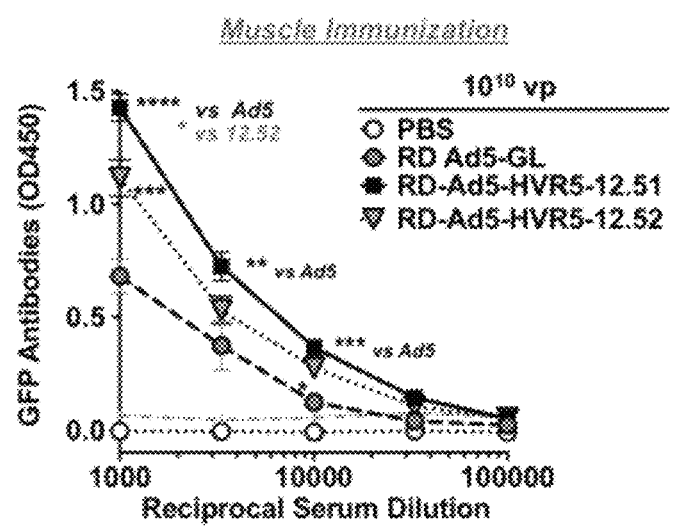
FIG. 5 shows gene-based immune responses 16 weeks after single IM immunization. Mice from FIG. 3 were bled 16 weeks after IM injection and their sera were analyzed in serial dilutions by ELISA to detect antibodies against GFP protein. *$p<0.05$, $p<0.01$, *$p<0.001$ by one-way ANOVA. ****$p<0.0001$ by one-way ANOVA. All Ad-injected mice generated significant anti-GFP antibodies when compared to the PBS group at sera dilutions of 1:10,000 to 1:1000. Comparisons of Ad5-GL-HVR-12.51 and 12.52 to Ad5-GL are shown with black asterisks. Comparison between Ad5-GL-HVR-12.51 and Ad5-GL-HVR-12.52 are shown with a gray asterisk. A gray dashed and dotted line at OD 0.06 shows the 95% confidence interval discriminating antibodies that are different from the PBS group.

Gene-Based Immunization after Intramuscular Injection in Mice 16 weeks after IM injection, sera were collected the mice treated as described above and as shown in FIG. 3 and analyzed in serial dilutions by ELISA for antibodies against transgene-encoded GFP (FIG. 5). All Ad-injected mice generated significant anti-GFP antibodies when compared to the PBS group at sera dilutions of 1:10,000 to 1:1000 (p<0.0001 by one-way ANOVA). However, Ad5-GL-HVR-12.51 produced higher antibodies than either Ad5 or Ad5-HVR5-12.52. At 1:1000 to 1:10,000 dilutions of sera, Ad5-GL-HVR-12.51 was significantly higher than Ad5-GL (p<0.01 to 0.0001 by one-way ANOVA). At a 1:1000 dilution of sera, 12.51 was significantly higher than 12.52 (p<0.05). Ad5-GL-12.52 was significantly higher than Ad5-GL at 1:1000 and 1:10,000 dilutions of sera (p<0.05 to 0.001).

This example demonstrates that peptides selected in a compatible structural context on phage libraries can be translated into the Ad hexon protein. For example, for the 12.51 peptide, this insertion site increases muscle transduction while decreasing off target infection in the liver. Thus, such a recombinant Ad which targets muscle tissue may be used as a vector for gene-based muscle vaccination or for gene therapy application/delivery to the muscle.

A further aspect of the invention relates to recombinant and/or chimeric Ads which comprise other cell targeting peptides inserted into Ad657 HVRs and into Ad6 and C68 HI loops are described in Table 1.

TABLE 1

Other Cell Targeting Peptides Inserted into Ad657 HVRs and into Ad6 and C68 HI Loops

| | |
|---|---|
| VSV cell binding peptide | GTWLNPGFPPQSCGYATVT (SEQ ID NO: 4) |
| RGD-4C integrin binding peptide | CDCRGDCFC (SEQ ID NO: 5) |
| 12.51 phage-selected peptide | TARGEHKEEELI (SEQ ID NO: 1) |
| 12.52 phage-selected peptide | LRQTGAASAVWG (SEQ ID NO: 2) |
| 12.53 phage-selected peptide | ARRADTQWRGLE (SEQ ID NO: 3) |
| alpha4 binding peptide | NMSLDVNRKA (SEQ ID NO: 6) |
| L10.1 lung binding peptide | WTMGLDQLRDSSWAHGGFSA (SEQ ID NO: 9) |
| L10.2 lung binding peptide | RSVSGTEWVPMNEQHRGAIW (SEQ ID NO: 10) |
| L10.5 lung binding peptide | TELRTHTSKELTIRTAASSD (SEQ ID NO: 11) |
| S5.1 muscle binding peptide | DRAIGWQDKLYKLPLGSIHN (SEQ ID NO: 12) |
| DU9C.1 prostate cancer binding peptide | MGSWEKAALWNRVSASSGGA (SEQ ID NO: 13) |
| DU9C.2 prostate cancer binding peptide | MAMGGKPERPADSDNVQVRG (SEQ ID NO: 14) |
| DU9A.7 prostate cancer binding peptide | MASRGDAGEGSTQSNTNVPS (SEQ ID NO: 15) |
| XS.1 dendritic cell binding peptide | GPEDTSRAPENQQKTFHRRW (SEQ ID NO: 17) |
| REDV endothelial cell binding peptide | REDVY (SEQ ID NO: 46) |
| SKBR5C1 breast cancer cell binding peptide | GQIPITEPELCCVPWTEAFY (SEQ ID NO: 20) |
| 231R10.1 breast cancer cell binding peptide | PQPPNSTAHPNPHKAPPNTT (SEQ ID NO: 21) |
| HepaCD8 hepatocellular cancer binding peptide | VRWFPGGEWGVTHPESLPPP (SEQ ID NO: 22) |
| HI Met 231 3-4 breast cancer binding peptide | ISLSSHRATWVV (SEQ ID NO: 47) |

TABLE 1-continued

B Cell Cancer Selected Peptides:

| | | |
|---|---|---|
| 1-1 | GVSKRGLQCHDFISCSGVPW | (SEQ ID NO: 29) |
| 1-2 | NQSIPKVAGDSKVFCWWCAL | (SEQ ID NO: 30) |
| 1-3 | QSTPPTKHLTIPRHLRNTLI | (SEQ ID NO: 31) |
| 1-4 | DMSFQLVTPFLKALPTGWRG | (SEQ ID NO: 32) |
| 1-5 | GGHGRVLWPDGWFSLVGISP | (SEQ ID NO: 33) |
| 1-6 | QIMMGPSLGYYMPSESIFAY | (SEQ ID NO: 35) |
| 2-11 | ISWDIWRWWYTSEDRDAGSA | (SEQ ID NO: 36) |
| 2-14 | VWGMTTSDHQRKTERLDSPE | (SEQ ID NO: 37) |
| 2-20 | MTSAQTSEKLKAETDRHTAE | (SEQ ID NO: 38) |
| 2-9 | MGSRSAVGDFESAEGSRRP | (SEQ ID NO: 39) |
| 3b-6 | MGRTVQSGDGTPAQTQPSVN | (SEQ ID NO: 40) |
| 4*-5 | MARTVTANVPGMGEGMVVVP | (SEQ ID NO: 41) |
| Small BAP biotin acceptor peptide | GLNDIFEAQKIEWH | (SEQ ID NO: 24) |
| calmodulin binding peptide | CAAARWKKAFIAVSAANRFKKIS | (SEQ ID NO: 25) |

DNA encoding the indicated peptides and its complementary DNA was synthesized flanked by cohesive ends for ligation into Ad plasmids, for example, XA hexon plasmids or pAd6-NdePfl fiber shuttle plasmids. These annealed oligonucleotides were ligated into HVRs or the HI loop of Ads. These plasmids were used to recombine into various Ad backbone plasmids.

Some peptides serve to target novel receptors on cells. Others like the small BAP can be used for avidin targeting and purification if the virus is grown in cells expressing bacterial biotin ligase BirA. The calmodulin peptide allows the virus to bind to calmodulin or calmodulin-fusion proteins for retargeting or for virus purification.

Thus, such a recombinant Ads which targets specific tissues/cell receptors may be used as a vector for gene-based vaccination or for gene therapy application in the targeted cells and/or tissues.

Example 3

Insertion of Individual HVRs from Different Ad Serotypes with the Insertion of Cell Targeting/Detargeting Peptides or Novel Amino Acids Hexon shuttle plasmid maps (FIG. 34) show the combination of the insertion of individual HVRs from different Ad serotypes with the insertion of cell targeting/detargeting peptides or novel amino acids such as cysteine into the hexon for targeted chemical modification and shielding.

Figure 34:
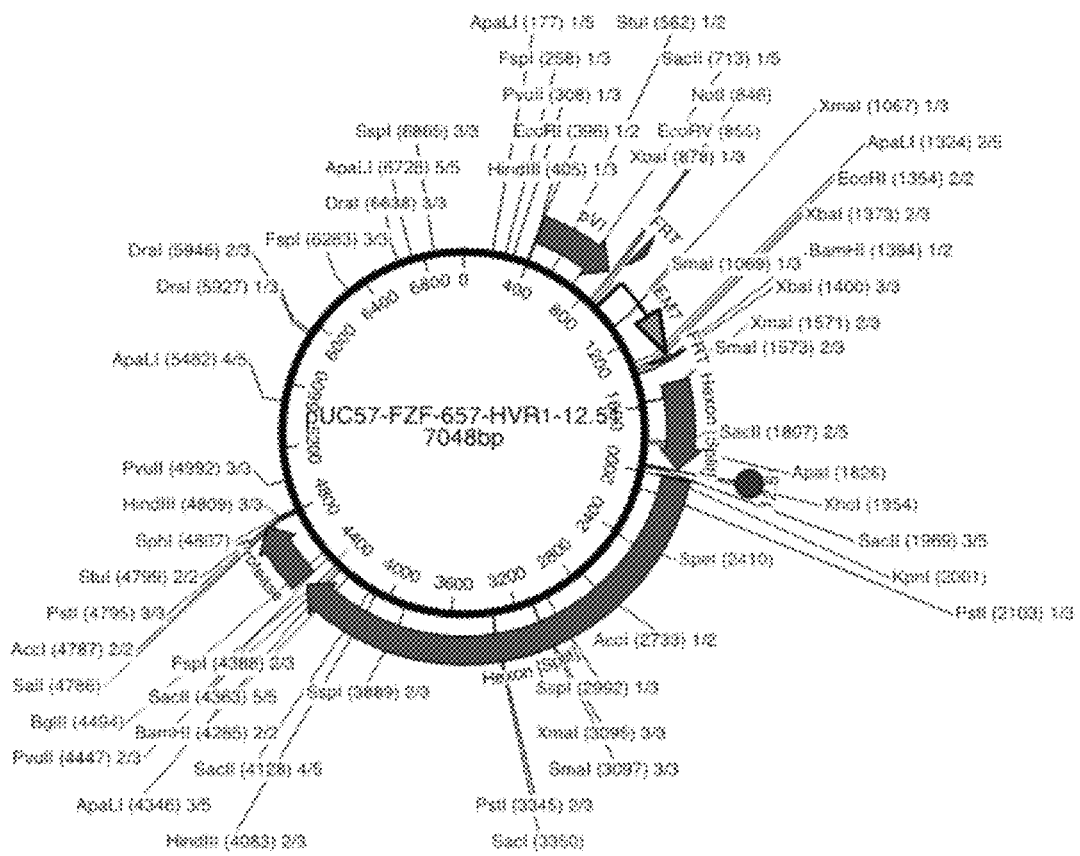
FIG. 34 shows plasmid maps for representative combinatorial hexons and peptide combinations. Shown are hexons with HVR1 from Ad6 and HVRs 2-7 from Ad57 as well as insertions of cell targeting peptides into individual HVRs.
Figure 34:
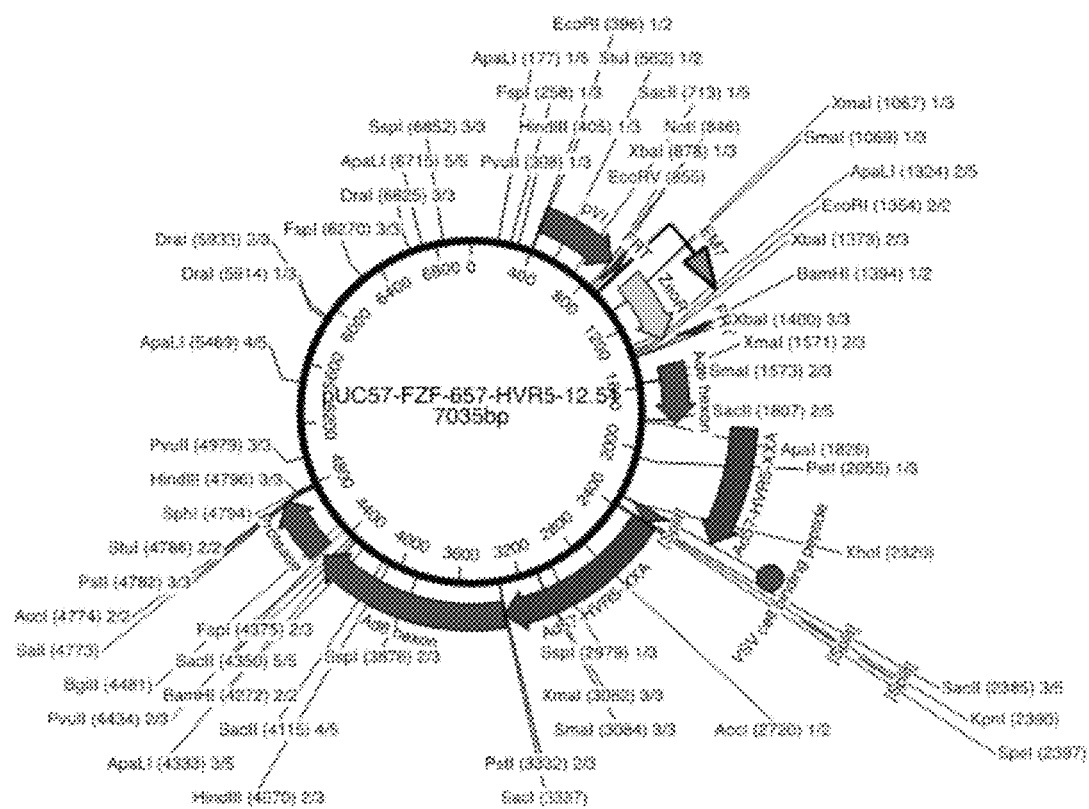
Figure 34:
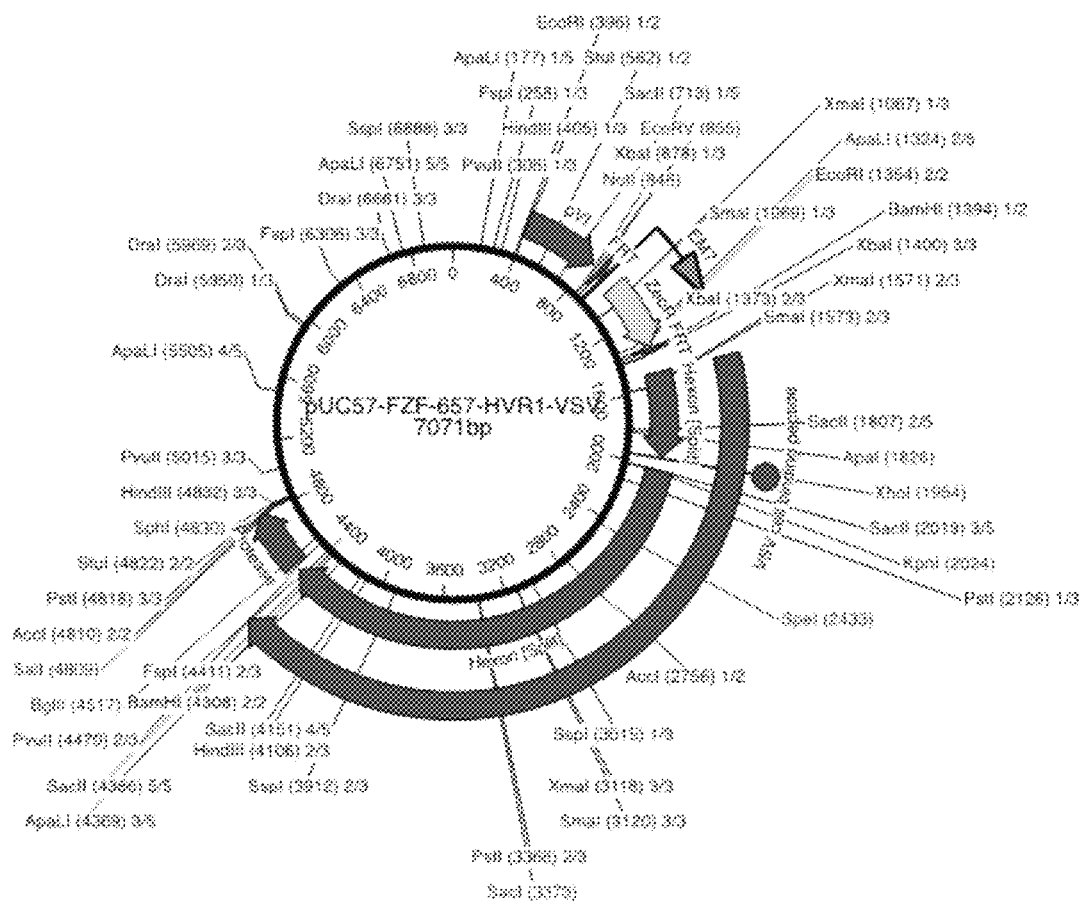
Figure 34:
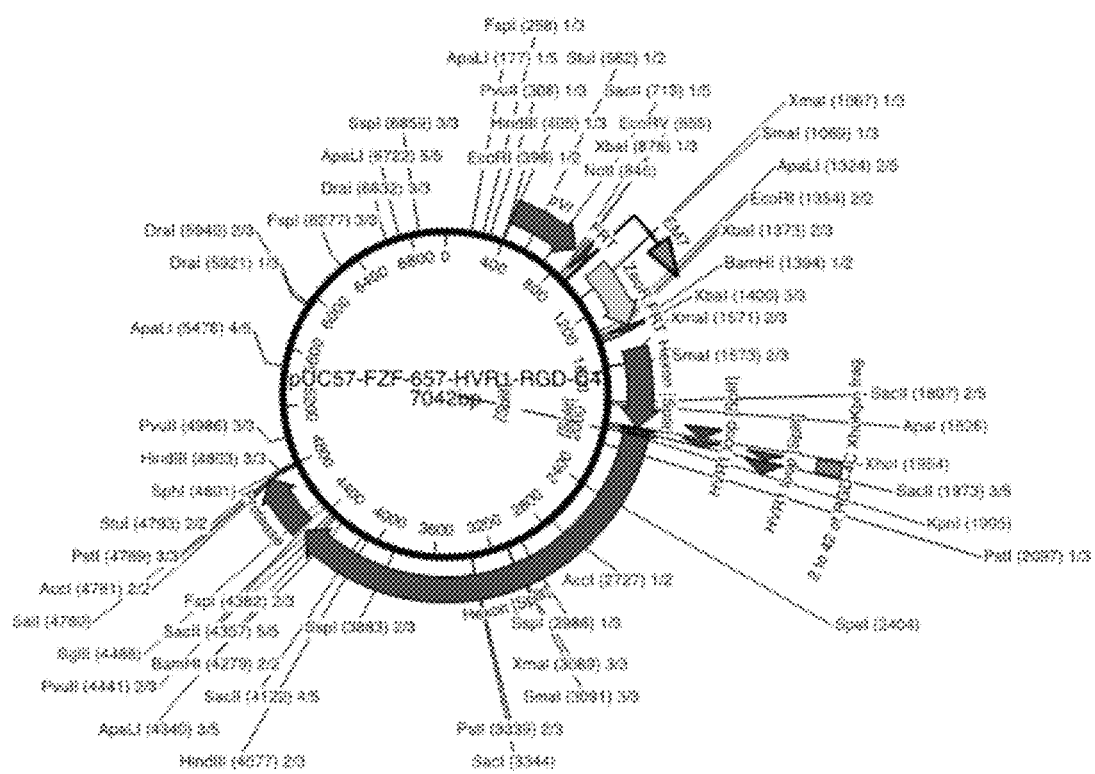
Figure 34:
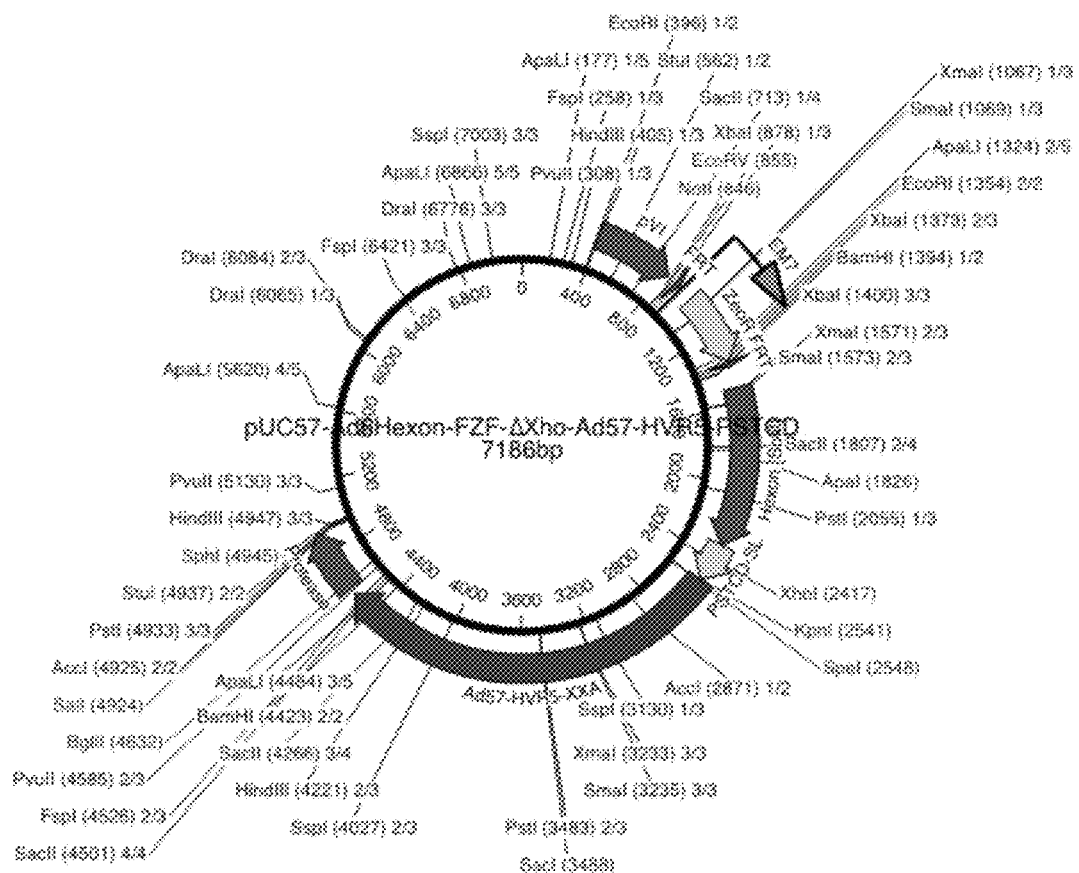
Figure 34:
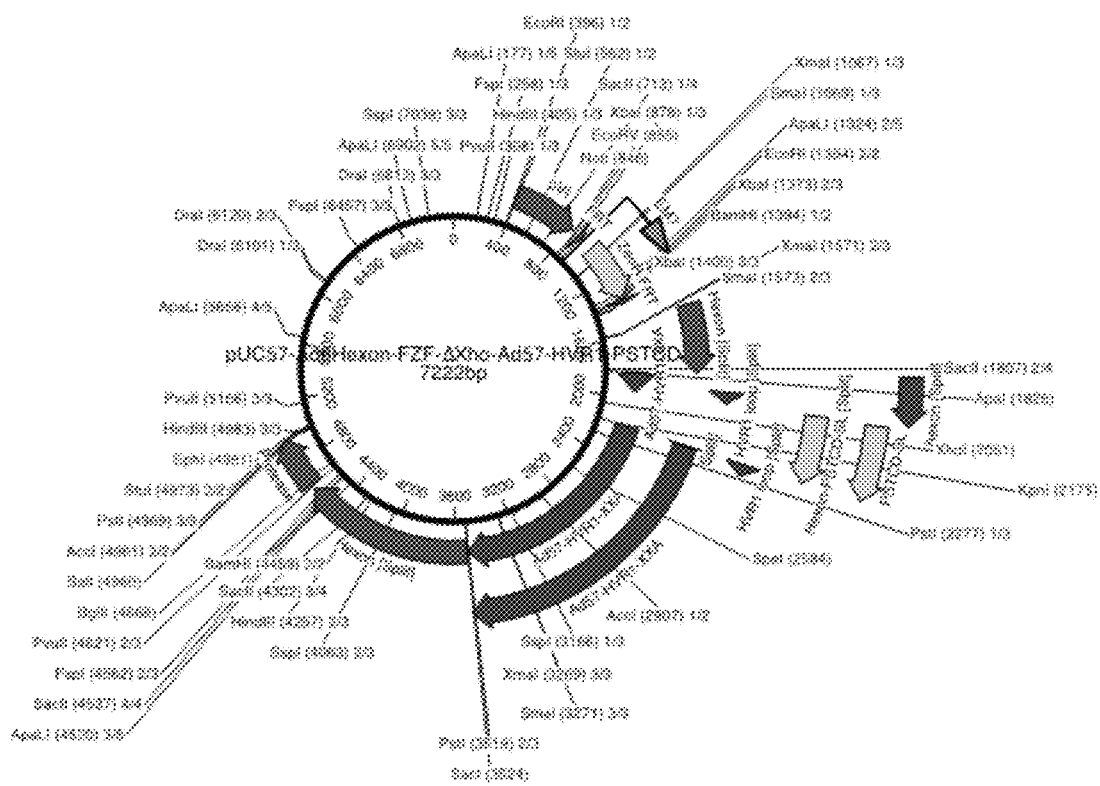
Figure 34:
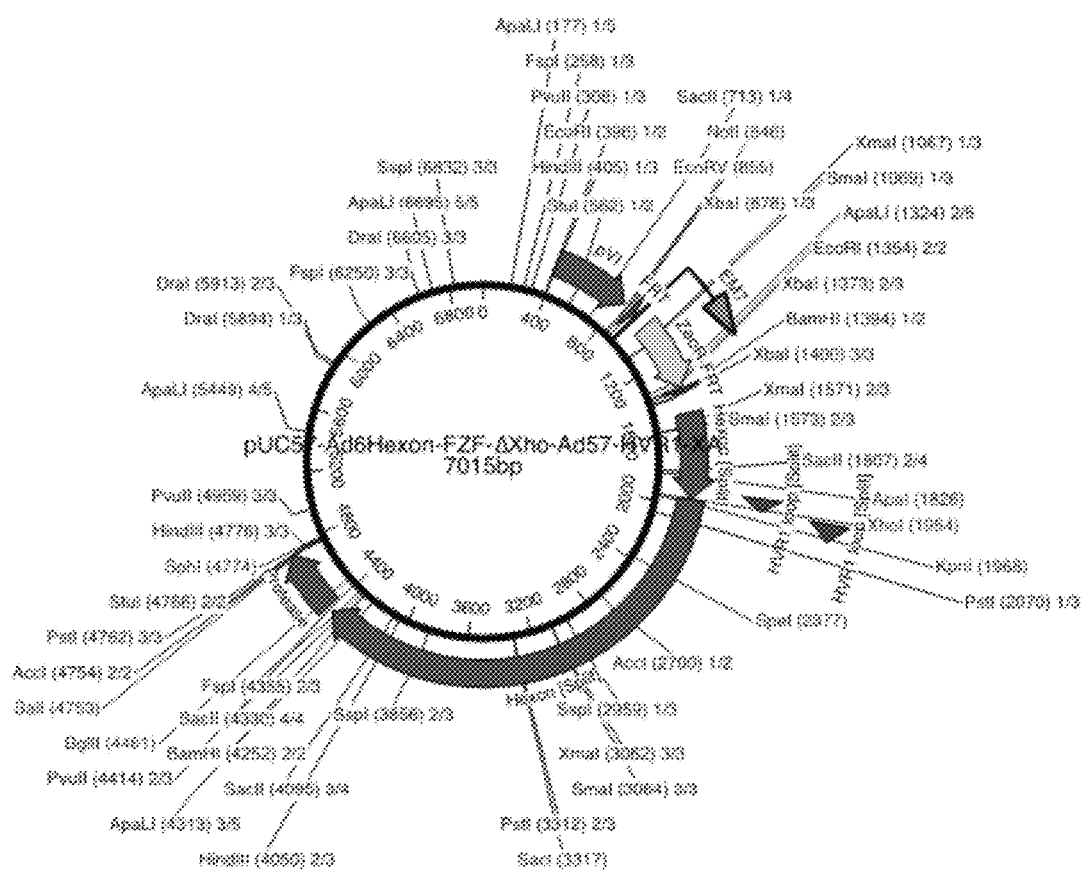
Figure 34:
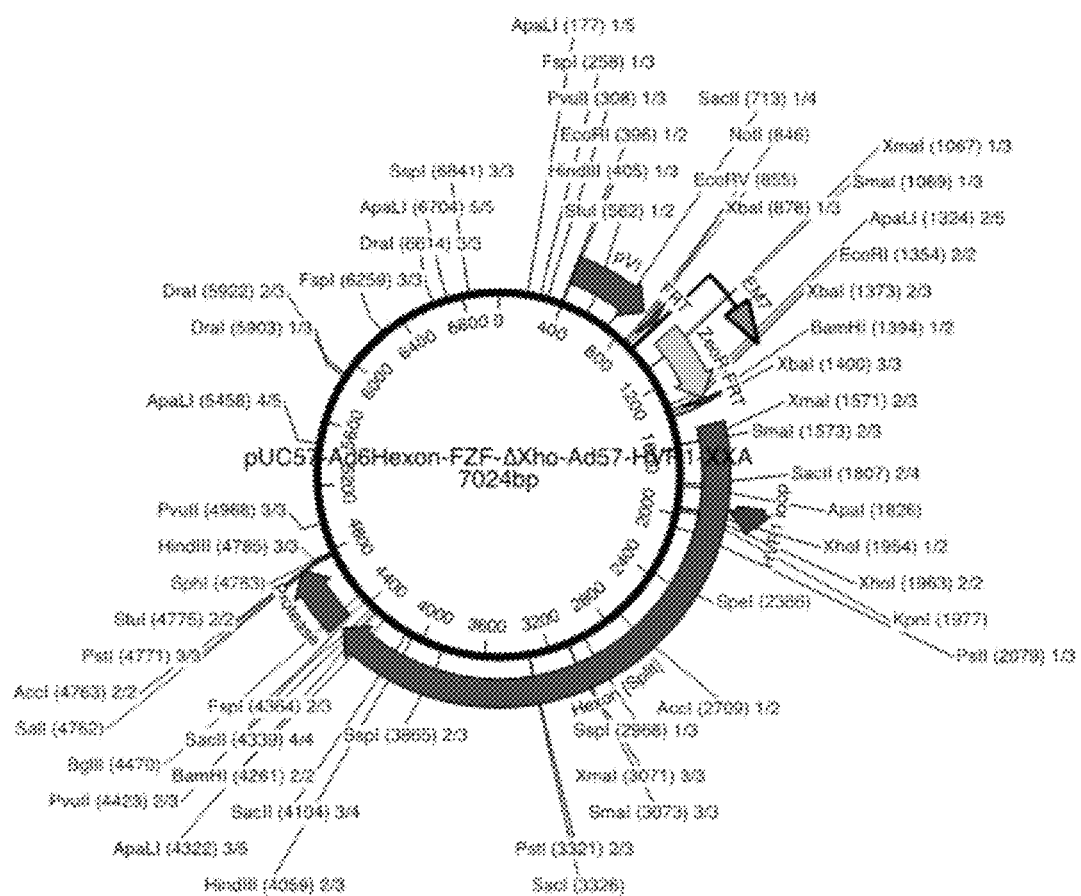
Figure 34:
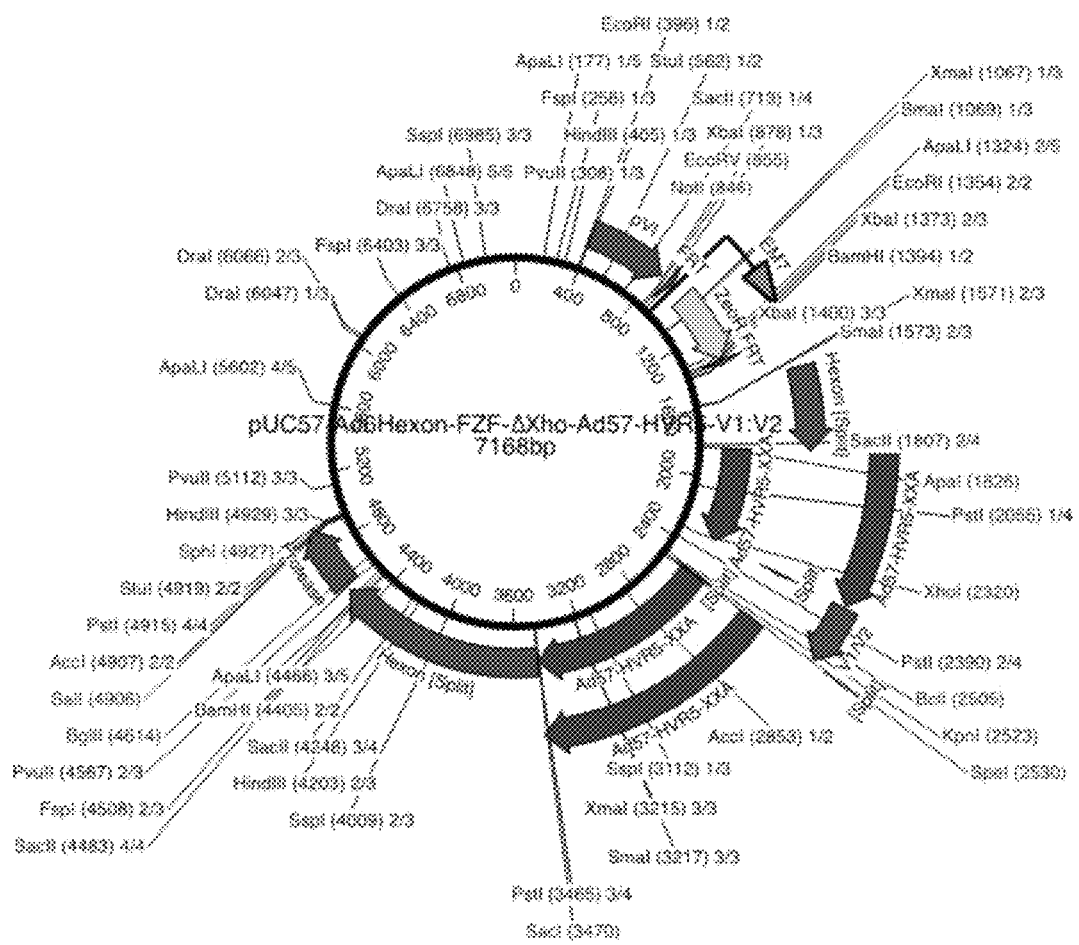

In certain embodiments, cell binding peptides 12.51, VSV, RGD (see Table 1) are inserted into HVR 1 or HVR 5, which embodiments serve as examples of inserting these and other peptides in any of the HVRs of an Ad (FIG. 34). Another example shows insertion of a biotin acceptor peptide (BAP) is inserted into these HVRs allowing for vector retargeting with avidin or streptavidin and biotinylated ligands or with avidin- or streptavidin fusion proteins. BAP insertion also allows the viruses to be purified on monomeric avidin or streptavidin columns for vector production. Likewise, Ad57-HVR1-XXA and XA shows the example of inserting a cysteine into this site to allow targeted chemical modification with maleimide or other cysteine-reactive agents (FIG. 34).

These embodiments have been applied also in the context of Ads which combine different HVRs from different Ads (i.e., shuffling HVRs). For example, HVR1 of Ad6 with HVRs 2-7 of Ad57 or HVR1 and 7 of Ad6 with HVRs 2-6 of Ad57. In a further embodiment, a 6/57/6 virus has HVRs 1 and 7 from Ad6 and HVRs 2-6 from Ad657.

Example 4

Figure 35:
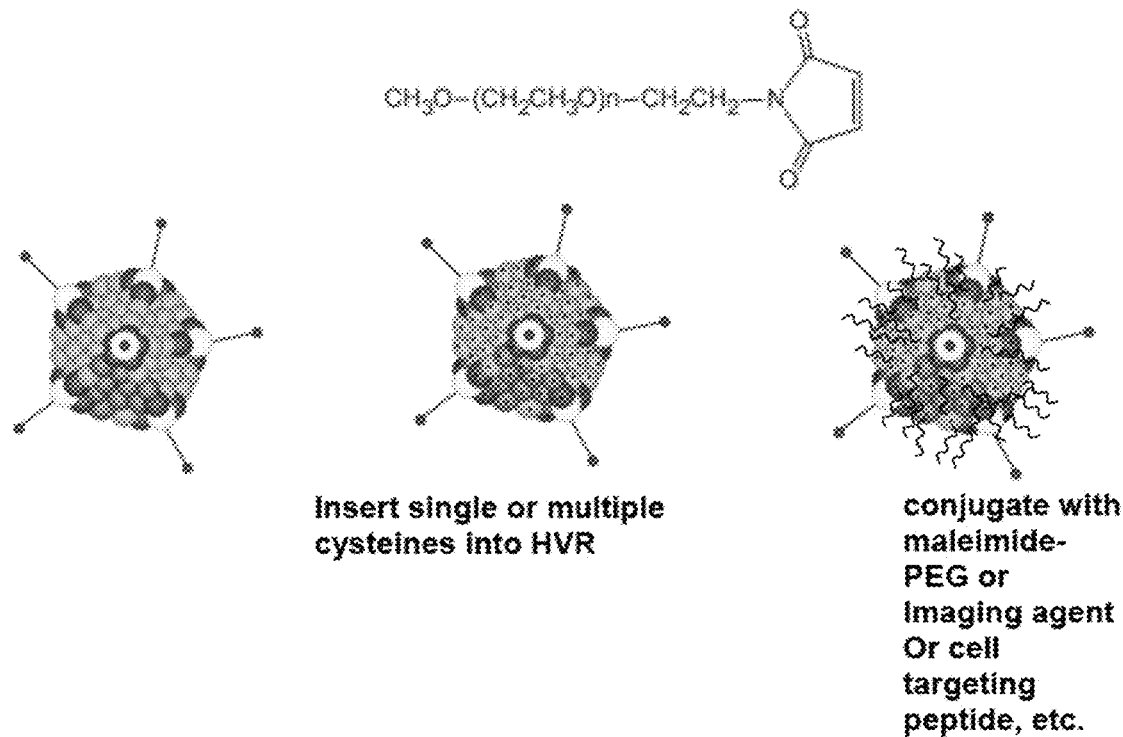
FIG. 35 shows chimeric HVR constructs that combine different HVRs from different Ad serotypes to modulate natural interactions with cells and blood factors improve pharmacology combined with insertion of cell binding and cell detargeting peptides in different HVRs to change cell entry and cell avoidance. In this example, a single cysteine amino acid is inserted into the HVR1 and HVR5 of Ad657 to modulate pharmacology and allow targeted conjugation of polymers like polyethylene glycol or other moieties like imaging agents like fluorophores.

Targeted Chemical Conjugation of Cysteine-modified Hexon-modified Ad657-HVR5C FIG. 35 is a depiction of Ad variants showing the combination of insertion of individual HVRs from different Ad serotypes with the insertion of novel amino acids such as cysteine into the hexon for targeted chemical modification and shielding.

Comparison of the effects of non-targeted chemical conjugation to targeted chemical conjugation on shielding and function of cysteine-modified hexon-modified Ad657-HVR1C (FIG. 36). This example demonstrates the ability to target polymer and other chemical modifications to cysteines inserted into an Ad hexon. Untargeted PEG inactivates virus infection whereas cysteine-targeting PEGylation retains virus functions.

Figure 54:
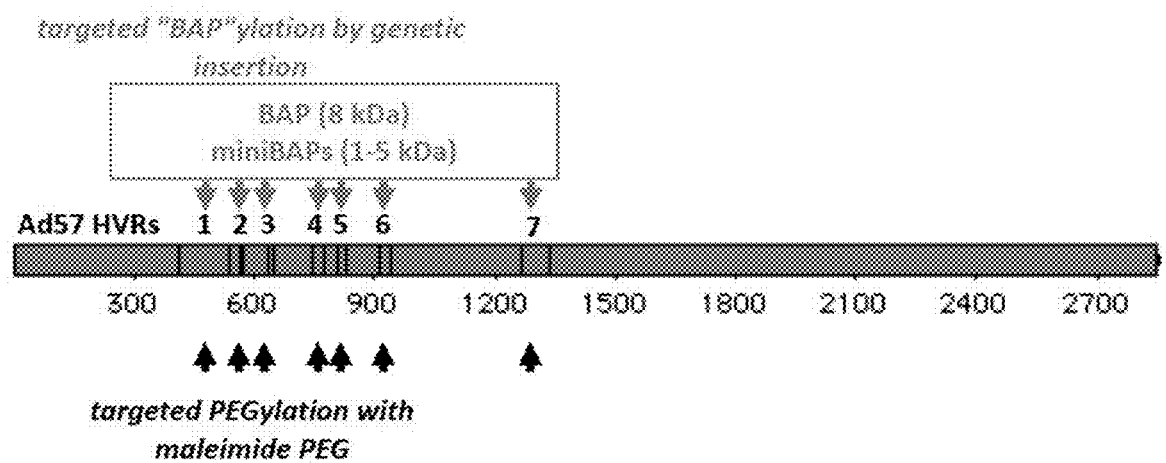
FIG. 54 depicts sites on Ad HVRs which may be modified, for example, by PEGylation or "BAPylation" with biotin acceptor peptides (BAPs).

In an aspect of the invention, the use of polymers or inserted peptides/proteins to detarget, retarget, and shield from antibodies, proteins, cells is contemplated. FIG. 54 depicts sites of Ad HVRs which may be modified, for example, by PEGylation or "BAPylation".

In an embodiment, the different Ad serotypes and/or variants comprise polymer shielding to allow multi dosing of Ad6 and Ad657 variants. An exemplary therapeutic cycle where Ad6 and Ad657 can be used for multiple rounds of treatment by serotype-switching in combination with covalent polymer conjugation is shown (FIG. 41B).

Ad657-HVR1C expressing GFPLuciferase was produced from a cells and purified on CsCl gradients. The virus was covalently modified with 5 kDa polyethylene glycol (PEG). The virus was treated with either NHS-PEG that reacts randomly with amines/lysines on viral proteins or with maleimide PEG that reacts specifically with cysteine that was inserted into HVR1 using the XXA shuttle plasmid. These unmodified or modified viruses were then purified by a final CsCl spin followed by desalting. The indicated virus were separated on SDS-PAGE gels, stained with Sypro-Ruby, and visualized by imaging (FIG. 36A). This shows that NHS-PEGylation randomly modifies many viral proteins as demonstrated by increases in the apparent mass of the proteins (indicated by arrows). In contrast, targeted maleimide PEG reaction with the cysteine in HVR1 modifies only hexon and does not damage other viral capsomer proteins. The effects of PEGylation on virus function was evaluated.

The indicated viruses were incubated with A549 cells and their ability to infect the cells was measured by luciferase assay. This shows that random NHS-PEGylation reduces virus activity more than 90% whereas maleimide-PEG does not (FIG. 36B).

Figure 58:
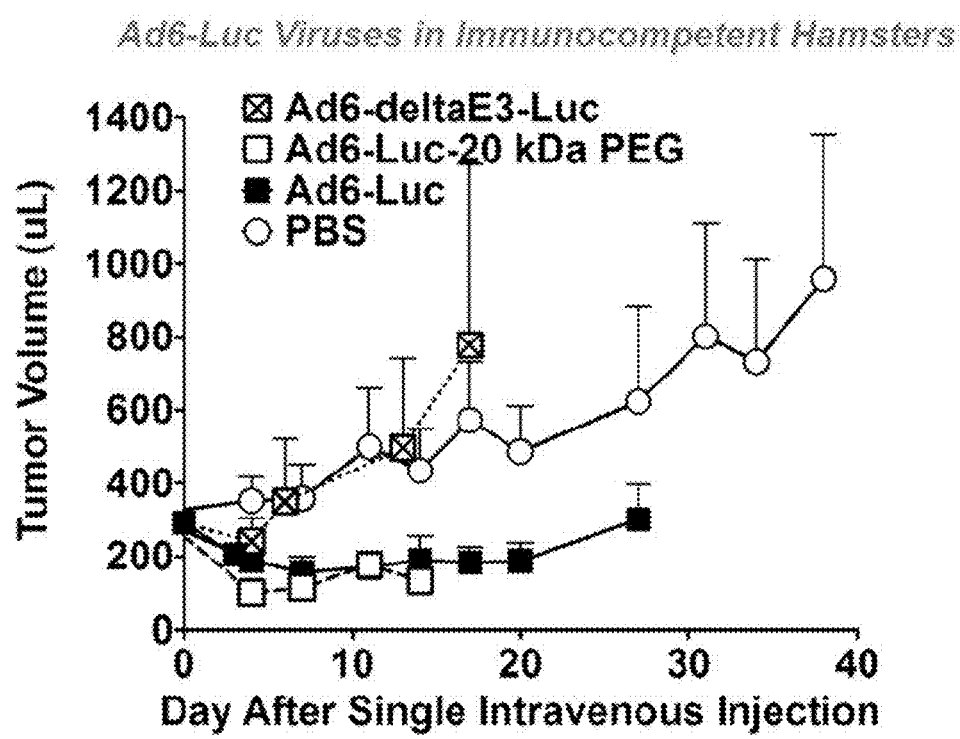
FIG. 58 demonstrates the effects of PEGylation and E3 deletion on oncolytic viral anti-tumor activity by Ad6-Luc viruses in immunocompetent hamsters. Ad6-Luc and Ad6-Luc-20K PEG both have all E3 genes and E4 34K intact. Ad6-deltaE3-Luc has partial deletion of E3 12.5K and E4 34K and full deletion of E3 6.7K, 19K, 11.6K (ADP), 10.4K (RIDα), 14.5K (RIDβ), and 14.7K genes. Oncolytic efficacy is lost in this immunocompetent animal model when these immune evasion genes are not present in oncolytic adenovirus.

Immune competent Syrian hamsters were engrafted with subcutaneous HaK kidney cancer tumors. When these reached 200 µl volume, they were injected a single time by the intravenous route with the indicated Ad6 viruses constructed with and without E3 (DE3) and with or without random NHS-PEGylation. Tumor sizes were measured over time. The data shows that deleting all E3 genes in the oncolytic virus Ad6-deltaE3-Luc makes the virus less effective at reducing tumor volume than the oncolytic parent virus, Ad6-Luc. The data also shows that Ad6 can be PEGylated and retain efficacy (see Ad6-Luc vs. Ad6-Luc-20 kDa PEG) (FIG. 58).

Figure 50:
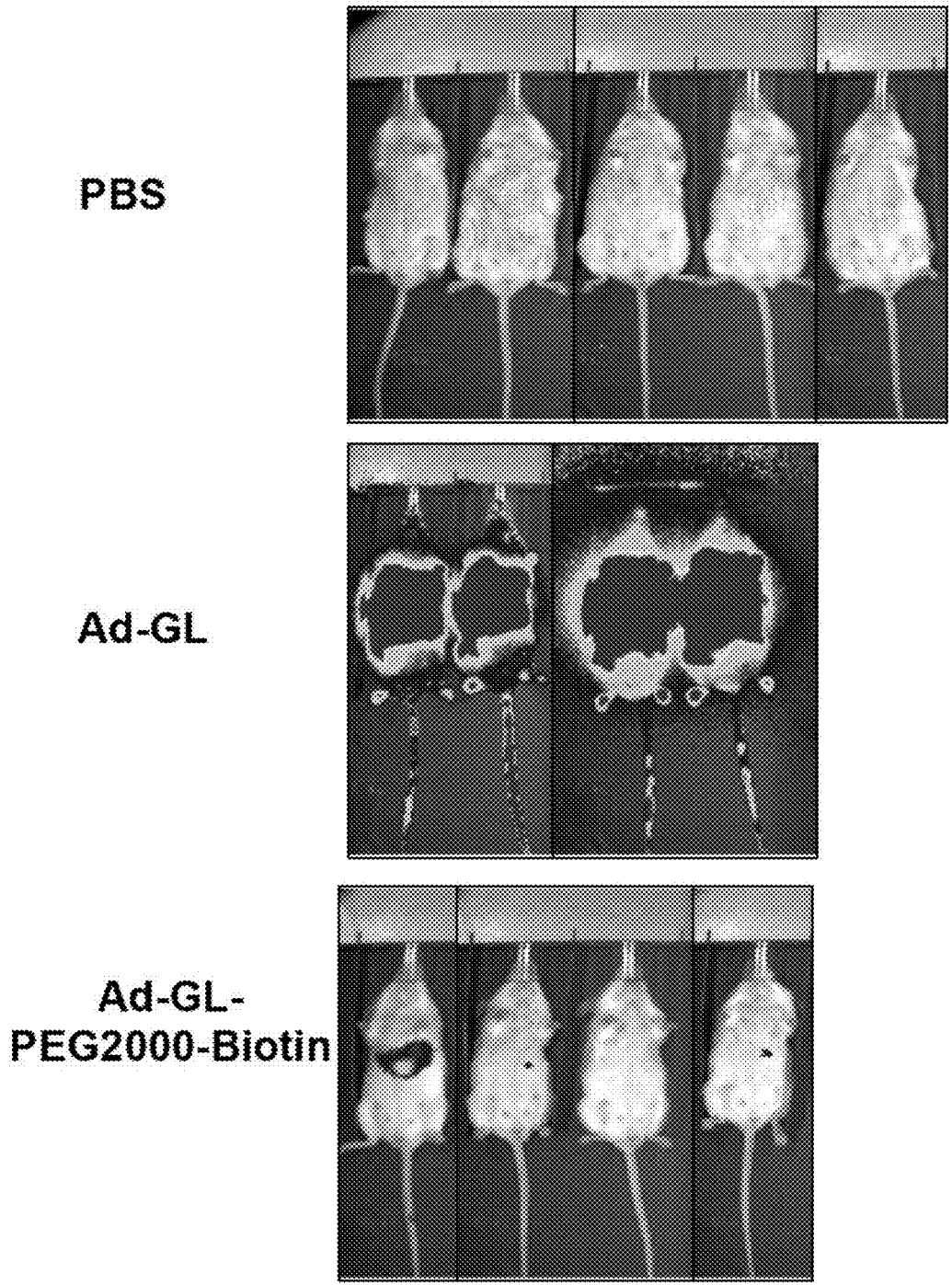
FIG. 50 demonstrates that PEGylation de-targets adenovirus to liver in vivo.

Targeted chemical conjugation of cysteine-modified hexon-modified Ads, for example Ad657-HVR5C. Ad657-HVR5C expressing GFPLuciferase was produced from cells and purified on CsC1 gradients. The virus was covalently modified with maleimide-IR800 near-infrared fluorophore, maleimide-biotin, or 5 kDa maleimide-PEG that reacts specifically with cysteine that was inserted into HVR5 using its XXA shuttle plasmid. The indicated Ads and modified Ads were separated on SDS-PAGE gels, stained with Sypro-Ruby, and visualized by imaging (FIG. 37A). SDS-PAGE of viral proteins followed by near infrared imaging demonstrates that the HVR-C can be tagged with an imaging agent (FIG. 37B). The effects of PEGylation on in vivo Ad virus function was demonstrated by injecting PEGylated Ad virus intraperitoneally. The ability to infect cells in tumor bearing mice is demonstrated by detectable luciferase activity by imaging. FIG. 37C demonstrates the ability to target polymer and other chemical modifications to cysteines inserted into the Ad657 hexon region. What is more, it is demonstrated that PEGylation de-targets adenovirus to liver in vivo (FIG. 50).

Example 5

Expression of Human Granulocyte-Macrophage Colony Stimulating Factor (GMCSF) by Ad657

Figure 27:
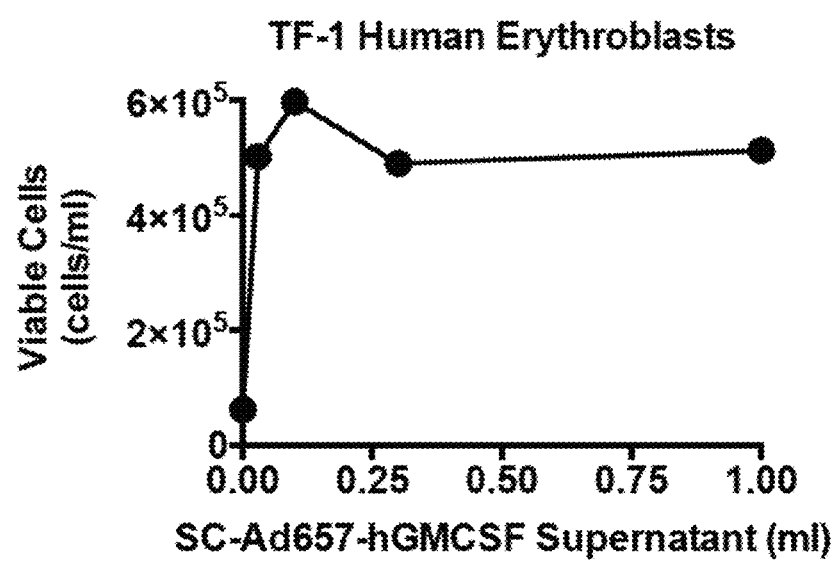
FIG. 27 shows expression of human GMCSF from Ad657 inducing proliferation of GMCSF-dependent TF-1 human erythroblasts.

Ad657 carrying the cDNA for human GMCSF was used to infect A549 cells and varied amounts of the supernatant were added to GMCSF growth-dependent TF-1 cells. Increased cell number indicates expression of the functional human cytokine (FIG. 27). The data demonstrates that recombinant Ads may be utilized for expression of heterologous proteins.

Example 6

Oncolytic Adenovirus Ad657 for Systemic Virotherapy Against Cancer Cells

Figure 6:
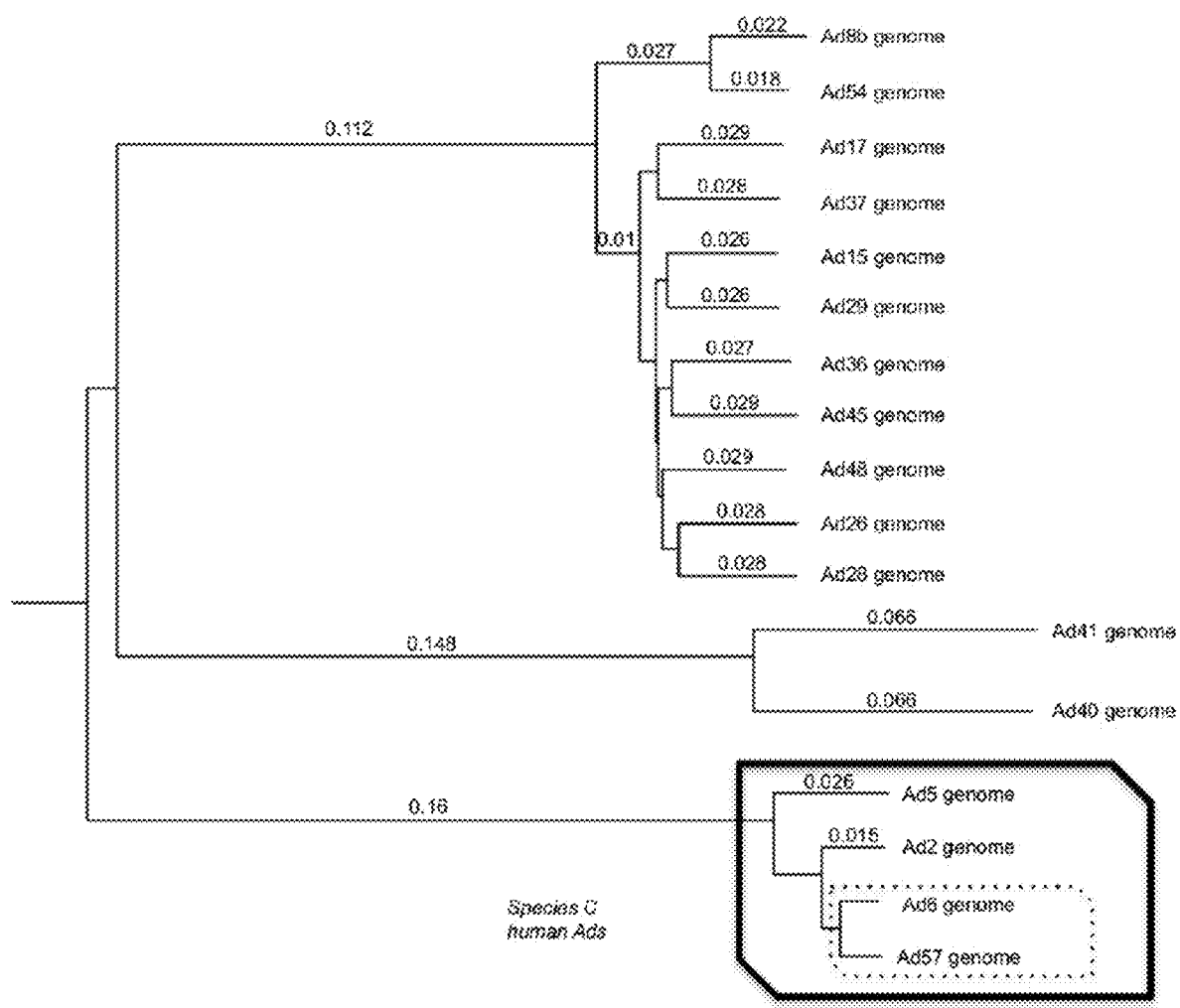
FIG. 6 shows a phylogenetic tree of whole genome sequences of human adenovirus serotypes.

An alignment of selected full Ad genomes produces a phylogenetic tree that clusters Ad57 with other species C viruses with most homology with Ad6 is shown in FIG. 6.

Figure 7:
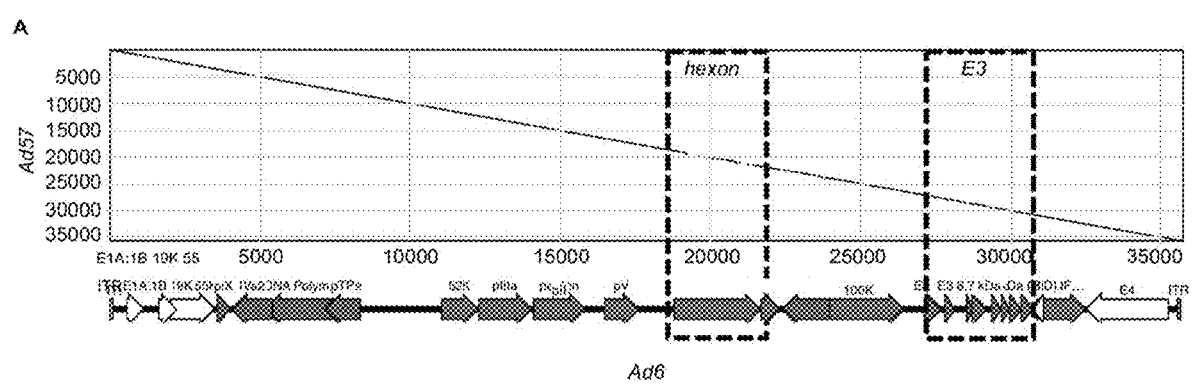
FIG. 7 shows an alignment of Ad5, 6, and 57 showing variation in hexon and E3 regions. (A) A Pustell DNA alignment of the genomes of Ad6 and Ad57. Boxes indicate hexon and E3 regions where variation is highest between the two viruses. (B) ClustalW amino acid alignment of the hypervariable region in hexon proteins from Ad5, Ad6, and Ad57. Alignments were performed on MacVector.

Ad57 appears nearly identical to Ad6 with sequence divergence in hexon hypervariable regions (HVRs) and in E3 immune evasion genes (FIG. 7). Other exposed viral capsid proteins including fiber, penton base, Ma, and IX are virtually identical between Ad6 and Ad57. The neutralization data are consistent with the fact that most adenovirus-neutralizing antibodies target the HVRs on Ads. The low cross-reactivity between Ad6 antisera and Ad57 is thought to be due to antibodies that may target their common fiber protein (Lukashev et al., 2008 *J Gen Virol.* 89:380-388).

In this example, the utility of Ad657 as an oncolytic against human prostate cancer is demonstrated. The Ad6 HVRs were replaced with those from Ad57 to generate a chimeric species C oncolytic virus called Ad657. Ad657 and Ad6 were tested as systemic oncolytic therapies by single i.v. injection in nude mice bearing human prostate cancer tumors. The liver and tumor tropism of this virus were evaluated in mouse models of prostate cancer as follows.

DU145 human prostate carcinoma cells were purchased from American Type Culture Collection (ATCC; Manassas, Va., USA) and verified to be specific pathogen free by IMPACT testing by RADIL. 293 cells were obtained from Microbix, Toronto, Ontario, Canada. Cells were maintained in DMEM with 10% FBS (Invitrogen, Grand Island, N.Y., USA).

Figure 59:
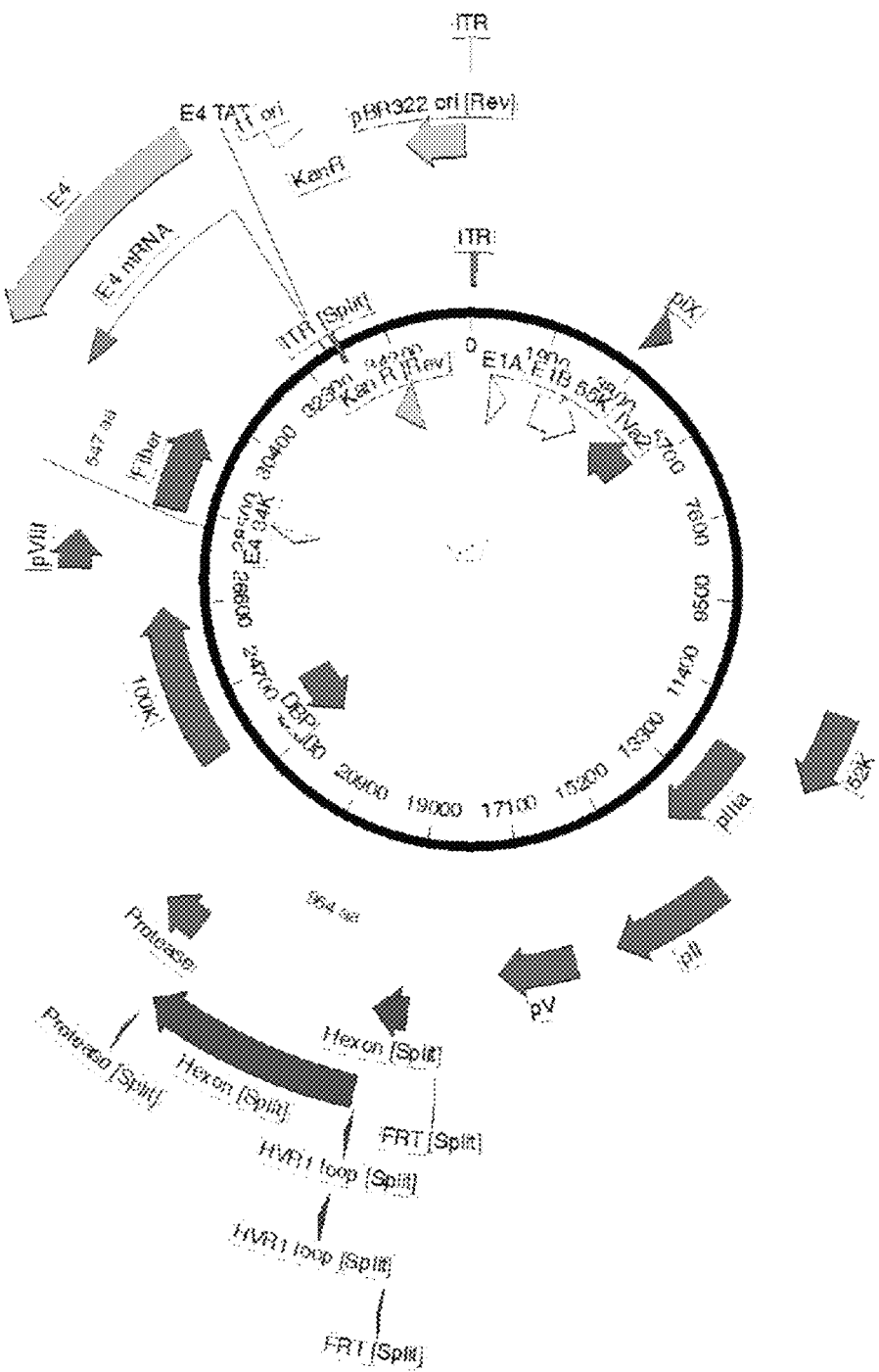
FIG. 59 is a plasmid map of Ad657 with partial deletion of E3 12.5K and E4 34K and full deletion of E3 6.7K, 19K, 11.6K (ADP), 10.4K (RIDα), 14.5K (RIDβ), and 14.7K genes.
Figure 60:
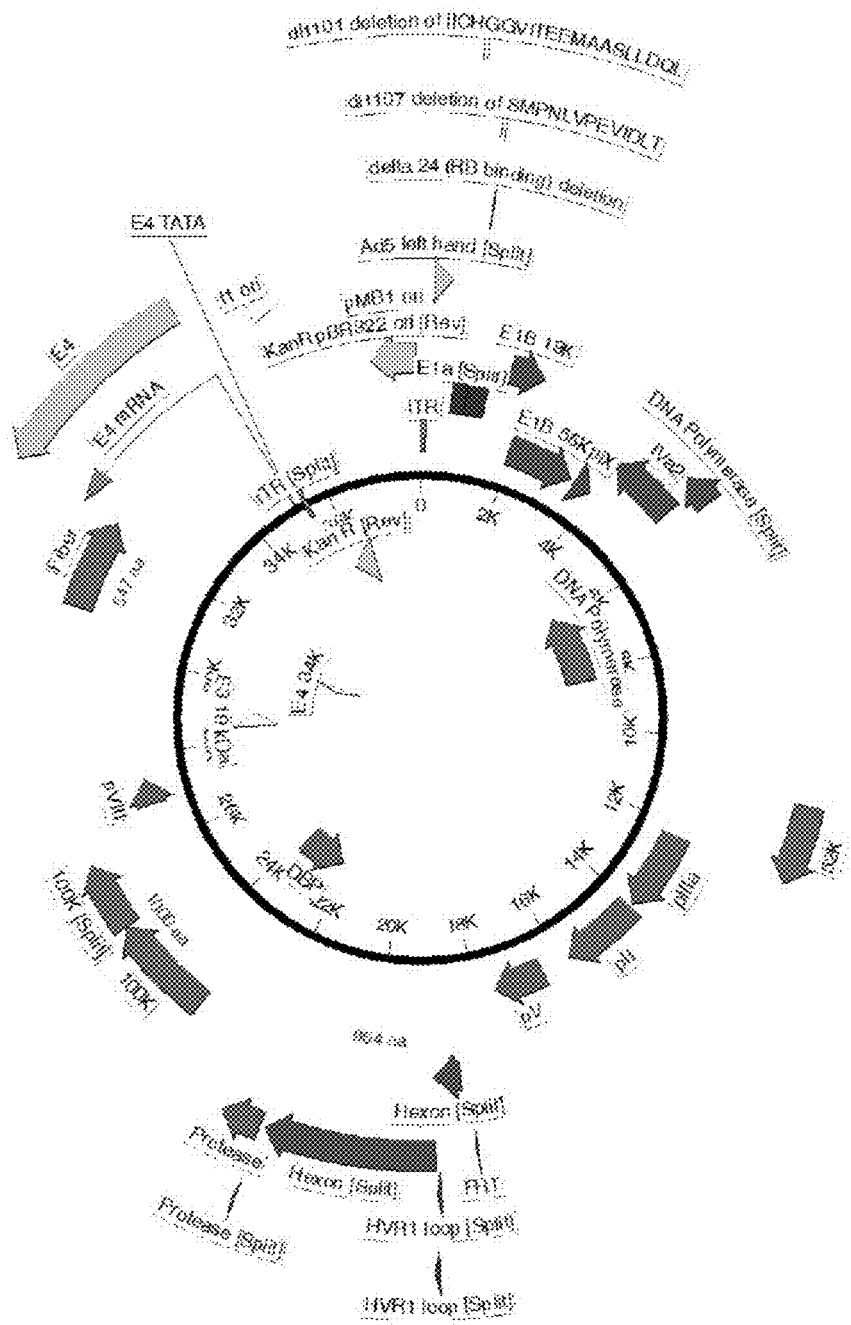
FIG. 60 depicts CRAd 657 constructs with and without dl1101/1107 CRAd modifications and with and without deletions of selected E3 immune evasion genes.
Figure 61:
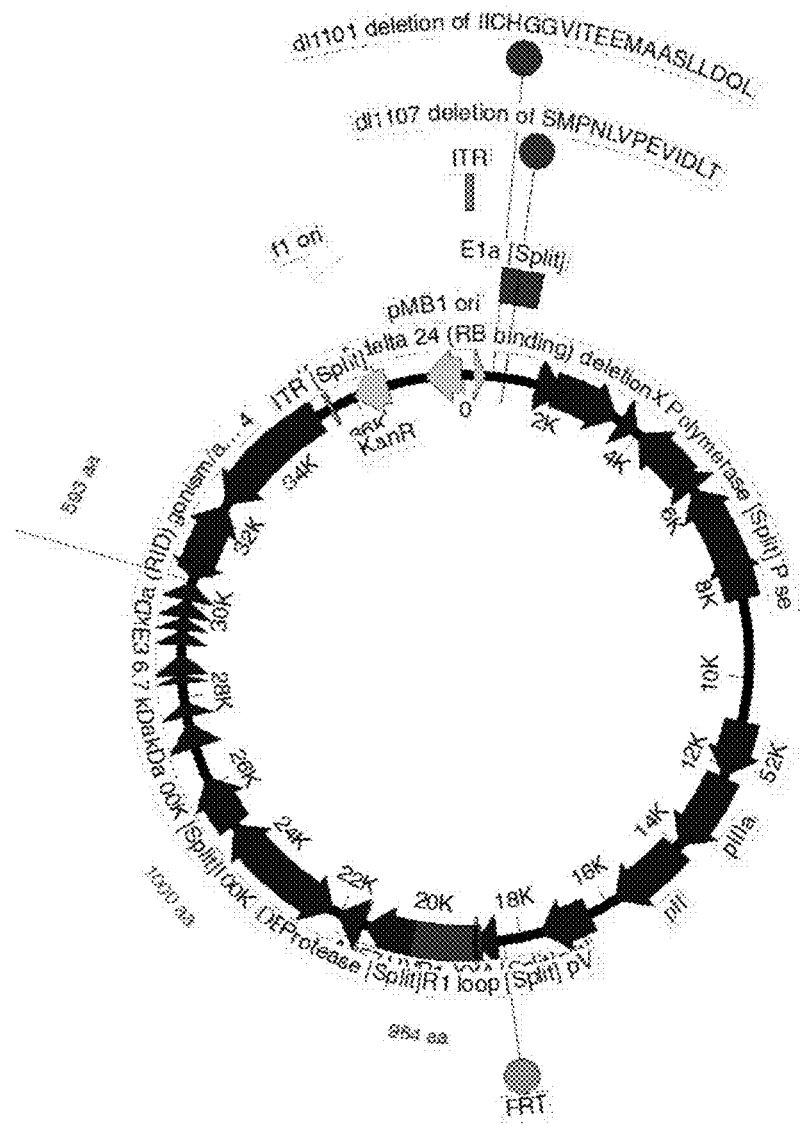
FIG. 61 depicts CRAd657 with E3 insertion site. These are with and without dl1101/1107 CRAd modifications described herein and with and without E3 immune evasion modifications.
Figure 62:
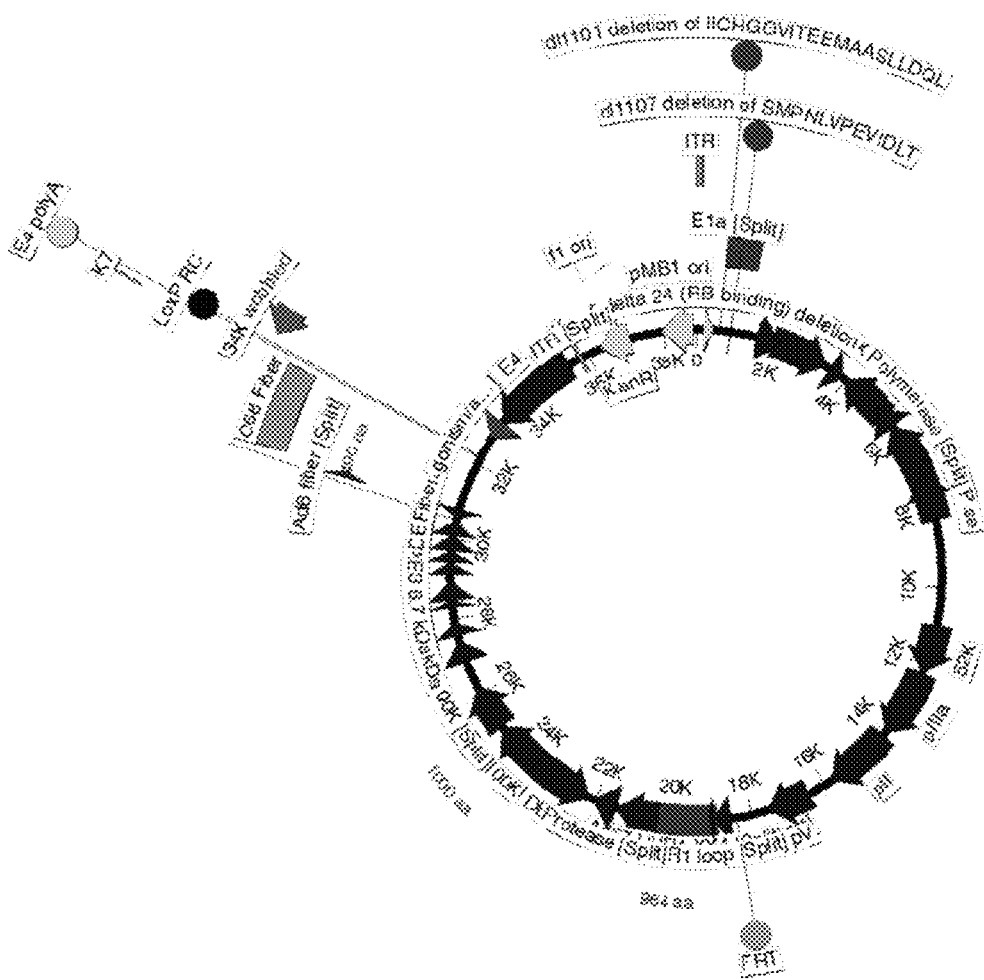
FIG. 62 depicts CRAd657+/−Ad35 Fiber or Chimpanzee C68 Fiber+/−K7 peptide. These are with and without dl1101/1107 CRAd modifications described in previous slides and with and without E3 immune evasion modifications. In some cases, a codon-wobbled E4 34K gene is included after E4 and before fiber to compensate for E4 34K partial deletion when deleted E3B genes.
Figure 63:
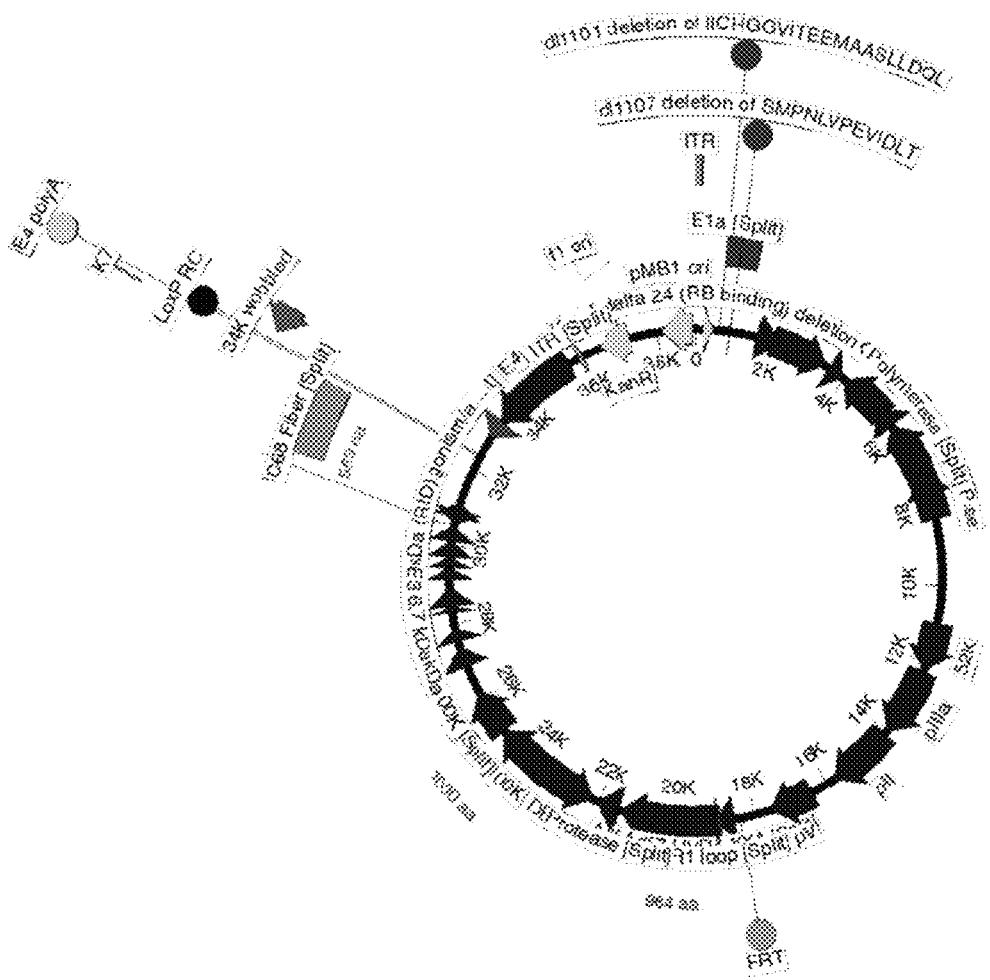
FIG. 63 depicts CRAd657+/−Ad35 Fiber or Chimpanzee C68 Fiber+/−K7 peptide. These are with and without dl1101/1107 CRAd modifications described in previous slides and with and without E3 immune evasion modifications.
Figure 64:
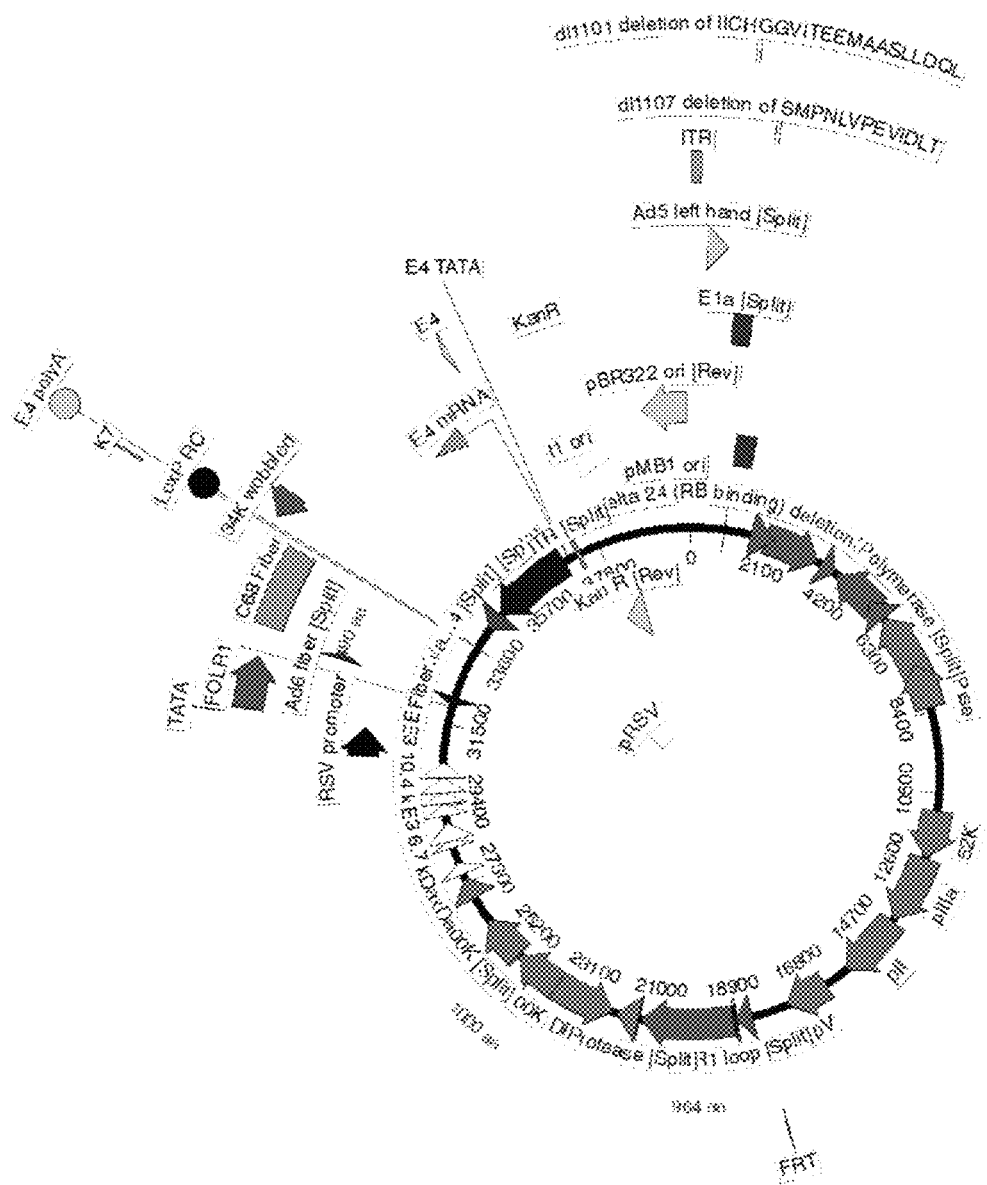
FIG. 64 depicts CRAd657+/−Ad35 Fiber or Chimpanzee C68 Fiber+/−K7 peptide Expressing Folate Receptor alpha.
Figure 65:
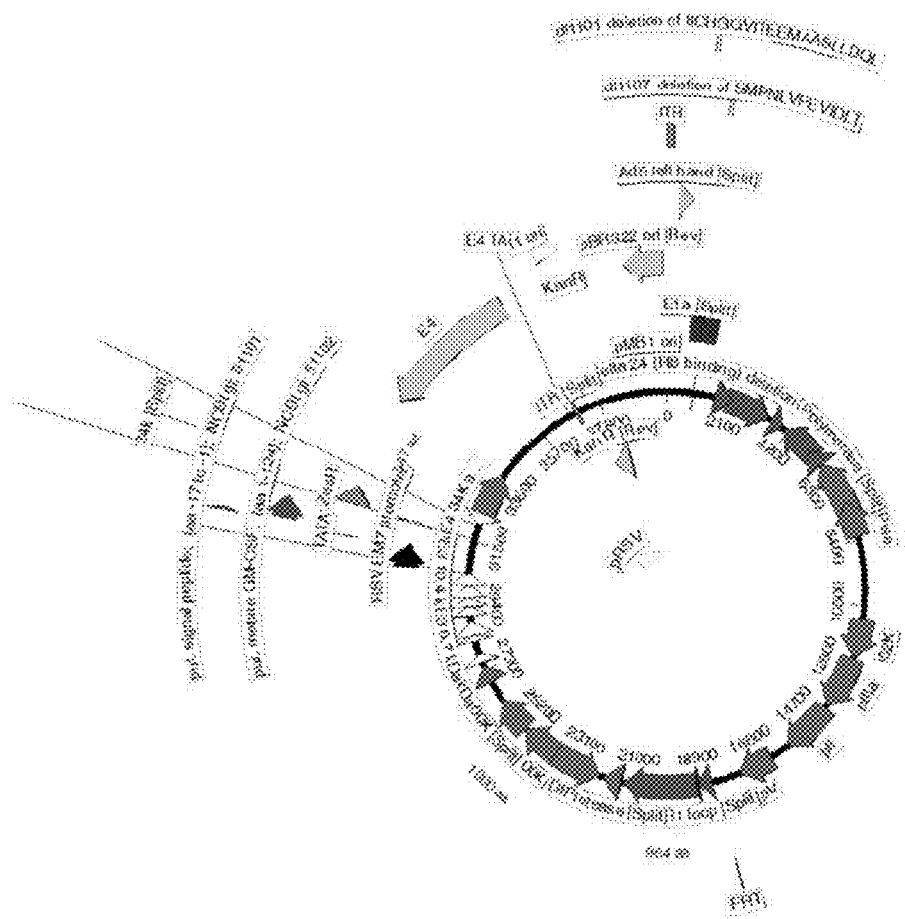
FIG. 65 depicts CRAd657+/−Ad35 Fiber or Chimpanzee C68 Fiber+/−K7 peptide Expressing Granulocyte Macrophage Colony Stimulating Factor (GMCSF).
Figure 66:
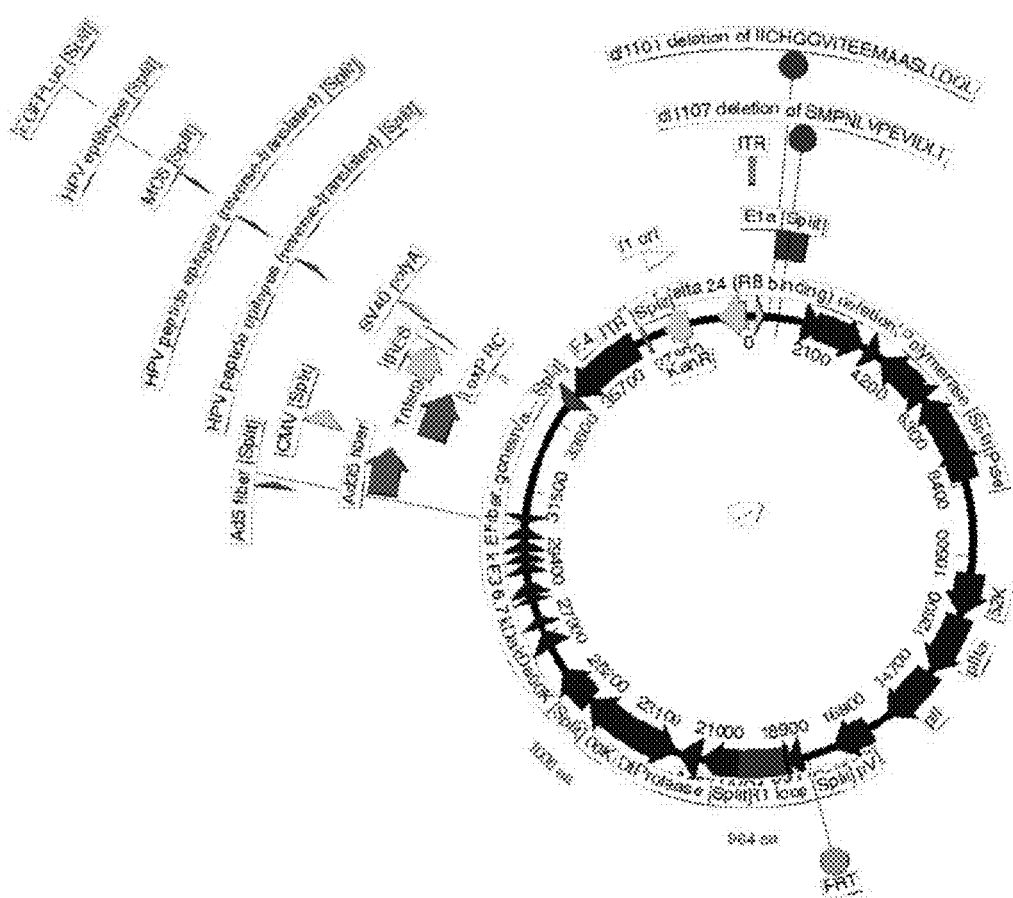
FIG. 66 depicts CRAd657+/−Ad35 Fiber or Chimpanzee C68 Fiber+/−K7 peptide Expressing 4-1BBL or GMCSF or IL21 or CD40L and combinations in one virus.
Figure 67:
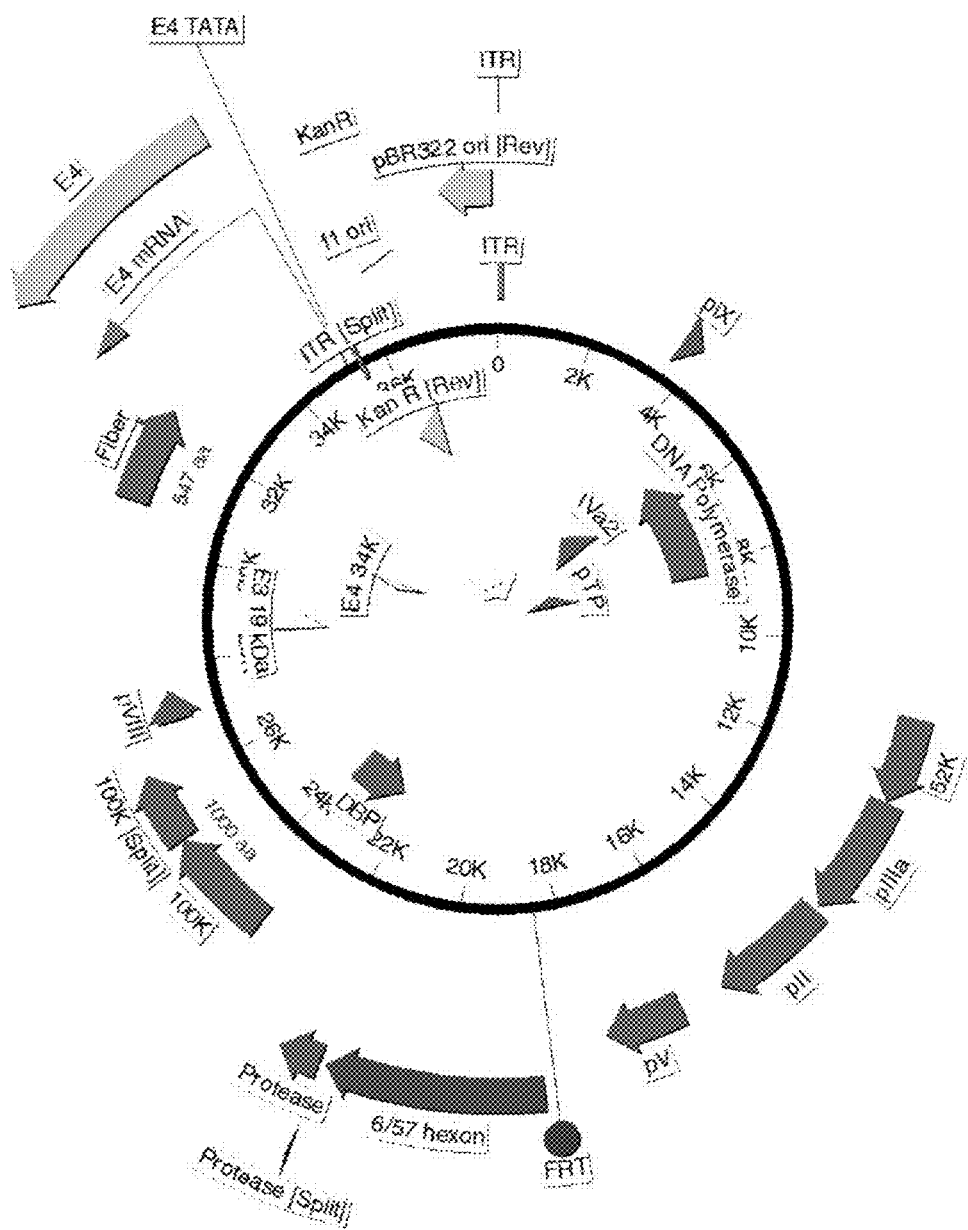
FIG. 67 depicts Ad6/57 with Ad6 HVR1 and Ad57 HVRs2-7+/−Ad35 Fiber or Chimpanzee C68 Fiber+/−K7 peptide.
Figure 68:
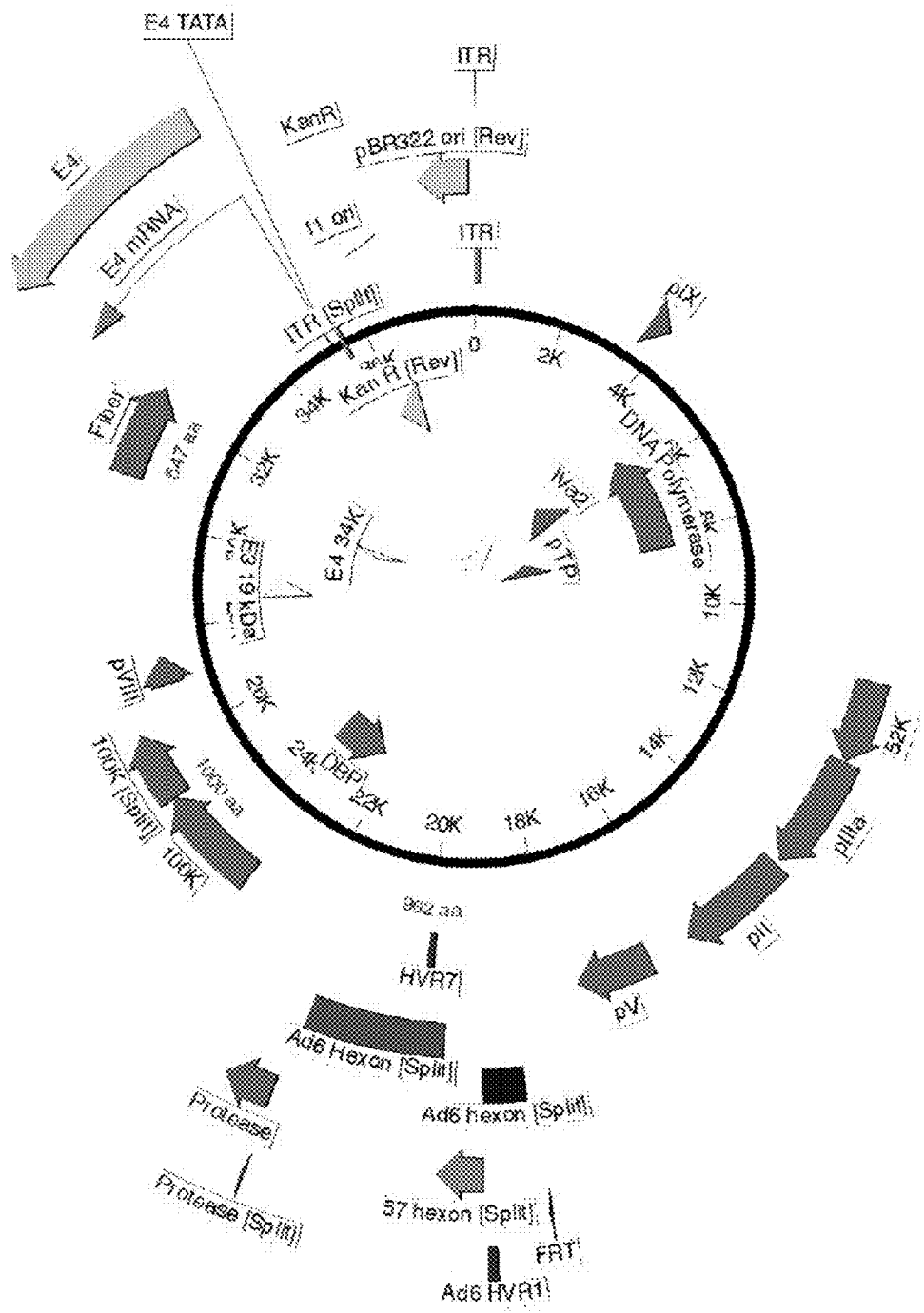
FIG. 68 depicts Ad6/57/6 with Ad6 HVR1, Ad57 HVRs2-6, Ad6 HVR7+/−Ad35 Fiber or Chimpanzee C68 Fiber+/−K7 peptide.
Figure 69:
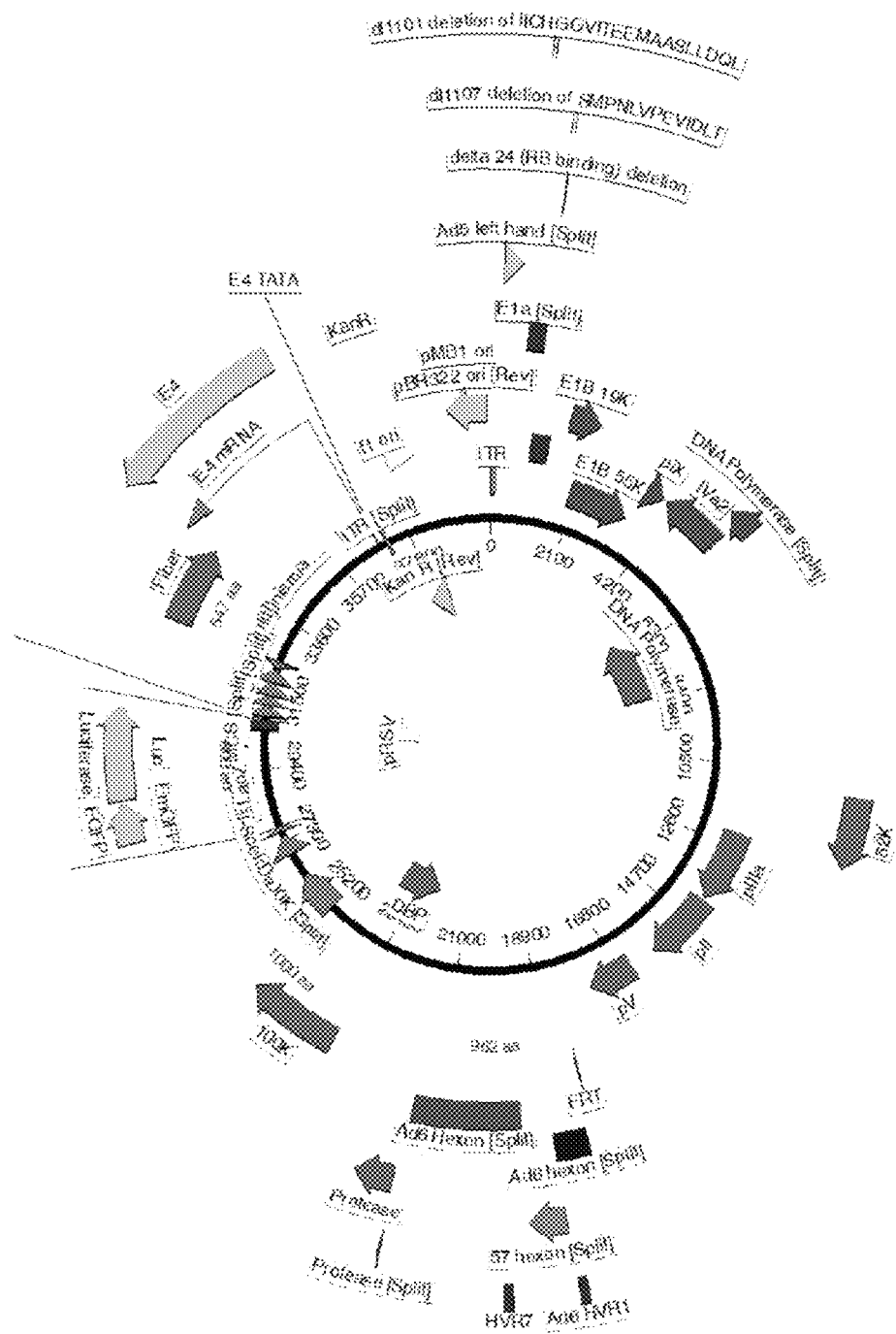
FIG. 69 depicts Ad6/57/6 with Ad6 HVR1, Ad57 HVRs2-6, Ad6 HVR7+/−Ad35 Fiber or Chimpanzee C68 Fiber+/−K7 peptide expressing GFPLuciferase.

The genome of Ad6, Tonsil 99 strain (ATCC VR-1083), was cloned as described elsewhere (see, e.g., Weaver et al., 2013 *PLoS One.* 8:e73313). A cassette corresponding to the Ad57 hexon between a natural ApaI and SacI sites was synthesized by Genscript. This fragment was cloned into the shuttle plasmid pUC57-Ad6 Hexon-FZF containing the Ad6 pVI and hexon genes with a FRT-Zeocin® resistance gene-FRT cassette between them for homologous recombination in bacteria as described elsewhere (see, e.g., Campos et al., 2004 *Hum Gene Ther.* 15:1125-1130; and Khare et al., 2012 *J Virol.* 86:2293-2301). The Ad6 ApaI-SacI fragment was replaced with the Ad57 fragment generating the plasmid pUC57-Ad6/57 Hexon-FZF. This was recombined into the Ad6 genome by red recombination (Campos et al., 2004 *Hum Gene Ther.* 15:1125-1130). FIG. 59 shows a plasmid map of Ad657 with E3 deletion. Viruses were rescued by transfection into 293 cells and produced from a 10 plate CellStack (Corning Life Sciences, Lowell, Mass., USA). Viruses expressing a green fluorescent protein-luciferase (GFP-Luc) fusion protein have a CMV-GFP-Luc expression cassette inserted between the Ad fiber and E4 and an E3 deletion to make space for this insertion. Viruses were purified on two CsCl gradients, and viral particle (vp) numbers were calculated by OD260.

To examine in vitro oncolytic activity, cells were treated at the indicated multiplicities of infection (MOI) in terms of vp/cell in DMEM with 5% FBS and antibiotic-antimycotic (Invitrogen, Grand Island, N.Y., USA). Five days later, media was removed and the cells were treated with crystal violet (0.05% crystal violet, 3.7% formaldehyde, in phosphate-buffered saline; Invitrogen, Grand Island, N.Y., USA) for 10 minutes. The cells were washed twice with PBS and then incubated overnight at 37° C. in 0.1% sodium dodecyl sulfate in PBS to solubilize the crystal violet. Crystal violet absorbance was measured at OD595 on a Beckman Coulter DTX 880 plate reader. Cell viability (%) was calculated by dividing the OD of the samples by the mean OD of untreated control cells on the same 96-well plate and multiplying this number by 100.

Animals were housed in the Mayo Clinic Animal Facility under Association for Assessment and Accreditation of Laboratory Animal Care guidelines. The studies were approved by the Mayo Clinic Animal Use and Care Committee under the provisions of the Animal Welfare Act, PHS Animal Welfare Policy. Subcutaneous tumors were initiated in 4-week-old nude mice (Harlan Sprague Dawley, Indianapolis, IN, USA) by injecting subcutaneously (s.c.) with $1 \times 10^7$ DU145 cells in 100 μL of DMEM/50% Matrigel (BD Biosciences, San Jose, Calif., USA). Tumor volumes were calculated using the equation width$^2$×length×½. When tumors reached ~200 μL in volume, mice were distributed into different groups and were treated by a single i.v. injection tail vein. Animals were euthanized when the tumor volume reached 2000 μL or if animals were moribund, in distress, or if the skin ruptured over the tumor.

For blood alanine aminotransferase (ALT) measurements, groups of six C57BL/6 mice were injected i.v. with $10^{11}$ vp of Ad5, Ad6, or Ad657 by tail vein and blood was collected 3 days later for ALT measurement using ALT Activity Assay (Sigma-Aldrich, St. Louis, Mo., USA).

Statistical analysis was performed with Prism (Graphpad) by repeated measures ANOVA or one-way ANOVA followed by Tukey's HSD test. Kaplan-Meier survival curves were plotted and compared by log rank test.

Figure 8:
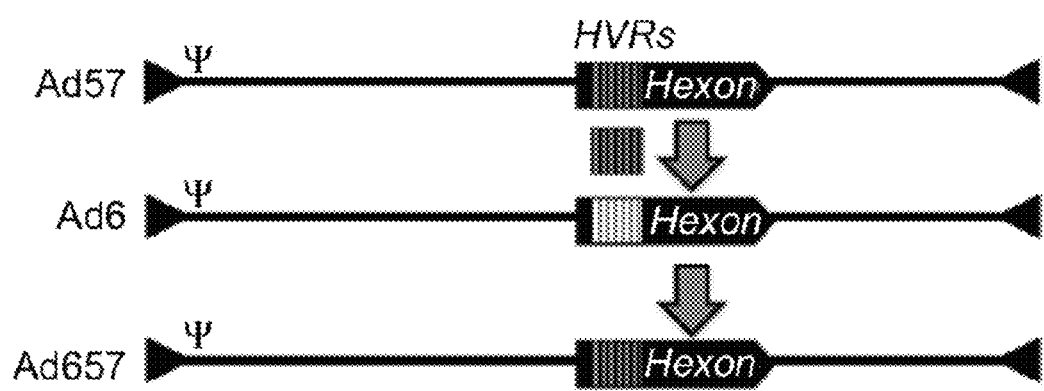
FIG. 8 shows a cartoon of the construction of Ad657 by replacement of the Ad6 HVRs with Ad57 HVRs. Abbreviation: HVRs, hypervariable regions.

The capsomer genes of Ad57 are nearly identical to Ad6 with the exception of their hexon HVRs (FIGS. 6 and 7). To generate a chimeric virus of Ad57 and Ad6, a cassette corresponding to the Ad57 hexon HVRs was recombined into the wild-type Ad6 genome (FIG. 8). This virus was rescued and produced in 293 cells and purified on CsCl gradients. Given that the base viral genome is Ad6, these hexon chimeric viruses are referred to as Ad657 (FIG. 59).

Figure 10:
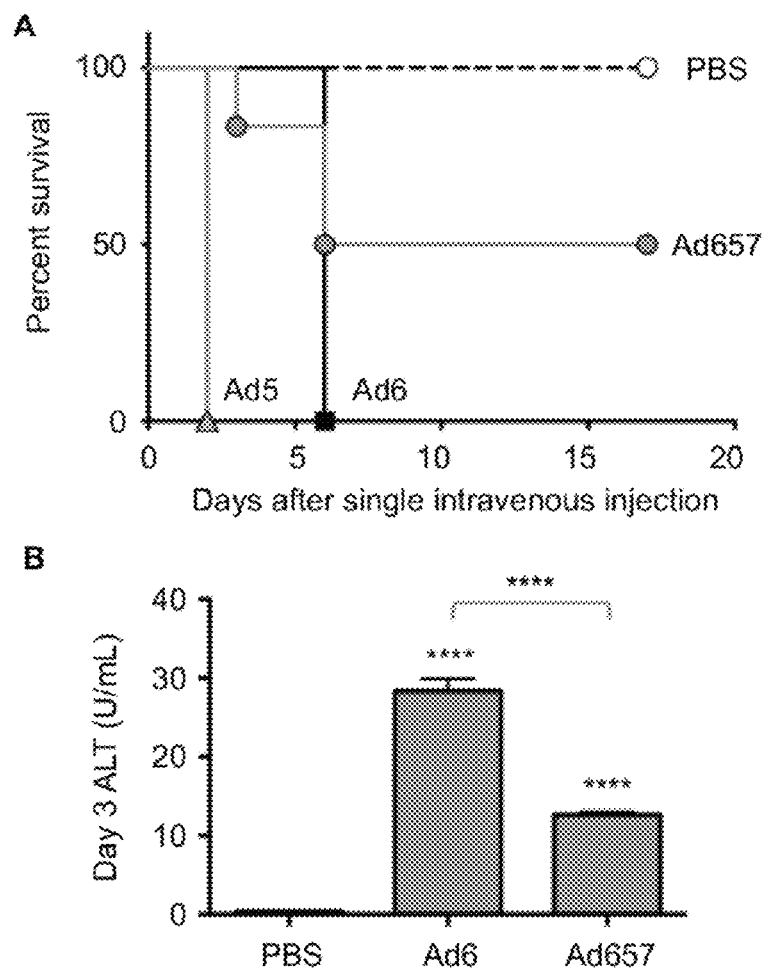
FIG. 10 shows effects of oncolytic Ads on liver damage. C57BL/6 mice (n=6 per group) were injected with 1011 vp of each virus by tail vein. (A) Kaplan-Meier survival. (B) Blood was drawn for ALT measurements 3 days after injection (****p<0.001 by ANOVA). Abbreviations: ALT, alanine aminotransferase; vp, viral particle.

In vitro oncolytic activity was evaluated by infecting LNCap and DU145 cells with 10, 100 or 1000 vp/cell. To compare liver damage by Ad5, Ad6, and Ad657, a high dose of $10^{11}$ vp of each virus were injected by tail vein into immunocompetent C57BL/6 mice. Ad5-injected animals became moribund within 2 days and had to be euthanized (FIG. 10A). Survival for Ad5 and Ad6 was significantly lower when compared with PBS (p=0.0001 and 0.0009, respectively, by log-rank analysis). Survival for Ad657 was also reduced when compared with PBS (p=0.0578). Survival after exposure to Ad6 or Ad657 was significantly better than in Ad5-treated mice (p=0.0001 and 0.0001, respectively). Ad6 and Ad657 survival were not statistically different (p=0.248).

Figure 12:
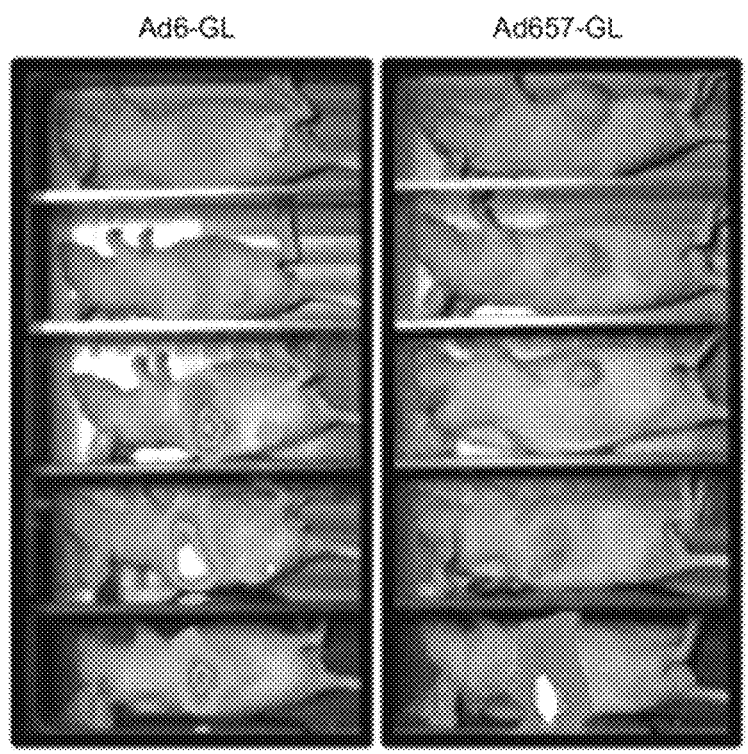
FIG. 12 shows luciferase imaging nude mice. Four days after single i.v. injection of $3 \times 10^{10}$ vp of Ad6 and Ad657-GFP-Luc with deletions of part of 12.5K, 6.7K, 19K, 11.6K (ADP), 10.4K (RIDα), 14.5K (RIDβ), and 14.7K and a partial deletion of E4 34K. Abbreviations: i.v., intravenous; vp, viral particle.

ALT was measured in the blood 3 days after injection in surviving Ad6 and Ad657 animals. Ad5-treated animals were not tested, since most of the group needed to be sacrificed. This assay showed that Ad6 provoked relatively low levels of liver damage in terms of liver ALT enzyme release in the blood (FIG. 10B). Both Ad6 and Ad657 groups had low, but significant, ALT levels when compared with PBS-treated mice (p<0.001 by one-way ANOVA with Tukey's multiple comparison test for both viruses). Ad657 had lower ALT levels than Ad6 (p<0.001 by ANOVA). This is consistent with higher levels of Ad6 infection in the liver than Ad657 after i.v. injection of luciferase expressing viruses (FIG. 12). One Ad657 animal was lost following bleeding on day 3. By 6 days, most of the Ad6 animals became moribund (FIG. 10A). In contrast, 50% of Ad657 animals survived beyond 2 weeks of the treatment.

Figure 11:
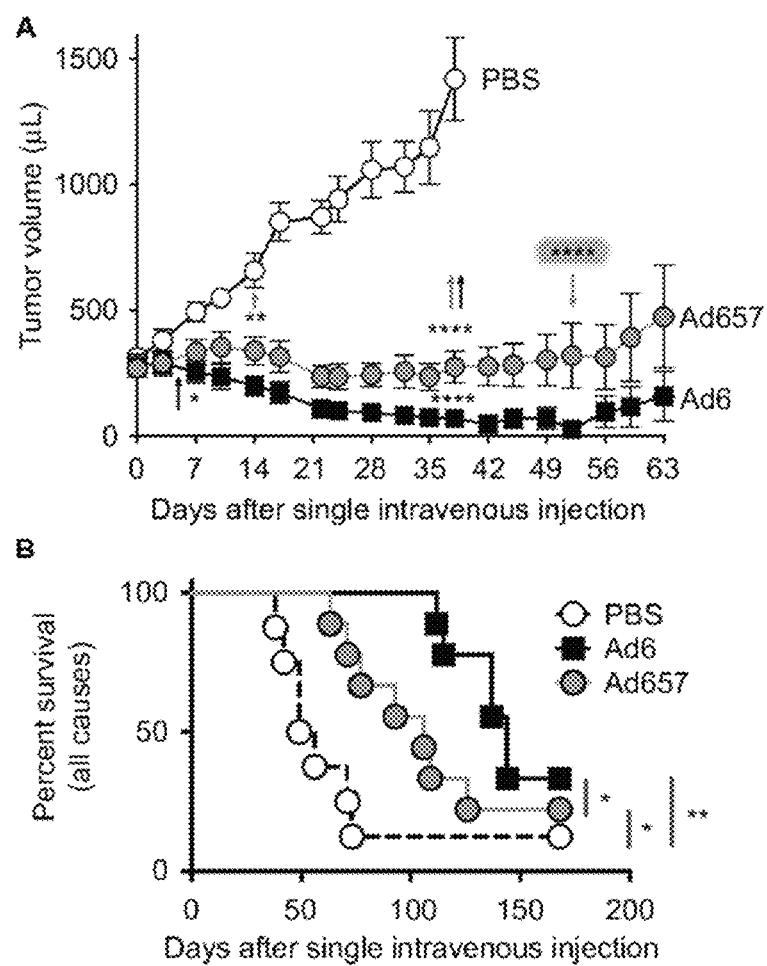
FIG. 11 shows anticancer activity of Ad6 and Ad657 in DU145 tumor xenografts in nude mice after single i.v. administration. Nude mice (n=9 per group) bearing established DU145 tumors were injected i.v. with a single dose of $3 \times 10^{10}$ vp of the indicated viruses or with PBS. (A) Effect of a single i.v. injection on tumor growth. Tumor dimensions were measured with calipers and tumor volume was calculated as width$^2 \times$length$\times$½. The data are shown as mean±SE. *p<0.05, ****p=0.0001 by ANOVA or by T-test as described in the text. Black asterisks with a black arrow pointing up indicate the statistical difference between the Ad6 group and the PBS group on a selected day described in the text. Gray asterisks and an arrow pointing up indicate differences between the Ad657 group and the PBS group on the indicated day. The shadowed white asterisks with a gray arrow pointing down indicates the statistical difference between the Ad6 and Ad657 groups on the indicated day. (B) Effect of a single i.v. injection on survival. Animals were euthanized when the tumor volume reached 2000 μL or when other sacrifice criteria were met (e.g., ulceration) and Kaplan-Meier survival curves were plotted (*p<0.05, **p<0.01 by log-rank analysis). Abbreviation: i.v., intravenous.

To compare the oncolytic activity of Ad6 and Ad657 against human DU145 prostate tumors, nude mice were engrafted s.c. with DU145 cells. Animals were distributed into groups with similar tumor sizes averaging 200 μL and groups of nine mice were treated a single time by the i.v. route with a dose of $3 \times 10^{10}$ vp of Ad6 or Ad657 (FIG. 11).

This single i.v. injection of Ad6 and Ad657 reduced tumor sizes when compared with PBS-injected control animals. Tumors were significantly smaller in the Ad6 group within 7 days when compared with the PBS group (p<0.05 by two-way ANOVA with Tukey's multiple comparison test). Tumors in the Ad657 group were significantly different from those in the PBS group by day 14 (p<0.01 by ANOVA). Both Ad6 and Ad657 maintained significant differences with PBS through day 38 (p<0.0001 by two-way ANOVA). This comparison ended on day 38 when the first animal in the PBS group had to be sacrificed since later comparison would be skewed due to the change in animal numbers. Tumor sizes in the Ad6 and Ad657 groups were not significantly different until day 38, when Ad657 had a significantly higher tumor volume (p<0.05) by two-way ANOVA (FIG. 11A). This difference between Ad6 and Ad657 tumor sizes persisted until day 52 (p=0.04 by T-test), and then the tumors were not significantly different after this time.

Figure 13:
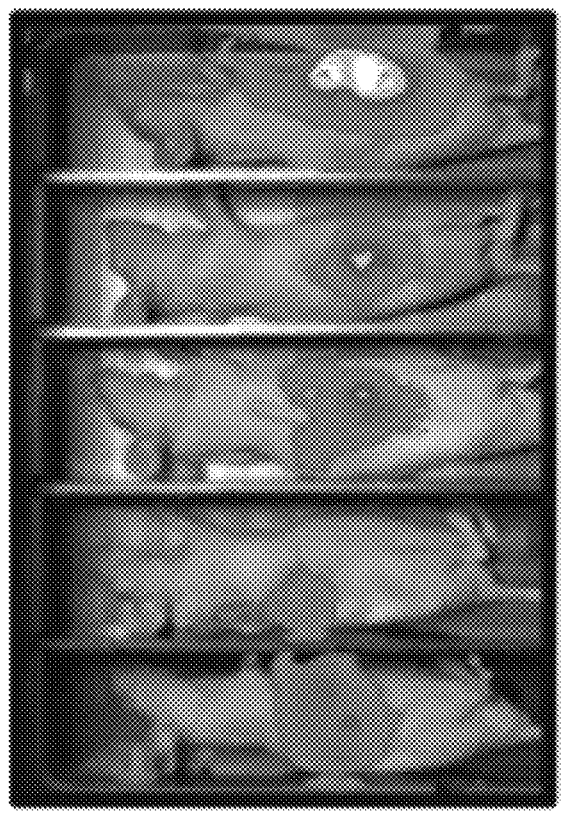
FIG. 13 shows luciferase imaging nude mice. Fourteen days after single i.v. injection of $3 \times 10^{10}$ vp of Ad657-GFP-Luc. Abbreviations: i.v., intravenous; vp, viral particle.

When survival due to all causes was assessed, both Ad6 and Ad657 significantly extended survival when compared with PBS-treated animals (FIG. 11B, p<0.01 and 0.05, respectively, by log-rank analysis). Ad6 survival due to all causes was significantly better than Ad657 (p<0.05). However, this was an artifact of survival attributed to all because three of the Ad657 animals had to be sacrificed per Institutional Animal Care and Use Committee (IACUC) guidelines due to the formation of ulcers on the skin over the tumor rather than due to excess tumor size. In some cases, ulceration is actually associated with effective tumor control. Like Ad6, Ad657 expressing GFP-luciferase produced significant luciferase activity in distant DU145 subcutaneous tumors after a single i.v. injection (FIG. 12 and FIG. 13). This suggests that both Ad6 and Ad657 can mediate oncolytic effects in prostate tumors after a single systemic treatment.

This example demonstrates that Ad657 may be used as a local or systemic oncolytic virotherapy for prostate cancers. These data also demonstrate surprising effects of serotype-switching with oncolytic species C Ads.

Figure 28:
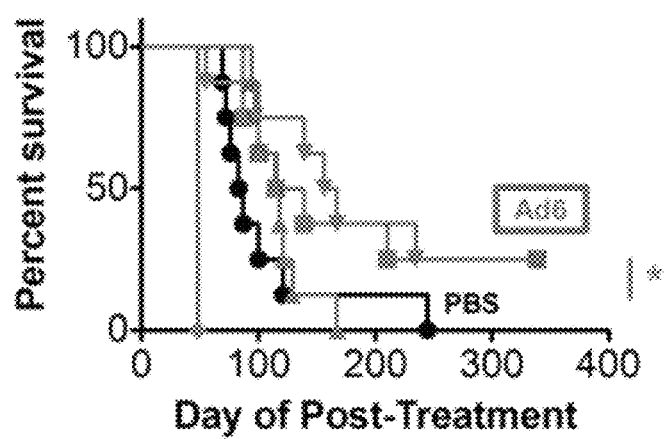
FIG. 28 is a graph showing Ad6 single IV injection vs. A549 lung tumors.
Figure 29:
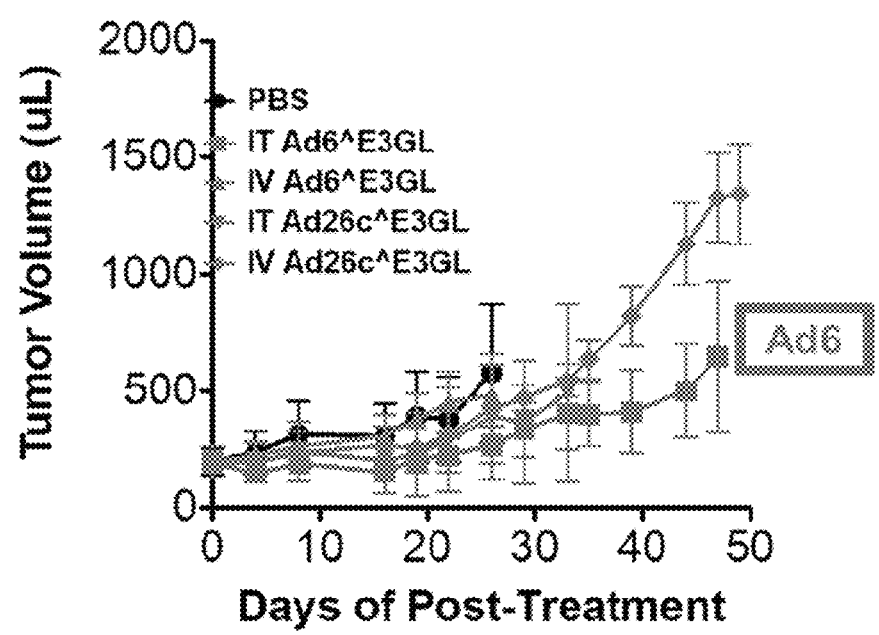
FIG. 29 is a graph showing Ad6 single IV or IT injection vs. Pancl pancreatic tumors.
Figure 30:
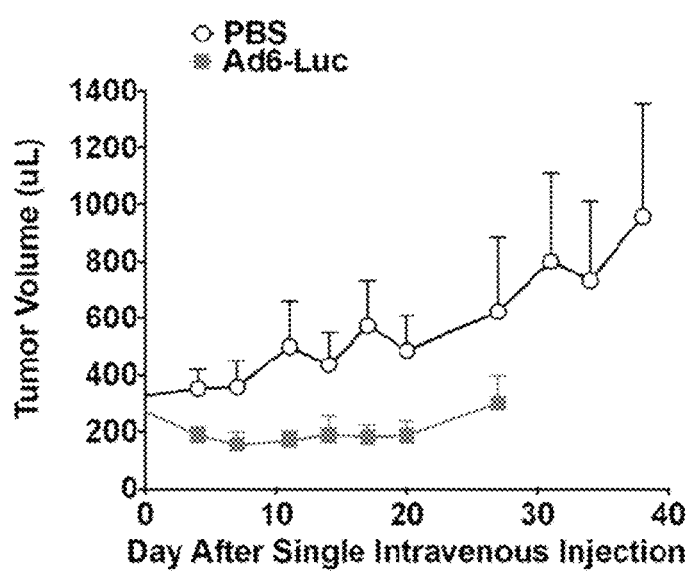
FIG. 30 is a graph showing Ad6 single IV injection vs. kidney cancer in immune competent hamsters.

The oncolytic activity of Ads was evaluated in tumor cells and/or cancerous tumors. Ad6 single IV injection vs. A549 lung tumor cells was evaluated (FIG. 28); Ad6 single IV or intratumoral (IT) injection vs. Panc 1 pancreatic tumors was evaluated (FIG. 29), and Ad6 single IV injection vs. kidney cancer in immune competent hamsters was evaluated (FIG. 30).

Figure 38:
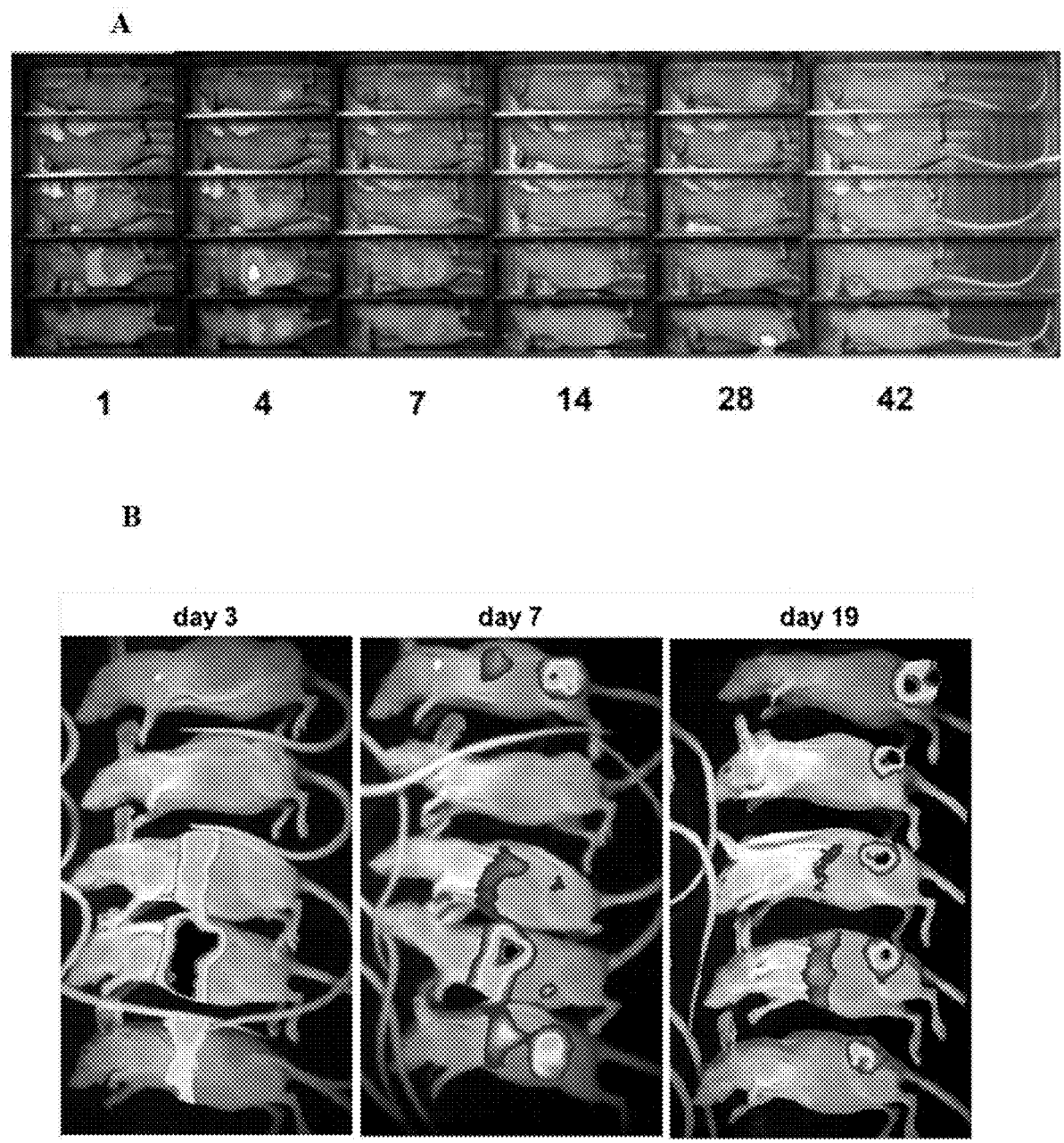
FIG. 38 shows luciferase imaging of nude mice. A) 1, 4, 7, 14, 28, and 42 days after single I.V. injection of Ad6 treatment vs. distant DU145 prostate tumors. B) 3, 7, and 19 days after I.V. injection of replicating Ad5-GFPLUC into mice bearing LNCaP prostate tumors.

FIG. 38 shows luciferase imaging of nude mice. A) 1, 4, 7, 14, 28, and 42 days after single I.V. injection of Ad6 treatment vs. distant DU145 prostate tumors. B) 3, 7, and 19 days after I.V. injection of replicating Ad5-GFPLUC into mice bearing LNCaP prostate tumors.

It may be concluded that Ad6 gets to distant target cells after IV injection.

Figure 31:
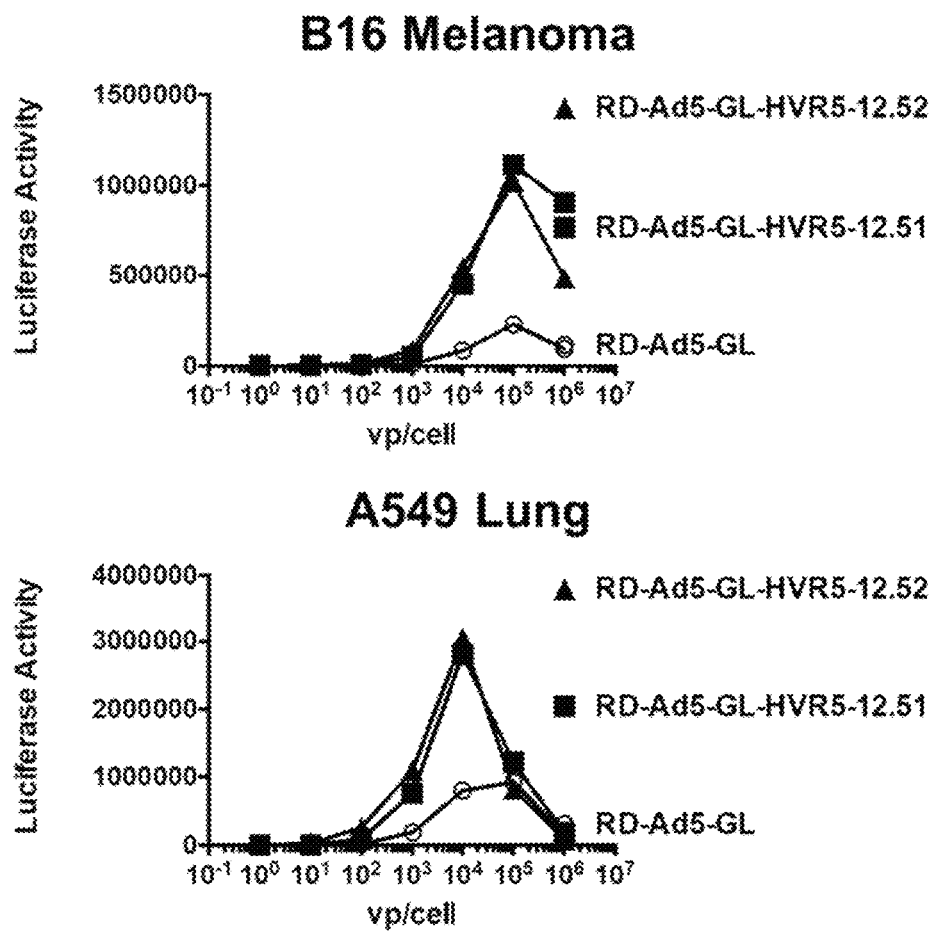
FIG. 31 is a graph showing luciferase activity in B16 melanoma and A549 lung tumor/cancer cells by Ads displaying 12.51 cell binding peptides in HVR5 of the hexon.

In another embodiment, Ads expressing luciferase with and without peptide library generated peptides 12.51 and 12.52 inserted in HVR5 of hexon were incubated on indicated cell lines, B16 melanoma and A549 lung carcinoma cells, with the indicated numbers of virus particles (vp) and luciferase activity was measured. Improved infection of cancer cells by Ads bearing peptide-modified hexons is demonstrated (FIG. 31).

Improved Infection of Cancer Cells by Ads Bearing Peptide-Modified Hexons

Figure 32:
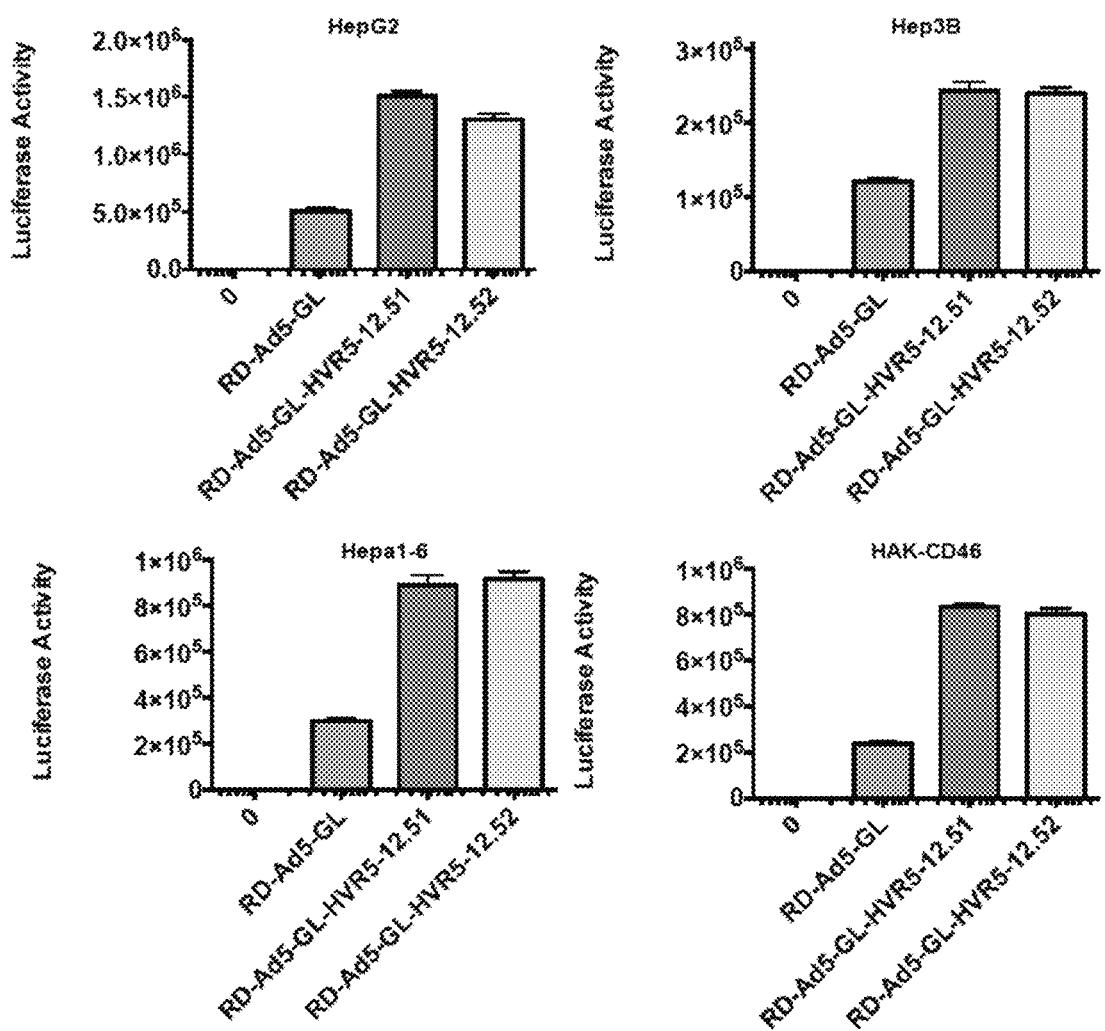
FIG. 32 is a graph showing luciferase activity in hepatocellular carcinoma and kidney cancer by Ads displaying 12.51 cell binding peptides in HVR5 of the hexon.
Figure 33:
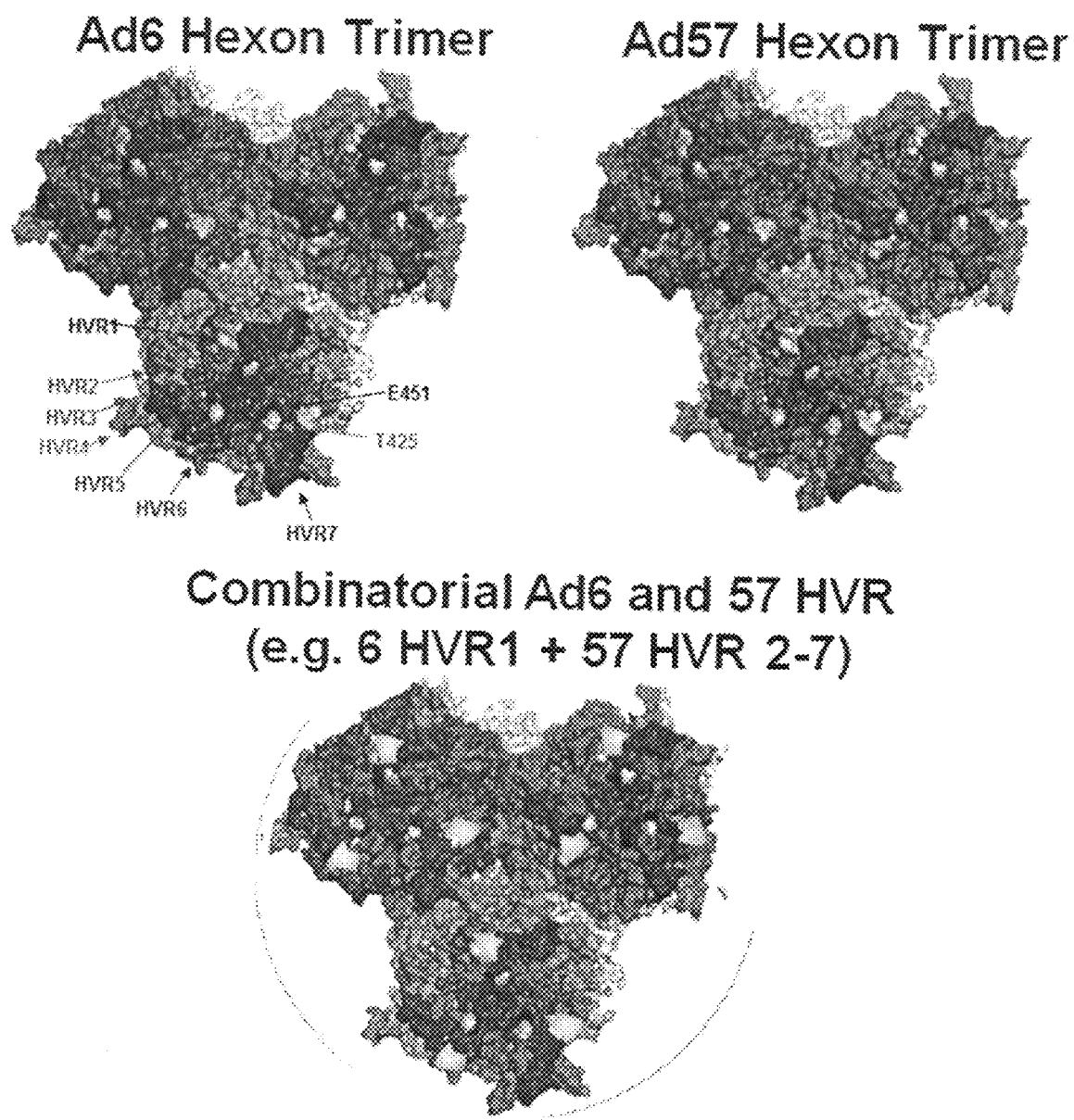
FIG. 33 shows a cartoon combining the insertion of individual HVRs from different Ad serotypes with the insertion of cell targeting/detargeting peptides or novel amino acids such as cysteine into the hexon for targeted chemical modification and shielding. Depicted are chimeric HVR constructs that combine different HVRs from different Ad serotypes to modulate natural interactions with cells and blood factors improve pharmacology combined with insertion of cell binding and cell detargeting peptides in different HVRs to change cell entry and cell avoidance. If one HVR is substituted from 100 Ads, this would create 100 different hexon chimeras. If all 7 HVRs each receive a different Ad HVR, this combinatorial library would equal $7^{100}$ variants. If one 1 peptide were introduced into 7 HVRs this would equal $7 \times 7^{100}$ variants. If 10 different peptides were introduced into 7 HVRs, this would equal $10 \times 7 \times 7^{100}$ variants, etc.
Figure 33:
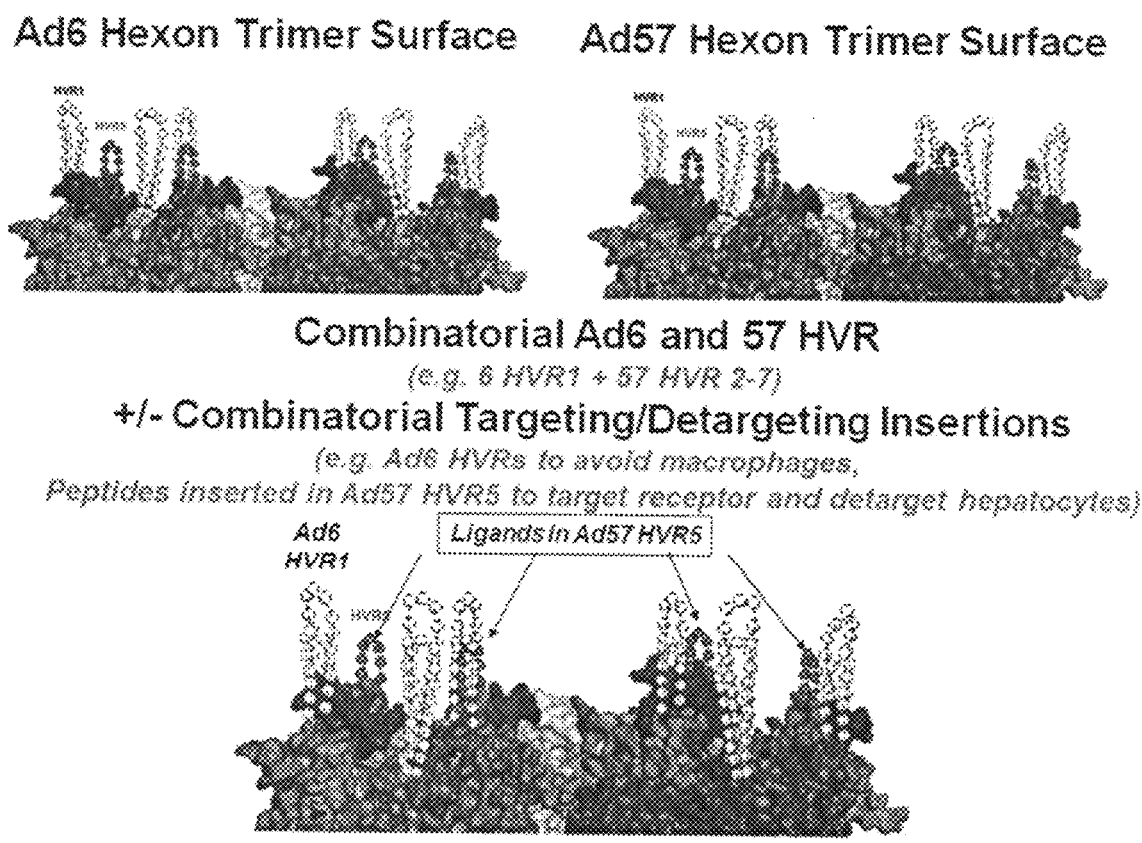

Ads expressing luciferase with and without peptide library generated peptides 12.51 and 12.52 inserted in HVR5 of hexon were incubated on indicated hepatocellular carcinoma cell lines with $10^4$ vp of each virus and luciferase activity was measured Improved infection of cancer cells by Ads bearing peptide-modified hexons is demonstrated (FIG. 32).

Example 7

Divergent HIV-1 Directed Immune Responses Generated by Systemic and Mucosal Immunization with Replicating Single-Cycle Adenoviruses in Rhesus Macaques Most gene-based adenovirus vaccines are replication-defective Ad (RD-Ad) vectors that have their E1 gene deleted to prevent them from replicating and causing Ad infections. Helper-dependent adenoviruses (HD-Ads) have all Ad genes deleted and are also replication-defective. An E1-deleted Ad vaccine can infect a cell, deliver its one copy of an antigen gene, and express a single copy (e.g., "1×") of this antigen. They are safe, but do not replicate transgenes or their expression.

In contrast, an E1+replication-competent Ad (RC-Ad) vaccine can infect the same cell, replicate the antigen gene DNA 10,000-fold, produce substantially more antigen, and provoke stronger immune responses than E1-deleted vectors. While RC-Ad is more potent than RD-Ad, replication-competent Ads can run the real risk of causing frank adenovirus infections in humans To take advantage of transgene DNA replication, but avoid the risk of adenovirus infections, single-cycle Ad (SC-Ad) vectors with a deletion of a gene for a key viral late protein, pIIIa, were developed (Crosby et al., 2014. *Virology* 462-463:158-165; Crosby et al., 2015 *J Virol* 89:669-675; Anguiano-Zarate et al., 2018 *J Infectious Dis* 218:1883-1889; and Crosby et al., 2017 *Genes* (Basel) 8:E79). SC-Ads retain their E1 genes to allow it to replicate its genome, but the absence of pIIIa blocks the production of infectious progeny viruses. SC-Ads replicate their genomes and transgenes as well as RC-Ad (up to 10,000-fold; Crosby et al., 2014. *Virology* 462-463:158-165). RC- and SC-Ad produce more transgene protein than RD-Ad vectors (Crosby et al., 2014. *Virology* 462-463:158-165). SC-Ads generate more robust and more persistent immune responses than either RD-Ad or RC-Ads (Crosby et al., 2015 *J Virol* 89:669-675). In head-to-head comparisons, SC-Ad produces significantly higher antibodies and better protection against influenza virus (Crosby et al., 2017 *J Virol* 91:e00720-16).

In this study, rhesus macaques were immunized with SC-Ads expressing Glade B envelope sequences that were obtained from an HIV-1 patient before and after their antibody response underwent an expansion neutralization breadth. Macaques were immunized by a single systemic IM immunization or by single mucosal intranasal (IN) immunization. The animals were then boosted by the same or alternative routes with SC-6 Ad followed by protein boost. This example describes how these various SC-Ad immunization strategies affected the generation of HIV binding, antibody-dependent cellular cytotoxicity (ADCC) and neutralizing antibodies as well as their effects on cellular immune responses including T follicular helper (pTfh) cells in blood and lymph nodes.

Single-Cycle Adenovirus Expressing HIV-1 Envelope Protein gp140

Clade B gp160 envelope sequences that arose before (G4) and immediately preceding a peak in the expansion of antibody neutralization breadth (F8) from HIV patient VC10014 (Malherbe et al., 2014 *J Virol* 88:12949-12967) were used as immunogens. Motif-optimized G4 and F8 gp160 sequences were recombined into SC-Ads based on human Ad serotypes 6 and 57 (see, e.g., Crosby et al., 2014. *Virology* 462-463:158-165; Crosby et al., 2015 *J Virol* 89:669-675; Anguiano-Zarate et al., 2018 *J Infectious Dis* 218:1883-1889; and Nguyen et al., 2018 *Oncolytic Virotherapy* 7:43-51). A control SC-Ad expressing Ebola glycoprotein was also used. Viruses were rescued and purified as described elsewhere (see, e.g., Crosby et al., 2014. *Virology* 462-463:158-165; Crosby et al., 2015 *J Virol* 89:669-675; and Anguiano-Zarate et al., 2018 *J Infectious Dis* 218:1883-1889).

The envelope gene F8 cloned from an HIV Clade B-infected subject used in the SC-Ad vector was motif-optimized and modified by site-directed mutagenesis to express uncleaved, trimeric gp140. Details of expression, purification, and antigenic characterization have been described elsewhere (see, e.g., Malherbe et al., 2014 *J Virol* 88:12949-12967).

Female adult rhesus macaques (Macaca mulatta) of Indian origin were maintained at the Michael Keeling Center for Comparative Medicine and Research at the University of Texas MD Anderson Cancer Center, Bastrop TX in the specific pathogen-free breeding colony. All animal handling was carried out in accordance with the policies and procedures of the Mayo Clinic and the University of Texas MD Anderson Cancer Center, the provisions of the Animal Welfare Act, PHS Animal Welfare Policy, the principles of the NIH Guide for the Care and Use of Laboratory Animals.

Macaques were anesthetized with ketamine and immunized by the intranasal (IN) or intramuscular (IM) route with $2\times10^{10}$ virus particles (vp) of the indicated SC-Ad vaccine. Animals were boosted with 50 μg of purified, trimeric recombinant F8 gp140 combined with Adjuplex™ adjuvant by the IM route as described elsewhere (see, e.g., Malherbe et al., 2014 *J Virol* 88:12949-12967; and Hessell et al., 2016 *J Immunol* 196:3064-3078).

Peripheral venous blood samples were collected in EDTA. Before isolation of peripheral blood mononuclear cells (PBMC), plasma was separated and stored immediately at −80° C. PBMCs were prepared from the blood on Ficoll-Hypaque density-gradients. Saliva and vaginal swabs collected with Wek-Cel Spears in 1 ml of PBS containing protease inhibitors, vortexed, and supernatants were collected after a 2,000 r.p.m. centrifugation as described elsewhere (see, e.g., Kozlowski et al., 1997 *Infect Immun* 65:1387-1394). Samples were kept frozen at −80 C. until further use.

ELISPOT Assay for Detecting Antigen-Specific IFN-γ Producing Cells

Freshly-isolated PBMCs were stimulated with either F8 gp140 protein (1 μg/mL) or heat inactivated Ad6 ($7.0\times10^8$ vp/well) to determine the numbers of IFN-γ-producing cells by the Enzyme Linked Immuno Spot (ELISPOT) assay using the methodology described elsewhere (see, e.g., Nehete et al., 2017 *Comp Med* 67:67-78; Nehete et al., 2013

PLoS One 8:e79836; and Nehete et al., 2017 *J Am Assoc Lab Anim Sci* 56:509-519). Briefly, aliquots of PBMCs ($10^5$/ well) were seeded in duplicate wells of 96-well plates (polyvinylidene difluoride backed plates, MAIP S 45, Millipore, Bedford, Mass.) pre-coated with the primary IFN-γ antibody and the lymphocytes were stimulated with either Con A, F8 gp140 protein, or heat inactivated Ad6. After incubation for 30-36 hours at 37° C., the cells were removed and the wells were thoroughly washed with PBS and developed as per protocol provided by the manufacturer. Results are expressed as IFN-γ spot-forming cells (SFCs) per $10^5$ PBMCs after subtraction of the duplicate wells with medium only (negative control) and are considered positive if greater than twice the background and greater than 5 SFCs/$10^5$ PBMCs.

Antibody ELISAs

HIV-1 envelope binding antibody titers were measured in plasma samples collected at regular intervals against F8 gp140 or SF162 gp140 as described elsewhere (Malherbe et al., 2014 *J Virol* 88:12949-12967; and Hessell et al., 2016 *J Immunol* 196:3064-3078).

Neutralization Assay

HIV neutralization was performed using the TZM-bl neutralization assay as described elsewhere (Malherbe et al., 2014 *J Virol* 88:12949-12967; and Hessell et al., 2016 *J Immunol* 196:3064-3078). All values were calculated as compared to virus-only wells.

Antibody Dependent Cellular Cytotoxicity (ADCC)

CEM.NKR.CCR5.CD4+-Luc, target cells were infected with 50 ng $SHIV_{SF162P3}$ and cultured for 4 days as described elsewhere (see, e.g., Alpert et al., 2012 *PLoS Pathog* 8:e1002890). Two-fold serial dilutions of each sample were added to the infected targets for 20 minutes at room temperature. CD16-KHYG-1 effector cells were added at a 10:1 effector to target ratio and these were incubated for additional 8 hours. The cells were lysed and luciferase activity was measured on the Bio-Tek plate reader.

Flow Cytometry

Cells collected from rectal and lymph node biopsies were incubated overnight with 0.2 μg gp140 or media alone in the presence of GolgiPlug™ (BD Biosciences, San Jose, Calif., USA) for the last 4 hours. After culture, cells were harvested and incubated on ice for 45 minutes with a panel of human antibodies that cross-react with rhesus macaque samples. The panels included the following fluorochrome labeled antibodies: CD8 (Qdot655), α4β7 (PE) and CXCR5 (PE), all obtained from the Nonhuman Primate Reagent Resource; CD69 (BV737, clone FN50) and FoxP3 (PECy5, clone: PCH101) obtained from eBioscience, IL-21 (BV421, clone: 3A3-N2.1), CD45 (BV786, D058-1283) and CD3 (clone SP34-2, PE-Cy7-labeled) all from BD Bioscience (San Jose, Calif.); CD4 (Pacific Blue, clone OKT4) from ThermoFisher Scientific (Waltham, Mass.). Dilutions for antibodies were determined by following manufacturer's recommendations. Dead cells were excluded by using live-dead fixable dead cells stain kit obtained from Invitrogen (Carlsbad, Calif.). Subsequently, the cells were washed twice with PBS containing 2% FBS and 2 mM EDTA and then fixed and permeabilized with FoxP3 Fix/Perm Kit (ThermoFisher Scientific, Waltham, Mass.). The intracellular markers FoxP3 and IL-21 were stained in permeabilization buffer. Both compensation controls (OneComp eBeads, (ThermoFisher Scientific, Waltham, Mass.) and fluorescence minus one (FMO) controls were utilized. All the samples were collected on an LSR Fortessa X-20 analyzer (BD Biosciences, San Jose, Calif.) and were analyzed using FlowJo software (FlowJo, LLC, Ashland, Oreg.). Approximately $2\times10^5$ to $1\times10^6$ events were collected per sample.

$SHIV_{SF162P3}$ Rectal Challenge $SHIV_{SF162P3}$ virus was derived from R157 harvest 3 (3.16.12). This stock had a P27 content of 66 ng/ml, RNA content Log ~9.35, TCID50 in Indian origin rhesus PBMC: 1288/ml, and TCID50 in TZM-bl cells: $4.1\times10^4$/ml. 1 ml of a 1:300 dilution of the stock was used. This equaled 4.3 TCID50 on rhesus PBMCs and 137 TCID50 on TZM-bl cells. This dose was used for weekly intrarectal (IR) challenge. Plasma samples were analyzed for SHIV viral RNA copy numbers by Leidos Biomedical Research, Inc., Frederick National Laboratory. Animals with RNA copies above 10 were considered to be infected and the number of challenges required to infect that animal were used as events for Kaplan-Meier survival analysis. Once infected, the animal was no longer challenged. Plasma viral loads were monitored periodically by the same method until the end of the study.

$SHIV_{SF162P3}$ Viral Load in Tissues

At the end of study PBMCs and post-mortem tissues were collected. PBMC and gut samples were analyzed for $SHIV_{SF162P3}$ viral RNA by qPCR. Prism 7 Graphical software was used for all statistical analyses.

SC-Ad Expressing HIV-1 gp160

Figure 24:
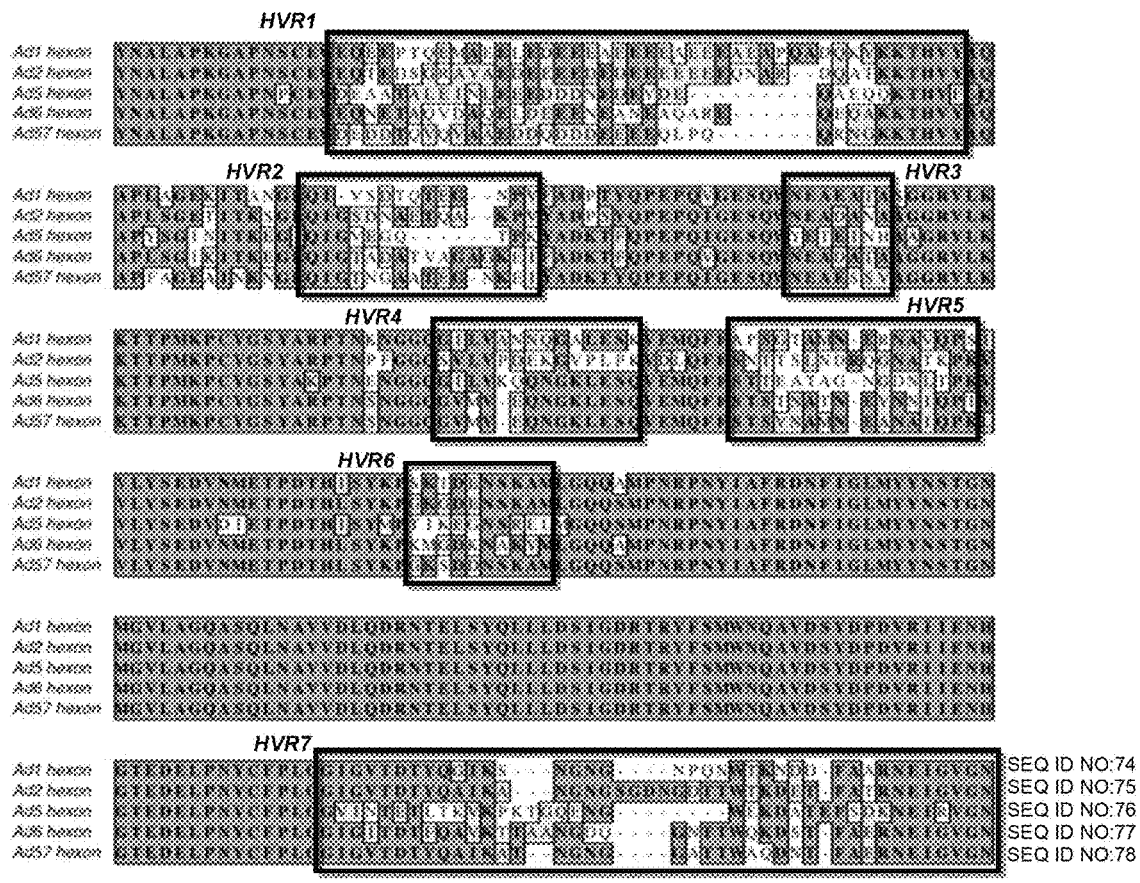
FIG. 24 shows single-cycle adenovirus vaccines used in Example 7. A) Cartoon of SC-Ad serotypes 6 and 657 carrying F8 and G4 Glade B HIV envelope genes. B) Alignment of Glade C Ad hexons including the Ad6 and 57 hexons displayed on vaccines.

Clade B envelope protein sequences (G4 gp160) were identified before and immediately preceding a peak in the expansion of antibody neutralization breadth (F8 gp160) from HIV patient VC10014. These gp160 sequences were inserted into SC-Ad6 and SC-Ad657 under the control of the strong cytomegalovirus promoter (FIG. 24A). Ad57 is a species C human Ad that is nearly identical to Ad6 with variation in its hexon hypervariable regions (HVRs) and in its E3 immunevasion genes (FIG. 24B). Most Ad neutralizing antibodies target Ad's hexon HVRs (Pichla-Gollon et al., 2007 *J Virol* 81:1680-1689; and Sumida et al., 2005 *J Immunol* 174:7179-7185). Given this, Ad6's HVRs were replaced with those from Ad57 to generate a chimeric species C Ad vector termed Ad657. Both SC-Ad6 and SC-Ad657 retain all Ad genes including E1 and lack functional pIIIA and E3 genes (FIG. 24A). Both SC-Ads can therefore replicate their genomes to amplify gp160 expression, but do not generate progeny Ad viruses. Both viruses were rescued and produced in 293-IIIA cells and purified on CsCl gradients. When used to infect A549 cells, both vectors produced gp160 as determined by Western blotting.

Different Ad vectors were previously tested in rhesus macaques by the systemic intramuscular (IM) route and by a variety of mucosal routes including oral gavage, oral enteric coated capsules, intranasal (IN), and intravaginal (IVAG). Testing of SC-Ad-G4 by IM, IN, and IVAG routes in small animals revealed that priming by IVAG route generated negligible antibody responses. In contrast, IN immunization in both mice and hamsters generated strong antibody responses. Given these data and the potential difficulty in performing IVAG immunizations in humans, the IN route was selected for the mucosal immunization route in the subsequent macaque studies.

Figure 14:
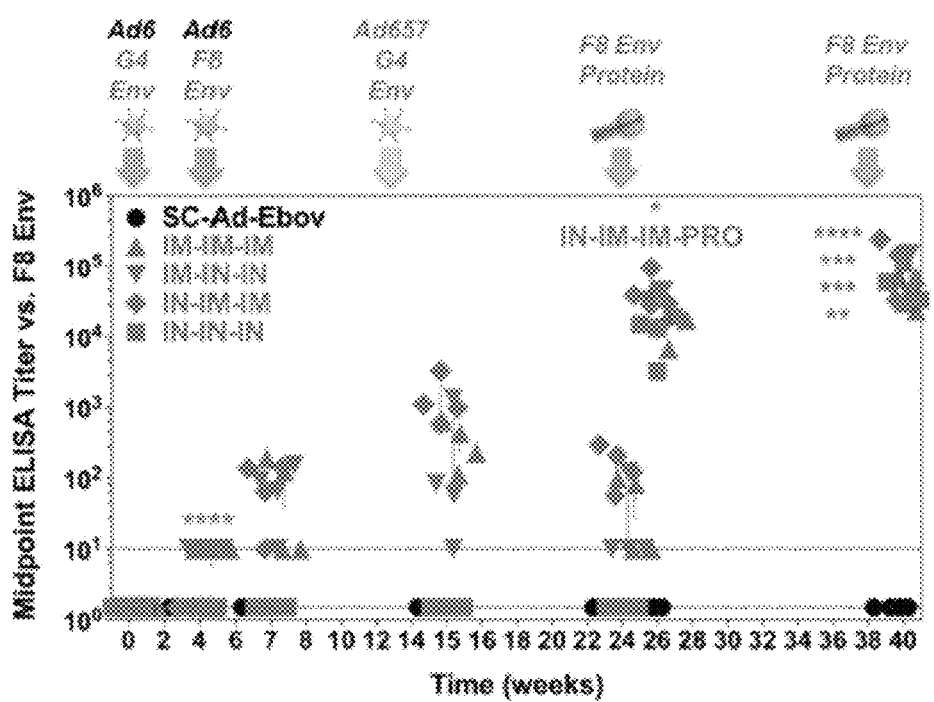
FIG. 14 shows plasma HIV Env binding titers Immunizations with different SC-Ads and gp140 proteins are shown above the graph with large arrows. Midpoint F8 gp140 binding titers by ELISA are shown for each animal before and after each immunization. The dashed line indicates the minimal detection limit for antibodies in this assay. Symbols are scattered in the x direction at each time point to allow individual measurements to be observed. SC-Ad6-Ebov is a negative control Ad vaccine. This group of animals was not boosted with gp140. *p<0.05, p<0.01, *p<0.001, ****p<0.0001 by one way ANOVA in comparison to the SC-Ad6-Ebov group.

Single Mucosal and Systemic Immunization in Rhesus Macaques $2\times10^{10}$ vp of SC-Ad6-G4 Env was used to vaccinate groups of 8 female rhesus macaques by single IM or IN immunization (FIG. 14). This dose is relatively low, being approximately 7.5-fold lower than recent use of RC-Ad HIV envelope vaccines delivered by mixed IN and IM immunization. A negative control vector group was immunized IN with SC-Ad6 expressing Ebola glycoprotein (gp). Four weeks later, plasma samples were assayed for Env binding antibodies against F8 gp140 (FIG. 14). This showed significantly higher midpoint binding titers in the IM immunized route group after single immunization (p<0.01 by ANOVA). SF162 neutralizing antibody (NAb) titers were also elevated at this time point, but did not reach significance by ANOVA for the individual route groups.

IM vs. IN Boost with SC-Ad6 at Week 4

It was been reported that anti-adenovirus neutralizing antibodies that are produced by one Ad IM immunization can be avoided by boosting by a different route (Xiang et al., 2003 *J Virol* 77:10780-10789). To test this route concept to enable the re-use of the same Ad serotype in macaques, each SC-Ad6-primed group was divided into 2 groups of 4. These were each boosted with SC-Ad6 expressing the alternate F8 Env at week 4 by either the IM or the IN route. Plasma samples collected 3 weeks after this boost showed elevations in midpoint binding titers in the animals that were prime-boosted by the IM-IM, IM-IN, and IN-IM groups. No detectable antibodies were observed in the IN-IN group (FIG. 14).

SC-Ad657 Boost at Week 13

The animals were then boosted by serotype-switching with SC-Ad657 expressing G4 Env at week 13. The same route was used as in the previous boost. Week 15 titers showed that IM primed animals had elevated Env binding titers near 350, but these levels were not significantly different than controls (FIG. 14). In contrast, antibodies in the IN-IM-IM group were significantly higher than both the vector control and the IN-IN-IN group (p<0.01). The IN-IN-IN group again showed no Env antibodies even after 3 immunizations.

Recombinant Trimeric Env Protein Boost at Week 24

Most HIV vaccine studies augment Ad immunizations with protein boosts to amplify antibody responses. For example, in a recent study, RD-Ad26 vectors were used twice and boosted three times with adjuvanted gp140 protein (Barouch et al., 2015 *Science* 349(6245):320-4). In an effort to determine whether this strategy would enhance the SC-Ad vaccines, all of the SC-Ad-Env groups were boosted with 50 µg of recombinant F8 trimeric gp140 protein mixed with ADJUPLEX™ adjuvant by the IM route. The F8 trimeric protein boosted midpoint binding titers by two orders of magnitude in all of the groups (FIG. 14). This protein immunization also boosted the IN-IN-IN to levels comparable to the other groups even though Env binding antibodies were not detected after the earlier SC-Ad immunizations.

Binding and Neutralizing Antibodies in Plasma after a Second Protein Boost

Figure 15:
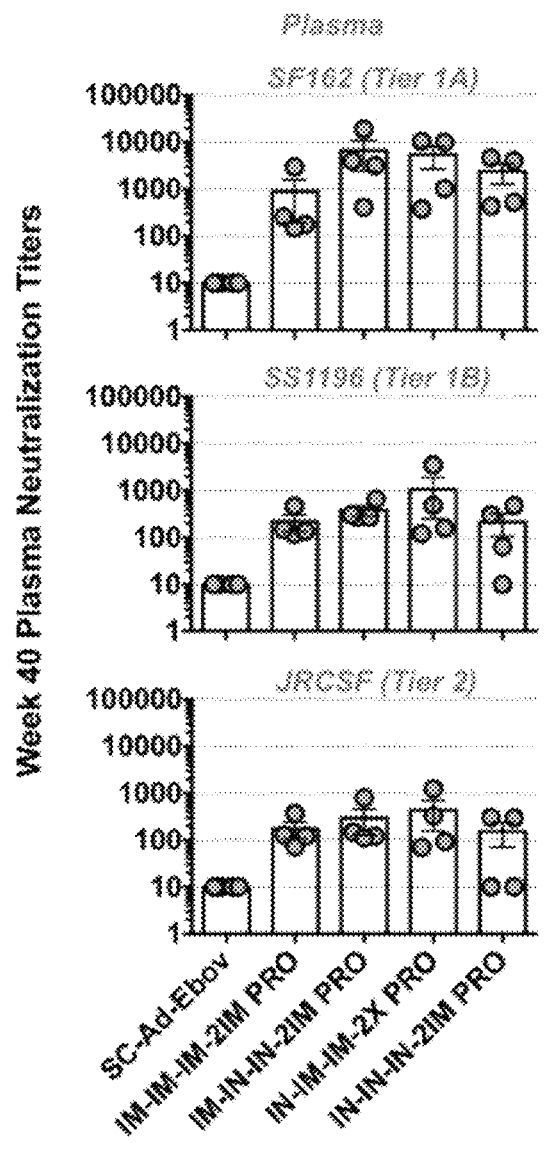

The animals were boosted with protein a second time at week 38. This increased F8 binding plasma antibody titers to nearly $10^5$ by week 40 and all groups became significantly different than controls (FIG. 14). Neutralizing antibody (NAb) titers against Tier 1A SF162 virus were increased to 100 to 10,000 at week 40 (FIG. 15). NAbs against Tier 1B virus SS1196 and Tier 2 JRCSF virus increased to 100 in most animals with the exception of two animals in the IN-IN-IN group whose titers were at background levels (FIG. 15).

ADCC Activity after the Second Protein Boost

Figure 16:
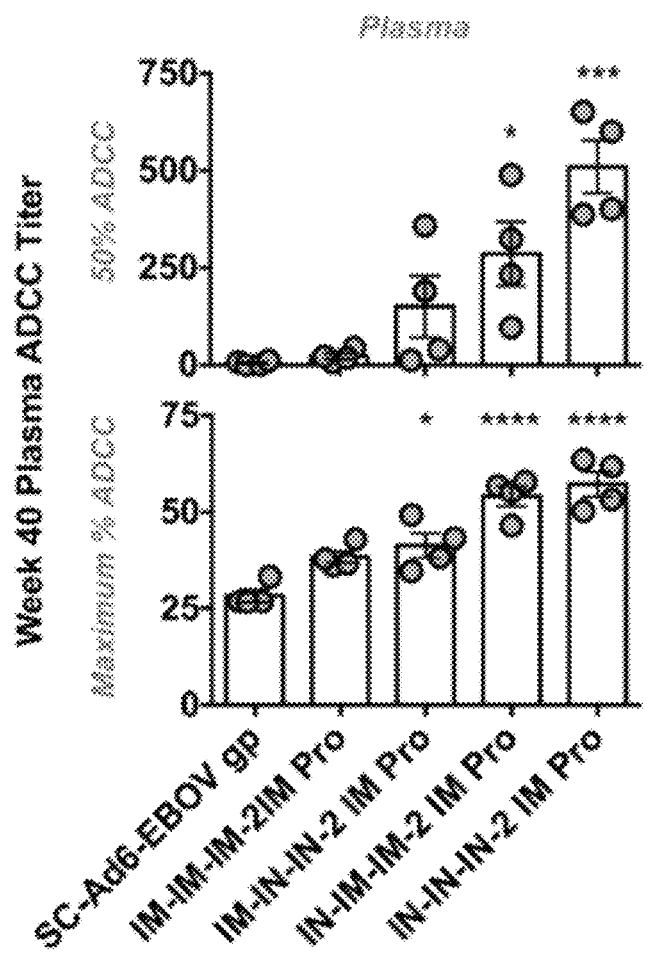
FIG. 16 shows plasma ADCC activity. Plasma samples were tested with CD16-KHYG-1 effector cells to kill CEM.NKR.CCR5.CD4+-Luc, target cells infected with SHIVSF162P3. Each dot represents the mean value for each animal. *p<0.05, *p<0.001, **p<0.0001 by one-way ANOVA vs. the SC-Ad6-Ebov group.

Antibody-dependent cellular cytotoxicity (ADCC) activity in week 40 plasma was tested against $SHIV_{SF162P3}$ infected cells. ADCC activity was generally higher in animals that had at least one IN mucosal SC-Ad immunization (FIG. 16). All animals that received a mucosal immunization had significantly higher maximum % ADCC than SC-Ad-Ebola control animals (p<0.05, 0.0001, 0.0001 for IM-IN-IN, IN-IM-IM, and IN-IN-IN, respectively). When compared by 50% ADCC titers, only the IN SC-Ad primed groups had significantly higher ADCC activity than controls (p<0.05 and 0.001 by ANOVA for (IN-IM-IM and IN-IN-IN groups).

Antibody Responses in Saliva and Vaginal Washes after a Second Protein Boost

Figure 25:
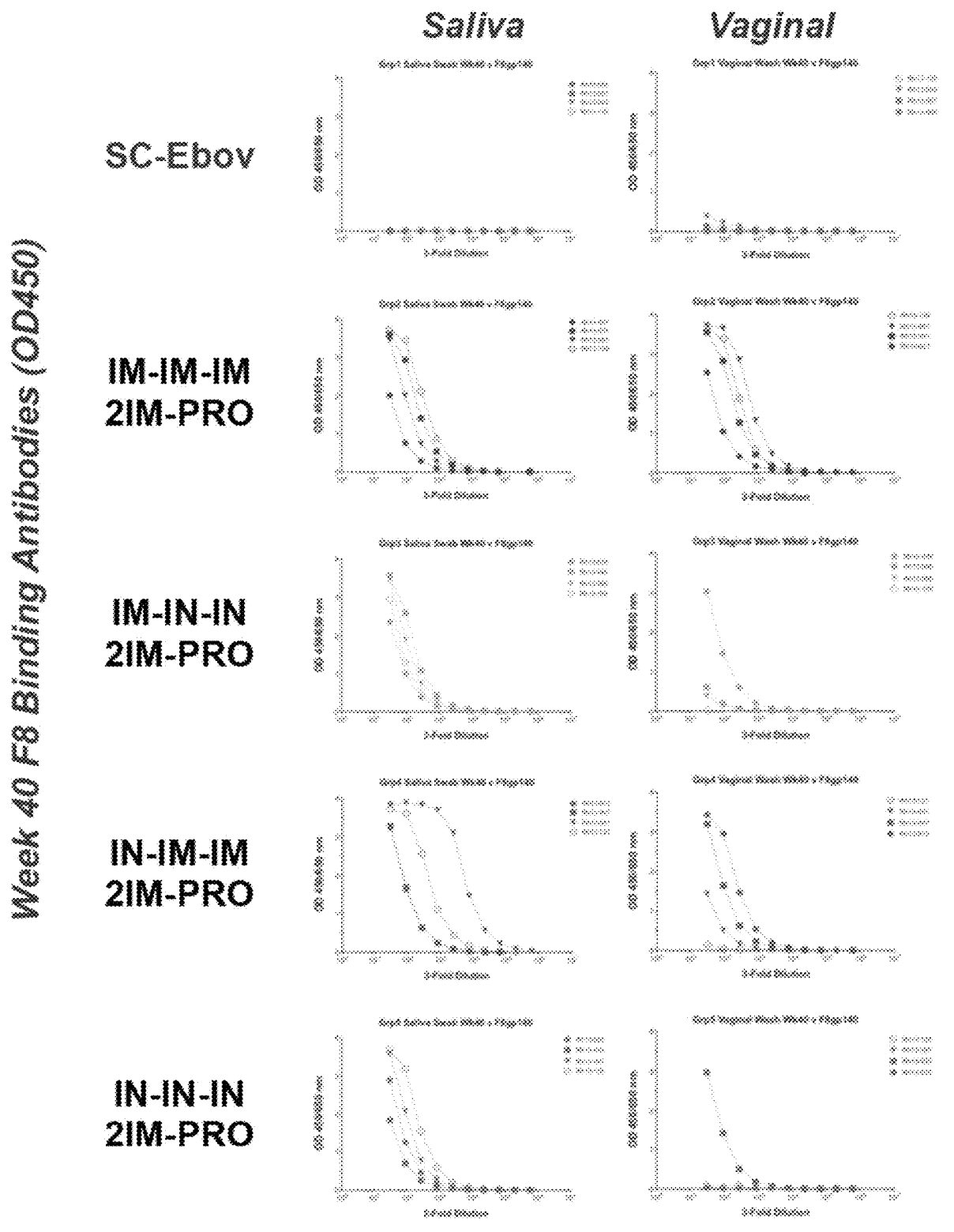

The data above monitored systemic antibody responses in plasma. Saliva and vaginal wash samples were also collected at week 40 and measured for antibodies in these mucosal sites. When saliva and vaginal washes were assayed for F8 and SF162 env binding by ELISA, these responses were observed in most groups with the exception of the SC-Ad-Ebola control group (FIG. 25).

Figure 17:
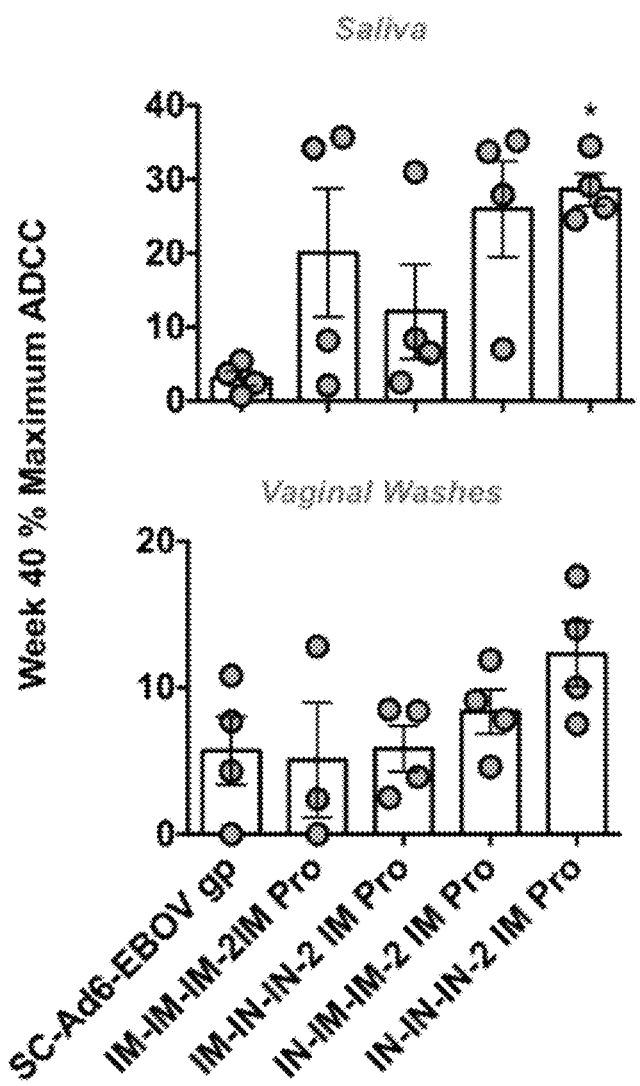
FIG. 17 shows mucosal ADCC activity. Vaginal wash and saliva samples were tested with CD16-KHYG-1 effector cells to kill CEM.NKR.CCR5.CD4+-Luc, target cells infected with SHIVSF162P3. Each dot represents the mean value for each animal. *p<0.05 by one-way ANOVA vs. the SC-Ad6-Ebov group.

There appeared to be a regional effect on these mucosal antibodies. In animals that were immunized with SC-Ad mostly by the IN route (IM-IN-IN and IN-IN-IN), binding antibodies were higher in the saliva near this site of immunization, but lower in the more distant vaginal site (FIG. 25). When ADCC activity was measured in these mucosal samples, these responses were highly variable (FIG. 17). Despite this, higher ADCC activity was observed in the IN-IN-IN group when compared to control animals (p<0.05 by ANOVA).

Systemic Cellular Immune Responses after One Protein Boost

Figure 18:
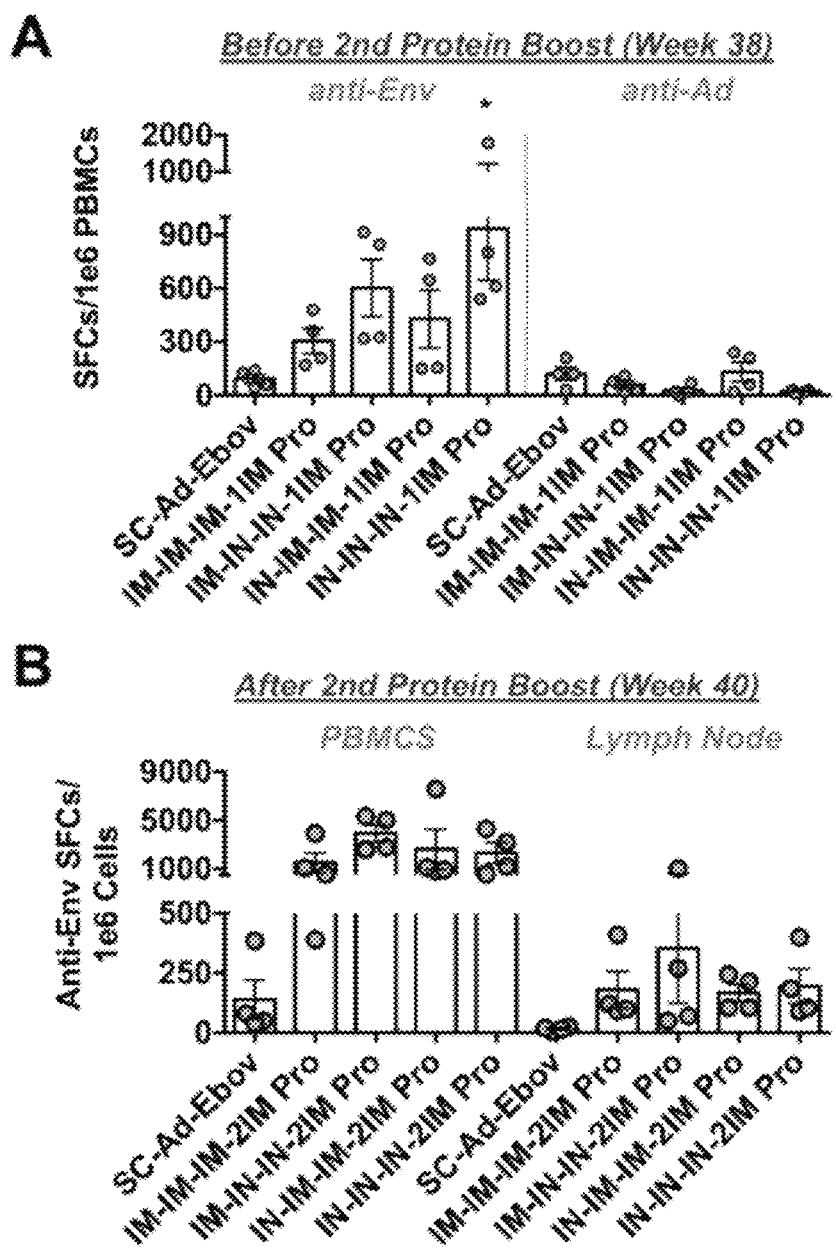
FIG. 18 shows IFN-γ Secreting Cells from PBMCs and Lymph Nodes. PBMCs and lymph node cells were analyzed by ELISPOT by staining for IFN-γ. Anti-Env indicates cells that were stimulated with conserved HIV Env peptides, and SC-Ads. The total number of spot forming cells (SFCs) in each of the stimulated wells were counted and adjusted to control medium as background. Each dot represents the mean value for each animal. *p<0.05 by one-way ANOVA.

Week 38 PBMCs were assayed for T cells against Env and against adenovirus by ELISPOT on samples collected just prior to a second F8 Env protein boost. All Env-immunized animals had Env-specific IFN-γ secreting cells in their PBMCs (FIG. 18A). The level of Env-specific IFN-γ SFCs were generally increased in animals that received at least one mucosal immunization. However, IFN-γ SFCs were only significantly higher only in the IN-IN-IN SC-Ad group when they were compared to SC-Ad Ebola immunized control animals (p<0.05 by ANOVA). Anti-Ad SFCs were relatively low in all groups when compared to anti-Env SFCs at this time point.

Systemic Cellular Immune Responses after a Second Protein Boost

At week 40, PBMCs and inguinal lymph node cells were assayed for Env-specific IFN-γ SFCs by ELISPOT (FIG. 18B). This protein boost increased Env-specific SFCs in PBMCs and in lymph nodes to similar levels in all of the Env-immunized animals.

Mucosal Cellular Trafficking

Figure 19:
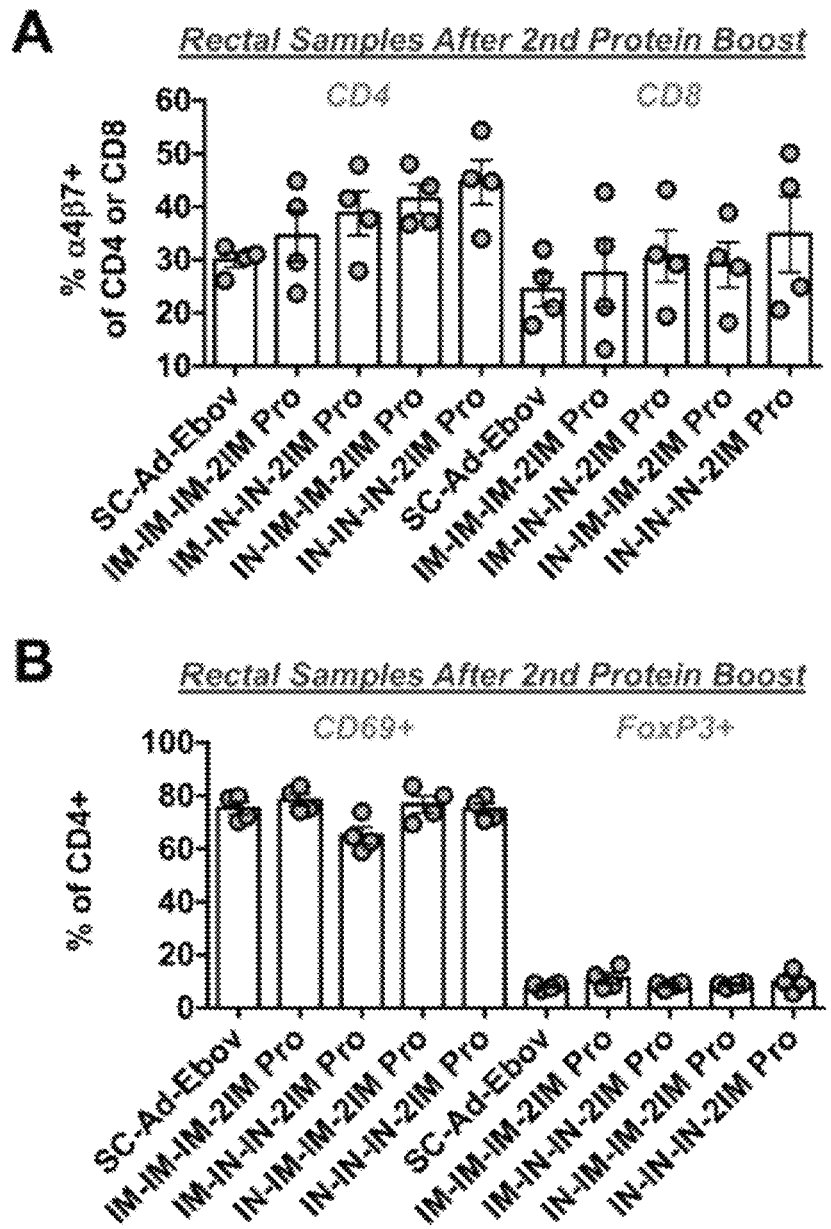
FIG. 19 shows mucosal T cell trafficking and activation. T cells were harvested from rectal biopsies collected after the second protein boost and analyzed by flow cytometry for CD4, CD8, α4β7 integrin, CD69, and FoxP3. Each dot represents the mean value for each animal.

Flow cytometry on rectal biopsy samples at week 40 showed similar numbers of α4β17 CD4 and CD8 cells in rectal sites (FIG. 19A). There was a trend towards increasing numbers in the IN primed groups, but these did not reach significance. The numbers of activated CD69+ CD4+ cells in rectal tissues were similar between the groups (FIG. 19B). Similarly, FoxP3+ CD4+ cells in this mucosal site were not appreciably different (FIG. 19B).

Antigen-Specific Tfh Cell Distributions

Figure 20:
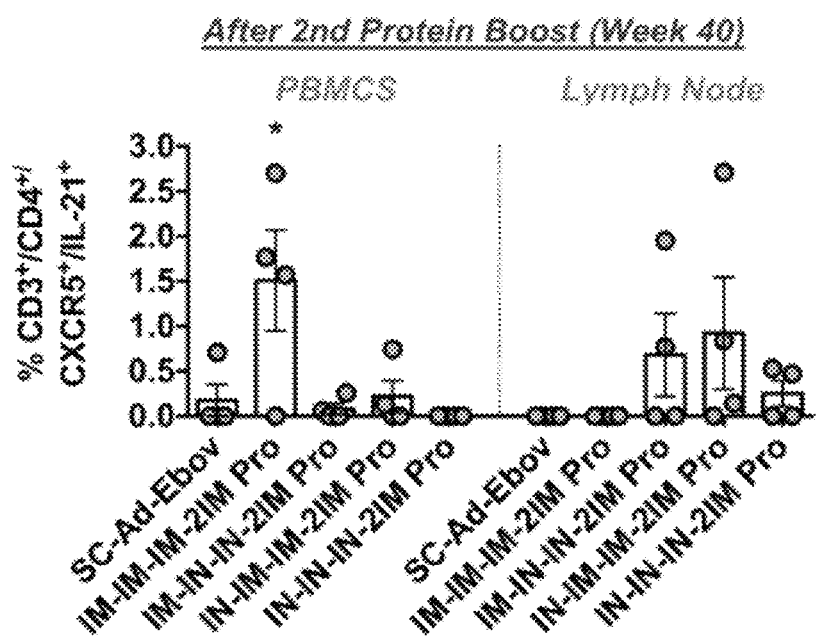
FIG. 20 shows Tfh cell response in the blood and in lymph nodes. PBMCs and lymph node cells collected at week 40 were stimulated with HIV-1 Env protein and then examined for co-expression of CD3+, CD4+, CXCR5+, and IL-21. Each dot represents the mean value for each animal. *p<0.05 by one-way ANOVA.

CXCR5+ IL-21+ CD4+ T follicular helper (Tfh) cells were measured in PBMCs and lymph node samples at week 40 (FIG. 20). The animals that were immunized by Ad and protein by only the IM route had significantly higher peripheral Tfh (pTfh) cells in PBMCs than other groups (FIG. 20). In lymph nodes, Tfh cells were lowest in the control and IM only group. In contrast, approximately one half of the animals that received at least one IN mucosal immunization have detectable Tfh in their lymph nodes after the last protein boost (FIG. 20).

Rectal Challenge with SHIV$_{SF162P3}$

Figure 21:
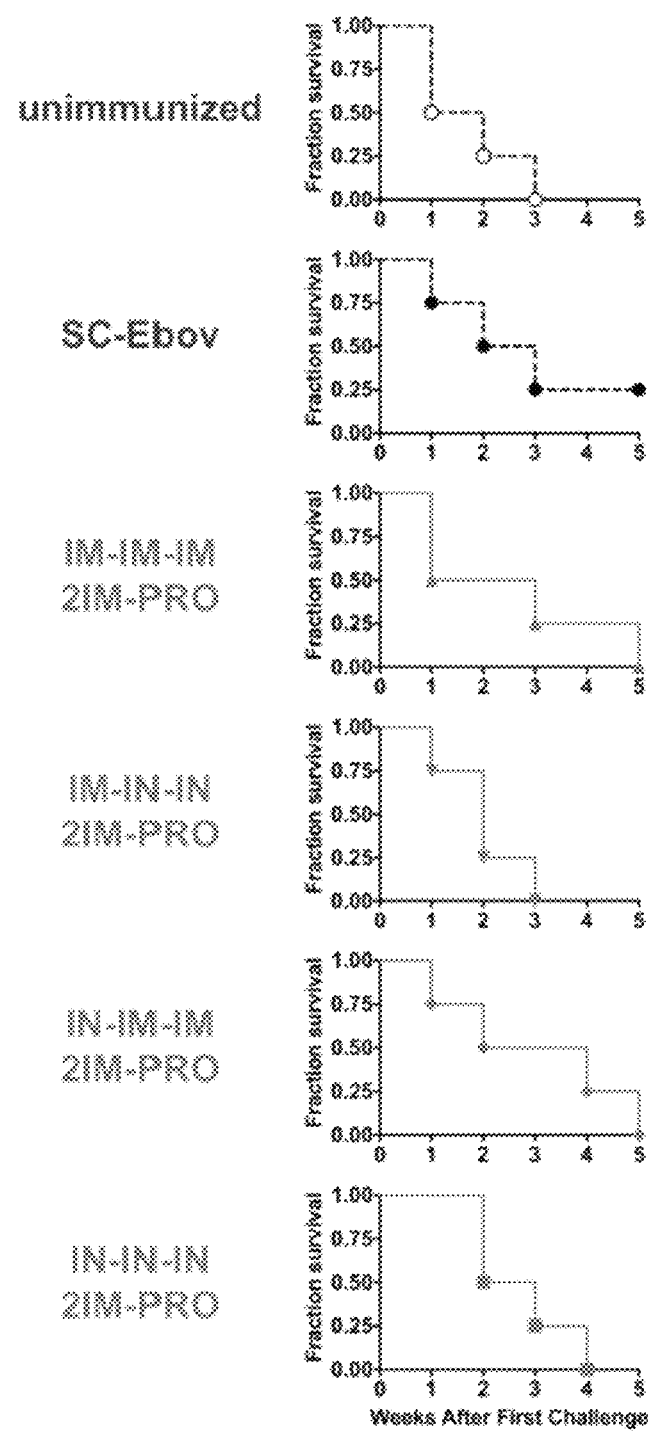
Figure 22:
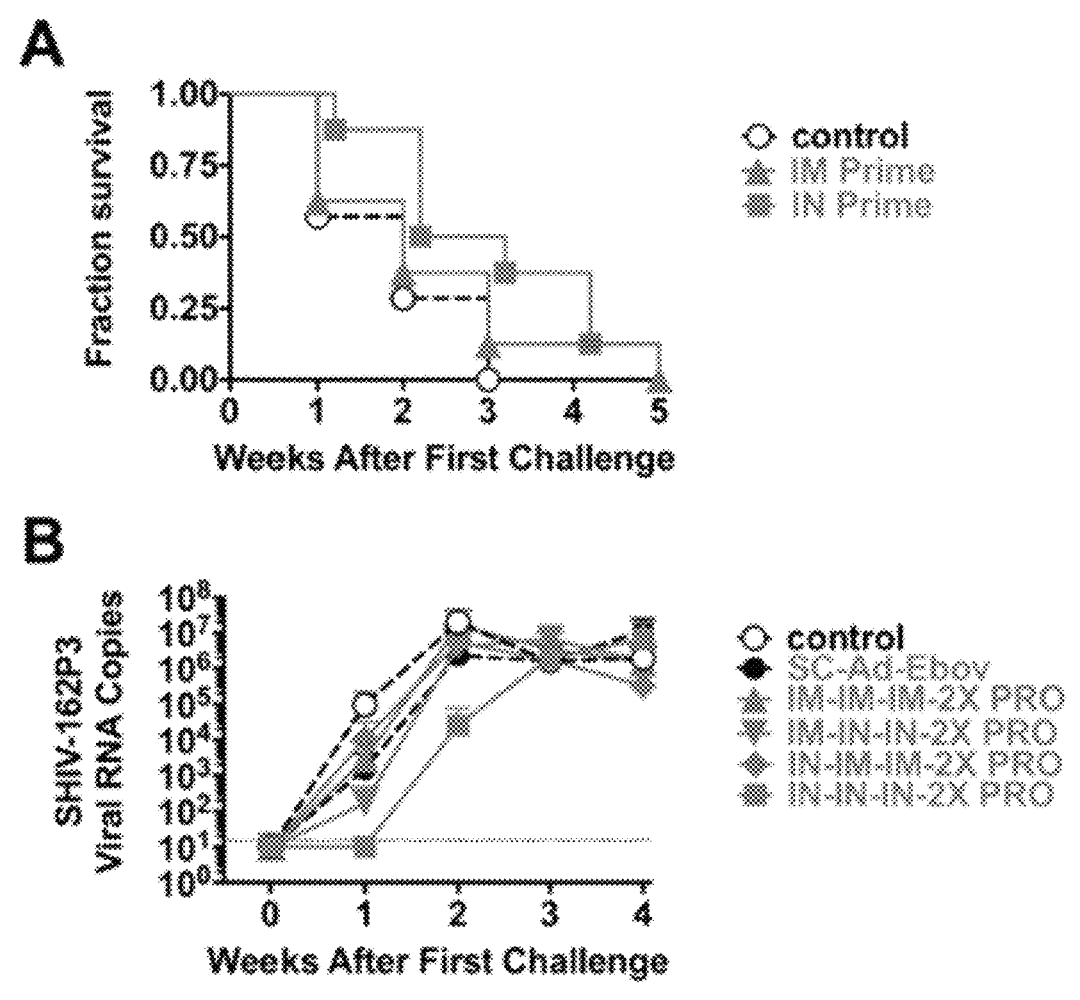

The immunized macaques were challenged rectally with HIV isolate SHIV$_{SF162P3}$. Four unimmunized control animals were added to the study and each group was challenged weekly by rectal inoculation with 1 ml a 1:300 dilution of SHIV$_{SF162P3}$ challenge stock provided by NIH. This challenge equaled 4.3 TCID$_{50}$ on rhesus PBMCs and 137 TCID$_{50}$ on TZM-bl cells. After the first challenge, 2 animals in an un-immunized control group and 2 animals in the IM-IM-IM group became infected (FIG. 21). One animal in each of the mixed route groups (IM-IN-IN and IN-IM-IM) became infected after one challenge. None of the animals in the IN-IN-IN group were infected after the first challenge. Viral loads in plasma indicated that all animals except the Ebola group animal reached high viral loads after 3 challenges (FIG. 22B). Animals in the IN-IN-IN group had a delay in reaching these high viral loads.

As challenges continued, animals in all groups became infected with the exception of one animal in the Ebola group that remained uninfected after 7 challenges. Trim5α and MHC alleles were examined retrospectively (Table 2). This analysis did not reveal overtly protective genes in the resistant Ebola group animal. Most animals could not be classified with alleles that might keep them moderately protected, but most groups had at least one animal with a higher likelihood of protection by virtue of these alleles. It should be noted that 2/4 animals in the IM-IM-IM and IN-IN-IN groups had Trim5a and MHC alleles that might predict a higher likelihood of innate protection against SIVsmm and perhaps SHIV$_{SF162P3}$ (Table 2).

TABLE 2

Retrospective Screening for SIV Protective Gene Alleles.

| Vaccine Group | Animal Number | MHC typing | TRIM5alpha | Degree of viral protection |
|---|---|---|---|---|
| Unimmunized | RHJ663 | Not done | Cyp A/TFP | High |
| | RH3-39 | Not done | Q/TFP | Moderate |
| | RHJ403 | Not done | CypA/Q | Moderate |
| | RHJ791 | Not done | Q/TFP | Moderate |
| SC-Ad-Ebov | RH13-005 | A11, B01, B17 | Q/TFP | Moderate |
| | RH13-007 | A08, A11, B01, B17 | Q/TFP | Moderate |
| | RH13-043 | A08, A11, B17 | Q/TFP | Moderate |
| | RH13-135 | A08, A11, B17 | Q/TFP | Moderate |
| IM-IM-IM | RH13-027 | A11, B01, B17 | TFP/TFP | High |
| | RH13-031 | A08, A11, B01 | Cyp A/Q | Moderate |
| | RH13-051 | A08, A11, B17 | Cyp A/Q | Moderate |
| | RH13-139 | A08, A11, B17 | TFP/TFP | High |
| IM-IN-IN | RH13-039 | A11, B01, B17 | Cyp A/Q | Moderate |
| | RH13-045 | A08, A11, B01, B17 | Q/Q | Susceptible |
| | RH13-095 | A08, A11, B17 | Q/TFP | Moderate |
| | RH13-159 | A08, A11 | Cyp A/TFP | High |
| IN-IM-IM | RH13-013 | A11, B17 | Cyp A/Q | Moderate |
| | RH13-067 | A08, A11, B01, B17 | Q/TFP | Moderate |
| | RH13-091 | A11, B01, B17 | TFP/TFP | High |
| | RH13-121 | A08, A11, B17 | Q/TFP | Moderate |
| IN-IN-IN | RH13-025 | A11, B17 | Cyp A/Q | Moderate |
| | RH13-033 | A08, A11, B17 | Cyp A/TFP | High |
| | RH13-087 | A08, A11, B01, B17 | TFP/TFP | High |
| | RH13-125 | A08, A11, B17 | Q/TFP | Moderate |

When the animals were grouped based on whether they were primed by the IM or IN route with SC-Ad and Kaplan-Meier survival was analyzed, infection of the eight IM primed animals paralleled that of control animals (FIG. 22A). In contrast, infection was somewhat delayed in the eight animals that were primed with SC-Ad-Env by the mucosal IN route.

Post-Mortem Viral Loads in Tissues

Figure 23:
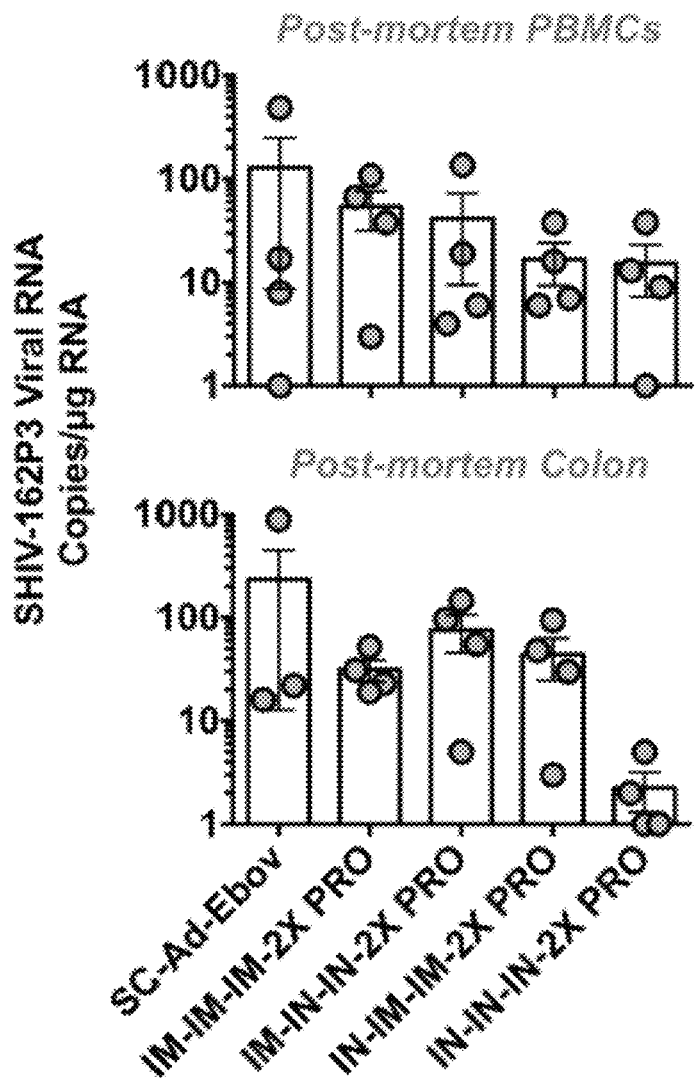
FIG. 23 shows SHIV viral load in tissues. RNA from PBMCs and post-mortem tissues were collected and qPCR was performed to detect analyzed for SHIV viral RNA.

The challenge study was terminated 9 weeks after first challenge. PBMCs and gut tissues were isolated, RNA was purified, and evaluated for SHIV viral genomes (FIG. 22B). Post-mortem PBMCs had varied levels of SHIV viral RNA with somewhat lower levels in the IN-IN-IN group than in the IM-IM-IM group. Mean viral RNA in the colon was 15-fold lower in the IN-IN-IN group than the IM-IM-IM group (FIG. 23). This difference did not reach significance by ANOVA, but two-tailed T test gave a p value of 0.0079.

This example demonstrates that replicating SC-Ad vectors can be used as a robust and safe platform for vaccination against HIV-1 and other infectious diseases. SC-Ad is able to amplify antigen and cytokine genes up to 10,000-fold in infected human cells. The immune response is amplified well-above those mediated by RD-Ad vectors that are currently being tested as HIV-1 vaccines in humans HIV vaccines can be transitioned to vaccine platforms that amplify HIV antigen genes by utilizing SC-Ad vectors, for example, SC-Ad vectors based on recombinant Ads having low seroprevelance.

Example 8

Figure 26:
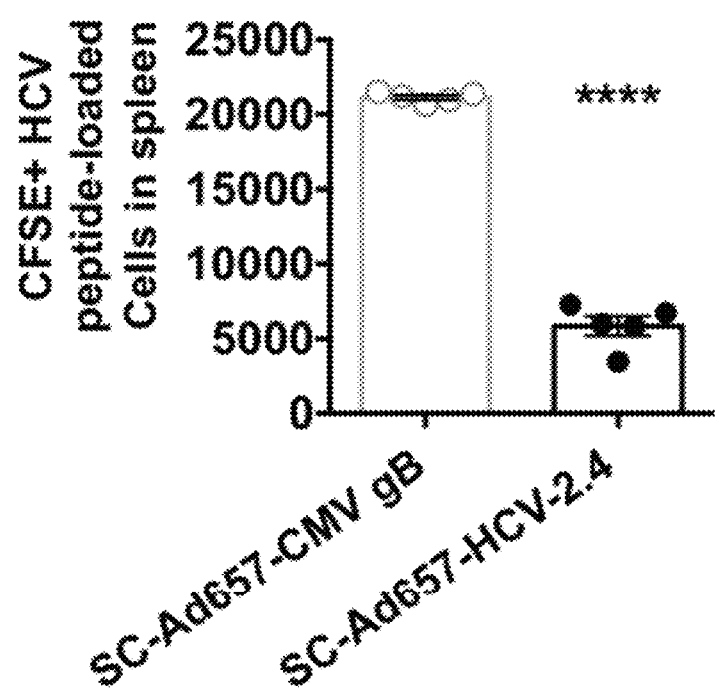
FIG. 26 shows Ad657 expressing antigen genes from hepatitis C and cytomegalovirus (CMV) gB generating in vivo cytotoxic T lymphocyte (CTL) activity. Shown is killing of hepatitis C peptide-loaded target cells in mice vaccinated with Ad657-HCV rather than CMV gB.

In Vivo Cytotoxic T Lymphocyte (CTL) Assay for Immune Responses against Hepatitis C Virus (HCV) Antigen Mice were immunized with Ad657 expressing the CMV cytomegalovirus (CMV) glycoprotein B (gB) cDNA or HCV antigen 2.4. Syngeneic cells were pulsed with HCV peptide and labeled with carboxyfluorescein succinimidyl ester (CFSE) prior to injection into the immunized mice. Cognate CTL activity is observed against HCV by loss of labeled cells in the HCV, but not CMV immunized animals (FIG. 26).

Example 9

Conditionally Replicating Ads (CRAds)

Figure 39:
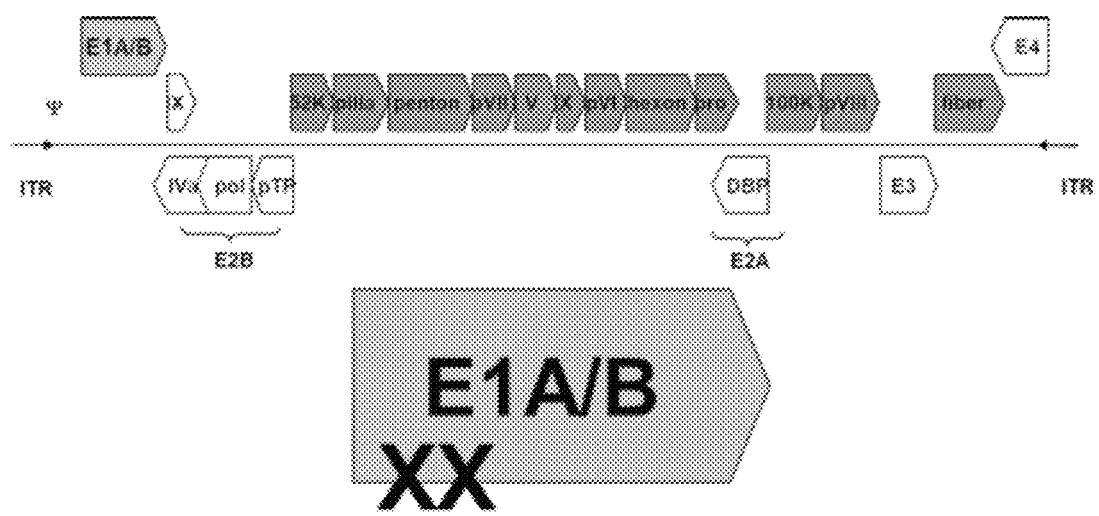
FIG. 39 shows a schematic of cancer-specific conditionally-replicating Ads (CRAds) dl1101+dl1107 having a modification in the E1A gene.

Schematic of mutations in Ad6, Ad657 and variants thereof involving mutations in the E1 protein to convert the virus to a conditionally-replicating Ad (CRAd) is shown in FIG. 39 and FIG. 43. These include dl1101 and/or the dl1107 that block binding to p300 and pRB, respectively.

FIG. 56 shows the N-terminal amino acid sequences of E1A in a wild-type Ad, as well as Ad variants E1A dl1101, E1A dl1107 and E1A dl1101/1107.

Figure 55:
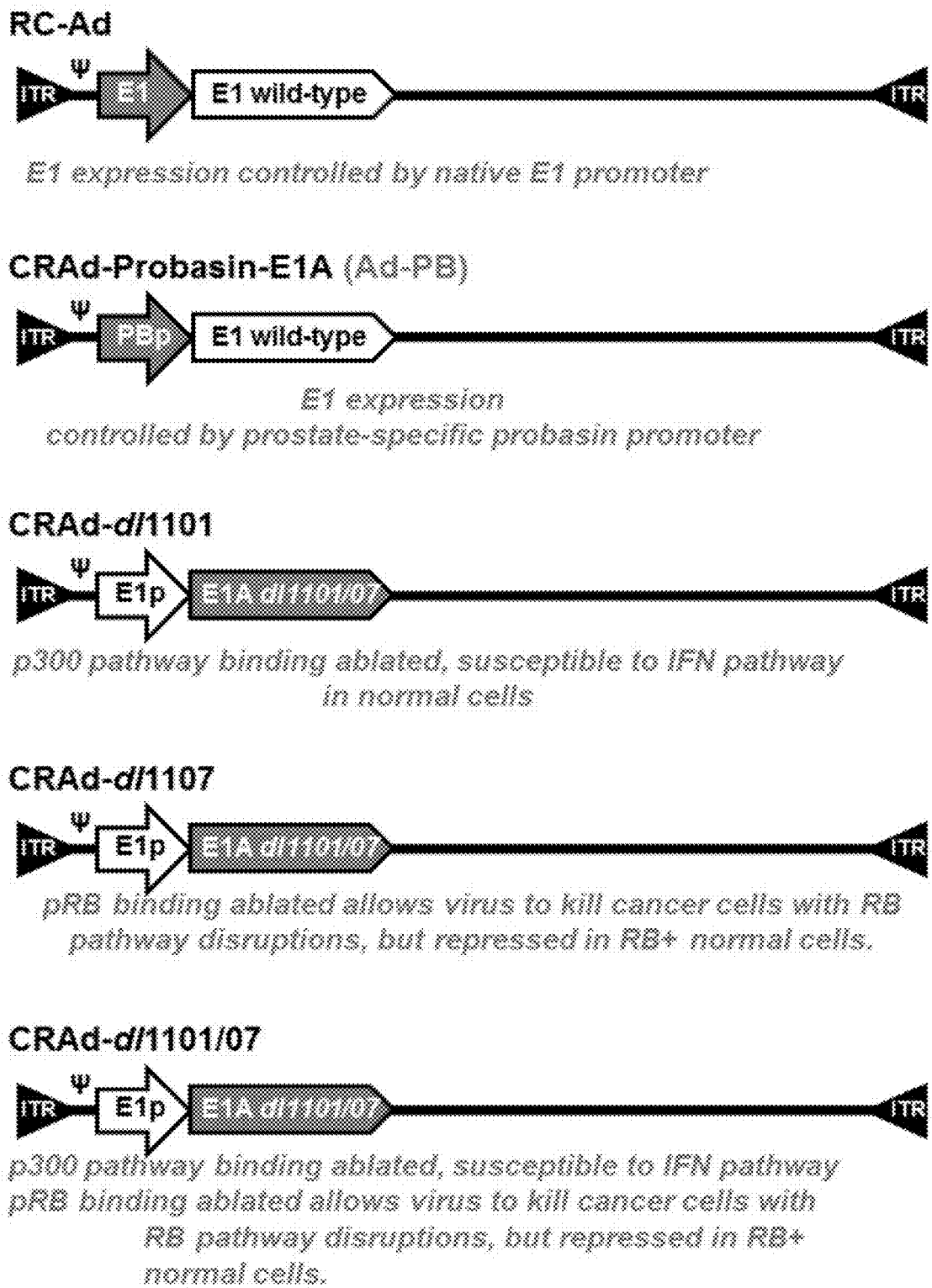
FIG. 55 is a schematic of variants of Ads having mutations in the E1 protein to convert the virus to a conditionally-replicating Ad (CRAd).

Also shown is the replacement of the Ad E1 promoter with the prostate-specific promoter probasin-E1 DNA sequence of SEQ ID NO:48 to generate the CRAd, Ad-PB (FIG. 55). The probasin promoter is androgen dependent, so will work in androgen-sensitive tumors like LNCaP, but not in androgen-resistant tumors like DU145.

Figure 40:
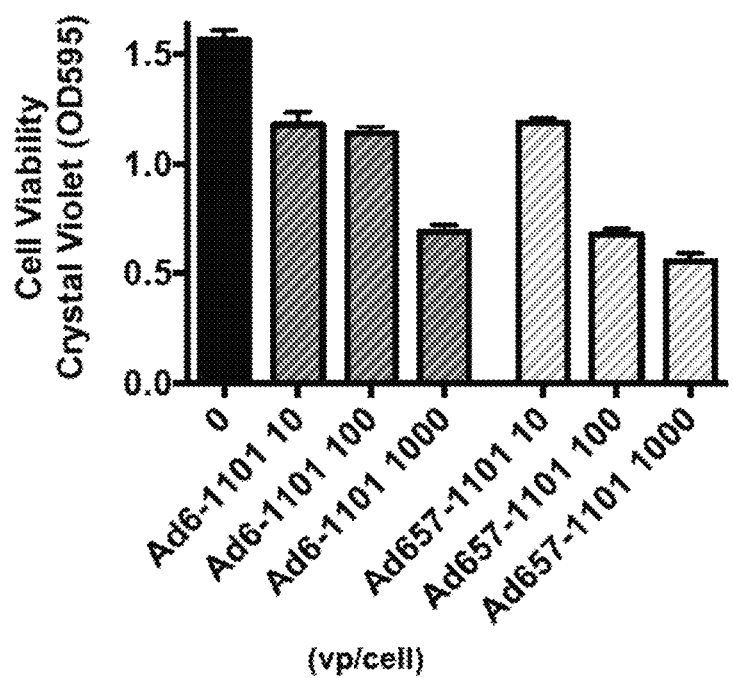
FIG. 40 is a graph showing that Ad6 and Ad657 can both be used as CRAds for targeted cancer therapy.

A549 cells were infected with the indicated Ad6 or Ad657 variants at the indicated concentrations of virus (vp/cell) and cell viability was measured by crystal violet staining after 5 days (FIG. 40).

Killing of non-cancerous cells by replication-defective Ad (RD-Ad), Ad6, CRAd6-dl1101/dl1107 or CRAd6-PB. Modification of Ad6 and Ad657 to be conditionally-replicating Ads (CRAds) is demonstrated (FIG. 44).

Killing of cancerous cells by replication-competent Ad5, Ad6, Ad657, and the indicated CRAds is shown in FIG. 45. The modification of Ad6 and Ad657 to be conditionally-replicating Ads (CRAds) is demonstrated.

Figure 46:
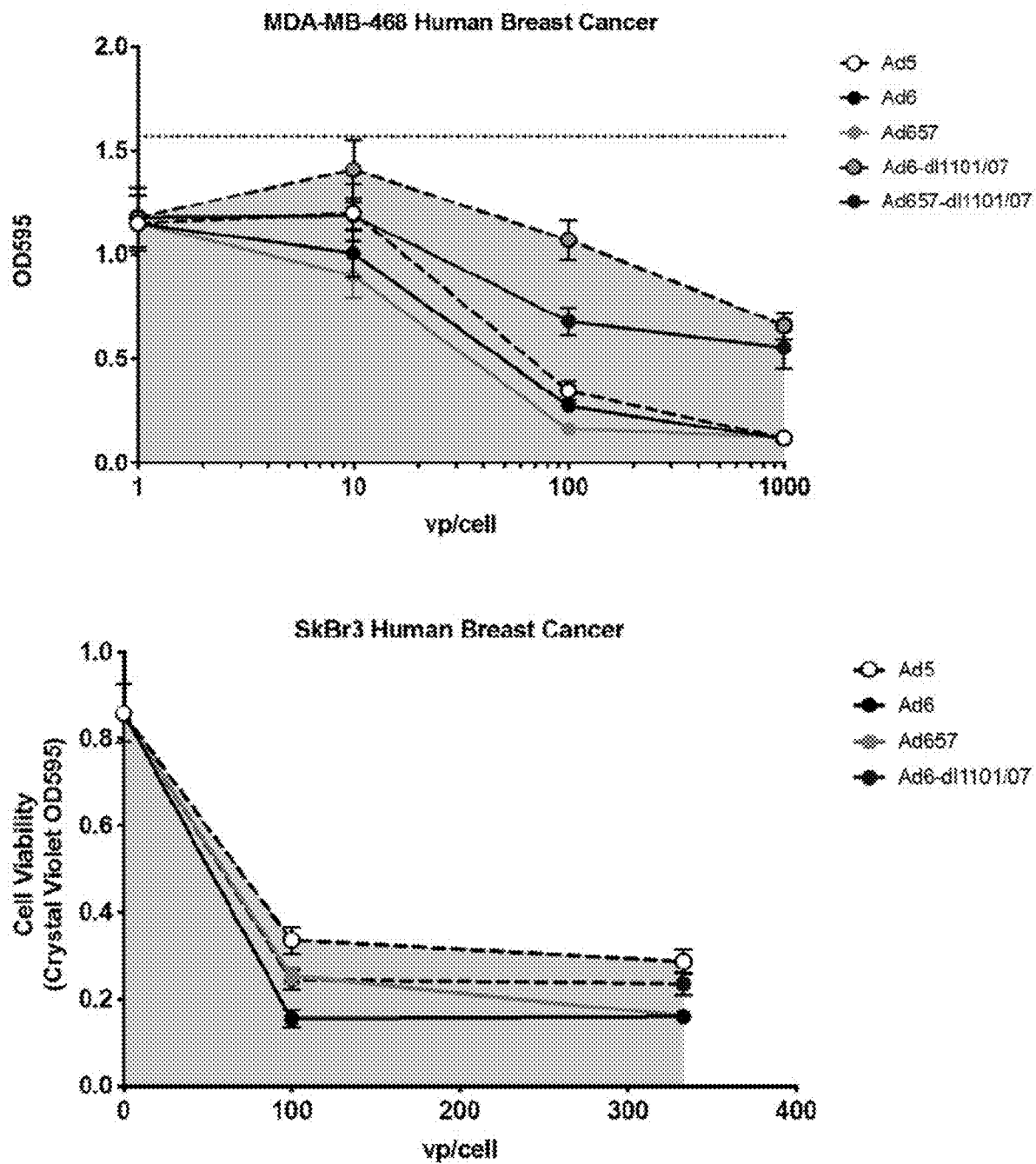
FIG. 46 demonstrates modification of Ad6 and Ad657 to be conditionally-replicating Ads (CRAds).

The results shown in FIG. 46 demonstrate modification of Ad6 and Ad657 to be conditionally-replicating Ads (CRAds) in breast cancer cells.

Figure 47:
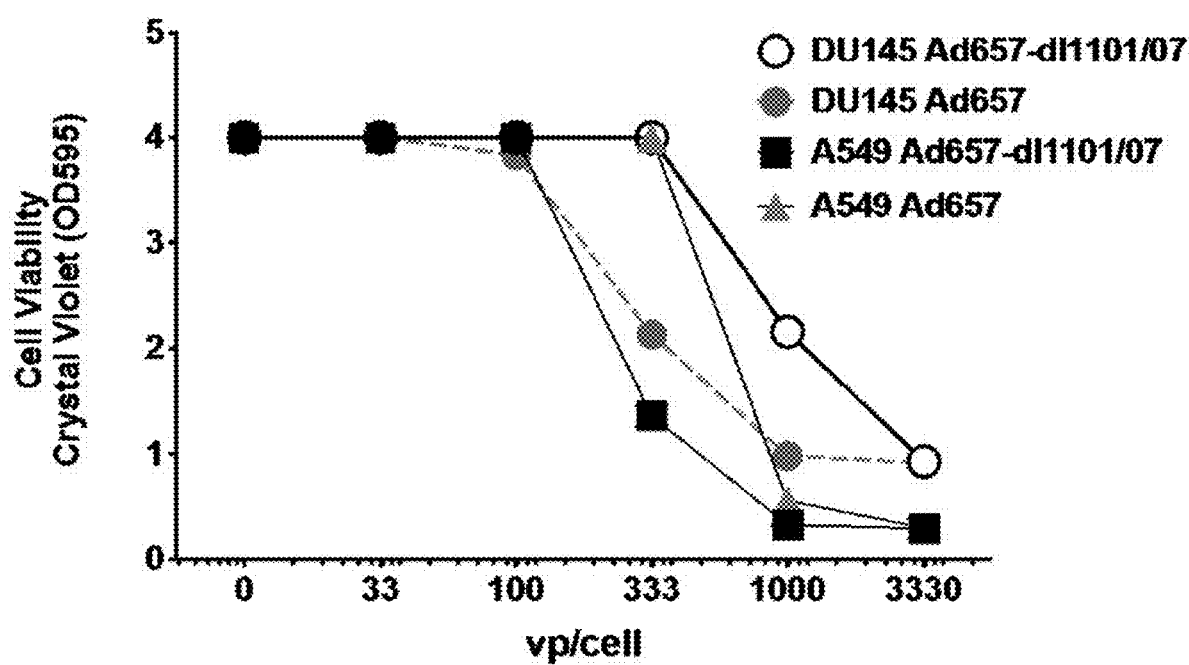
FIG. 47 demonstrates modification of Ad6 and Ad657 to be conditionally-replicating Ads (CRAds).

The results shown in FIG. 47 demonstrate modification of Ad6 and Ad657 to be conditionally-replicating Ads (CRAds) in prostate cancer cells and lung cancer cells.

Figure 48:
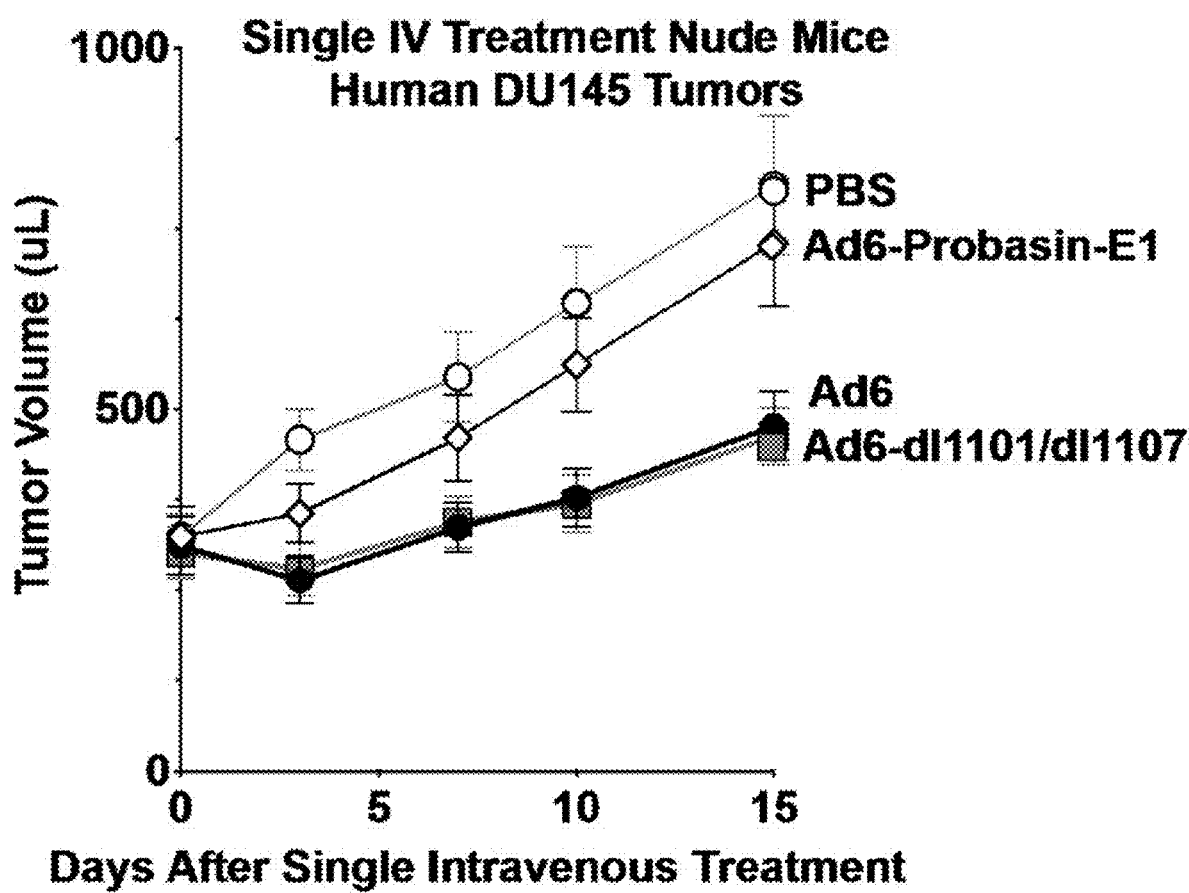
FIG. 48 demonstrates in vivo effects of replication-competent Ad6 or the indicated CRAds on growth of DU145 tumors in mice.

In vivo effects of replication-competent Ad6 or the indicated CRAds on growth of DU145 tumors in mice. FIG. 48 demonstrates modification of Ad6 and Ad657 to be conditionally-replicating Ads (CRAds) in vivo after a single intravenous injection in mice bearing human prostate tumors.

Figure 49:
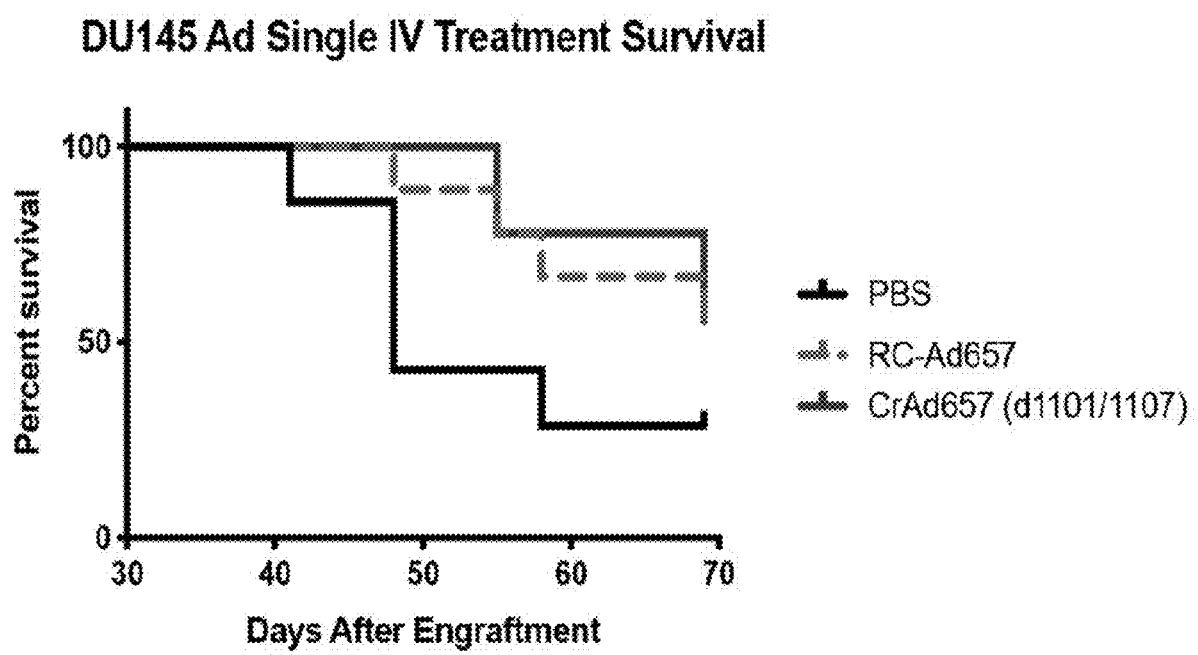
FIG. 49 demonstrates in vivo effects of replication-competent Ad657 and conditionally-replicating Ad657-dl1101/07 both with intact E3 regions in vivo after a single intravenous injection in mice bearing human prostate tumors.

In vivo effects of replication-competent Ad6 or the indicated CRAds on survival of mice with DU145 tumors. FIG. 49 demonstrates modification of Ad6 and Ad657 to be conditionally-replicating Ads (CRAds) in vivo after a single intravenous injection in mice bearing human prostate tumors.

Figure 51:
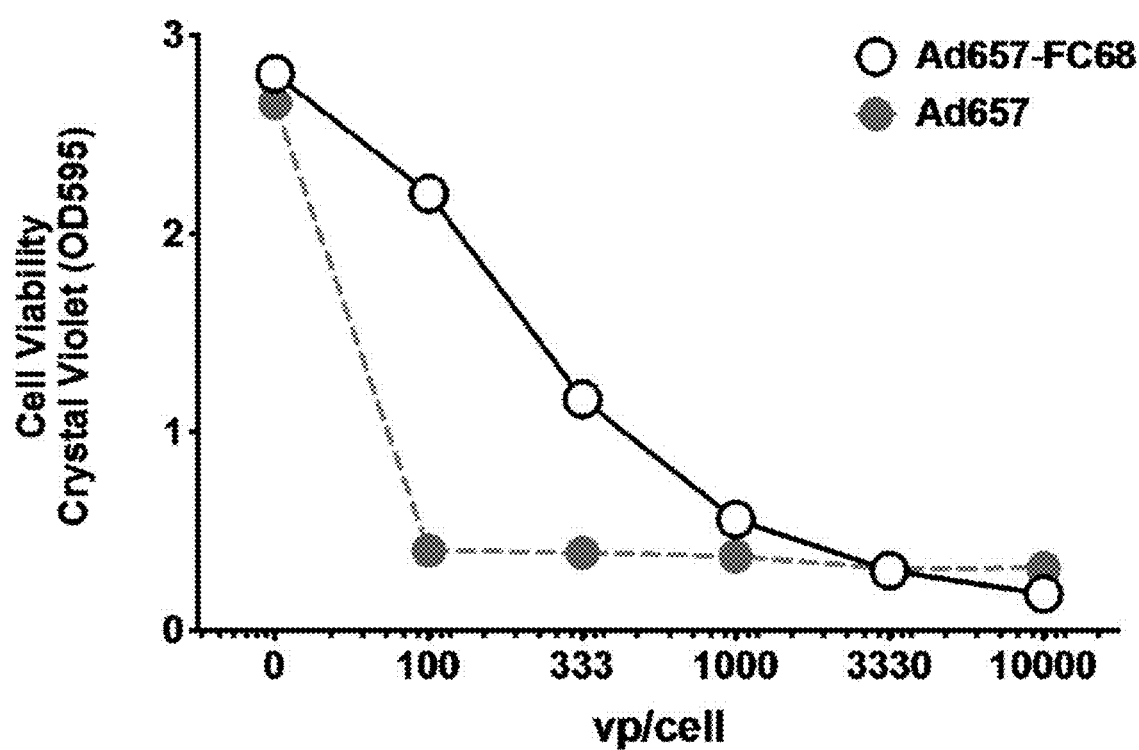
FIG. 51 demonstrates modification of Ad657 with the shorter fiber from chimpanzee AdC68 and the addition of a codon-wobbled E4 34.K gene changes in vitro efficacy.

FIG. 51 demonstrates that modification of Ad657 with the shorter fiber from chimpanzee AdC68 reduces efficacy.

Figure 52:
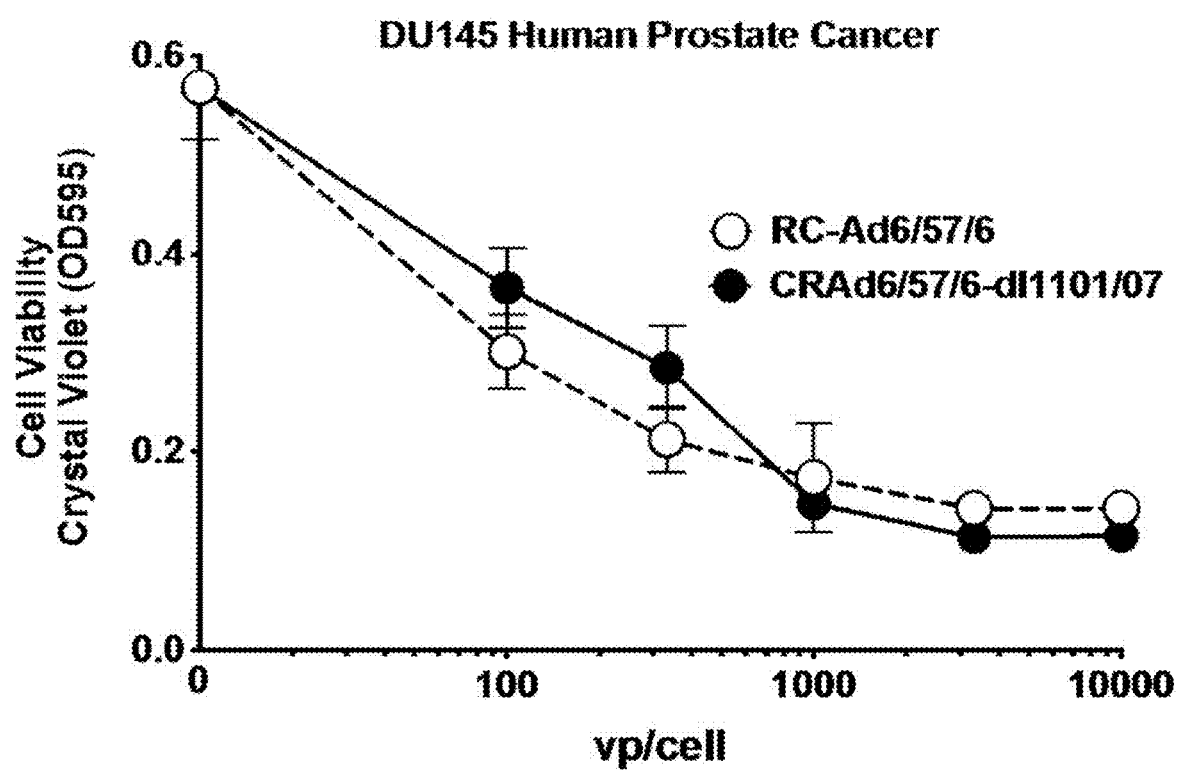
FIG. 52 demonstrates 6/57/6 virus killing human prostate cancer cells with and without CRAd modifications.

In an embodiment, an Ad 6/57/6 virus has HVRs 1 and 7 from Ad6 and HVRs 2-6 from Ad657. FIG. 52 demonstrates Ad 6/57/6 virus killing human lung cancer cells with and without CRAd modifications.

Tumor cell killing by Ad variants involving mutations in the E3 protein Immune competent Syrian hamsters were engrafted with subcutaneous HaK kidney cancer tumors. When these reached 200 µl volume, they were injected a single time by the intravenous route with the indicated Ad6 viruses constructed with and without E3 (DE3) and with or without random NHS-PEGylation. Tumor sizes were measured over time. The data shows that deleting all E3 genes makes the oncolytic virus less effective (Ad6-deltaE3-Luc vs Ad6-Luc) (FIG. 58).

The Ad fiber protein is a complex of three apparently identical subunits which mediates the initial attachment step. The Dative Ad6 fiber protein comprises the amino acid sequence set forth in SEQ ID NO:60 and binds CAR.

In a further aspect of the invention, fiber-modified recombinant Ads having different fiber proteins which are not native to the parental Ad were generated. Recombinant Ads, including CRAds, comprising capsid proteins from different Ad strains were generated, for example, recombinant Ads comprising a heterologous Ad35 fiber polypeptide or Chimpanzee C68 fiber polypeptide, +/− a K7 peptide (FIGS. 62-69).

A chimeric Ad, AdF35 fiber chimera, has the amino acid sequence of SEQ ID NO:61 and is shorter than Ad5 and Ad6 fiber proteins and retargets virus to CD46.

A fiber-modified recombinant Ad, comprising K7 Fiber having the sequence of SEQ ID NO:62, targets virus to heparin sulfate proteoglycans and negative charges on cells.

A recombinant, chimeric Ad, 6/FC68 Fiber comprising the sequence of SEQ ID NO:63, is a chimeric Ad having a fiber protein from chimpanzee adenovirus C68. The fiber protein is shorter than Ad5 or Ad6 fiber proteins and binds CAR.

A recombinant, chimeric Ad, 6/FC68-K7 Fiber comprising the sequence of SEQ ID NO:64, is a chimeric Ad having a fiber protein from chimpanzee adenovirus C68. The fiber protein is shorter than Ad5 or Ad6 fiber proteins. The 6/FC68-K7 Fiber binds CAR and is retargeted to heparin sulfate and negative charges.

A recombinant, chimeric Ad, 6/FC68-HI-K7 Fiber comprising the sequence of SEQ ID NO:65, is a chimeric Ad having a fiber protein from chimpanzee adenovirus C68. The fiber protein is shorter than Ad5 or Ad6 fiber proteins. The 6/FC68-HI-K7 Fiber binds CAR and is retargeted to heparin sulfate and negative charges.

Example 10

Serotype-Switching of Adenoviruses

Figure 41:
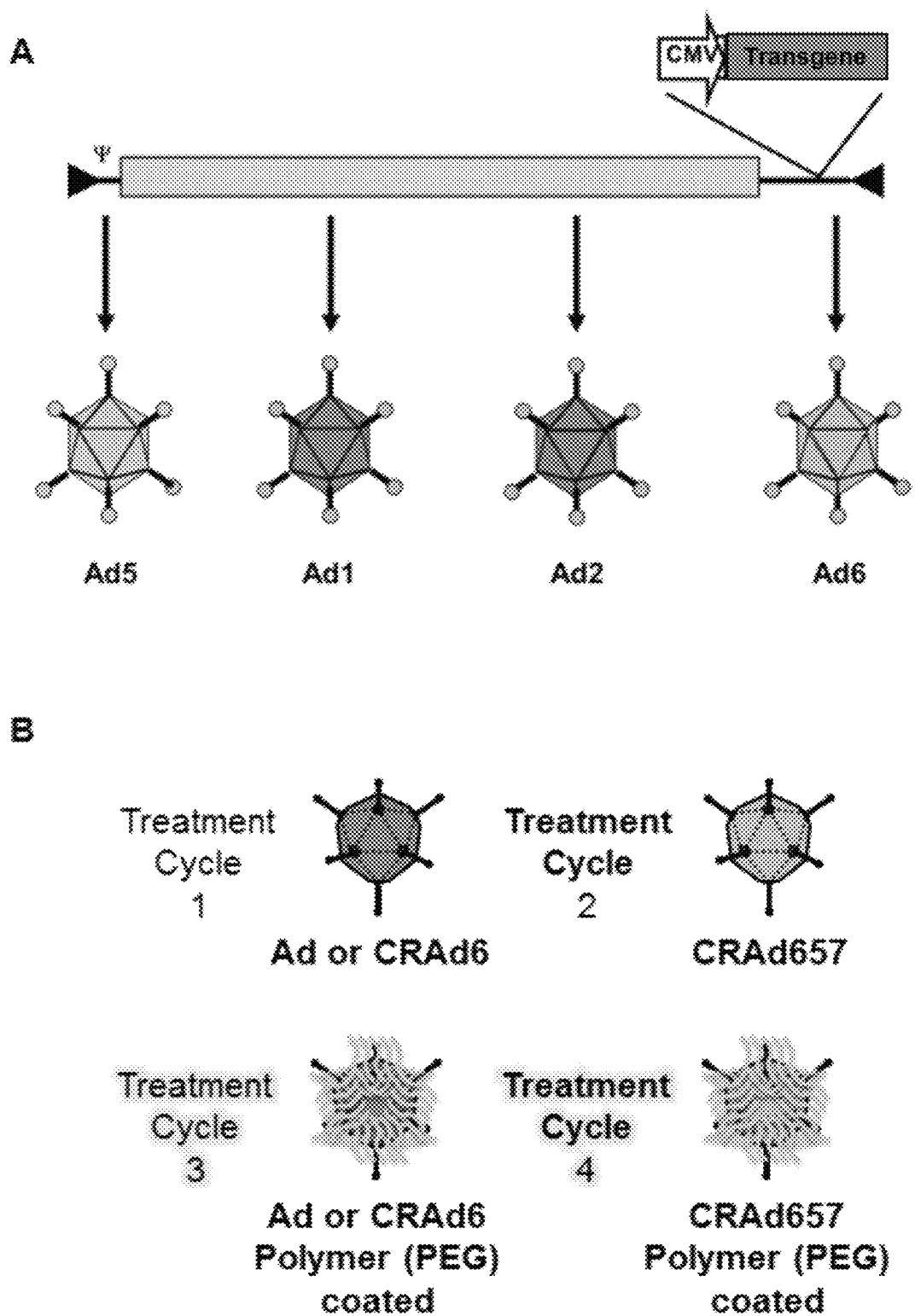
FIG. 41 is a schematic showing Ad therapeutic cycles. A) A schematic of serotype-switching with Ads. B) A schematic of an exemplary therapeutic cycle where Ad6 and Ad657 can be used for multiple rounds of treatment by serotype-switching in combination with covalent polymer conjugation.

FIG. 41 is a schematic showing Ad therapeutic cycles. In an embodiment serotype-switching with different Ads over the course of a treatment is exemplified (FIG. 41A). Prostate Tumor Targeting after Serotype-switching of Oncolytic Adenoviruses.

Figure 42:
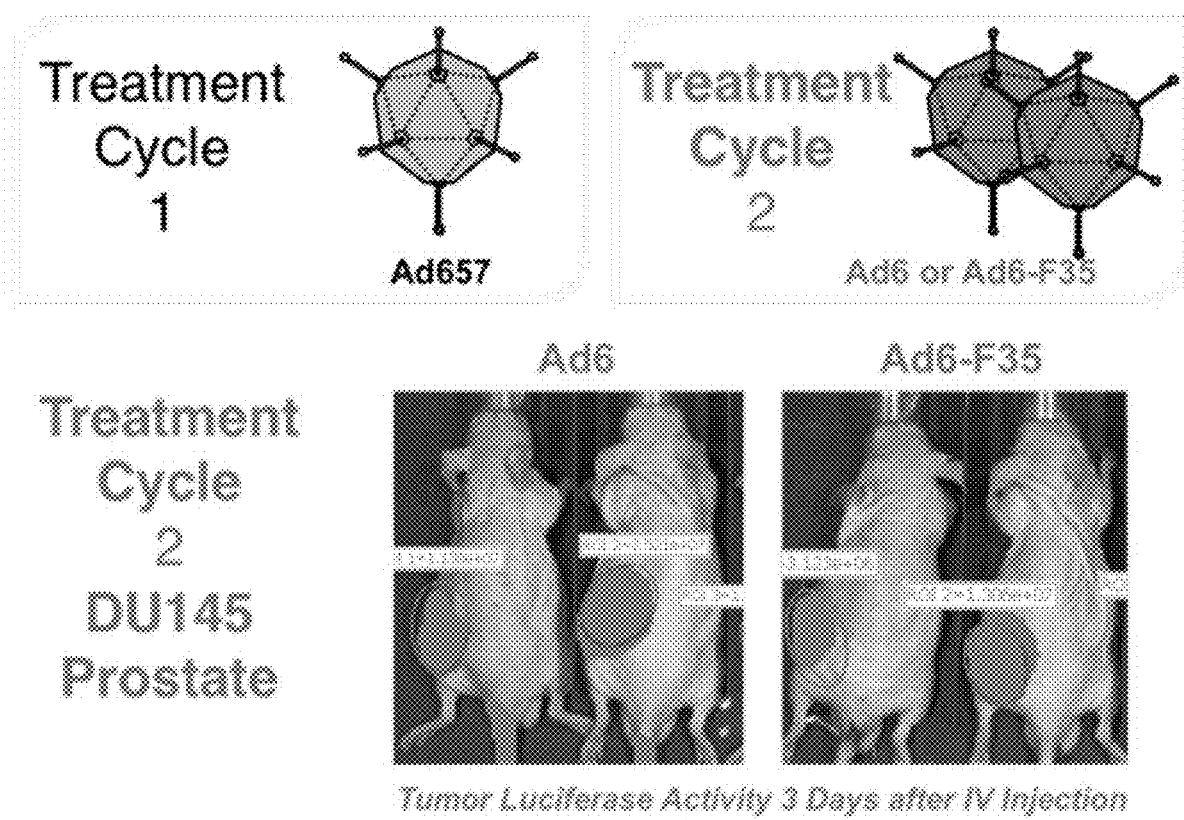
FIG. 42 demonstrates serotype-switching and on-target luciferase activity in the DU145 prostate tumors after a single IV injection of Ad6 and Ad6-F35 with deletions in E3A genes (12.5K, 6.7K, 19K, 11.6K), but retention of E3B genes (10.4K, 14.5K, and 14.7K) and retention of E4 34K. Mice whose tumors resisted prior single IV injection with Ad657 and CRAd657 both with intact E3 genes were injected with the indicated vectors by single IV injection.

Mice bearing DU145 prostate tumors on their flanks were treated by a single intravenous (IV) injection with Ad657 or CRAd657. These mice were treated a second time with alternate Ad6 oncolytic virus or Ad6-F35 expressing GFPLuciferase and luciferase activity was measured by imaging. Ad6 has Ad6 hexon and fiber that targets CAR. Ad6-F35 has Ad6 hexon and the Ad35 fiber that targets CD46. FIG. 42 demonstrates the capability to serotype-switch oncolytics with viruses targeting a tumor with lower off-target infection of the liver.

In another example of serotype-switching, mice bearing LNCaP prostate tumors on their flanks were treated by a single intravenous (IV) injection with 3e10 viral particles (vp) of Ad657 or CRAd657. These mice were treated a second time 5 months later with 3e10 vp alternate Ad6/57/6 oncolytic virus expressing GFPLuciferase and fiber variants K7 (with 7 lysines added), F35 (with the Ad35 fiber), or KKTK-C68 (chimpanzee C68 fiber fused after the Ad6 KKTK flexibility domain. KKTK-C68 virus also has an added codon-optimized E4 34K gene to enhance viral productivity. Luciferase activity was measured by imaging 7 days later. All Ad6/57/6's have a hexon with HVR1 and 7 from Ad6 and HVRs 2-6 from Ad57. Ad6/57/6 and KKTK-C68 have fibers that targets CAR. Ad6/57/6-F35 has the Ad35 fiber that targets CD46. K7 increases binding to negative charges on cells including binding heparin sulfate proteoglycans. FIG. 70 demonstrates the capability to serotype-switch oncolytics with viruses targeting a tumor with lower off-target infection of the liver.

Serotype-Switching During Vaccination of Non-human Primates.

In FIGS. 14 through 25, rhesus macaques were immunized with replicating single-cycle Ad6 expressing HIV envelope and then boosted by serotype-switching with single-cycle Ad657 expressing HIV envelope. Following these immunizations, each animal was boosted with envelope protein. Each figure shows the generation of adaptive antibody or cellular immune responses and how the animals repelled rectal challenge with $SHIV_{SF162P3}$ virus. FIG. 14 documents the value of the serotype-switch where changing to Ad657 generated marked increases in antibody responses.

Example 11

Oncolytic Cancer Vaccines

Figure 53:
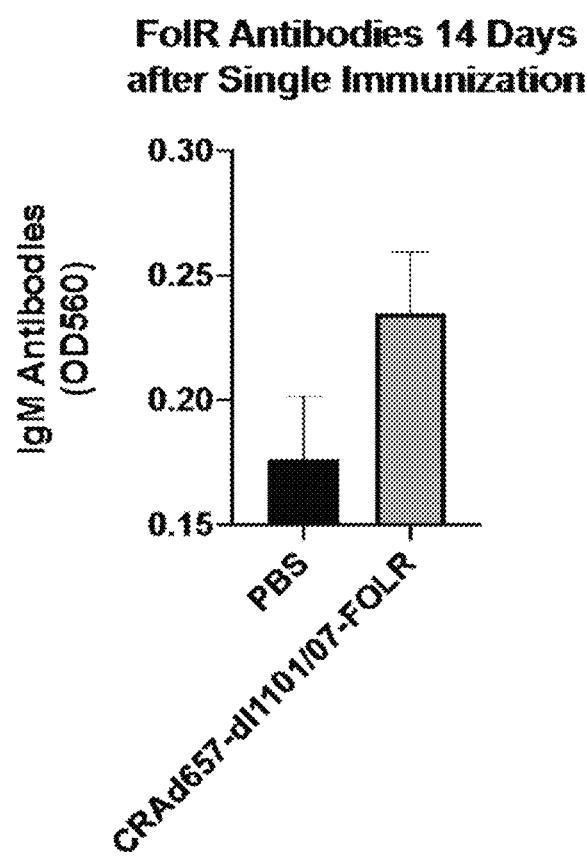
FIG. 53 demonstrates the production of antibody responses against the human cancer antigen folate receptor alpha after a single intramuscular immunization of BALB/c mice by CRAd657-dl1101/07-FOLR with an intact E3 region.

BALB/c mice were immunized with $10^{10}$ virus particles of CRAd-657-dl1101/1107-FolR with intact E3 and expressing the human folate receptor alpha or with PBS by the intramuscular route. Sera was collected 2 weeks after one immunization and analyzed for anti-Folate Receptor alpha antibodies by ELISA using anti-IgM antibody for detection (all antibodies are IgM at this type of early time point after immunization). Data shows the generation of antibodies against the known cancer antigen folate receptor alpha by this CRAd. p—0.07 by T test (FIG. 53).

Example 12

Effects of E3 Immune Evasion Genes on Oncolytic Activity

FIG. 57 shows as schematic of different E3 immune evasion genes in Ads. E3 19K protects infected cells from T cells and NK cells. RID proteins protect infected cells from death-inducing ligands (FAS, TRAIL, TNFR, and EGFR). 14.7K inhibits intrinsic activation of apoptosis in infected cells. Species C Ads also express the 11.6K known as the adenovirus death protein (ADP). Over-expression of ADP accelerates cell death, but overall cell death is equal. Species 49K binds to CD46 on T cells and NK cells leading to down-regulation of these cells and less-efficient cell killing of cells deficient in class I MHC by NK cells.

FIG. 58 demonstrates that partial deletion of E3 12.5K and full deletion of E3 6.7K, 19K, 11.6K (ADP), 10.4K (RIDα), 14.5K (RIDβ), and 14.7K genes reduces oncolytic efficacy in an immunocompetent hamster model of kidney cancer when these immune evasion genes are not present in oncolytic adenovirus.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A recombinant adenovirus (Ad), wherein capsid hexon polypeptides of an Ad strain Ad6 comprise at least two capsid hexon hypervariable region (HVR) polypeptides from Ad strain Ad57.

2. The recombinant Ad of claim 1, wherein the capsid hexon polypeptides of the Ad strain Ad6 comprise capsid hexon hypervariable region (HVR) polypeptides 1-7 from Ad strain Ad57.

3. The recombinant Ad of claim 2, which is Ad657.

4. The recombinant Ad of claim 1, wherein the capsid hexon polypeptides of the Ad strain Ad6 comprise capsid hexon hypervariable region (HVR) polypeptides 2-6 from Ad strain Ad57.

5. The recombinant Ad of claim 4, which is Ad6/57/6.

6. A pharmaceutical composition comprising the recombinant Ad of claim 1 and a pharmaceutically acceptable carrier, filler, and/or vehicle.

7. A conditionally-replicating Adenovirus (CRAd) comprising a recombinant Adenovirus (Ad) which has been modified in an E1A gene encoding an E1A polypeptide, wherein the CRAd exhibits amino acid substitutions in the E1A polypeptide relative to wild-type E1A polypeptide of an Ad strain, and wherein the CRAd capsid hexon polypeptides are from an Ad strain Ad6 and wherein the capsid hexon polypeptides comprise at least two capsid hexon hypervariable region (HVR) polypeptides from Ad strain Ad57.

8. The CRAd of claim 7, wherein the N-terminal portion of the E1A polypeptide comprises an amino acid sequence set forth in SEQ ID NO:43, SEQ ID NO:44 or SEQ ID NO:45.

9. The CRAd of claim 7, wherein the capsid hexon polypeptides of the Ad strain Ad6 comprise capsid hexon hypervariable region (HVR) polypeptides 1-7 from Ad strain Ad57.

10. The CRAd of claim 7, wherein the capsid hexon polypeptides of the Ad strain Ad6 comprise capsid hexon hypervariable region (HVR) polypeptides 2-6 from Ad strain Ad57.

11. The CRAd of claim 7, wherein the recombinant Adenovirus (Ad) has been modified in an E1A gene to comprise a dl1101 deletion in a nucleic acid encoding an E1 polypeptide, modified to comprise a dl1107 deletion in a nucleic acid encoding an E1 polypeptide, or modified to comprise a dl1101 deletion and a dl1107 deletion in a nucleic acid encoding an E1 polypeptide.

12. A pharmaceutical composition comprising the recombinant Ad of claim 7 and a pharmaceutically acceptable carrier, filler, and/or vehicle.

* * * * *